US009862938B2

(12) United States Patent
Smith et al.

(10) Patent No.: US 9,862,938 B2

(45) Date of Patent: *Jan. 9, 2018

(54) THERMOSTABLE REVERSE TRANSCRIPTASES AND USES THEREOF

(71) Applicant: LIFE TECHNOLOGIES CORPORATION, Carlsbad, CA (US)

(72) Inventors: Michael D. Smith, Rockville, MD (US); Robert Jason Potter, San Marcos, CA (US); Gulshan Dhariwal, Potomac, MD (US); Gary F. Gerard, Frederick, MD (US); Kim Rosenthal, Laytonsville, MD (US); Jun E. Lee, San Diego, CA (US)

(73) Assignee: Life Technologies Corporation, Carlsbad, CA (US)

( * ) Notice: Subject to any disclaimer, the term of this patent is extended or adjusted under 35 U.S.C. 154(b) by 2 days.

This patent is subject to a terminal disclaimer.

(21) Appl. No.: 14/272,433

(22) Filed: May 7, 2014

(65) Prior Publication Data

US 2014/0363854 A1 Dec. 11, 2014

Related U.S. Application Data

(63) Continuation of application No. 12/979,899, filed on Dec. 28, 2010, now Pat. No. 8,753,845, which is a continuation of application No. 11/492,194, filed on Jul. 25, 2006, now abandoned, which is a continuation of application No. 10/661,819, filed on Sep. 15, 2003, now abandoned, and a continuation-in-part of application No. 11/437,681, filed on May 22, 2006, now abandoned, which is a continuation of application No. 09/845,157, filed on May 1, 2001, now Pat. No. 7,078,208.

(60) Provisional application No. 60/410,283, filed on Sep. 13, 2002, provisional application No. 60/207,196, filed on May 26, 2000.

(51) Int. Cl.
*C12N 9/12* (2006.01)
*C12P 19/34* (2006.01)

(52) U.S. Cl.
CPC ............ *C12N 9/1276* (2013.01); *C12P 19/34* (2013.01); *C12Y 207/07049* (2013.01)

(58) Field of Classification Search
None
See application file for complete search history.

(56) References Cited

U.S. PATENT DOCUMENTS 5,244,797 A 9/1993 Kotewicz et al.
5,405,776 A 4/1995 Kotewicz et al.
5,688,005 A 11/1997 Ellis
6,063,608 A 5/2000 Kotewicz et al.
6,136,582 A 10/2000 Gao et al.
7,056,716 B2 6/2006 Potter et al.
7,078,208 B2 7/2006 Smith et al.
8,835,148 B2 9/2014 Janulaitis et al.

FOREIGN PATENT DOCUMENTS

CN 1422336 6/2003
EP 0962526 12/1999
JP 2000-139457 5/2000
WO 98/23733 6/1998
WO 98/47912 10/1998
WO 99/10366 3/1999
WO 01/68895 9/2001
WO 01/92500 12/2001
WO 2004/024749 3/2004
WO 2009/125006 10/2009

OTHER PUBLICATIONS

Blain et al. (Nuclease Activities of Moloney Murine Leukemia Virus Reverse Transcriptase, Mutants with Altered Substrate Specificities, Journal of Biological Chemistry, vol. 268, No. 31, pp. 23585-23592, 1993.*

Arion, et al., "The K65R Mutation Confers Increased DNA Polymerase Processivity to HIV-1 Reverse Transcriptase", *The Journal of Biological Chemistry*, vol. 271, No. 33, Aug. 16, 1996, 19860-19864.

Arnold, et al., "How enzymes adapt: lessons from directed evolution", *Trends in Biochemical Sciences*, vol. 26, No. 2, Feb. 2001, 100-106.

Bailey, et al., "Interpretation of nitrocellulose filter assays of protein-nucleic acid binding", *Analytical Biochemistry*, vol. 93, No. 1, 1979, 204-206.

Bakhanashvili, et al., "Fidelity of the reverse transcriptase of human immunodeficiency virus type 2", *FEBS Letters*, vol. 306, No. 2-3, Jul. 20, 1992, 151-156.

Bakhanashvili, et al., "Fidelity of the RNA-Dependent DNA Synthesis Exhibited by the Reverse Reverse Transcriptases of Human Immunodeficiency Virus Types 1 and 2 and of Murine Leukemia Virus: Mispair Extension Frequencies", *Biochemistry*, vol. 31, No. 39,, 1992, 9393-9398.

Bakhanashvili, et al., "Mutational studies of human immunodeficiency virus type 1 reverse transcriptase: the involvement of residues 183 and 184 in the fidelity of DNA synthesis", *FEBS Letters*, vol. 391, vol. 3, Aug. 12, 1996, 257-262.

(Continued)

*Primary Examiner* — Richard Hutson

(57) ABSTRACT

The present invention is in the fields of molecular and cellular biology. The invention is generally related to reverse transcriptase enzymes and methods for the reverse transcription of nucleic acid molecules, especially messenger RNA molecules. Specifically, the invention relates to reverse transcriptase enzymes which have been mutated or modified to increase thermostability, decrease terminal deoxynucleotidyl transferase activity, and/or increase fidelity, and to methods of producing, amplifying or sequencing nucleic acid molecules (particularly cDNA molecules) using these reverse transcriptase enzymes or compositions. The invention also relates to nucleic acid molecules produced by these methods and to the use of such nucleic acid molecules to produce desired polypeptides. The invention also concerns kits comprising such enzymes or compositions.

12 Claims, 22 Drawing Sheets

(56) References Cited

OTHER PUBLICATIONS

Bakhanashvili, et al., "The fidelity of the reverse transcriptases of human immunodeficiency viruses and murine leukemia virus, exhibited by the mispair extension frequencies, is sequence dependent and enzyme related", *FEBS Letters*, vol. 319, Nos. 1-2, 1993, 201-205.
Barnes "The Fidelity of Taq Polymerase Catalyzing PCR is Improved by an N-Terminal Deletion", *Gene*, vol. 112, No. 1, Mar. 1, 1992, 29-35.
Basu, et al., "Sulphydryl groups in the template-primer-binding domain of murine leukemia virus reverse transcriptase", *Biochemical Journal*, vol. 296, Pt. 3, Dec. 15, 1993, 577-583.
Beard, et al., "Vertical-scanning Mutagenesis of a Critical Tryptophan in the Minor Groove Binding Track of HIV-1 Reverse Transcriptase. Molecular Nature of polymerase-Nucleic Acid Interactions", *The Journal of Biological Chemistry*, vol. 273, No. 46, Nov. 13, 1998, 30435-30442.
Bebenek, et al., "A minor groove binding track in reverse transcriptase" *Nature Structural & Molecular Biology*, vol. 4, No. 3, Mar. 1997, 194-197.
Bebenek, et al., "Reduced Frameshift Fidelity and Processivity of HIV-1 Reverse Transcriptase Mutants Containing Alanine Substitutions in Helix H of the Thumb Subdomain", *The Journal of Biological Chemistry*, vol. 270, No. 33, Aug. 18, 1995, 19516-19523.
Bebenek, et al., "The Fidelity of DNA Synthesis Catalyzedby Derivatives of *Escherichia coli* DNA Polymerase I", *The Journal of Biological Chemistry*, vol. 265, No. 23, Aug. 15, 1990, 13878-13887.
Bebenek, et al., "The Fidelity of Retroviral Reverse Transcriptases", *in Reverse Transcriptase*, Skalka, A.M., and Goff, S.P. (eds), Cold Spring Harbor Laboratory Press, Plainview, NY, 1993, 85-102.
Ben-Artzi, et al., "Characterization of the double stranded RNA dependent RNAse activity associated with recombinant reverse transcriptases", *Nucleic Acids Research*, vol. 20, No. 19, Oct. 11, 1992, 5115-5118.
Berger, et al., "Reverse Transcriptase and its Associated Ribonuclease H: Interplay of Two Enzyme Activities Controls the Yield of Single-Stranded Complementary Deoxyribonucleic Acid", *Biochemistry*, vol. 22, No. 10, May 10, 1983, 2365-2372.
Blain, et al., "Effects on DNA Synthesis and Translocation Caused by Mutations in the RNAse H Domain of Moloney Murine Luekemia Virus Reverse Transcriptase", *Journal of Virology*, vol. 69, No. 7, Jul. 1995, 4440-4452.
Blain, et al., "Nuclease Activities of Moloney Murine Leukemia Virus Reverse Transcriptase", *The Journal of Biological Chemistry*, vol. 268, No. 31, Nov. 5, 1993, 23585-23592.
Cadwell, et al., "Randomization of Genes by PCR Mutagenesis", *PCR Methods Applications*, vol. 2, No. 1, Aug. 1992, 28-33.
Caliendo, et al., "Effects of Zidovudine-Selected Human Immunodeficiency Virus Type 1 Reverse Trasncriptase Amino Acid Substitutions on Processive DNA Synthesis and Viral Replication", *Journal of Virology*, vol. 70, No. 4, Apr. 1996, 2146-2153.
Cambillau, et al., "Structural and Genomic Correlates of Hyperthermostability" *The Journal of Biological Chemistry*, vol. 275, Oct. 20, 2000, 32383-32396.
Carroll, et al., "A Mutant of DNA Polymerase I (Klenow Fragment) with Reduced Fidelity", *Biochemistry*, vol. 30, No. 3, 1991, 804-813.
Carter, et al., "Engineering Enzyme Specificity by 'Substrate-Assisted Catalysis'", *Science*, vol. 237, No. 4813, Jul. 1987, 394-399.
Chen, et al., "Amino Acids Essential for RNAse H Activity of Hepadnaviruses are Also Required for Efficient Elongation of Minus-Strand Viral DNA", *Journal of Virology*, vol. 70, No. 9, Sep. 1996, 6151-6156.
Chowdhury, et al., "Elucidation of the Role of Arg 110 of Murine Leukemia Virus Reverse Transcriptase in the Catalytic Mechanism: Biochemical Characterization of Its Mutant Enzymes", *Biochemistry*, vol. 35, No. 51 ,, Dec. 24, 1996, 16610-16620.
Creighton, et al., "Base Mispair Extension Kinetics", *The Journal of Biological Chemistry*, vol. 267, No. 4, Feb. 5, 1992, 2633-2639.
D'Alessio, et al., "Second-strand cDNA synthesis with *E. coli* DNA polymerase I and RNase H: the fate of information at the mRNA 5' terminus and the effect of *E. coli* DNA ligase", *Nucleic Acids Research*, vol. 16, No. 5, Mar. 11, 1988, 1999-2014.
Destefano, et al., "Characterization of an RNase H deficient mutant of human immunodeficiency virus-1 reverse transcriptase having an aspartate to asparagine change at position 498", *Biochimica et Biophysica Acta*, vol. 1219, No. 2, Oct. 18, 1994, 380-388.
Destefano, et al., "Parameters that influence processive synthesis and site-specific termination by human immunodeficiency virus reverse transcriptase on RNA and DNA templates", *Biochimica et Biophysica Acta*, vol. 1131, No. 3, Jul. 15, 1992, 270-280.
Destefano, et al., "Polymerization and RNase H Activities of the Reverse Transcriptase from Avian Myeloblastosis, human immunodeficiency, and Moloney Murine Leukemia Viruses are Functionally Uncoupled", *The Journal of Biological Chemistry*, vol. 266, No. 12, Apr. 25, 1991, 7423-7431.
Diaz, et al., "Strand Transfer is enhanced by mismatched nucleotide at the 3' primer terminus: a possible link between HIV reverse transcriptase fidelity and recombination", *Nucleic Acids Research*, vol. 24, No. 15,, Aug. 1996, 3086-3092.
Ding, et al., "Structure and functional implications of the polymerase active site region in a complex of HIV-1 RT with a double-stranded DNA template-primer and an antibody fab fragment at 2.8 Å resolution", *Journal of Molecular Biology*, vol. 284, No. 4, Dec. 11, 1998, 1095-1111.
Drosopoulos, et al., "Increased Misincorporation Fidelity Observed for Nucleoside Analog Resistance Mutations M184V and E89G in Human Immunodeficiency Virus Type 1 Reverse Transcriptase Does Not Correlate with the Overall Error Rate Measured In Vitro", *Journal of Virology*, vol. 72, No. 5, May 1998, 4224-4230.
Drosopoulos, et al., "Increased Polymerase Fidelity of E89G, a Nucleoside Analog-Resistant Variant of Human Immunodeficiency Virus Type 1 Reverse Transcriptase", *Journal of Virology*, vol. 70, No. 7, Jul. 1996, 4834-4838.
Eckert, et al., "Fidelity of DNA synthesis catalyzed by human DNA polymerase alpha and HIV-1 reverse transcriptase: effect of reaction pH", *Nucleic Acids Research*, vol. 21, No. 22, Nov. 11, 1993, 5212-5220.
Eger, et al., "Mechanism of DNA replication fidelity for three mutants of DNA polymerase I: Klenow fragment KF(exo+), KF(polA5), and KF(exo−)", *Biochemistry*, vol. 30, No. 5, 1991, 1441-1448.
Feng, et al., "Mechanistic Studies Examining the Efficiency and Fidelity of DNA Synthesis by the 3TC-Resistant Mutant (184V) of HIV-1 Reverse Transcriptase", *Biochemistry*, vol. 38, No. 29, Jul. 20, 1999, 9440-9448.
Finston, et al., "RNA-Primed Initiation of Moloney Murine Leukemia Virus Plus Strands by Reverse Transcriptase In Vitro", *Journal of Virology*, vol. 51, No. 1, Jul. 1984, 26-33.
Gao, et al., "Replication Defect of Moloney Murine Leukemia Virus with a Mutant Reverse Transcriptase That Can Incorporate Ribonucleotides and Deoxyribonucleotides", *Journal of Virology*, vol. 72, No. 7, Jul. 1998, 5905-5911.
Georgiadis, et al., "Mechanistic implications from the Structure of a Catalytic Fragment of Moloney Murine Leukemia Virus Reverse Transcriptase", *Structure*, vol. 3, No. 9, Sep. 5, 1995, 879-892.
Gerard, et al., "cDNA Synthesis by Cloned Moloney Murine Leukemia Virus Reverse Transcriptase Lacking RNase H Activity", *Focus*, vol. 11, 1989, 66-69.
Gerard, et al., "cDNA Synthesis by Moloney Murine Leukemia Virus RNase H-Minus Reverse Transcriptase Possessing Full DNA Polymerase Activity", *Focus*, vol. 14, No. 3,, 1992, 91-93.
Gerard et al., "Influence of Stability in *Escherichia coli* of the Carboxy-Terminal Structure of Cloned Moloney Murine Leukemia Virus Reverse Transcriptase", *DNA*, vol. 5, No. 4, Aug. 1986, 271-279.
Gerard, et al., "Poly (2'-O-Methylcytidylate) Oligodeoxyguanylate as a Template for the Ribonucleic Acid Directed Deoxoyribonucleic Acid Polymerase in Ribonucleic Acid Tumor Virus Particles and a

(56) References Cited

OTHER PUBLICATIONS

Specific Probe for Ribonucleic Acid Directed Enzyme in Trans. Murin cells", *Biochemistry*, vol. 13, No. 8, 1974, 1632-1641.
Gerard, et al., "Reverse Transcriptase (EC 2.7.7.49): The Use of Cloned Moloney Murine Leukemia Virus Reverse Transcriptase to Synthesize DNA from RNA", *Methods in Molecular Biology*, vol. 16, 1993, 73-93.
Gerard, et al., "Reverse Transcriptase. The Use of Cloned Moloney Murine Leukemia Virus Reverse Transcriptase to Synthesize DNA from RNA", *Molecular Biotechnology*, vol. 8, No. 1, Aug. 1997, 61-77.
Gerwin, et al., "Mutant of B-Tropic Murine Leukemia Virus Synthesizing an Altered Polymerase Molecule", *Journal of Virology*, vol. 31, No. 3,, Sep. 1979, 741-751.
Goff, et al., "Mutants of murine leukemia viruses and retroviral replication", *Biochimica et Biophysica Acta*, vol. 907, No. 2, Jul. 8, 1987, 93-123.
Goff, , "Retroviral Reverse Transcriptase: Synthesis, Structure, and Function", *Journal of Acquired Immune Deficiency Syndromes*, vol. 3, No. 8, 1990, 817-831.
Goobar-Larsson, et al., "Disruption of a Salt Bridge between Asp 488 and Lys 465 in HIV-1 Reverse Transcriptase Alters Its Proteolytic Processing and Polymerase Activity", *Virology*, vol. 196, No. 2, Oct. 1993, 731-738.
Gotte, et al., "The M184V Mutation in the Reverse Transcriptase of Human Immunodeficiency Virus Type 1 Imparis Rescue of Chain-Terminated DNA Synthesis", *Journal of Virology*, vol. 74, No. 8, Apr. 2000, 3579-3585.
Guo, et al., "Defects in Primer-Template Binding, Processive DNA Synthesis, and RNAse H Activity Associated with Chimeric Reverse Transcriptases Having the Murine Leukemia Virus Polymerase Domain Joined to *Escherichia coli* RNAse H", *Biochemistry*, vol. 34, No. 15, Apr. 18, 1995, 5018-5029.
Halvas, et al., "Development of an In Vivo Assay to Identify Structural Deteminants in Murine Leukemia Virus Reverse Transcriptase Important for Fidelity", *Journal of Virology*, vol. 74, No. 1, Jan. 2000, 312-319.
Hamburgh, et al., "The influence of 3TC-resistance mutations E89G and M184V in the human immunodeficiency virus reverse transcriptase on mispair extension efficiency", *Nucleic Acids Research*, vol. 26, No. 19, Oct. 1, 1998, 4389-4394.
Harrison, et al., "Pausing of reverse transcriptase on retroviral RNA templates is influenced by secondary structures both 5' and 3' of the catalytic site", *Nucleic Acids Research*, vol. 26, No. 14, Jul. 1998, 3433-3442.
Hite, et al., "Factors affecting fidelity of DNA synthesis during PCR amplification of d(C-A)n d(G-T)n microsatellite repeats", *Nucleic Acids Research*, vol. 24, No. 12, Jun. 15, 1996, 2429-2434.
Houts, et al., "Reverse Transcriptase from Avian Myeloblastosis Virus", *Journal of Virology*, vol. 29, No. 2, Feb. 1979, 517-522.
Hsu, et al., "Higher fidelity of RNA-dependent DNA mispair extension by M184V drug-resistant than wild-type reverse transcriptase of human immunodeficiency virus type 1", *Nucleic Acids Research*, vol. 25, No. 22, Nov. 15, 1997, 4532-4536.
Huang, et al., "Structure of a Covalently Trapped Catalytic Complex of HIV-1 Reverse Transcriptase: Implications for Drug Resistance", *Science*, vol. 282, No. 5394, Nov. 27, 1998, 1669-1675.
Jacobo-Molina, et al., "Crystal structure of human immunodeficiency virus type 1 reverse trasncriptase complexed with double-stranded DNA at 3.0 A resolution shows bent DNA", *Proceedings of the National Academy of Sciences*, vol. 90, No. 13, Jul. 1993, 6320-6324.
Jin, et al., "Analysis of the Role of Glutamine 190 in the Catalytic Mechanism of Murine Leukemia Virus Reverse Transcriptase", *The Journal of Biological Chemistry*, vol. 274, Jul. 1999, 20861-20868.
Kaushik, et al., "Role of Glutamine 151 of Human Immunodeficiency Virus Type-1 Reverse Transcriptase in Substrate Selection as Assessed by Site-Directed Mutagenesis", *Biochemistry*, vol. 39, No. 11, Mar. 21, 2000, 2912-2920.
Kaushik, et al., "Role of Glutamine-151 of Human Immunodeficiency Virus Type-1 Reverse Transcriptase in RNA-Directed DNA Synthesis", *Biochemistry*, vol. 36, No. 47, Nov. 25, 1997, 14430-14438.
Kaushik, et al., "Tyrosine 222, a Member of the YXDD Motif of MuLV RT, Is Catalytically Essential and Is a Major Component of the Fidelity Center", *Biochemistry*, vol. 38, No. 9, Mar. 2, 1999, 2617-2627.
Kaushik, et al., "Valine of the YVDD Motif of Moloney Murine Leukemia Virus Reverse Transcriptase: Role in the Fidelity of DNA Synthesis", *Biochemistry*, vol. 39, No. 17, May 2, 2000, 5155-5165.
Kerr, et al., "RNA Dependent DNA Replication Fidelity of HIV-1 Reverse Transcriptase: Evidence of Discrimination between DNA and RNA Substrates", *Biochemistry*, vol. 36, No. 46, Nov. 18, 1997, 14056-14063.
Kim, et al., "Fidelity of Mutant HIV-1 Reverse Transcriptases: Interaction with the Single-Stranded Template Influences the Accuracy of DNA Synthesis", *Biochemistry*, vol. 37, No. 17, 1998, 5831-5839.
Kim, et al., "New Human Immunodeficiency Virus Type 1 Reverse Transcriptase (HIV-1 RT) Mutants with Increased Fidelity of DNA Synthesis", *Journal of Biological Chemistry*, vol. 274, No. 39, Sep. 24, 1999, 27666-27673.
Kneller, et al., "Improvements in Protein Secondary Structure Prediction by an Enhanced Neural Network", *Journal of Molecular Biology*, vol. 214, No. 1, Jul. 5, 1990, 171-182.
Kohlstaedt, et al., "Crystal Structure at 3.5 Lambda Resolution of HIV-1 Reverse Transcriptase Complexed with an Inhibitor", *Science*, vol. 256, Jun. 26, 1992, 1783-1790.
Kotewicz, et al., "Isolation of cloned Moloney murine leukemia virus reverse transcriptase lacking ribonuclease H activity", *Nucleic Acids Research*, vol. 16, No. 1, IRL Press Limited, Oxford, England, Jan. 11, 1988, 265-277.
Krug, et al., "First-Strand cDNA Synthesis Primed with Oligo(dT)", *Methods in Enzymology*, vol. 152, 1987, 316-325.
Kumar, et al., "How do thermophilic proteins deal with heat?", *Cellular and Molecular Life Sciences*, vol. 58, No. 9, Aug. 2001, 1216-1233.
Kunkel, et al., "[19] Rapid and Efficient Site-Specific Mutagenesis without Phenotypic Selection", *Methods in Enzymology*, vol. 154, 1987, 367-383.
Kunkel, et al., "Efficient site-directed mutagenesis using uracil-containing DNA", *Methods in Enzymology*, vol. 204, 1991, 125-139.
Lawyer, et al., "Isolation, Characterization, and Expression in *Escherichia coli* of the DNA Polymerase Gene from Thermus aquaticus", *The Journal of Biological Chemistry*, vol. 264, No. 11, Apr. 15, 1989, 6427-6437.
Le Grice, et al., "[9] Human Immunodeficiency Virus Reverse Transcriptase", *Reverse Transcriptase*, Shalka, A. M., and Golf, S. P., Eds.,, Cold Spring Harbor, New York: Cold Spring Harbor Laboratory Press, 1993, 163-191.
Lehmann, et al., "Engineering proteins for thermostability: the use of sequence alignments versus rational design and directed evolution", *Current Opinion in Biotechnology*, vol. 12, No. 4, Aug. 2001, 371-375.
Leung, et al., "A method for random mutagenesis of a defined DNA segment using a modified polymerase chain reaction.", *Technique—A Journal of Methods in Cell and Molecular Biology*, vol. 1, Aug. 1989, 11-15.
Levin, et al., "Murine Leukemia Virus Mutant with a Frameshift in the Reverse Transcriptase Coding Region: Implications for pol Gene Structure", *Journal of Virology*, vol. 51, No. 2, Aug. 1984, 470-478.
Lewis, et al., "Uniquely Altered DNA Replication Fidelity Conferred by an Amino Acid Change in the Nucleotide Binding Pocket of Human Immunodeficiency virus Type I Reverse Transcriptase", *The Journal of Biological Chemistry*, vol. 274, No. 46, Nov. 12, 1999, 32924-32930.
Li, et al., "The Rapid isolation of Specific Genes from cDNA Libraries with the GeneTrapper cDNA Positive Selection System", *Focus*, vol. 17, No. 2, 1995, 45-49.

(56) References Cited

OTHER PUBLICATIONS

Martin-Hernandez, et al., "Human immunodeficiency virus type 1 reverse transcriptase: role of Tyr115 in deoxynucleotide binding and misinsertion fidelity of DNA synthesis", *The EMBO Journal*, vol. 15, No. 16, Aug. 15, 1996, 4434-4442.

Martin-Hernandez, et al., "Mispair extension fidelity of human immunodeficiency virus type 1 reverse transcriptases with amino acid substitutions affecting Tyr115", *Nucleic Acids Research*, vol. 25, No. 7, Apr. 1, 1997, 1383-1389.

McDonell, et al., "Analysis of restriction Fragments of T7 DNA and Determination of Molecular Weights of Electrophoresis in Neutral and Alkaline Gels", *Journal of Molecular Biology*, vol. 110, No. 1, Feb. 15, 1977, 119-146.

Messer, et al., "Functional Analysis of Reverse Transcription by a Frameshift pol Mutant of Murine Leukemia Virus", *Virology*, vol. 146, No. 1, Oct. 15, 1985, 146-152.

Molling, et al., "Association of Viral Reverse Transcriptase with an Enzyme degrading the RNA Moiety of RNA-DNA Hybrids", *Nature New Biology*, vol. 234, Dec. 22, 1971, 240- 243.

Myers, et al., "Reverse Transcription and DNA Amplification by a Thermus thermophilus DNA Polymerase", *Biochemistry*, vol. 30, No. 31, Aug. 6, 1991, 7661-7666.

Ngo, et al., "Computational Complexity, Protein Structure Prediction and the Levinthal Paradox", *The Protein Folding Problem and Tertiary Structure*, Merz et al. ed., 1994, 14-16.

Ngo, et al., "Computational Complexity, Protein Structure Prediction, and Levinthal Paradox", *The Protein Folding Problem and Tertiary Structure Prediction*; Birkhauser, Boston, MA, 1994, 433 and 492-495.

Oude Essink, et al., "Increased polymerase fidelity of the 3TC-resistant variants of HIV-1 reverse transcriptase", *Nucleic Acids Research*, vol. 25, No. 16, Aug. 15, 1997, 3212-3217.

Pandey, et al., "Role of Methionine 184 of Human Immunodeficiency Virus Type-1 Reverse Transcriptase in the Polymerase Function and Fidelity of DNA Synthesis", *Biochemistry*, vol. 35, No. 18, May 6, 1996, 2168-2179.

Patel, et al., "Insights into DNA Polymerization Mechanisms from Structure and Function Analysis of HIV-1 Reverse Transcriptase", *Biochemistry*, vol. 34, No. 16, Apr. 1995, 5351-5363.

PCT/US03/28802 "International Search Report dated Mar. 18, 2005".

Perler, et al., "Thermostable DNA Polymerases", *Advances in Protein Chemistry*, vol. 48, 1996, 377-435.

Perrino, et al., "Extension of mismatched 3' termini of DNA is a major determinant of the infidelity of human immunodeficiency virus type 1 reverse transcriptase" *Proceedings of the National Academy of Sciences*, vol. 86, No. 21, Nov. 1, 1989, 8343-8347.

Pfeiffer, et al., "Structure-Based Moloney Murine Leukemia Virus Reverse Transcriptase Mutants with Altered Intracellular Direct-Repeat Deletion Frequencies", *Journal of Virology*, vol. 74, No. 20, Oct. 2000, 9629-9636.

Polesky, et al., "Identification of Residues Critical for the Polymerase Activity of the Klenow Fragment of DNA Polymerase I from *Escherichia coli", The Journal of Biological Chemistry*, vol. 265, No. 24, Aug. 25, 1990, 14579-14591.

Pop, et al., "Kinetic Analysis of Pausing and Fidelity of Human Immunodeficiency Virus Type 1 Reverse Transcription", *Biochemistry*, vol. 35, No. 15, Apr. 16, 1996, 5054-5062.

Prasad, et al., "Genetic Analysis of Retroviral Reverse Transcriptase Structure and Function", *Reverse Transcriptase*, Skalka, A. M., and Golf, S.P., Eds., Cold Spring Harbor, Cold Spring Harbor, 1993, 135-162.

Prasad, et al., "Linker insertion mutagenesis of the human immunodeficiency virus reverse trasncriptase expressed in bacteria: Definition of the minimal polymerase domain", *Proceedings of the National Academy of Sciences*, vol. 86, No. 9, May 1, 1989, 3104-3108.

Quan, et al., "Dominance of the E89G Substitutions in HIV-1 Reverse Transcriptase in Regard to Increased Polymerase Processivity and Patterns of Pausing", *The Journal of Biological Chemistry*, vol. 273, No. 34, Aug. 21, 1998, 21918-21925.

Repaske et al., "Inhibition of RNase H Activity and Viral Replication by Single Mutations in the 3' Region of Moloney Murine Leukemia Virus Reverse Transcriptase", *Journal of Virology*, vol. 63, No. 3, Mar. 1989, 1460-1464.

Resnick, et al., "Involvement of Retrovirus Reverse Transcriptase-Associated RNase H in the Initiation of Strong-Stop (+) DNA Synthesis and the Generation of the Long Terminal Repeat", *Journal of Virology*, vol. 51, No. 3, Sep. 1984, 813-821.

Rezende, et al., "The impact of multidideoxynucleoside resistance-conferring mutations in human immunodeficiency virus type 1 reverse transcriptase on polymerase fidelity and error specificity", *Journal of Virology*, vol. 72, No. 4, Apr. 1998, 2890-2895.

Rezende, et al., "The influenceof 3TC resistance mutation M184I on the fidelity and error specificity of human immunodeficiency virus type 1 reverse transcriptase", *Nucleic Acids Research*, vol. 26, No. 12, Jun. 1998, 3066-3072.

Rost, , "[31] PHD: Predicting One-Dimensional Protein Structure by Profile-based Neural Networks", *Methods in Enzymology*, vol. 266, 1996, 525-539.

Rubinek, et al., "The Fidelity of 3' Misinsertion and Mispair Extension During DNA Synthesis Exhibited by two Drug-Resistant Mutants of the Reverse Transcriptase of Human Immunodeficiency Virus Type 1 with Leu74→Val and Glu89→Gly", *European Journal of Biochemistry* (*the FEBS Journal*), vol. 247, No. 1, Jul. 1997, 238-247.

Schwartzberg, et al., "Construction and Analysis of Deletion Mutations in the pol Gene of Moloney Murine Leukemia Virus: A New Viral Function Required for Productive Infection", *Cell*, vol. 37, No. 3, Jul. 1984, 1043-1052.

Shinnick, et al., "Nucleotide sequence of Moloney murine leukaemia virus", *Nature*, vol. 293, Oct. 15, 1981, 543-548.

Skalka, , "10, Endonuclease Activity Associated with Reverse Transcriptase of Avian Sarcoma-Leukosis Viruses", *Reverse Trans*, Skalka, A.M., and Golf, S.P., Eds., Cold Spring Harbor, New York, Cold Spring Harbor Laboratory Press, 1993, 193-204.

Sooknanan, et al., "Fidelity of Nucleic Acid Amplification with Avian Myeloblastosis Virus Reverse Transcriptase and T7 RNA Polymerase", *BioTechniques*, vol. 17, No. 6, Dec. 1994, 1077-1080 and 1083-1085.

Stemmer, , "Rapid evolution of a protein in vitro by DNA shuffling", *Nature*, vol. 370, No. 6488, Aug. 4, 1994, 389-391.

Strauss, et al., "Variable affecting the selectivity and efficiency of retention of DNA fragment by *E.coli* RNA polymerase in the nitrocellulose filter-binding assay", *Gene*, vol. 13, No. 1, Jan.-Feb. 1981, 75-87.

Suzuki, et al., "Fidelity Mutants in Thermus aquaticus DNA Polymerase I", *Microbial & Comparative Genomics*, vol. 2, No. 3, Abstract# C-30, Ninth Genome Sequencing & Analysis Conference, 1997, 226.

Suzuki, et al., "Low Fidelity Mutants in the O-Helix of Thermus aquaticus DNA Polymerase I", *The Journal of Biological Chemistry*, vol. 272, No. 17, Apr. 25, 1997, 11228-11235.

Taube, et al., "The fidelity of misinsertion and mispair extension throughout DNA synthesis exhibited by mutants of the reverse transcriptase of human immunodeficiency virus type 2 resistant to nucleoside analogs", *European Journal of Biochemistry*, vol. 250, No. 1, Nov. 1997, 106-114.

Telesnitsky, et al., "RNase H Domain Mutations Affect the Interaction Between Moloney Murine Leukemia Virus Reverse Transcriptase and Its Primer-Template" *Proceedings of the National Academy of Sciences*, vol. 90, No. 4, Feb. 15, 1993, 1276-1280.

Tosh, et al., "One-tube and One-buffer System of RT-PCR Amplification of ID Gene of Foot-and-Mouth Disease Virus Field Isolates", *Acta Virologica*, vol. 41, No. 3, Jun. 1997, 153-155.

Unknown, , "Moloney murine leukaemia virus reverse transcriptase, M289L mutant", *Database Geneseq*, retrieved from EBI accession No. GSP: AAU74994. Database accession No. AAU74994, Apr. 9, 2002.

Unknown, , "Unverified English Language translation of JP P2000-139457 (Document AN1)", *Ralph McElroy Translation Company*.

(56) References Cited

OTHER PUBLICATIONS

Varela-Echavarria, et al., "Comparison of Moloney Murine Leukemia Virus Mutation Rate with the Fidelity of Its Reverse Transcriptase In Vitro" *Journal of Biological Chemistry*, vol. 267, Dec. 5, 1992, 24681-24688.
Verma, et al., "Studies on Reverse Transcriptase of RNA Tumor Viruses. III. Properties of Purified Moloney Murine Leukemia Virus DNA Polymerase and Associated RNase H", *Journal of Virology*, vol. 15, No. 4, Apr. 1975, 843-854.
Wainberg, et al., "Enhanced Fidelity of 3TC-Selected Mutant HIV-1 Reverse Transcriptase", *Science*, vol. 271, No. 5253, Mar. 1, 1996, 1282-1285.
Weber, et al., "Fidelity of human immunodeficiency virus type 1 reverse transcriptase in copying natural DNA", *Nucleic Acids Research*, vol. 17, No. 4, Feb. 25, 1989, 1379-1393.
Wells, et al., "Addictivity of Mutational Effects in Proteins", *Biochemistry*, vol. 29, No. 37, Sep. 18, 1990, 8509-8517.
Wu, et al., "Human Immunodeficiency Virus Type 1 Nucleocapsid Protein Reduces Reverse Transcriptase Pausing at a Secondary Stucture near the Murine Leukemia Virus Polypurine Tract", *Journal of Virology*, vol. 70, No. 10, Oct. 1996, 7132-7142.
Yamagishi, , "Improvement of thermal stability of protein by evolutionary molecular engineering", *Biophysical Society of Japan*, vol. 36, No. 3, 1996, 144-148.

* cited by examiner

SEQUENCE LISTING

```
<160> NUMBER OF SEQ ID NOS: 46

<210> SEQ ID NO 1
<211> LENGTH: 2151
<212> TYPE: DNA
<213> ORGANISM: Artificial Sequence
<220> FEATURE:
<223> OTHER INFORMATION: Mutant Reverse Transcriptase Derived from
      Moloney Murine Leukemia Virus
<220> FEATURE:
<221> NAME/KEY: CDS
<222> LOCATION: (1)..(2148)

<400> SEQUENCE: 1

atg ggg ggt tct cat cat cat cat cat cat ggt atg gct agc atg act       48
Met Gly Gly Ser His His His His His His Gly Met Ala Ser Met Thr
1               5                   10                  15

ggt gga cag caa atg ggt cgg gat ctg tac gac gat gac gat aag cat       96
Gly Gly Gln Gln Met Gly Arg Asp Leu Tyr Asp Asp Asp Asp Lys His
            20                  25                  30

atg acc cta aat ata gaa gat gag tat cgg cta cat gag acc tca aaa      144
Met Thr Leu Asn Ile Glu Asp Glu Tyr Arg Leu His Glu Thr Ser Lys
        35                  40                  45

gag cca gat gtt tct cta ggg tcc aca tgg ctg tct gat ttt cct cag      192
Glu Pro Asp Val Ser Leu Gly Ser Thr Trp Leu Ser Asp Phe Pro Gln
    50                  55                  60

gcc tgg gcg gaa acc ggg ggc atg gga ctg gca gtt cgc caa gct cct      240
Ala Trp Ala Glu Thr Gly Gly Met Gly Leu Ala Val Arg Gln Ala Pro
65                  70                  75                  80

ctg atc ata ctt ctg aaa gca acc tct acc ccc gtg tcc ata aaa caa      288
Leu Ile Ile Leu Leu Lys Ala Thr Ser Thr Pro Val Ser Ile Lys Gln
                85                  90                  95

tac ccc atg tca caa gaa gcc aga ctg ggg atc aag ccc cac ata cag      336
Tyr Pro Met Ser Gln Glu Ala Arg Leu Gly Ile Lys Pro His Ile Gln
            100                 105                 110
```

```
aga ctg ttg gac cag gga ata ctg gta ccc tgc cag tcc ccc tgg aac      384
Arg Leu Leu Asp Gln Gly Ile Leu Val Pro Cys Gln Ser Pro Trp Asn
        115                 120                 125

acg ccc ctg cta ccc gtc aag aaa ccc ggg act aat gat tac agg cct      432
Thr Pro Leu Leu Pro Val Lys Lys Pro Gly Thr Asn Asp Tyr Arg Pro
    130                 135                 140

gtc caa gat ctg aga gag gtc aac aaa cgc gta gaa gac atc cac ccc      480
Val Gln Asp Leu Arg Glu Val Asn Lys Arg Val Glu Asp Ile His Pro
145                 150                 155                 160

acc gta ccc aac ccc tac aac ctc ttg agt ggg ctc cca ccg tcc cac      528
Thr Val Pro Asn Pro Tyr Asn Leu Leu Ser Gly Leu Pro Pro Ser His
                165                 170                 175

cag tgg tac act gtt cta gac tta aaa gat gcc ttt ttc tgc ctg aga      576
Gln Trp Tyr Thr Val Leu Asp Leu Lys Asp Ala Phe Phe Cys Leu Arg
            180                 185                 190

ctc cac ccg acg tct cag cct ctc ttc gcc ttt gaa tgg aga gac cca      624
Leu His Pro Thr Ser Gln Pro Leu Phe Ala Phe Glu Trp Arg Asp Pro
        195                 200                 205

gag atg gga atc tct ggc caa cta acc tgg acc aga ctc cca cag gga      672
Glu Met Gly Ile Ser Gly Gln Leu Thr Trp Thr Arg Leu Pro Gln Gly
    210                 215                 220

ttc aaa aac agt ccc acc ctg ttt gat gag gca ctg cgc aga gac cta      720
Phe Lys Asn Ser Pro Thr Leu Phe Asp Glu Ala Leu Arg Arg Asp Leu
225                 230                 235                 240

gca gac ttc cgg atc cag cac cca gac ttg atc ctg cta cag tac gta      768
Ala Asp Phe Arg Ile Gln His Pro Asp Leu Ile Leu Leu Gln Tyr Val
                245                 250                 255

gat gac tta ctg ctg gcc gcc act tct gag ctc gac tgc caa caa ggt      816
Asp Asp Leu Leu Leu Ala Ala Thr Ser Glu Leu Asp Cys Gln Gln Gly
            260                 265                 270

act cgg gcc ctg tta caa acc cta gga gac ctc ggg tat cgg gcc tcg      864
Thr Arg Ala Leu Leu Gln Thr Leu Gly Asp Leu Gly Tyr Arg Ala Ser
        275                 280                 285

gcc aag aaa gcc caa att tgc cag aaa cag gtc aag tat ctg ggg tat      912
Ala Lys Lys Ala Gln Ile Cys Gln Lys Gln Val Lys Tyr Leu Gly Tyr
    290                 295                 300

ctt cta aaa gag ggt cag aga tgg ctg act gag gcc aga aaa gag act      960
Leu Leu Lys Glu Gly Gln Arg Trp Leu Thr Glu Ala Arg Lys Glu Thr
305                 310                 315                 320

gtg atg ggg cag cct act ccg aag acc ccg cgg caa cta agg gag ttc     1008
Val Met Gly Gln Pro Thr Pro Lys Thr Pro Arg Gln Leu Arg Glu Phe
                325                 330                 335

cta ggg acg gca ggc ttc tgt cgc ctc tgg atc cct ggg ttt gca gaa     1056
Leu Gly Thr Ala Gly Phe Cys Arg Leu Trp Ile Pro Gly Phe Ala Glu
            340                 345                 350

atg gca gcc ccc ttg tac cct ctc acc aaa acg ggg act ctg ttt aat     1104
Met Ala Ala Pro Leu Tyr Pro Leu Thr Lys Thr Gly Thr Leu Phe Asn
        355                 360                 365

tgg ggc cca gac caa caa aag gcc tat caa gaa atc aag caa gct ctt     1152
Trp Gly Pro Asp Gln Gln Lys Ala Tyr Gln Glu Ile Lys Gln Ala Leu
    370                 375                 380

cta act gcc cca gcc ctg ggg ttg cca gat ttg act aag ccc ttt gaa     1200
Leu Thr Ala Pro Ala Leu Gly Leu Pro Asp Leu Thr Lys Pro Phe Glu
385                 390                 395                 400

ctc ttt gtc gac gag aag cag ggc tac gcc aaa ggt gtc cta acg caa     1248
Leu Phe Val Asp Glu Lys Gln Gly Tyr Ala Lys Gly Val Leu Thr Gln
                405                 410                 415

aaa ctg gga cct tgg cgt cgg ccg gtg gcc tac ctg tcc aaa aag cta     1296
Lys Leu Gly Pro Trp Arg Arg Pro Val Ala Tyr Leu Ser Lys Lys Leu
```

-continued

```
            420                 425                 430

gac cca gta gca gct ggg tgg ccc cct tgc cta cgg atg gta gca gcc     1344
Asp Pro Val Ala Ala Gly Trp Pro Pro Cys Leu Arg Met Val Ala Ala
        435                 440                 445

att gcc gta ctg aca aag gat gca ggc aag cta acc atg gga cag cca     1392
Ile Ala Val Leu Thr Lys Asp Ala Gly Lys Leu Thr Met Gly Gln Pro
    450                 455                 460

cta gtc att ctg gcc ccc cat gca gta gag gca cta gtc aaa caa ccc     1440
Leu Val Ile Leu Ala Pro His Ala Val Glu Ala Leu Val Lys Gln Pro
465                 470                 475                 480

ccc gat cga tgg ctt tcc aac gcc cgg atg act cac tat cag gcc ttg     1488
Pro Asp Arg Trp Leu Ser Asn Ala Arg Met Thr His Tyr Gln Ala Leu
                485                 490                 495

ctt ttg gac acg gac cgg gtc cag ttc gga ccg gtg gta gcc ctg aac     1536
Leu Leu Asp Thr Asp Arg Val Gln Phe Gly Pro Val Val Ala Leu Asn
            500                 505                 510

ccg gct aca ctg ctc cca ctg cct gag gaa ggg ctg cag cac aac tgc     1584
Pro Ala Thr Leu Leu Pro Leu Pro Glu Glu Gly Leu Gln His Asn Cys
        515                 520                 525

ctt gat atc ctg gcc gaa gcc cac gga acc cga ccc gac cta acg gac     1632
Leu Asp Ile Leu Ala Glu Ala His Gly Thr Arg Pro Asp Leu Thr Asp
    530                 535                 540

cag ccg ctc cca gac gcc gac cac acc tgg tac acg ggt gga tcc agt     1680
Gln Pro Leu Pro Asp Ala Asp His Thr Trp Tyr Thr Gly Gly Ser Ser
545                 550                 555                 560

ctc ttg caa gag gga cag cgt aag gcg gga gct gcg gtg acc acc gag     1728
Leu Leu Gln Glu Gly Gln Arg Lys Ala Gly Ala Ala Val Thr Thr Glu
                565                 570                 575

acc gag gta atc tgg gct aaa gcc ctg cca gcc ggg aca tcc gct cag     1776
Thr Glu Val Ile Trp Ala Lys Ala Leu Pro Ala Gly Thr Ser Ala Gln
            580                 585                 590

cgg gct cag ctg ata gca ctc acc cag gcc cta agg atg gca gaa ggt     1824
Arg Ala Gln Leu Ile Ala Leu Thr Gln Ala Leu Arg Met Ala Glu Gly
        595                 600                 605

aag aag cta aat gtt tat acg aat tcc cgt tat gct ttt gct act gcc     1872
Lys Lys Leu Asn Val Tyr Thr Asn Ser Arg Tyr Ala Phe Ala Thr Ala
    610                 615                 620

cat atc cat gga gaa ata tac aga agg cgt ggg ttg ctc aca tca gaa     1920
His Ile His Gly Glu Ile Tyr Arg Arg Arg Gly Leu Leu Thr Ser Glu
625                 630                 635                 640

ggc aaa gag atc aaa aat aag gac gag ata ttg gcc cta cta aaa gcc     1968
Gly Lys Glu Ile Lys Asn Lys Asp Glu Ile Leu Ala Leu Leu Lys Ala
                645                 650                 655

ctc ttt ctg ccc aaa aga ctt agc ata atc cat tgt cca gga cat caa     2016
Leu Phe Leu Pro Lys Arg Leu Ser Ile Ile His Cys Pro Gly His Gln
            660                 665                 670

aag gga cac agc gcc gag gct aga ggc aac cgg atg gct gac caa gcg     2064
Lys Gly His Ser Ala Glu Ala Arg Gly Asn Arg Met Ala Asp Gln Ala
        675                 680                 685

gcc cga aag gca gcc atc aca gag aat cca gac acc tct acc ctc ctc     2112
Ala Arg Lys Ala Ala Ile Thr Glu Asn Pro Asp Thr Ser Thr Leu Leu
    690                 695                 700

ata gaa aat tca tca ccc aat tcc cgc tta att aat taa                 2151
Ile Glu Asn Ser Ser Pro Asn Ser Arg Leu Ile Asn
705                 710                 715


<210> SEQ ID NO 2
<211> LENGTH: 716
<212> TYPE: PRT
<213> ORGANISM: Artificial Sequence
```

<220> FEATURE:
<223> OTHER INFORMATION: Mutant Reverse Transcriptase Derived from
      Moloney Murine Leukemia Virus

<400> SEQUENCE: 2

```
Met Gly Gly Ser His His His His His His Gly Met Ala Ser Met Thr
1               5                   10                  15

Gly Gly Gln Gln Met Gly Arg Asp Leu Tyr Asp Asp Asp Asp Lys His
            20                  25                  30

Met Thr Leu Asn Ile Glu Asp Glu Tyr Arg Leu His Glu Thr Ser Lys
        35                  40                  45

Glu Pro Asp Val Ser Leu Gly Ser Thr Trp Leu Ser Asp Phe Pro Gln
    50                  55                  60

Ala Trp Ala Glu Thr Gly Gly Met Gly Leu Ala Val Arg Gln Ala Pro
65                  70                  75                  80

Leu Ile Ile Leu Leu Lys Ala Thr Ser Thr Pro Val Ser Ile Lys Gln
                85                  90                  95

Tyr Pro Met Ser Gln Glu Ala Arg Leu Gly Ile Lys Pro His Ile Gln
            100                 105                 110

Arg Leu Leu Asp Gln Gly Ile Leu Val Pro Cys Gln Ser Pro Trp Asn
        115                 120                 125

Thr Pro Leu Leu Pro Val Lys Lys Pro Gly Thr Asn Asp Tyr Arg Pro
    130                 135                 140

Val Gln Asp Leu Arg Glu Val Asn Lys Arg Val Glu Asp Ile His Pro
145                 150                 155                 160

Thr Val Pro Asn Pro Tyr Asn Leu Leu Ser Gly Leu Pro Pro Ser His
                165                 170                 175

Gln Trp Tyr Thr Val Leu Asp Leu Lys Asp Ala Phe Phe Cys Leu Arg
            180                 185                 190

Leu His Pro Thr Ser Gln Pro Leu Phe Ala Phe Glu Trp Arg Asp Pro
        195                 200                 205

Glu Met Gly Ile Ser Gly Gln Leu Thr Trp Thr Arg Leu Pro Gln Gly
    210                 215                 220

Phe Lys Asn Ser Pro Thr Leu Phe Asp Glu Ala Leu Arg Arg Asp Leu
225                 230                 235                 240

Ala Asp Phe Arg Ile Gln His Pro Asp Leu Ile Leu Leu Gln Tyr Val
                245                 250                 255

Asp Asp Leu Leu Leu Ala Ala Thr Ser Glu Leu Asp Cys Gln Gln Gly
            260                 265                 270

Thr Arg Ala Leu Leu Gln Thr Leu Gly Asp Leu Gly Tyr Arg Ala Ser
        275                 280                 285

Ala Lys Lys Ala Gln Ile Cys Gln Lys Gln Val Lys Tyr Leu Gly Tyr
    290                 295                 300

Leu Leu Lys Glu Gly Gln Arg Trp Leu Thr Glu Ala Arg Lys Glu Thr
305                 310                 315                 320

Val Met Gly Gln Pro Thr Pro Lys Thr Pro Arg Gln Leu Arg Glu Phe
                325                 330                 335

Leu Gly Thr Ala Gly Phe Cys Arg Leu Trp Ile Pro Gly Phe Ala Glu
            340                 345                 350

Met Ala Ala Pro Leu Tyr Pro Leu Thr Lys Thr Gly Thr Leu Phe Asn
        355                 360                 365

Trp Gly Pro Asp Gln Gln Lys Ala Tyr Gln Glu Ile Lys Gln Ala Leu
    370                 375                 380

Leu Thr Ala Pro Ala Leu Gly Leu Pro Asp Leu Thr Lys Pro Phe Glu
```

```
385                 390                 395                 400

Leu Phe Val Asp Glu Lys Gln Gly Tyr Ala Lys Gly Val Leu Thr Gln
                405                 410                 415

Lys Leu Gly Pro Trp Arg Arg Pro Val Ala Tyr Leu Ser Lys Lys Leu
            420                 425                 430

Asp Pro Val Ala Ala Gly Trp Pro Pro Cys Leu Arg Met Val Ala Ala
        435                 440                 445

Ile Ala Val Leu Thr Lys Asp Ala Gly Lys Leu Thr Met Gly Gln Pro
    450                 455                 460

Leu Val Ile Leu Ala Pro His Ala Val Glu Ala Leu Val Lys Gln Pro
465                 470                 475                 480

Pro Asp Arg Trp Leu Ser Asn Ala Arg Met Thr His Tyr Gln Ala Leu
                485                 490                 495

Leu Leu Asp Thr Asp Arg Val Gln Phe Gly Pro Val Val Ala Leu Asn
            500                 505                 510

Pro Ala Thr Leu Leu Pro Leu Pro Glu Glu Gly Leu Gln His Asn Cys
        515                 520                 525

Leu Asp Ile Leu Ala Glu Ala His Gly Thr Arg Pro Asp Leu Thr Asp
    530                 535                 540

Gln Pro Leu Pro Asp Ala Asp His Thr Trp Tyr Thr Gly Gly Ser Ser
545                 550                 555                 560

Leu Leu Gln Glu Gly Gln Arg Lys Ala Gly Ala Ala Val Thr Thr Glu
                565                 570                 575

Thr Glu Val Ile Trp Ala Lys Ala Leu Pro Ala Gly Thr Ser Ala Gln
            580                 585                 590

Arg Ala Gln Leu Ile Ala Leu Thr Gln Ala Leu Arg Met Ala Glu Gly
        595                 600                 605

Lys Lys Leu Asn Val Tyr Thr Asn Ser Arg Tyr Ala Phe Ala Thr Ala
    610                 615                 620

His Ile His Gly Glu Ile Tyr Arg Arg Arg Gly Leu Leu Thr Ser Glu
625                 630                 635                 640

Gly Lys Glu Ile Lys Asn Lys Asp Glu Ile Leu Ala Leu Leu Lys Ala
                645                 650                 655

Leu Phe Leu Pro Lys Arg Leu Ser Ile Ile His Cys Pro Gly His Gln
            660                 665                 670

Lys Gly His Ser Ala Glu Ala Arg Gly Asn Arg Met Ala Asp Gln Ala
        675                 680                 685

Ala Arg Lys Ala Ala Ile Thr Glu Asn Pro Asp Thr Ser Thr Leu Leu
    690                 695                 700

Ile Glu Asn Ser Ser Pro Asn Ser Arg Leu Ile Asn
705                 710                 715


<210> SEQ ID NO 3
<211> LENGTH: 21
<212> TYPE: PRT
<213> ORGANISM: Unknown
<220> FEATURE:
<223> OTHER INFORMATION: N-terminal tag sequence

<400> SEQUENCE: 3

Met Ala Ser Gly Thr Gly Gly Gln Gln Met Gly Arg Asp Leu Tyr Asp
1               5                   10                  15

Asp Asp Asp Lys His
            20
```

```
<210> SEQ ID NO 4
<211> LENGTH: 4
<212> TYPE: PRT
<213> ORGANISM: Unknown
<220> FEATURE:
<223> OTHER INFORMATION: Factor Xa cleavage site

<400> SEQUENCE: 4

Ile Glu Gly Arg
1


<210> SEQ ID NO 5
<211> LENGTH: 4
<212> TYPE: PRT
<213> ORGANISM: Unknown
<220> FEATURE:
<223> OTHER INFORMATION: Thrombin cleavage site

<400> SEQUENCE: 5

Leu Val Pro Arg
1


<210> SEQ ID NO 6
<211> LENGTH: 47
<212> TYPE: DNA
<213> ORGANISM: Unknown
<220> FEATURE:
<223> OTHER INFORMATION: 47mer DNA template

<400> SEQUENCE: 6

gagttacagt gtttttgttc cagtctgtag cagtgtgtga atggaag                47


<210> SEQ ID NO 7
<211> LENGTH: 18
<212> TYPE: DNA
<213> ORGANISM: Unknown
<220> FEATURE:
<223> OTHER INFORMATION: 18mer DNA primer

<400> SEQUENCE: 7

cttccattca cacactgc                                                18


<210> SEQ ID NO 8
<211> LENGTH: 21
<212> TYPE: DNA
<213> ORGANISM: Unknown
<220> FEATURE:
<223> OTHER INFORMATION: Sequencing primer

<400> SEQUENCE: 8

gaagatcgca ctccagccag c                                            21


<210> SEQ ID NO 9
<211> LENGTH: 304
<212> TYPE: DNA
<213> ORGANISM: Unknown
<220> FEATURE:
<223> OTHER INFORMATION: Mutations introduced by SuperScript II into
      LacZ Alpha DNA
<220> FEATURE:
<221> NAME/KEY: misc_feature
<222> LOCATION: (139)..(139)
<223> OTHER INFORMATION: May be an inserted cytosine, may not be present
<220> FEATURE:
<221> NAME/KEY: misc_feature
<222> LOCATION: (212)..(212)
<223> OTHER INFORMATION: May be an inserted thymine, may not be present
<220> FEATURE:
<221> NAME/KEY: misc_feature
```

```
<222> LOCATION: (234)..(234)
<223> OTHER INFORMATION: May be 1, 3 or 4 inserted adenines, may not be
      present
<220> FEATURE:
<221> NAME/KEY: misc_feature
<222> LOCATION: (277)..(277)
<223> OTHER INFORMATION: May be an inserted cytosine or adenine, may not
      be present
<220> FEATURE:
<221> NAME/KEY: misc_feature
<222> LOCATION: (281)..(281)
<223> OTHER INFORMATION: May be 1, 3 or 5 inserted thymines, may not be
      present
<220> FEATURE:
<221> NAME/KEY: misc_feature
<222> LOCATION: (285)..(285)
<223> OTHER INFORMATION: May be an inserted cytosine, may not be present
<220> FEATURE:
<221> NAME/KEY: misc_feature
<222> LOCATION: (304)..(304)
<223> OTHER INFORMATION: May be deleted

<400> SEQUENCE: 9

agcgcaaygc aattaatgtg agttagctya ctcattaggc accccaggyy ytacacttta     60

tgcttccggc tcgyrtgttg tgtggaattg tgagcggata acaattycac acmsgaaaca    120

gctaysacca tgattacgns caagcytgca tgcctgcagg tcgactctag aggatccccg    180

ggtaccgagc tcgaattyac tggycgtcgt tntwacaacg tcgtgwctgg gaanaaccct    240

ggcgttaccy macytaatcg ccytgcagya ymtcycncyt nttcngccrg ctgkcgtaat    300

agcg                                                                 304


<210> SEQ ID NO 10
<211> LENGTH: 20
<212> TYPE: DNA
<213> ORGANISM: Unknown
<220> FEATURE:
<223> OTHER INFORMATION: 18 mer DNA primer

<400> SEQUENCE: 10

gaacaaaaac actgtaactc                                                 20


<210> SEQ ID NO 11
<211> LENGTH: 20
<212> TYPE: PRT
<213> ORGANISM: Unknown
<220> FEATURE:
<223> OTHER INFORMATION: N-terminal tag sequence

<400> SEQUENCE: 11

Met Ala Ser Gly Thr Gly Gly Gln Gln Met Gly Arg Asp Leu Tyr Asp
1               5                   10                  15

Asp Asp Asp Lys
            20


<210> SEQ ID NO 12
<211> LENGTH: 21
<212> TYPE: DNA
<213> ORGANISM: Homo sapiens

<400> SEQUENCE: 12

gctcgtcgtc gacaacggct c                                               21


<210> SEQ ID NO 13
<211> LENGTH: 25
<212> TYPE: DNA
<213> ORGANISM: Homo sapiens
```

<400> SEQUENCE: 13
caaacatgat ctgggtcatc ttctc 25

<210> SEQ ID NO 14
<211> LENGTH: 24
<212> TYPE: DNA
<213> ORGANISM: Homo sapiens

<400> SEQUENCE: 14
gtgaaggtcg gagtcaacgg attt 24

<210> SEQ ID NO 15
<211> LENGTH: 24
<212> TYPE: DNA
<213> ORGANISM: Homo sapiens

<400> SEQUENCE: 15
cacagtcttc tgggtggcag tgat 24

<210> SEQ ID NO 16
<211> LENGTH: 20
<212> TYPE: DNA
<213> ORGANISM: Homo sapiens

<400> SEQUENCE: 16
atggcgatcg tcgaaccgga 20

<210> SEQ ID NO 17
<211> LENGTH: 31
<212> TYPE: DNA
<213> ORGANISM: Homo sapiens

<400> SEQUENCE: 17
cactgtctta atatgaatgg gacctactga g 31

<210> SEQ ID NO 18
<211> LENGTH: 26
<212> TYPE: DNA
<213> ORGANISM: Homo sapiens

<400> SEQUENCE: 18
gagccaagca gacaagcaaa gcaagc 26

<210> SEQ ID NO 19
<211> LENGTH: 27
<212> TYPE: DNA
<213> ORGANISM: Homo sapiens

<400> SEQUENCE: 19
tgttttaatt caatcccacg cccctgt 27

<210> SEQ ID NO 20
<211> LENGTH: 20
<212> TYPE: DNA
<213> ORGANISM: Homo sapiens

<400> SEQUENCE: 20
aaggctggcg gattactgcc 20

<210> SEQ ID NO 21
<211> LENGTH: 21
<212> TYPE: DNA

<213> ORGANISM: Homo sapiens

<400> SEQUENCE: 21
gatgctgctg gtgatgtact c 21

<210> SEQ ID NO 22
<211> LENGTH: 21
<212> TYPE: DNA
<213> ORGANISM: Homo sapiens

<400> SEQUENCE: 22
gaggagggcg aggtggacgg c 21

<210> SEQ ID NO 23
<211> LENGTH: 27
<212> TYPE: DNA
<213> ORGANISM: Homo sapiens

<400> SEQUENCE: 23
gaactaacac acagcgatgg gtgggaa 27

<210> SEQ ID NO 24
<211> LENGTH: 32
<212> TYPE: DNA
<213> ORGANISM: Homo sapiens

<400> SEQUENCE: 24
ggagtttatc atcaccgcgg aaatactgag ag 32

<210> SEQ ID NO 25
<211> LENGTH: 30
<212> TYPE: DNA
<213> ORGANISM: Homo sapiens

<400> SEQUENCE: 25
tatttcactg acaggcaata ccgtccaagg 30

<210> SEQ ID NO 26
<211> LENGTH: 20
<212> TYPE: DNA
<213> ORGANISM: Homo sapiens

<400> SEQUENCE: 26
cgccaaattt ctcccctgaa 20

<210> SEQ ID NO 27
<211> LENGTH: 21
<212> TYPE: DNA
<213> ORGANISM: Homo sapiens

<400> SEQUENCE: 27
ccgtagtgct gggcaatgtt c 21

<210> SEQ ID NO 28
<211> LENGTH: 27
<212> TYPE: DNA
<213> ORGANISM: Homo sapiens

<400> SEQUENCE: 28
gctgcagctt catatgatca gttgtta 27

<210> SEQ ID NO 29
<211> LENGTH: 20

<212> TYPE: DNA
<213> ORGANISM: Homo sapiens

<400> SEQUENCE: 29
aatggcgctt aggactttgg 20

<210> SEQ ID NO 30
<211> LENGTH: 24
<212> TYPE: DNA
<213> ORGANISM: Homo sapiens

<400> SEQUENCE: 30
tggaggctgg gaacgtgaag gaaa 24

<210> SEQ ID NO 31
<211> LENGTH: 27
<212> TYPE: DNA
<213> ORGANISM: Homo sapiens

<400> SEQUENCE: 31
acaggaatga ccgagggtaa tcttggc 27

<210> SEQ ID NO 32
<211> LENGTH: 17
<212> TYPE: DNA
<213> ORGANISM: Rattus sp.

<400> SEQUENCE: 32
gcggcgctgg aggagaa 17

<210> SEQ ID NO 33
<211> LENGTH: 22
<212> TYPE: DNA
<213> ORGANISM: Rattus sp.

<400> SEQUENCE: 33
aggtggcggc tcaaacacaa ag 22

<210> SEQ ID NO 34
<211> LENGTH: 24
<212> TYPE: DNA
<213> ORGANISM: Homo sapiens

<400> SEQUENCE: 34
cgggtggtaa ctggctgctg tgga 24

<210> SEQ ID NO 35
<211> LENGTH: 24
<212> TYPE: DNA
<213> ORGANISM: Homo sapiens

<400> SEQUENCE: 35
tggaggctgg gaacgtgaag gaaa 24

<210> SEQ ID NO 36
<211> LENGTH: 23
<212> TYPE: DNA
<213> ORGANISM: Homo sapiens

<400> SEQUENCE: 36
gcggacctcc cgcttctgcc gga 23

<210> SEQ ID NO 37

<211> LENGTH: 28
<212> TYPE: DNA
<213> ORGANISM: Homo sapiens

<400> SEQUENCE: 37
ccaagtaaaa cagcatcgga acaccagg 28

<210> SEQ ID NO 38
<211> LENGTH: 25
<212> TYPE: DNA
<213> ORGANISM: Homo sapiens

<400> SEQUENCE: 38
aaagtcgatc agcagttgcc agggg 25

<210> SEQ ID NO 39
<211> LENGTH: 23
<212> TYPE: DNA
<213> ORGANISM: Homo sapiens

<400> SEQUENCE: 39
cccacagtca ccgccgctta cct 23

<210> SEQ ID NO 40
<211> LENGTH: 25
<212> TYPE: DNA
<213> ORGANISM: Homo sapiens

<400> SEQUENCE: 40
cttcatccct ccccaacccc aatct 25

<210> SEQ ID NO 41
<211> LENGTH: 21
<212> TYPE: DNA
<213> ORGANISM: Homo sapiens

<400> SEQUENCE: 41
gaggagggcg aggtggacgg c 21

<210> SEQ ID NO 42
<211> LENGTH: 27
<212> TYPE: DNA
<213> ORGANISM: Homo sapiens

<400> SEQUENCE: 42
gaactaacac acagcgatgg gtgggaa 27

<210> SEQ ID NO 43
<211> LENGTH: 20
<212> TYPE: DNA
<213> ORGANISM: Homo sapiens

<400> SEQUENCE: 43
cgccaaattt ctcccctgaa 20

<210> SEQ ID NO 44
<211> LENGTH: 21
<212> TYPE: DNA
<213> ORGANISM: Homo sapiens

<400> SEQUENCE: 44
ccgtagtgct gggcaatgtt c 21

-continued

```
<210> SEQ ID NO 45
<211> LENGTH: 21
<212> TYPE: DNA
<213> ORGANISM: Homo sapiens

<400> SEQUENCE: 45

gctcgtcgtc gacaacggct c                                              21


<210> SEQ ID NO 46
<211> LENGTH: 25
<212> TYPE: DNA
<213> ORGANISM: Homo sapiens

<400> SEQUENCE: 46

accacatgat ctgggtcatc ttctc                                          25
```

THERMOSTABLE REVERSE TRANSCRIPTASES AND USES THEREOF

CROSS-REFERENCE TO RELATED APPLICATIONS

The present application is a continuation application of U.S. patent application Ser. No. 12/979,899, filed Dec. 28, 2010 which is a continuation of U.S. patent application Ser. No. 11/492,194, filed Jul. 25, 2006 which is a continuation of U.S. patent application Ser. No. 10/661,819, filed Sep. 15, 2003 which claims priority from Provisional Application No. 60/410,283, filed Sep. 13, 2002. U.S. patent application Ser. No. 11/492,194 is also a continuation-in-part of U.S. patent application Ser. No. 11/437,681, filed May 22, 2006, which is a continuation of U.S. application Ser. No. 09/845,157, filed May 1, 2001, now U.S. Pat. No. 7,078,208, which claims priority from Provisional Application No. 60/207,196, filed May 26, 2000, the entire disclosures of which are incorporated herein by reference.

BACKGROUND OF THE INVENTION

Field of the Invention

The present invention is in the fields of molecular and cellular biology. The invention is generally related to reverse transcriptase enzymes and methods for the reverse transcription of nucleic acid molecules, especially messenger RNA molecules. Specifically, the invention relates to reverse transcriptase enzymes which have been mutated or modified to increase thermostability, decrease terminal deoxynucleotidyl transferase activity, and/or increase fidelity, and to methods of producing, amplifying or sequencing nucleic acid molecules (particularly cDNA molecules) using these reverse transcriptase enzymes or compositions. The invention also relates to nucleic acid molecules produced by these methods and to the use of such nucleic acid molecules to produce desired polypeptides. The invention also relates to nucleic acid molecules encoding the reverse transcriptases of the invention, to vectors containing such nucleic acid molecules, and to host cells containing such nucleic acid molecules. The invention also concerns kits or compositions comprising such enzymes.

Related Art cDNA and cDNA Libraries

In examining the structure and physiology of an organism, tissue or cell, it is often desirable to determine its genetic content. The genetic framework of an organism is encoded in the double-stranded sequence of nucleotide bases in the deoxyribonucleic acid (DNA) which is contained in the somatic and germ cells of the organism. The genetic content of a particular segment of DNA, or gene, is typically manifested upon production of the protein which the gene encodes. In order to produce a protein, a complementary copy of one strand of the DNA double helix is produced by RNA polymerase enzymes, resulting in a specific sequence of ribonucleic acid (RNA). This particular type of RNA, since it contains the genetic message from the DNA for production of a protein, is called messenger RNA (mRNA).

Within a given cell, tissue or organism, there exist myriad mRNA species, each encoding a separate and specific protein. This fact provides a powerful tool to investigators interested in studying genetic expression in a tissue or cell. mRNA molecules may be isolated and further manipulated by various molecular biological techniques, thereby allowing the elucidation of the full functional genetic content of a cell, tissue or organism.

One common approach to the study of gene expression is the production of complementary DNA (cDNA) clones. In this technique, the mRNA molecules from an organism are isolated from an extract of the cells or tissues of the organism. This isolation often employs solid chromatography matrices, such as cellulose or agarose, to which oligomers of thymidine (T) have been complexed. Since the 3' termini on most eukaryotic mRNA molecules contain a string of adenosine (A) bases, and since A base pairs with T, the mRNA molecules can be rapidly purified from other molecules and substances in the tissue or cell extract. From these purified mRNA molecules, cDNA copies may be made using the enzyme reverse transcriptase (RT), which results in the production of single-stranded cDNA molecules. This reaction is typically referred to as the first strand reaction. The single-stranded cDNAs may then be converted into a complete double-stranded DNA copy (i.e., a double-stranded cDNA) of the original mRNA (and thus of the original double-stranded DNA sequence, encoding this mRNA, contained in the genome of the organism) by the action of a DNA polymerase. The protein-specific double-stranded cDNAs can then be inserted into a plasmid or viral vector, which is then introduced into a host bacterial, yeast, animal or plant cell. The host cells are then grown in culture media, resulting in a population of host cells containing (or in many cases, expressing) the gene of interest.

This entire process, from isolation of mRNA from a source organism or tissue to insertion of the cDNA into a plasmid or vector to growth of host cell populations containing the isolated gene, is termed "cDNA cloning." The set of cDNAs prepared from a given source of mRNAs is called a "cDNA library." The cDNA clones in a cDNA library correspond to the genes transcribed in the source tissue. Analysis of a cDNA library can yield much information on the pattern of gene expression in the organism or tissue from which it was derived.

Retroviral Reverse Transcriptase Enzymes

Three prototypical forms of retroviral reverse transcriptase have been studied thoroughly. Moloney Murine Leukemia Virus (M-MLV) reverse transcriptase contains a single subunit of 78 kDa with RNA-dependent DNA polymerase and RNase H activity. This enzyme has been cloned and expressed in a fully active form in *E. coli* (reviewed in Prasad, V. R., *Reverse Transcriptase*, Cold Spring Harbor, N.Y.: Cold Spring Harbor Laboratory Press, p. 135 (1993)). Human Immunodeficiency Virus (HIV) reverse transcriptase is a heterodimer of p66 and p51 subunits in which the smaller subunit is derived from the larger by proteolytic cleavage. The p66 subunit has both a RNA-dependent DNA polymerase and an RNase H domain, while the p51 subunit has only a DNA polymerase domain. Active HIV p66/p51 reverse transcriptase has been cloned and expressed successfully in a number of expression hosts, including *E. coli* (reviewed in Le Grice, S. F. J., *Reverse Transcriptase*, Cold Spring Harbor, N.Y.: Cold Spring Harbor Laboratory press, p. 163 (1993)). Within the HIV p66/p51 heterodimer, the 51-kD subunit is catalytically inactive, and the 66-kD subunit has both DNA polymerase and RNase H activity (Le Grice, S. F. J., et al., *EMBO Journal* 10:3905 (1991); Hostomsky, Z., et al., *J. Virol.* 66:3179 (1992)). Avian Sarcoma-Leukosis Virus (ASLV) reverse transcriptase, which includes but is not limited to Rous Sarcoma Virus (RSV) reverse transcriptase, Avian Myeloblastosis Virus (AMV) reverse transcriptase, Avian Erythroblastosis Virus (AEV) Helper Virus MCAV reverse transcriptase, Avian Myelocytomatosis Virus MC29 Helper Virus MCAV reverse transcriptase, Avian Reticuloendotheliosis Virus (REV-T)

Helper Virus REV-A reverse transcriptase, Avian Sarcoma Virus UR2 Helper Virus UR2AV reverse transcriptase, Avian Sarcoma Virus Y73 Helper Virus YAV reverse transcriptase, Rous Associated Virus (RAV) reverse transcriptase, and Myeloblastosis Associated Virus (MAV) reverse transcriptase, is also a heterodimer of two subunits, α (approximately 62 kDa) and β (approximately 94 kDa), in which α is derived from β by proteolytic cleavage (reviewed in Prasad, V. R., *Reverse Transcriptase*, Cold Spring Harbor, N.Y.: Cold Spring Harbor Laboratory Press (1993), p. 135). ASLV reverse transcriptase can exist in two additional catalytically active structural forms, ββ and α (Hizi, A. and Joklik, W. K., *J. Biol. Chem.* 252: 2281 (1977)). Sedimentation analysis suggests αβ and ββ are dimers and that the α form exists in an equilibrium between monomeric and dimeric forms (Grandgenett, D. P., et al., *Proc. Nat. Acad. Sci. USA* 70:230 (1973); Hizi, A. and Joklik, W. K., *J. Biol. Chem.* 252:2281 (1977); and Soltis, D. A. and Skalka, A. M., *Proc. Nat. Acad. Sci. USA* 85:3372 (1988)). The ASLV αβ and ββ reverse transcriptases are the only known examples of retroviral reverse transcriptase that include three different activities in the same protein complex: DNA polymerase, RNase H, and DNA endonuclease (integrase) activities (reviewed in Skalka, A. M., *Reverse Transcriptase*, Cold Spring Harbor, N.Y.: Cold Spring Harbor Laboratory Press (1993), p. 193). The α form lacks the integrase domain and activity.

Various forms of the individual subunits of ASLV reverse transcriptase have been cloned and expressed. These include a 98-kDa precursor polypeptide that is normally processed proteolytically to β and a 4 kDa polypeptide removed from the β carboxy end (Alexander, F., et al., *J. Virol.* 61:534 (1987) and Anderson, D. et al., *Focus* 17:53 (1995)), and the mature β subunit (Weis, J. H. and Salstrom, J. S., U.S. Pat. No. 4,663,290 (1987); and Soltis, D. A. and Skalka, A. M., *Proc. Nat. Acad. Sci. USA* 85:3372 (1988)). (See also Werner S, and Wohrl B. M., *Eur. J. Biochem.* 267:4740-4744 (2000); Werner S, and Wohrl B. M., *J. Virol.* 74:3245-3252 (2000); Werner S. and Wohrl B. M., *J. Biol. Chem.* 274: 26329-26336 (1999).) Heterodimeric RSV αβ reverse transcriptase has also been purified from *E. coli* cells expressing a cloned RSV β gene (Chemov, A. P., et al., *Biomed. Sci.* 2:49 (1991)).

Reverse Transcription Efficiency

As noted above, the conversion of mRNA into cDNA by reverse transcriptase-mediated reverse transcription is an essential step in the study of proteins expressed from cloned genes. However, the use of unmodified reverse transcriptase to catalyze reverse transcription is inefficient for a number of reasons. First, reverse transcriptase sometimes degrades an RNA template before the first strand reaction is initiated or completed, primarily due to the intrinsic RNase H activity present in reverse transcriptase. In addition, mis-priming of the mRNA template molecule can lead to the introduction of errors in the cDNA first strand while secondary structure of the mRNA molecule itself may make some mRNAs refractory to first strand synthesis.

Removal of the RNase H activity of reverse transcriptase can eliminate the first problem and improve the efficiency of reverse transcription (Gerard, G. F., et al., *FOCUS* 11(4):60 (1989); Gerard, G. F., et al., *FOCUS* 14(3):91 (1992)). However such reverse transcriptases ("RNase H−" forms) do not address the additional problems of mis-priming and mRNA secondary structure.

Another factor which influences the efficiency of reverse transcription is the ability of RNA to form secondary structures. Such secondary structures can form, for example, when regions of RNA molecules have sufficient complementarity to hybridize and form double stranded RNA. Generally, the formation of RNA secondary structures can be reduced by raising the temperature of solutions which contain the RNA molecules. Thus, in many instances, it is desirable to reverse transcribe RNA at temperatures above 37° C. However, art known reverse transcriptases generally lose activity when incubated at temperatures much above 37° C. (e.g., 50° C.).

SUMMARY OF THE INVENTION

The present invention provides, in part, reverse transcriptase enzymes, compositions comprising such enzymes and methods useful in overcoming limitations of reverse transcription discussed above. In general, the invention provides compositions for use in reverse transcription of a nucleic acid molecule, these compositions comprising one or more (e.g., one, two, three, four, five, ten, fifteen, etc.) polypeptides having at least one reverse transcriptase activity. Such compositions may further comprise one or more (e.g., one, two, three, four, five, etc.) nucleotides (e.g. one or more fluorescent1-labeled nucleotides, one or more radiolabeled nucleotides, etc.), a suitable buffer, and/or one or more (e.g., one, two, three, four, five, ten, fifteen, etc.) DNA polymerases. Compositions of the invention may also comprise one or more (e.g., one, two, three, four, five, ten, fifteen, etc.) oligonucleotide primers, and/or one or more templates, and/or one or more nucleic acid molecules (which may be complementary to all or a portion of such templates).

Reverse transcriptases of the invention are preferably modified or mutated such that the thermostability of the enzyme is increased or enhanced and/or the fidelity of the enzyme is increased or enhanced. In specific embodiments, reverse transcriptases of the invention may be single chained (single subunit) or multi-chained (multi-subunit) and may be reduced or substantially reduced in RNase H activity or may have no detectable RNase H activity or may be lacking in RNase H activity. Preferably enzymes of the invention are enzymes selected from the group consisting of Moloney Murine Leukemia Virus (M-MLV) RNase H− reverse transcriptase, Rous Sarcoma Virus (RSV) RNase H− reverse transcriptase, Avian Myeloblastosis Virus (AMV) RNase H− reverse transcriptase, Rous Associated Virus (RAV) RNase H− reverse transcriptase, Myeloblastosis Associated Virus (MAV) RNase H− reverse transcriptase or other ASLV RNase H− reverse transcriptases and Human Immunodeficiency Virus (HIV) RNase H− reverse transcriptase and mutants thereof. In preferred compositions, the reverse transcriptases are present at working concentrations.

In certain aspects, the invention includes reverse transcriptases which have been modified or mutated to increase or enhance thermostability. Examples of such reverse transcriptases include enzymes comprising one or more modifications or mutations at positions corresponding to amino acids selected from the group consisting of:

(a) leucine 52 of M-MLV reverse transcriptase;
(b) tyrosine 64 of M-MLV reverse transcriptase;
(c) lysine 152 of M-MLV reverse transcriptase;
(d) histidine 204 of M-MLV reverse transcriptase;
(e) methionine 289 of M-MLV reverse transcriptase;
(f) threonine 306 of M-MLV reverse transcriptase; and
(g) phenylalanine 309 of M-MLV reverse transcriptase.

In some embodiments, a modification or mutation may be the addition of an N- and/or C-terminal tag sequence.

In specific embodiments, the invention is directed to M-MLV reverse transcriptases wherein leucine 52 is replaced with proline, tyrosine 64 is replaced with arginine, lysine 152 is replaced with methionine, histidine 204 is replaced with arginine, methionine 289 is replaced with leucine, threonine 306 is replaced with either lysine or arginine, and/or phenylalanine 309 is replaced with asparagine or serine. Further included within the scope of the invention are reverse transcriptases, other than M-MLV reverse transcriptase, which contain alterations corresponding to those set out above.

In additional aspects, the invention also include thermostable reverse transcriptases which retain at least about 50%, at least about 60%, at least about 70%, at least about 85%, at least about 95%, at least about 97%, at least about 98%, at least about 99%, at least about 100%, at least about 150%, at least about 200%, at least about 250%, or at least about 300% of reverse transcriptase activity after heating to 50° C. for 5 minutes.

As noted above, enzymes of the invention include reverse transcriptases which exhibit reverse transcriptase activity either upon the formation of multimers (e.g., dimers) or as individual protein molecules (i.e., in monomeric form). Examples of reverse transcriptases which exhibit reverse transcriptase activity upon the formation of multimers include AMV, RSV and HIV reverse transcriptases. One example of a reverse transcriptase which exhibits reverse transcriptase activity as separate, individual proteins (i.e., in monomeric form) is M-MLV reverse transcriptase.

Multimeric reverse transcriptases of the invention may form homo-multimers or hetero-multimers. In other words, the subunits of the multimeric protein complex may be identical or different. One example of a hetero-dimeric reverse transcriptase is AMV reverse transcriptase, which is composed of two subunits that differ in primary amino acid sequence. More specifically, as already discussed, AMV reverse transcriptase may be composed of two subunits wherein one of these subunits is generated by proteolytic processing of the other. Thus, dimeric AMV reverse transcriptase may be composed of subunits of differing size which share regions of amino acid sequence identity.

The present invention relates in particular to mutant or modified reverse transcriptases wherein one or more (e.g., one, two, three, four, five, ten, twelve, fifteen, twenty, etc.) amino acid changes have been made which renders the enzyme more thermostable in nucleic acid synthesis, as compared to the unmutated or unmodified reverse transcriptases. Sites for mutation or modification to produce the thermostable reverse transcriptase enzymes of the present invention and/or reverse transcriptases which exhibit other characteristics (e.g., increased fidelity, decreased TdT activity, etc.) are listed for some reverse transcriptases in Table 1. As will be appreciated by those skilled in the art, one or more of the amino acids identified may be deleted and/or replaced with one or a number of amino acid residues. In a preferred aspect, any one or more of the amino acids identified in Table 1 may be substituted with any one or more amino acid residues such as Ala, Arg, Asn, Asp, Cys, Gln, Glu, Gly, His, Ile, Leu, Lys, Met, Phe, Pro, Ser, Thr, Trp, Tyr, and/or Val. The modifications described in Table 1 preferably produce thermostable reverse transcriptases of the invention. Similar or equivalent sites or corresponding sites in other reverse transcriptases can be mutated or modified to produce additional thermostable reverse transcriptases, as well as reverse transcriptases which exhibit other characteristics (e.g., increased fidelity, decreased TdT activity, etc.). Thus, a reverse transcriptase of the present invention may have one or more of the following properties: (a) increased thermostability or increased half-life at elevated temperatures; (b) reduced, substantially reduced, or no detectable RNase H activity, (c) reduced or substantially reduced terminal deoxynucleotidyl transferase activity, and/or (d) increased fidelity. In some embodiments, a reverse transcriptase of the invention may have a plurality of the properties listed above (e.g., a reverse transcriptase may have enhanced thermostability, reduced RNase H activity, and enhanced fidelity).

TABLE 1

| RT | Amino Acids |
|---|---|
| M-MLV | L52, Y64, L135, H143, K152, Q165, G181, H204, I218, N249, M289, T306, F309, A517, D524, T544, V546, W548, E562, H577, D583, L604, S606, G608, F625, L626, H629, H631, H638, G641 |
| AMV | V2, L4, W12, P14, H16, T17, W20, I21, Q23, W24, L26, P27, G29, V32, Q36, L42, Q43, L44, G45, H46, I47, P49, S50, L51, S52, C53, W54, F59, I61, A64, S65, G66, S67, Y68, L70, L71, A76, A79, P83, A86, V87, Q88, Q89, G90, A91, W101, P102, L108, Q120, S131, V132, N133, N134, Q135, P137, A138, Q142, Q148, T151, Y180, M181, S190, H191, G193, A196, I201, S202, P214, V217, Q218, P221, G222, Q224, L226, G227, Y228, G231, T233, Y234, A236, P237, G239, L240, P244, I246, T248, W250, Q252, G257, Q260, W261, P264, L266, G267, L272, Y277, Q279, L280, G282, S283, P285, N286, A288, N292, L293, M297, I302, V303, L305, S306, T308, L311, L320, I332, G333, V334, G336, Q337, G338, P345, W348, L349, F350, S351, P354, A357, F358, A360, W361, L362, V364, L365, T366, T370, A374, V377, G381, C392, P400, G402, L405, G412, I414, F423, I425, A426, P428, L433, H440, P441, V443, G444, P445, A451, S453, S454, T455, H456, G458, V459, V460, W462, W468, I470, I473, A474, L476, G477, A478, S479, V480, Q481, Q482, L483, A491, W495, P496, T497, T498, P499, T500, A507, F508, M512, L513, G520, V521, P522, S523, T524, A525, A527, F528, L534, S535, Q536, S538, V543, S548, H549, S550, V552, P553, F556, T557, N560, A562 |
| RSV | V2, L4, W12, P14, H16, T17, W20, I21, Q23, W24, L26, P27, G29, V32, Q36, L42, Q43, L44, G45, H46, I47, P49, S50, L51, S52, C53, W54, F59, I61, A64, S65, G66, S67, Y68, L70, L71, A76, A79, P83, A86, V87, Q88, Q89, G90, A91, W101, P102, L108, Q120, S131, V132, N133, N134, Q135, P137, A138, Q142, Q148, T151, Y180, M181, S190, H191, G193, A196, I201, S202, P214, V217, Q218, P221, G222, Q224, L226, G227, Y228, G231, T233, Y234, A236, P237, G239, L240, P244, I246, T248, W250, Q252, G257, Q260, W261, |

TABLE 1-continued

| RT | Amino Acids |
|---|---|
| | P264, L266, G267, L272, Y277, Q279, L280, G282, S283, P285, N286, A288, N292, L293, M297, I302, V303, L305, S306, T308, L311, L320, I332, G333, V334, G336, Q337, G338, P345, W348, L349, F350, S351, P354, A357, F358, A360, W361, L362, V364, L365, T366, T370, A374, V377, G381, C392, P400, G402, L405, G412, I414, F423, I425, A426, P428, L433, H440, P441, V443, G444, P445, A451, S453, S454, T455, H456, G458, V459, V460, W462, W468, I470, I473, A474, L476, G477, A478, S479, V480, Q481, Q482, L483, A491, W495, P496, T497, T498, P499, T500, A507, F508, M512, L513, G520, V521, P522, S523, T524, A525, A527, F528, L534, S535, Q536, S538, V543, S548, H549, S550, V552, P553, F556, T557, N560, A562 |
| HIV | I1, P3, L11, P13, G14, M15, Q22, W23, L25, T26, T38, G44, I46, S47, G50, P51, N53, P54, Y55, F60, I62, S67, T68, W70, L73, V89, Q90L91, G92, I93, S104, V110, G111, S133, I134, N135, N136, P139, G140, I141, Q144, N146, Q150,, Y182, M183, I194, G195, Q196, T,199, Q206, L209, P216, Q221, P224, P225, L227, M229, G230, Y231, H234, Q241, P242, V244, L245, S250, T252, N254, Q257, G261, N264, W265, Q268, P271, G272, Q277, C279, L281, L282, G284, T285, A287, L288, T289, V291, P293, L294, T295, L300, A303, I308, L309, P312, H314, Y317, L324, I328, Q329, G332, Q333, G334, Y341, P344, F345, Y353, M356, G358, A359, H360, T361, Q372, T376, V380, Q392, W405, Q406, A407, F415, V416, N417, T418, P419, P420, L424, W425, P432, V434, G435, A436, A444, A445, N446, T449, L451, N459, G461, Q463, V465, V466, P467, L468, T469, N470, T471, T472, N473, Q474, Y482, Q486, S488, G489, L490, Q499, Y500, G503, I504, S512, S514, L516, N518, Q519, Q523, I525, W534, P536, A537, H538, G540, I541, G542, Q546, L550, S552, A553, V554, I555 |

Those skilled in the art will appreciate that a different isolate of virus may encode a reverse transcriptase enzyme having a different amino acid at the positions identified above. Such isolates may be modified to produce the reverse transcriptases (e.g., thermostable reverse transcriptases) of the present invention.

Reverse transcriptases of the invention may have one or more of the following properties: (a) increased thermostability or increased half-life at elevated temperatures; (b) reduced, substantially reduced, or no detectable RNase H activity, (c) reduced or substantially reduced terminal deoxynucleotidyl transferase activity, and/or (d) increased fidelity.

Enzymes of the invention which have reduced or substantially reduced terminal deoxynucleotidyl transferase activity may comprise one or more modifications or mutations at positions corresponding to amino acids selected from the group consisting of:

(a) tyrosine 133 of M-MLV reverse transcriptase;

(b) threonine 197 of M-MLV reverse transcriptase; and (c) phenylalanine 309 of M-MLV reverse transcriptase.

In specific embodiments, the invention is directed to M-MLV reverse transcriptases wherein tyrosine 133 is replaced with alanine, threonine 197 is replaced with glutamic acid, and/or phenylalanine 309 is replaced with asparagine. As will be appreciated, one or more of the amino acids identified may be deleted and/or replaced with one or a number of amino acid residues. Further included within the scope of the invention are reverse transcriptases, other than M-MLV reverse transcriptase, which contain alterations corresponding to those set out above.

Additionally, enzymes which exhibit increased fidelity may comprise one or more modifications or mutations at positions corresponding to amino acids selected from the group consisting of:

(a) tyrosine 64 of M-MLV reverse transcriptase;

(b) arginine 116 of M-MLV reverse transcriptase;

(c) glutamine 190 of M-MLV reverse transcriptase; and (d) valine 223 of M-MLV reverse transcriptase.

As will be appreciated, one or more of the amino acids identified may be deleted and/or replaced with any one or a number of amino acid residues. Further, included in the invention are reverse transcriptases, other than M-MLV reverse transcriptase, that contain alterations corresponding to those set out above.

In some embodiments, the present invention provides a modified or mutated reverse transcriptase (e.g., preferably a modified or mutated retroviral reverse transcriptase) having a reverse transcriptase activity that has a half-life of greater than that of the corresponding un-modified or un-mutated reverse transcriptase at an elevated temperature, i.e., greater than 37° C. In some embodiments, the half-life of a reverse transcriptase of the present invention may be 5 minutes or greater and preferably 10 minutes or greater at 50° C. In some embodiments, the reverse transcriptases of the invention may have a half-life (e.g., at 50° C.) equal to or greater than about 25 minutes, preferably equal to or greater than about 50 minutes, more preferably equal to or greater than about 100 minutes, and most preferably, equal to or greater than about 200 minutes.

In some embodiments, the reverse transcriptases of the invention may have a half-life at 50° C. that is from about 10 minutes to about 200 minutes, from about 10 minutes to about 150 minutes, from about 10 minutes to about 100 minutes, from about 10 minutes to about 75 minutes, from about 10 minutes to about 50 minutes, from about 10 minutes to about 40 minutes, from about 10 minutes to about 30 minutes, or from about 10 minutes to about 20 minutes.

A modified or mutated reverse transcriptase of the invention (e.g., one having a half-life at 50° C. as described above) may be a modified or mutated retroviral reverse transcriptase. A reverse transcriptase according to the invention may be selected from a group consisting of M-MLV reverse transcriptase, ASV reverse transcriptase, HIV reverse transcriptase, Avian Sarcoma-Leukosis Virus (ASLV) reverse transcriptase, Rous Sarcoma Virus (RSV) reverse transcriptase, Avian Myeloblastosis Virus (AMV) reverse transcriptase, Avian Erythroblastosis Virus (AEV)

Helper Virus MCAV reverse transcriptase, Avian Myelocytomatosis Virus MC29 Helper Virus MCAV reverse transcriptase, Avian Reticuloendotheliosis Virus (REV-T) Helper Virus REV-A reverse transcriptase, Avian Sarcoma Virus UR2 Helper Virus UR2AV reverse transcriptase, Avian Sarcoma Virus Y73 Helper Virus YAV reverse transcriptase, Rous Associated Virus (RAV) reverse transcriptase, and Myeloblastosis Associated Virus (MAV) reverse transcriptase, and fragments of any of the above having reverse transcriptase activity.

Mutated or modified reverse transcriptases of the present invention may have a reverse transcriptase activity (e.g., RNA-dependent DNA polymerase activity) that has a longer half-life at 55° C. than the reverse transcriptase activity of a corresponding un-mutated or un-modified reverse transcriptases. For example, introduction of the H204R, M289K, T306K, and F309N mutation into $His_6$-$H^-$RT increases the half-life at 55° C. from 1.6 minutes to 8.1 minutes (see Table 9). At 55° C., the half-life of reverse transcriptase activity of a mutated or modified reverse transcriptase of the invention may be greater than about 2 minutes, greater than about 3 minutes, greater than about 4 minutes, greater than about 5 minutes, greater than about 6 minutes, greater than about 7 minutes, greater than about 8 minutes, greater than about 10 minutes, greater than about 15 minutes, greater than about 20 minutes, or greater than about 30 minutes. At 55° C., the half-life of reverse transcriptase activity of a reverse transcriptase of the invention may be from about 2 minutes to about 60 minutes, from about 2 minutes to about 45 minutes, from about 2 minutes to about 30 minutes, from about 2 minutes to about 20 minutes, from about 2 minutes to about 15 minutes, from about 2 minutes to about 10 minutes, from about 2 minutes to about 8 minutes, from about 2 minutes to about 7 minutes, from about 2 minutes to about 6 minutes, from about 2 minutes to about 5 minutes, from about 2 minutes to about 4 minutes, or from about 2 minutes to about 3 minutes. Such a reverse transcriptase may be a modified or mutant retroviral reverse transcriptase.

A modified or mutated reverse transcriptase of the invention (e.g., one having a half-life at 55° C. as described above) may be a modified or mutated retroviral reverse transcriptase. A mutated reverse transcriptase according to the present invention may be selected from a group consisting of M-MLV reverse transcriptase, ASV reverse transcriptase, HIV reverse transcriptase, Avian Sarcoma-Leukosis Virus (ASLV) reverse transcriptase, Rous Sarcoma Virus (RSV) reverse transcriptase, Avian Myeloblastosis Virus (AMV) reverse transcriptase, Avian Erythroblastosis Virus (AEV) Helper Virus MCAV reverse transcriptase, Avian Myelocytomatosis Virus MC29 Helper Virus MCAV reverse transcriptase, Avian Reticuloendotheliosis Virus (REV-T) Helper Virus REV-A reverse transcriptase, Avian Sarcoma Virus UR2 Helper Virus UR2AV reverse transcriptase, Avian Sarcoma Virus Y73 Helper Virus YAV reverse transcriptase, Rous Associated Virus (RAV) reverse transcriptase, and Myeloblastosis Associated Virus (MAV) reverse transcriptase and fragments of any of the above having reverse transcriptase activity.

Reverse transcriptases of the present invention may produce more product (e.g., full length product) at elevated temperatures than other reverse transcriptases. In one aspect, comparisons of full length product synthesis is made at different temperatures (e.g., one temperature being lower, such as between 37° C. and 50° C., and one temperature being higher, such as between 50° C. and 78° C.) while keeping all other reaction conditions similar or the same. The amount of full length product produced may be determined using techniques well known in the art, for example, by conducting a reverse transcription reaction at a first temperature (e.g., 37° C., 38° C., 39° C., 40° C., etc.) and determining the amount of full length transcript produced, conducting a second reverse transcription reaction at a temperature higher than the first temperature (e.g., 45° C., 50° C., 52.5° C., 55° C., etc.) and determining the amount of full length product produced, and comparing the amounts produced at the two temperatures. A convenient form of comparison is to determine the percentage of the amount of full length product at the first temperature that is produced at the second (i.e., elevated) temperature. The reaction conditions used for the two reactions (e.g., salt concentration, buffer concentration, pH, divalent metal ion concentration, nucleoside triphosphate concentration, template concentration, reverse transcriptase concentration, primer concentration, length of time the reaction is conducted, etc.) are preferably the same for both reactions. Suitable reaction conditions include, but are not limited to, a template concentration of from about 1 nM to about 1 μM, from about 100 nM to 1 μM, from about 300 nM to about 750 nM, or from about 400 nM to about 600 nM, and a reverse transcriptase concentration of from about 1 nM to about 1 μM, from about 10 nM to 500 nM, from about 50 nM to about 250 nM, or from about 75 nM to about 125 nM. The ratio of the template concentration to the reverse transcriptase concentration may be from about 100:1 to about 1:1, from about 50:1 to about 1:1, from about 25:1 to about 1:1, from about 10:1 to about 1:1, from about 5:1 to about 1:1, or from about 2.5:1 to 1:1. A reaction may be conducted from about 5 minutes to about 5 hours, from about 10 minutes to about 2.5 hours, from about 30 minutes to about 2 hours, from about 45 minutes to about 1.5 hours, or from about 45 minutes to about 1 hour. A suitable reaction time is about one hour. Other suitable reaction conditions may be determined by those skilled in the art using routine techniques and examples of such conditions are provided below.

When the amount of full length product produced by a reverse transcriptase of the invention at an elevated temperature is compared to the amount of full length product produced by the same reverse transcriptase at a lower temperature, at an elevated temperature, the reverse transcriptases of the invention may produce not less than about 25%, 35%, 45%, 55%, 65%, 75%, 85%, 95%, 100% of the amount of full length product produced at the lower temperature. In some cases, the reverse transcriptases of the invention may produce an amount of full length product at a higher temperature that is greater than the amount of full length product produced by the reverse transcriptase at a lower temperature (e.g., 1% to about 100% greater). In one aspect, reverse transcriptases of the invention produce approximately the same amount (e.g., no more than a 25% difference) of full length product at the lower temperature compared to the amount of full length product made at the higher temperature.

A reverse transcriptase of the present invention may be one that synthesizes an amount of full length product, wherein the amount of full length product synthesized at 50° C. is no less than 10% (e.g., from about 10% to about 95%, from about 10% to about 80%, from about 10% to about 70%, from about 10% to about 60%, from about 10% to about 50%, from about 10% to about 40%, from about 10% to about 30%, or from about 10% to about 20%) of the amount of full length product it synthesizes at 40° C. In some embodiments, a reverse transcriptase of the invention is one wherein the amount of full length product synthesized at 50° C. is no less than 50% (e.g., from about 50% to about 95%, from about 50% to about 80%, from about 50% to about 70%, or from about 50% to about 60%) of the amount of full length product it synthesizes at 40° C. In some embodiments, a reverse transcriptase of the invention is one wherein the amount of full length product synthesized at 50° C. is no less than 75% (e.g., from about 75% to about 95%, from about 75%, to about 90%, from about 75% to about 85%, or from about 75% to about 80%) of the amount of full length product it synthesizes at 40° C. In other embodiments, a reverse transcriptase of the invention is one wherein the amount of full length product synthesized at 50° C. is no less than 85% (e.g., from about 85% to about 95%, or from about 85% to about 90%) of the amount of full length product it synthesizes at 40° C.

A reverse transcriptase of the invention may be one that synthesizes an amount of full length product, wherein the amount of full length product synthesized at 52.5° C. is no less than 10% (e.g., from about 10% to about 30%, from about 10% to about to about 25%, from about 10% to about 20%, from about 10% to about 15%, from about 20% to about 60%, from about 20% to about 40%, from about 20% to about 30%, from about 30% to about 80%, from about 30% to about 60%, from about 30% to about 45%, from about 40% to about 90%, from about 40% to about 80%, from about 40% to about 60%, from about 40% to about 50% from about 50% to about 90%, or from about 50% to about 70%), of the amount of full length product it synthesizes at 40° C. In some embodiments, the amount of full length product synthesized at 52.5° C. is no less than 30% (e.g., from about 30% to about 70%, from about 30% to about 60%, from about 30% to about 50%, or from about 30% to about 40%) of the amount of full length product it synthesizes at 40° C. In some embodiments, the amount of full length product synthesized at 52.5° C. is no less than 50% (e.g., from about 50% to about 70%, from about 50% to about 65%, from about 50% to about 60%, or from about 50% to about 55%), of the amount of full length product it synthesizes at 40° C.

A reverse transcriptase of the invention may be one that synthesizes an amount of full length product, wherein the amount of full length product synthesized at 55° C. is no less than 1% (e.g., from about 1% to about 30%, from about 1% to about 25%, from about 1% to about 20%, from about 1% to about 15%, from about 1% to about 10%, or from about 1% to about 5%) of the amount of full length product it synthesizes at 40° C. In some embodiments, the amount of full length product synthesized at 55° C. is no less than 5% (e.g., from about 5% to about 30%, from about 5% to about to about 25%, from about 5% to about 20%, from about 5% to about 15%, or from about 5% to about 10%) of the amount of full length product it synthesizes at 40° C. In some embodiments, the amount of full length product synthesized at 55° C. is no less than 10% (e.g., from about 10% to about 30%, from about 10% to about to about 25%, from about 10% to about 20%, from about 10% to about 15%, from about 20% to about 60%, from about 20% to about 40%, from about 20% to about 30%, from about 30% to about 80%, from about 30% to about 60%, from about 30% to about 45%, from about 40% to about 90%, from about 40% to about 80%, from about 40% to about 60%, from about 40% to about 50% from about 50% to about 90%, or from about 50% to about 70%) of the amount of full length product it synthesizes at 40° C.

In another aspect, the reverse transcriptases of the invention are capable of producing more nucleic acid product (e.g., cDNA) and, preferably, more full length product, at one or a number of elevated temperatures (typically between 40° C. an 78° C.) compared to the corresponding un-mutated or un-modified reverse transcriptase (e.g., the control reverse transcriptase). Such comparisons are typically made under similar or the same reaction conditions and the amount of product synthesized by the control reverse transcriptase is compared to the amount of product synthesized by the reverse transcriptase of the invention. Preferably, the reverse transcriptases of the invention produce at least about 5%, at least 10%, at least 15%, at least 25%, at least 50%, at least 75%, at least 100%, or at least 200% more product or full length product compared to the corresponding control reverse transcriptase under the same reaction conditions and temperature. The reverse transcriptases of the invention preferably produce from about 10% to about 200%, from about 25% to about 200%, from about 50% to about 200%, from about 75% to about 200%, or from about 100% to about 200% more product or full length product compared to a control reverse transcriptase under the same reaction conditions and incubation temperature. The reverse transcriptases of the invention preferably produce at least 2 times, at least 3 times, at least 4 times, at least 5 times, at least 6 times, at least 7 times, at least 8 times, at least 9 times, at least 10 times, at least 25 times, at least 50 times, at least 75 times, at least 100 times, at least 150 times, at least 200 times, at least 300 times, at least 400 times, at least 500 times, at least 1000 times, at least 5,000 times, or at least 10,000 times more product or full length product compared to a control reverse transcriptase (e.g., the corresponding un-mutated or un-modified reverse transcriptase) under the same reaction conditions and temperature. The reverse transcriptases of the invention preferably produce from 2 to 10,000, 5 to 10,000, 10 to 5,000, 50 to 5,000, 50 to 500, 2 to 500, 5 to 500, 5 to 200, 5 to 100, or 5 to 75 times more product or full length product than a control reverse transcriptase under the same reaction conditions and temperature.

In one aspect, the reverse transcriptases of the invention produce, at 50° C., at least 25% more, preferably at least 50% more and more preferably at least 100% more nucleic acid product or full length product than a control reverse transcriptase (which is preferably the corresponding wild-type reverse transcriptase). In another aspect, at 52.5° C., the reverse transcriptases of the invention produce at least 1.5 times, at least 2 times, at least 2.5 times, at least 3 times, at least 4 times, at least 5 times, at least 6 times, at least 7 times, at least 8 times, at least 9 times, at least 10 times the amount of nucleic acid product or full length product compared to a control reverse transcriptase. In another aspect, at 55° C., the reverse transcriptases of the invention produce at least 2 times, at least 5 times, at least 10 times, at least 15 times, at least 20 times, at least 25 times, at least 50 times, at least 75 times, at least 100 times the amount of nucleic acid product or full length product compared to a control reverse transcriptase. Such comparisons are preferably made under the same reaction conditions and temperature.

Modified or mutated reverse transcriptases of the present invention may have an increased thermostability at elevated temperatures as compared to corresponding un-modified or un-mutated reverse transcriptases. They may show increased thermostability in the presence or absence an RNA template. In some instances, reverse transcriptases of the invention may show an increased thermostability in both the presence and absence of an RNA template. Those skilled in the art will appreciate that reverse transcriptase enzymes are typically more thermostable in the presence of an RNA template. The increase in thermostability may be measured by comparing suitable parameters of the modified or mutated reverse transcriptase of the invention to those of a corresponding un-modified or un-mutated reverse transcriptase. Suitable parameters to compare include, but are not limited to, the amount of product and/or full length product synthesized by the modified or mutated reverse transcriptase at an elevated temperature compared to the amount or product and/or full length product synthesized by the corresponding un-modified or un-mutated reverse transcriptase at the same temperature, and/or the half-life of reverse transcriptase activity at an elevated temperature of a modified or mutated reverse transcriptase at an elevated temperature compared to that of a corresponding un-modified or un-mutated reverse transcriptase.

A modified or mutated reverse transcriptase of the invention may have an increase in thermostability at 50° C. of at least about 1.5 fold (e.g., from about 1.5 fold to about 100 fold, from about 1.5 fold to about 50 fold, from about 1.5 fold to about 25 fold, from about 1.5 fold to about 10 fold) compared, for example, to the corresponding un-mutated or un-modified reverse transcriptase. A reverse transcriptase of the invention may have an increase in thermostability at 50° C. of at least about 10 fold (e.g., from about 10 fold to about 100 fold, from about 10 fold to about 50 fold, from about 10 fold to about 25 fold, or from about 10 fold to about 15 fold) compared, for example, to the corresponding un-mutated or un-modified reverse transcriptase. A reverse transcriptase of the invention may have an increase in thermostability at 50° C. of at least about 25 fold (e.g., from about 25 fold to about 100 fold, from about 25 fold to about 75 fold, from about 25 fold to about 50 fold, or from about 25 fold to about 35 fold) compared to a corresponding un-mutated or un-modified reverse transcriptase.

The present invention also contemplates a modified or mutated thermostable reverse transcriptase, wherein the reverse transcriptase has an increase in thermostability of greater than about 1.5 fold at 52.5° C. (e.g., from about 1.5 fold to about 100 fold, from about 1.5 fold to about 50 fold, from about 1.5 fold to about 25 fold, or from about 1.5 fold to about 10 fold) compared, for example, to the corresponding un-mutated or un-modified reverse transcriptase. A reverse transcriptase of the invention may have an increase in thermostability at 52.5° C. of at least about 10 fold (e.g., from about 10 fold to about 100 fold, from about 10 fold to about 50 fold, from about 10 fold to about 25 fold, or from about 10 fold to about 15 fold) compared, for example, to the corresponding un-mutated or un-modified reverse transcriptase. A reverse transcriptase of the invention may have an increase in thermostability at 52.5° C. of at least about 25 fold (e.g., from about 25 fold to about 100 fold, from about 25 fold to about 75 fold, from about 25 fold to about 50 fold, or from about 25 fold to about 35 fold) compared, for example, to the corresponding un-mutated or un-modified reverse transcriptase.

In other embodiments, the present invention provides a reverse transcriptase, wherein the reverse transcriptase has an increase in thermostability of greater than about 1.5 fold at 55° C. (e.g., from about 1.5 fold to about 100 fold, from about 1.5 fold to about 50 fold, from about 1.5 fold to about 25 fold, or from about 1.5 fold to about 10 fold) compared to a corresponding un-mutated or un-modified reverse transcriptase. In some embodiments, a reverse transcriptase of the invention may have an increase in thermostability at 55° C. of at least about 10 fold (e.g., from about 10 fold to about 100 fold, from about 10 fold to about 50 fold, from about 10 fold to about 25 fold, or from about 10 fold to about 15 fold) compared to a corresponding un-mutated or un-modified reverse transcriptase. In some embodiments, a reverse transcriptase of the invention may have an increase in thermostability at 55° C. of at least about 25 fold (e.g., from about 25 fold to about 100 fold, from about 25 fold to about 75 fold, from about 25 fold to about 50 fold, or from about 25 fold to about 35 fold) compared to a corresponding un-mutated or un-modified reverse transcriptase.

The present invention provides reverse transcriptase enzymes, compositions and kits comprising such enzymes, and methods useful in preparing labeled nucleic acid molecules by reverse transcription. In general, the invention relates to the use of polypeptides of the invention (e.g., reverse transcriptase enzymes having one or more of the mutations identified above) to synthesized labeled nucleic acid molecules. In some embodiments, polypeptides of the invention may be heterodimers and more specifically two subunit enzymes (e.g., dimers) such as HIV RT and ASLV RTs. In some embodiments, polypeptides of the invention may be single sub-unit enzymes (e.g., M-MLV reverse transcriptase). Preferably, such labeling involves the use of modified nucleotides (e.g., labeled nucleotides, particularly fluorescently labeled nucleotides, nucleotide analogs and the like) and one or more nucleic acid templates (preferably RNA and most preferably mRNA). In accordance with the invention, one or more labeled nucleic acid molecules are synthesized which are complementary to all or a portion of the one or more templates. The labeled nucleic acid molecules preferably have one or more labeled nucleotides incorporated into the synthesized molecule and in a preferred aspect, the labels are one or more fluorescent labels (which may be the same or different). In another aspect, nucleotides are used during nucleic acid synthesis using the reverse transcriptases of the invention to produce one or more nucleic acid molecules complementary to all or a portion of one or more templates. In such aspects, such nucleotides, which are incorporated in the synthesized nucleic acid molecules, may be modified (before or after incorporation) to contain one or more labels, which may then be detected.

The invention also relates to compositions for use in the invention and such compositions may comprise one or more polypeptides of the invention (e.g., single sub-unit such as M-MLV RT and/or multi-subunit RTs such as HIV and ASLV RTs). Such compositions may further comprise one or more nucleotides, a suitable buffer, and/or one or more DNA polymerases. The compositions of the invention may also comprise one or more primers. The reverse transcriptases in these compositions preferably have RNase H activity or are reduced or substantially reduced in RNase H activity, and most preferably are enzymes selected from the group consisting of Moloney Murine Leukemia Virus (M-MLV) reverse transcriptase, Rous Sarcoma Virus (RSV) reverse transcriptase, Avian Myeloblastosis Virus (AMV) reverse transcriptase, Rous Associated Virus (RAV) reverse transcriptase, Myeloblastosis Associated Virus (MAV) reverse transcriptase and Human Immunodeficiency Virus (HIV) reverse transcriptase or other ASLV reverse transcriptases. The reverse transcriptases of the invention may be composed of one or more subunits (which may be the same or different). When two subunit RTs are use in the practice of the invention, such enzymes may contain various forms and combinations of such subunits such as αβ, αα, ββ, etc. and mutants, variants or derivatives thereof. In preferred compositions, the reverse transcriptases are present at working concentrations.

The invention is also directed to methods for making one or more nucleic acid molecules and/or labeled nucleic acid molecules, comprising mixing one or more nucleic acid templates (preferably one or more RNA templates and most preferably one or more messenger RNA templates) with one or more polypeptides of the invention having reverse transcriptase activity and incubating the mixture under conditions sufficient to synthesize one or more first nucleic acid molecules complementary to all or a portion of the one or more nucleic acid templates, wherein said at least one of said synthesized molecules are optionally labeled and/or comprise one or more labeled nucleotides and/or wherein said synthesized molecules may optionally be modified to contain one or more labels. In a preferred embodiment, the one or more first nucleic acid molecules are single-stranded cDNA molecules. Nucleic acid templates suitable for reverse transcription according to this aspect of the invention include any nucleic acid molecule or population of nucleic acid molecules (preferably RNA and most preferably mRNA), particularly those derived from a cell or tissue. In a preferred aspect, a population of mRNA molecules (a number of different mRNA molecules, typically obtained from cells or tissue) are used to make a labeled cDNA library, in accordance with the invention. Preferred sources of nucleic acid templates include viruses, virally infected cells, bacterial cells, fungal cells, plant cells and animal cells.

The invention also concerns methods for making one or more double-stranded nucleic acid molecules (which may optionally be labeled). Such methods comprise (a) mixing one or more nucleic acid templates (preferably RNA or mRNA, and more preferably a population of mRNA templates) with one or more polypeptides of the invention having reverse transcriptase activity; (b) incubating the mixture under conditions sufficient to make one or more first nucleic acid molecules complementary to all or a portion of the one or more templates; and (c) incubating the one or more first nucleic acid molecules under conditions sufficient to make one or more second nucleic acid molecules complementary to all or a portion of the one or more first nucleic acid molecules, thereby forming one or more double-stranded nucleic acid molecules comprising the first and second nucleic acid molecules. In accordance with the invention, the first and/or second nucleic acid molecules may be labeled (e.g., may comprise one or more of the same or different labeled nucleotides and/or may be modified to contain one or more of the same or different labels). Thus, labeled nucleotides may be used at one or both synthesis steps. Such methods may include the use of one or more DNA polymerases as part of the process of making the one or more double-stranded nucleic acid molecules. The invention also concerns compositions useful for making such double-stranded nucleic acid molecules. Such compositions comprise one or more reverse transcriptases of the invention and optionally one or more DNA polymerases, a suitable buffer and/or one or more nucleotides (preferably including labeled nucleotides).

The invention is also directed to nucleic acid molecules and/or labeled nucleic acid molecules (particularly single- or double-stranded cDNA molecules) produced according to the above-described methods and to kits comprising these nucleic acid molecules. Such molecules or kits may be used to detect nucleic acid molecules (for example by hybridization) or for diagnostic purposes.

The invention is also directed to kits for use in the methods of the invention. Such kits can be used for making nucleic acid molecules and/or labeled nucleic acid molecules (single- or double-stranded). Kits of the invention may comprise a carrier, such as a box or carton, having in close confinement therein one or more containers, such as vials, tubes, bottles and the like. In kits of the invention, a first container may contain one or more of the reverse transcriptase enzymes of the invention or one or more of the compositions of the invention. Kits of the invention may also comprise, in the same or different containers, at least one component selected from one or more DNA polymerases (preferably thermostable DNA polymerases), a suitable buffer for nucleic acid synthesis and one or more nucleotides. Alternatively, the components of the kit may be divided into separate containers. In one aspect, kits of the invention comprise reverse transcriptases which have RNase H activity or are reduced or substantially reduced in RNase H activity (or lacking or having undetectable RNase H activity). Such RTs preferably are selected from the group consisting of M-MLV reverse transcriptase, RSV reverse transcriptase, AMV reverse transcriptase, RAV reverse transcriptase, MAV reverse transcriptase and HIV reverse transcriptase. In additional preferred kits of the invention, the enzymes (e.g. reverse transcriptases and/or DNA polymerases) in the containers are present at working concentrations.

In specific embodiments, reverse transcriptases of the invention may not include M-MLV reverse transcriptases, HIV reverse transcriptases, AMV reverse transcriptases, and/or RSV reverse transcriptases. Thus, for example, in certain embodiments, the invention is directed to reverse transcriptases with increased thermostability that are not a HIV reverse transcriptase. In other embodiments, the invention is directed to reverse transcriptases with increased thermostability that are not a M-MLV reverse transcriptase. In yet other embodiments, the invention is directed to reverse transcriptases with increased thermostability that are not an AMV reverse transcriptase. In still other embodiments, the invention is directed to reverse transcriptases with increased thermostability that are not a RSV reverse transcriptase.

The present invention is also directed to nucleic acid molecules (e.g., vectors) containing a gene or nucleic acid molecules encoding the mutant or modified reverse transcriptases of the present invention (or fragments thereof including fragments having polymerase activity) and to host cells containing such DNA or other nucleic acid molecules. Any number of hosts may be used to express the gene or nucleic acid molecule of interest, including prokaryotic and eukaryotic cells. In specific embodiments, prokaryotic cells are used to express the reverse transcriptases of the invention. One example of a prokaryotic host suitable for use with the present invention is *Escherichia coli*. Examples of eukaryotic hosts suitable for use with the present invention include fungal cells (e.g., *Saccharomyces cerevisiae cells, Pichia pastoris* cells, etc.), plant cells, and animal cells (e.g.; *Drosophila melanogaster* cells, *Spodoptera frugiperda* Sf9 and Sf21 cells, *Trichoplusa* High-Five cells, *C. elegans cells, Xenopus laevis* cells, CHO cells, COS cells, VERO cells, BHK cells, etc.). Preferably, polypeptides of the invention may be purified and/or isolated from a cell or organism expressing them, which may be a wild type cell or organism or a recombinant cell or organism. In some embodiments, such polypeptides may be substantially isolated from the cell or organism in which they are expressed.

The invention also relates to a method of producing reverse transcriptases of the invention, said method comprising:

(a) culturing a host cell comprising a gene or other nucleic acid molecule encoding a reverse transcriptase of the invention (preferably such reverse transcriptase gene or other nucleic acid molecule is contained by a vector within the host cell);

(b) expressing the gene or nucleic acid molecule; and (c) isolating or purifying said reverse transcriptase.

The invention is also directed to methods for making one or more (e.g., one, two, three, four, five, ten, twelve, fifteen, etc.) nucleic acid molecules, comprising mixing one or more (e.g., one, two, three, four, five, ten, twelve, fifteen, etc.) nucleic acid templates (preferably one or more RNA templates and most preferably one or more messenger RNA templates or a population of messenger RNA templates) with one or more (e.g., one, two, three, four, five, ten, fifteen, etc.) reverse transcriptases of the invention and incubating the mixture under conditions sufficient to make a first nucleic acid molecule or molecules complementary to all or a portion of the one or more nucleic acid templates. In some embodiments, the mixture is incubated at an elevated temperature, i.e., greater than 37° C. In specific embodiments, the elevated temperature may be from about 40° C. or greater, from about 45° C. or greater, from about 50° C. or greater, from about 51° C. or greater, from about 52° C. or greater, from about 53° C. or greater, from about 54° C. or greater, from about 55° C. or greater, from about 56° C. or greater, from about 57° C. or greater, from about 58° C. or greater, from about 59° C. or greater, from about 60° C. or greater, from about 61° C. or greater, from about 62° C. or greater, from about 63° C. or greater, from about 64° C. or greater, from about 65° C. or greater, from about 66° C. or greater, from about 67° C. or greater, from about 68° C. or greater, from about 69° C. or greater, from about 70° C. or greater, from about 71° C. or greater, from about 72° C. or greater, from about 73° C. or greater, from about 74° C. or greater, from about 75° C. or greater, from about 76° C. or greater, from about 77° C. or greater, or from about 78° C. or greater. An elevated temperature may be within a temperature range of from about 40° C. to about 45° C., from about 40° C. to about 48° C., from about 40° C. to about 50° C., from about 40° C. to about 52° C., from about 40° C. to about 55° C., from about 40° C. to about 58° C., from about 40° C. to about 60° C., from about 40° C. to about 65° C., from about 42° C. to about 45° C., from about 42° C. to about 48° C., from about 42° C. to about 50° C., from about 42° C. to about 52° C., from about 42° C. to about 55° C., from about 42° C. to about 58° C., from about 42° C. to about 60° C., from about 42° C. to about 65° C., from about 45° C. to about 48° C., from about 45° C. to about 50° C., from about 45° C. to about 52° C., from about 45° C. to about 55° C., from about 45° C. to about 58° C., from about 45° C. to about 60° C., from about 45° C. to about 65° C., from about 48° C. to about 50° C., from about 48° C. to about 52° C., from about 48° C. to about 55° C., from about 48° C. to about 58° C., from about 48° C. to about 60° C., from about 48° C. to about 65° C., from about 50° C. to about 52° C., from about 50° C. to about 55° C., from about 50° C. to about 58° C., from about 50° C. to about 60° C., from about 50° C. to about 65° C., from about 52° C. to about 55° C., from about 52° C. to about 58° C., from about 52° C. to about 60° C., from about 52° C. to about 65° C., from about 55° C. to about 58° C., from about 55° C. to about 60° C., from about 55° C. to about 65° C., from about 55° C. to about 70° C., from about 58° C. to about 60° C., from about 58° C. to about 65° C., from about 58° C. to about 70° C. An elevated temperature may be within a temperature range from about 37° C. to about 75° C., from about 40° C. to about 75° C., from about 45° C. to about 75° C., from about 50° C. to about 75° C., from about 51° C. to about 75° C., from about 52° C. to about 75° C., from about 53° C. to about 75° C., from about 54° C. to about 75° C., from about 55° C. to about 75° C. In other embodiments, the elevated temperature may be within the range of about 50° C. to about 70° C., from about 51° C. to about 70° C., from about 52° C. to about 70° C., from about 53° C. to about 70° C., from about 54° C. to about 70° C., from about 55° C. to about 70° C., from about 56° C. to about 65° C., from about 56° C. to about 64° C. or about 56° C. to about 62° C. In other embodiments, the elevated temperature may be within the range of about 46° C. to about 60° C., from about 47° C. to about 60° C., from about 49° C. to about 60° C., from about 51° C. to about 60° C., from about 53° C. to about 60° C., or from about 54° C. to about 60° C. In additional specific embodiments, the first nucleic acid molecule is a single-stranded cDNA. The invention further includes nucleic acid molecules prepared by the above methods and reaction mixtures used in and formed by such methods. Such conditions for incubation may include the use of one or more buffers or buffering salts, one or more primers (such as oligo dT primers) and/or one or more nucleotides (e.g.; one or more nucleoside triphosphates). The invention also concerns compositions for making one or more nucleic acid molecules comprising one or more components selected from the group consisting of one or more reverse transcriptases of the invention, one or more primers, one or more nucleotides and one or more suitable buffers.

Nucleic acid templates suitable for reverse transcription according to this aspect of the invention include any nucleic acid molecule or population of nucleic acid molecules (preferably RNA and most preferably mRNA), particularly those derived from a cell or tissue. In a specific aspect, a population of mRNA molecules (a number of different mRNA molecules, typically obtained from a particular cell or tissue type) is used to make a cDNA library, in accordance with the invention. Examples of cellular sources of nucleic acid templates include bacterial cells, fungal cells, plant cells and animal cells.

The invention also concerns methods for making one or more (e.g., one, two, three, four, five, ten, twelve, fifteen, etc.) double-stranded nucleic acid molecules. Such methods comprise (a) mixing one or more nucleic acid templates (preferably RNA or mRNA, and more preferably a population of mRNA templates) with one or more (e.g., one, two, three, four, five, ten, fifteen, etc.) reverse transcriptases of the invention; (b) incubating the mixture under conditions sufficient to make a first nucleic acid molecule or molecules complementary to all or a portion of the one or more templates; and (c) incubating the first nucleic acid molecule or molecules under conditions sufficient to make a second nucleic acid molecule or molecules complementary to all or a portion of the first nucleic acid molecule or molecules, thereby forming one or more double-stranded nucleic acid molecules comprising the first and second nucleic acid molecules. In some embodiments, the incubation of step (b) is performed at an elevated temperature. In some embodiments, conditions may comprise the use of one or more labeled nucleotides and the double stranded nucleic acid molecules may be labeled. In specific embodiments, the elevated temperature may be from about 40° C. or greater, from about 45° C. or greater, from about 50° C. or greater, from about 51° C. or greater, from about 52° C. or greater, from about 53° C. or greater, from about 54° C. or greater, from about 55° C. or greater, from about 56° C. or greater, from about 57° C. or greater, from about 58° C. or greater, from about 59° C. or greater, from about 60° C. or greater, from about 61° C. or greater, from about 62° C. or greater, from about 63° C. or greater, from about 64° C. or greater, from about 65° C. or greater, from about 66° C. or greater, from about 67° C. or greater, from about 68° C. or greater, from about 69° C. or greater, from about 70° C. or greater, from about 71° C. or greater, from about 72° C. or greater, from about 73° C. or greater, from about 74° C. or greater, from about 75° C. or greater, from about 76° C. or greater, from about 77° C. or greater, or from about 78° C. or greater. An elevated temperature may be within a temperature range of from about 40° C. to about 45° C., from about 40° C. to about 48° C., from about 40° C. to about 50° C., from about 40° C. to about 52° C., from about 40° C. to about 55° C., from about 40° C. to about 58° C., from about 40° C. to about 60° C., from about 40° C. to about 65° C., from about 42° C. to about 45° C., from about 42° C. to about 48° C., from about 42° C. to about 50° C., from about 42° C. to about 52° C., from about 42° C. to about 55° C., from about 42° C. to about 58° C., from about 42° C. to about 60° C., from about 42° C. to about 65° C., from about 45° C. to about 48° C., from about 45° C. to about 50° C., from about 45° C. to about 52° C., from about 45° C. to about 55° C., from about 45° C. to about 58° C., from about 45° C. to about 60° C., from about 45° C. to about 65° C., from about 48° C. to about 50° C., from about 48° C. to about 52° C., from about 48° C. to about 55° C., from about 48° C. to about 58° C., from about 48° C. to about 60° C., from about 48° C. to about 65° C., from about 50° C. to about 52° C., from about 50° C. to about 55° C., from about 50° C. to about 58° C., from about 50° C. to about 60° C., from about 50° C. to about 65° C., from about 52° C. to about 55° C., from about 52° C. to about 58° C., from about 52° C. to about 60° C., from about 52° C. to about 65° C., from about 55° C. to about 58° C., from about 55° C. to about 60° C., from about 55° C. to about 65° C., from about 55° C. to about 70° C., from about 58° C. to about 60° C., from about 58° C. to about 65° C., from about 58° C. to about 70° C. An elevated temperature may be within a temperature range from about 37° C. to about 75° C., from about 40° C. to about 75° C., from about 45° C. to about 75° C., from about 50° C. to about 75° C., from about 51° C. to about 75° C., from about 52° C. to about 75° C., from about 53° C. to about 75° C., from about 54° C. to about 75° C., from about 55° C. to about 75° C. In other embodiments, the elevated temperature may be within the range of about 50° C. to about 70° C., from about 51° C. to about 70° C., from about 52° C. to about 70° C., from about 53° C. to about 70° C., from about 54° C. to about 70° C., from about 55° C. to about 70° C., from about 56° C. to about 65° C., from about 56° C. to about 64° C. or about 56° C. to about 62° C. In other embodiments, the elevated temperature may be within the range of about 46° C. to about 60° C., from about 47° C. to about 60° C., from about 49° C. to about 60° C., from about 51° C. to about 60° C., from about 53° C. to about 60° C., or from about 54° C. to about 60° C. Such conditions may involve the use of one or more suitable buffers or buffer salts, on or more primers (such as oligo dT primers), and one or more nucleotides. Such methods may include the use of one or more (e.g., one, two, three, four, five, ten, twelve, fifteen, etc.) DNA polymerases as part of the process of making the one or more double-stranded nucleic acid molecules. Such DNA polymerases are preferably thermostable DNA polymerases and most preferably the nucleic acid synthesis accomplished with such DNA polymerases is conducted at elevated temperatures, i.e., greater than 37° C. The invention also concerns compositions useful for making such double-stranded nucleic acid molecules. Such compositions comprise one or more (e.g., one, two, three, four, five, ten, twelve, fifteen, twenty, etc.) reverse transcriptases of the invention and optionally one or more DNA polymerases, a suitable buffer, one or more (e.g., one, two, three, four, five, ten, twelve, fifteen, etc.) primers, and/or one or more (e.g., one, two, three, four, five, etc.) nucleotides. The invention further includes nucleic acid molecules prepared by the above methods and reaction mixtures used in and formed by such methods.

The invention also relates to methods for amplifying a nucleic acid molecule. Such amplification methods comprise mixing the double-stranded nucleic acid molecule or molecules produced as described above with one or more (e.g., one, two, three, four, five, ten, twelve, fifteen, etc.) DNA polymerases (preferably thermostable DNA polymerases) and incubating the mixture under conditions sufficient to amplify the double-stranded nucleic acid molecule. In a first embodiment, the invention concerns a method for amplifying a nucleic acid molecule, the method comprising (a) mixing one or more (e.g., one, two, three, four, five, ten, twelve, fifteen, twenty, etc.) nucleic acid templates (preferably one or more RNA or mRNA templates and more preferably a population of mRNA templates) with one or more reverse transcriptases of the invention and with one or more DNA polymerases and (b) incubating the mixture under conditions sufficient to amplify nucleic acid molecules complementary to all or a portion of the one or more templates. In some embodiments, the incubation of step (b) is performed at an elevated temperature. In specific embodiments, the elevated temperature may be from about 40° C. or greater, from about 45° C. or greater, from about 50° C. or greater, from about 51° C. or greater, from about 52° C. or greater, from about 53° C. or greater, from about 54° C. or greater, from about 55° C. or greater, from about 56° C. or greater, from about 57° C. or greater, from about 58° C. or greater, from about 59° C. or greater, from about 60° C. or greater, from about 61° C. or greater, from about 62° C. or greater, from about 63° C. or greater, from about 64° C. or greater, from about 65° C. or greater, from about 66° C. or greater, from about 67° C. or greater, from about 68° C. or greater, from about 69° C. or greater, from about 70° C. or greater, from about 71° C. or greater, from about 72° C. or greater, from about 73° C. or greater, from about 74° C. or greater, from about 75° C. or greater, from about 76° C. or greater, from about 77° C. or greater, or from about 78° C. or greater. An elevated temperature may be within a temperature range of from about 40° C. to about 45° C., from about 40° C. to about 48° C., from about 40° C. to about 50° C., from about 40° C. to about 52° C., from about 40° C. to about 55° C., from about 40° C. to about 58° C., from about 40° C. to about 60° C., from about 40° C. to about 65° C., from about 42° C. to about 45° C., from about 42° C. to about 48° C., from about 42° C. to about 50° C., from about 42° C. to about 52° C., from about 42° C. to about 55° C., from about 42° C. to about 58° C., from about 42° C. to about 60° C., from about 42° C. to about 65° C., from about 45° C. to about 48° C., from about 45° C. to about 50° C., from about 45° C. to about 52° C., from about 45° C. to about 55° C., from about 45° C. to about 58° C., from about 45° C. to about 60° C., from about 45° C. to about 65° C., from about 48° C. to about 50° C., from about 48° C. to about 52° C., from about 48° C. to about 55° C., from about 48° C. to about 58° C., from about 48° C. to about 60° C., from about 48° C. to about 65° C., from about 50° C. to about 52° C., from about 50° C. to about 55° C., from about 50° C. to about 58° C., from about 50° C. to about 60° C., from about 50° C. to about 65° C., from about 52° C. to about 55° C., from about 52° C. to about 58° C., from about 52° C. to about 60° C., from about 52° C. to about 65° C., from about 55° C. to about 58° C., from about 55° C. to about 60° C., from about 55° C. to about 65° C., from about 55° C. to about 70° C., from about 58° C. to about 60° C., from about 58° C. to about 65° C., from about 58° C. to about 70° C. An elevated temperature may be within a temperature range from about 37° C. to about 75° C., from about 40° C. to about 75° C., from about 45° C. to about 75° C., from about 50° C. to about 75° C., from about 51° C. to about 75° C., from about 52° C. to about 75° C., from about 53° C. to about 75° C., from about 54° C. to about 75° C., from about 55° C. to about 75° C. In other embodiments, the elevated temperature may be within the range of about 50° C. to about 70° C., from about 51° C. to about 70° C., from about 52° C. to about 70° C., from about 53° C. to about 70° C., from about 54° C. to about 70° C., from about 55° C. to about 70° C., from about 56° C. to about 65° C., from about 56° C. to about 64° C. or about 56° C. to about 62° C. In other embodiments, the elevated temperature may be within the range of about 46° C. to about 60° C., from about 47° C. to about 60° C., from about 49° C. to about 60° C., from about 51° C. to about 60° C., from about 53° C. to about 60° C., or from about 54° C. to about 60° C.

Preferably, reverse transcriptases of the invention, used in methods of the invention, and/or present in compositions of the invention (1) are reduced or substantially reduced in RNase H activity, (2) are reduced or substantially reduced in TdT activity, and/or (3) exhibit increased fidelity. Preferably, DNA polymerases used with the invention may comprise a first DNA polymerase having 3' exonuclease activity and a second DNA polymerase having substantially reduced 3' exonuclease activity. The invention further includes nucleic acid molecules prepared by the above methods and reaction mixtures used in and formed by such methods.

The invention also concerns compositions comprising one or more reverse transcriptases of the invention and one or more DNA polymerases for use in amplification reactions. Such compositions may further comprise one or more nucleotides and/or a buffer suitable for amplification. Compositions of the invention may also comprise one or more oligonucleotide primers. Compositions of the invention may further include nucleic acid molecules prepared by the above methods and reaction mixtures used in and formed by such methods.

The invention is also directed to nucleic acid molecules (particularly single- or double-stranded cDNA molecules) or amplified nucleic acid molecules produced according to the above-described methods and to vectors (particularly expression vectors) comprising these nucleic acid molecules or amplified nucleic acid molecules.

The invention is further directed to recombinant host cells comprising the above-described nucleic acid molecules, amplified nucleic acid molecules or vectors. Examples of such host cells include bacterial cells, yeast cells, plant cells and animal cells (including insect cells and mammalian cells).

The invention is additionally directed to methods of producing polypeptides encoded by the nucleic acid molecules produced by the methods of the invention. Such methods include those comprising culturing the above-described recombinant host cells and isolating the encoded polypeptides. The invention further includes polypeptides produced by such methods.

The invention also concerns methods for sequencing one or more (e.g., one, two, three, four, five, ten, twelve, fifteen, etc.) nucleic acid molecules using compositions or enzymes of the invention. Such methods comprise (a) mixing one or more nucleic acid molecules (e.g., one or more RNA or DNA molecules) to be sequenced with one or more reverse transcriptases of the invention, and, optionally, one or more nucleotides, one or more terminating agents, such as one or more dideoxynucleoside triphosphates, and one or more primers; (b) incubating the mixture under conditions sufficient to synthesize a population of nucleic acid molecules complementary to all or a portion of the one or more (e.g., one, two, three, four, five, ten, twelve, fifteen, twenty, thirty, fifty, one hundred, two hundred, etc.) nucleic acid molecules to be sequenced; and (c) separating the population of nucleic acid molecules to determine the nucleotide sequence of all or a portion of the one or more nucleic acid molecules to be sequenced. Such methods may also comprise (a) mixing a nucleic acid molecule (e.g., one or more RNA or DNA molecules) to be sequenced with one or more primers, one or more reverse transcriptases of the invention, one or more nucleotides and one or more terminating agents, such as one or more dideoxynucleoside triphosphates; (b) incubating the mixture under conditions sufficient to synthesize a population of nucleic acid molecules complementary to all or a portion of the nucleic acid molecule to be sequenced; and (c) separating members of the population of nucleic acid molecules to determine the nucleotide sequence of all or a portion of the nucleic acid molecule to be sequenced. In some embodiments, such incubation may be performed at elevated temperatures as described herein. The invention further includes sequence data generated by the above methods, as well as methods for generating such sequence data, and reaction mixtures used in and formed by such methods.

The invention is also directed to kits for use in methods of the invention. Such kits can be used for making, sequencing or amplifying nucleic acid molecules (single- or double-stranded), preferably at the elevated temperatures described herein. Kits of the invention may comprise a carrier, such as a box or carton, having in close confinement therein one or more (e.g., one, two, three, four, five, ten, twelve, fifteen, etc.) containers, such as vials, tubes, bottles and the like. In kits of the invention, a first container contains one or more of the reverse transcriptase enzymes of the present invention. Kits of the invention may also comprise, in the same or different containers, one or more DNA polymerases (preferably thermostable DNA polymerases), one or more (e.g., one, two, three, four, five, ten, twelve, fifteen, etc.) suitable buffers for nucleic acid synthesis, one or more nucleotides and one or more (e.g., one, two, three, four, five, ten, twelve, fifteen, etc.) oligonucleotide primers. Alternatively, the components of the kit may be divided into separate containers (e.g., one container for each enzyme and/or component). Kits of the invention also may comprise instructions or protocols for carrying out the methods of the invention. In preferred kits of the invention, the reverse transcriptases are reduced or substantially reduced in RNase H activity (or lacking or having undetectable RNase H activity), and are most preferably selected from the group consisting of M-MLV RNase H− reverse transcriptase, RSV RNase H− reverse transcriptase, AMV RNase H− reverse transcriptase, RAV RNase H− reverse transcriptase, MAV RNase H− reverse transcriptase and HIV RNase H− reverse transcriptase. In other preferred kits of the invention, the reverse transcriptases are reduced or substantially reduced in TdT activity, and/or exhibit increased fidelity, as described elsewhere herein.

In additional preferred kits of the invention, the enzymes (reverse transcriptases and/or DNA polymerases) in the containers are present at working concentrations.

Thus, the invention is further directed to kits for use in reverse transcription, amplification or sequencing of a nucleic acid molecule, the kit comprising one or more reverse transcriptases of the invention.

As indicated above, kits of the invention may contain any number of various components for practicing methods of the invention. One example of such a component is instructions for performing methods of the invention. Example of such instructions include those which direct individuals using the kits to perform methods for amplifying nucleic acid molecules using one or more reverse transcriptases of the invention.

As one skilled in the art would recognize, the full text of these instructions need not be included with the kit. One example of a situation in which kits of the invention would not contain such full length instructions is where directions are provided which inform individuals using the kits where to obtain instructions for using the kit. Thus, instructions for performing methods of the invention may be obtain from internet web pages, separately sold or distributed manuals or other product literature, etc. The invention thus includes kits which direct kit users to locations where they can find instructions which are not directly packaged and/or distributed with the kits. These instructions may be in any form including, but not limited to, electronic or printed forms.

The invention thus also provides, in part, kits for performing methods using the reverse transcriptases of the invention. In specific embodiments, kits of the invention contain instructions for performing methods for amplifying and/or sequencing nucleic acid molecules. These methods will often involve reacting RNA molecules with one or more reverse transcriptases of the invention.

In specific embodiments, reverse transcriptases of kits of the invention may comprise one or more modifications or mutations at positions corresponding to amino acids selected from the group consisting of:

(a) leucine 52 of M-MLV reverse transcriptase;

(b) tyrosine 64 of M-MLV reverse transcriptase;

(c) lysine 152 of M-MLV reverse transcriptase;

(d) arginine 204 of M-MLV reverse transcriptase;

(e) methionine 289 of M-MLV reverse transcriptase;

(f) threonine 306 of M-MLV reverse transcriptase; and (g) phenylalanine 309 of M-MLV reverse transcriptase.

Reverse transcriptases of the invention include any reverse transcriptase having one or a combination of the properties described herein. Such properties include, but are not limited to, enhanced thermostability, reduced or eliminated RNase H activity, reduced terminal deoxynucleotidyl transferase activity, and/or increased fidelity. Such reverse transcriptases include retroviral reverse transcriptases, bacterial reverse transcriptases, retrotransposon reverse transcriptases (e.g., reverse transcriptases of the Ty1 and/or Ty3 retrotransposons), and DNA polymerases having reverse transcriptase activity. Preferred reverse transcriptases of the invention include a single and multi-subunit reverse transcriptase and preferably retroviral reverse transcriptases. In particular, the invention relates to M-MLV-reverse transcriptases and ASLV-reverse transcriptases (such as AMV-RT and RSV-RT). Such reverse transcriptases of the invention preferably have reduced, substantially reduced, or no detectable RNase H activity.

Other embodiments of the present invention will be apparent to one of ordinary skill in light of the following drawings and description of the invention, and of the claims.

BRIEF DESCRIPTION OF THE DRAWINGS/FIGURES

Figure 3:
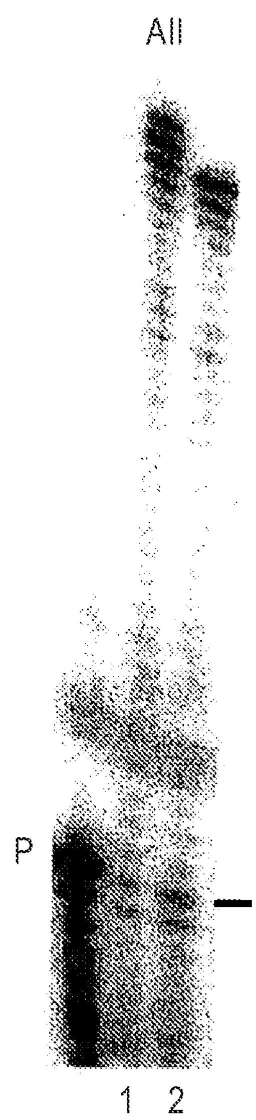

FIG. 3 represents a scanned phosphoimage of an extension assay using (1) SuperScript™ II reverse transcriptase, and (2) F309N. The [$^{32}$P]-labeled 18-mer primer annealed to a 47-mer DNA template (5 nM) was extended by equal units of reverse transcriptase at 37° C. for 30 minutes as seen in the extension reactions with all 4 nucleotides. The extension reactions were analyzed by denaturing 6% gel electrophoresis. P, non-extended primer.

Figure 4:
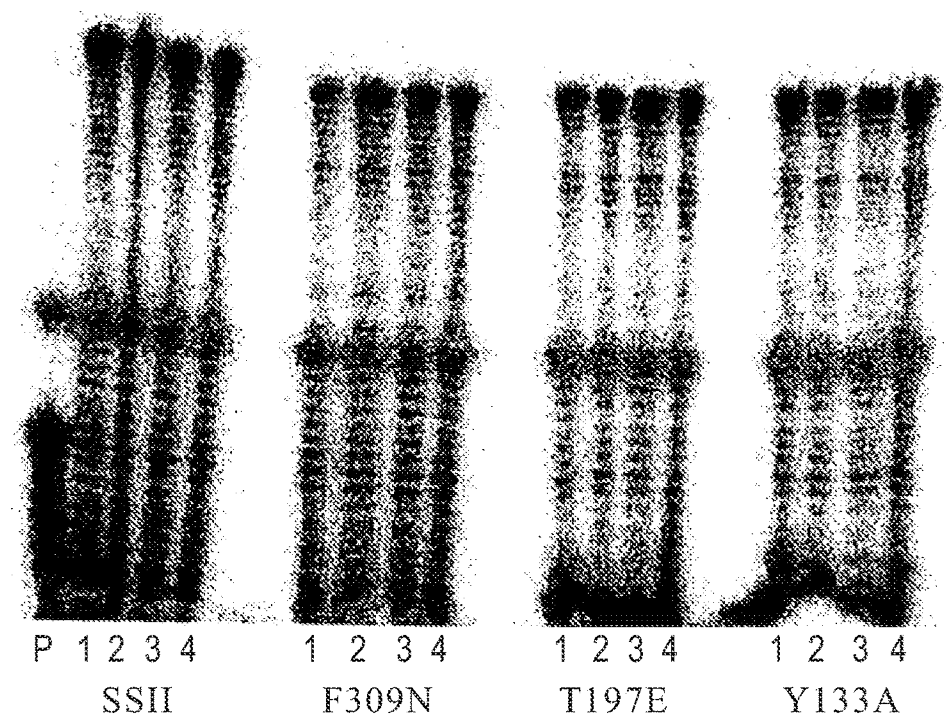

FIG. 4 represents a scanned phosphoimage showing a TdT extension assay of SuperScript™ II reverse transcriptase and the mutants F309N, T197E, and Y133A. The [$^{32}$P]-labeled 18-mer primer annealed to a 47-mer DNA template (5 nM) was extended with decreasing units of reverse transcriptase (lane (1) 646 units, lane (2) 200 units, lane (3) 50 units, and lane (4) 20 units) at 37° C. for 30 minutes with all four nucleotides (see the Methods section below in Example 3). The extension reactions were analyzed by denaturing 6% gel electrophoresis. In this assay, extension past the 47 nucleotide templates is considered non-template directed addition or TdT activity. P, non-extended primer.

Figure 5:
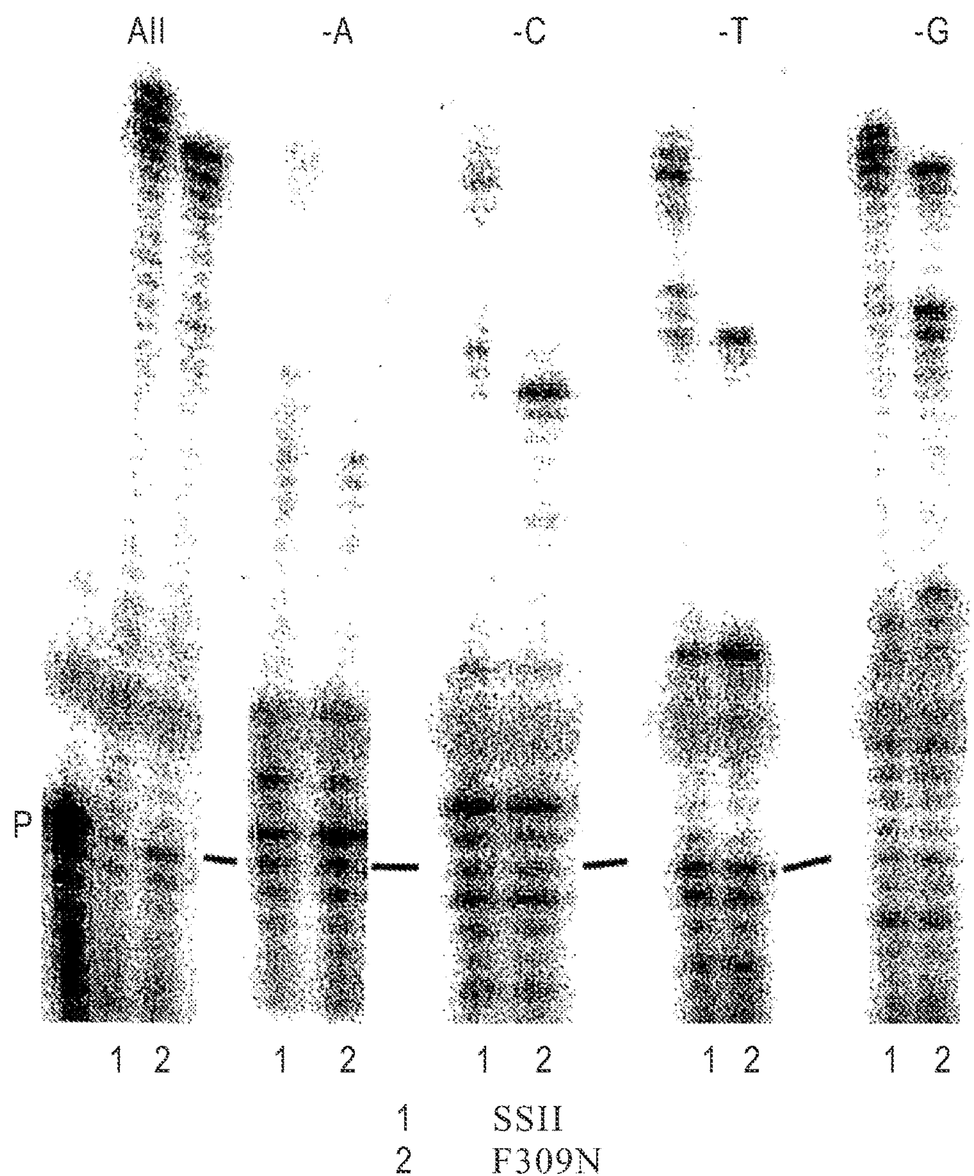

FIG. 5 represents a scanned phosphoimage showing misinsertion assays of SuperScript™ II reverse transcriptase (1) and mutant protein F309N reverse transcriptase (2) with DNA template. The [$^{32}$P]-labeled 18-mer primer annealed to a 47-mer DNA template (5 nM) was extended by equal units of reverse transcriptase protein at 37° C. for 30 min. as seen in the extension reactions with all four nucleotides. The extension reactions were also performed in the presence of only 3 complementary dNTPs; minus dCTP, minus dATP, minus TTP, and minus dGTP. The extension reactions were analyzed by denaturing 6% gel electrophoresis. In this assay, the higher efficiency of elongation of terminated primer with only three nucleotides will reflect the lower fidelity of the SuperScript™ II reverse transcriptase assayed. P, non-extended primer.

Figure 6:
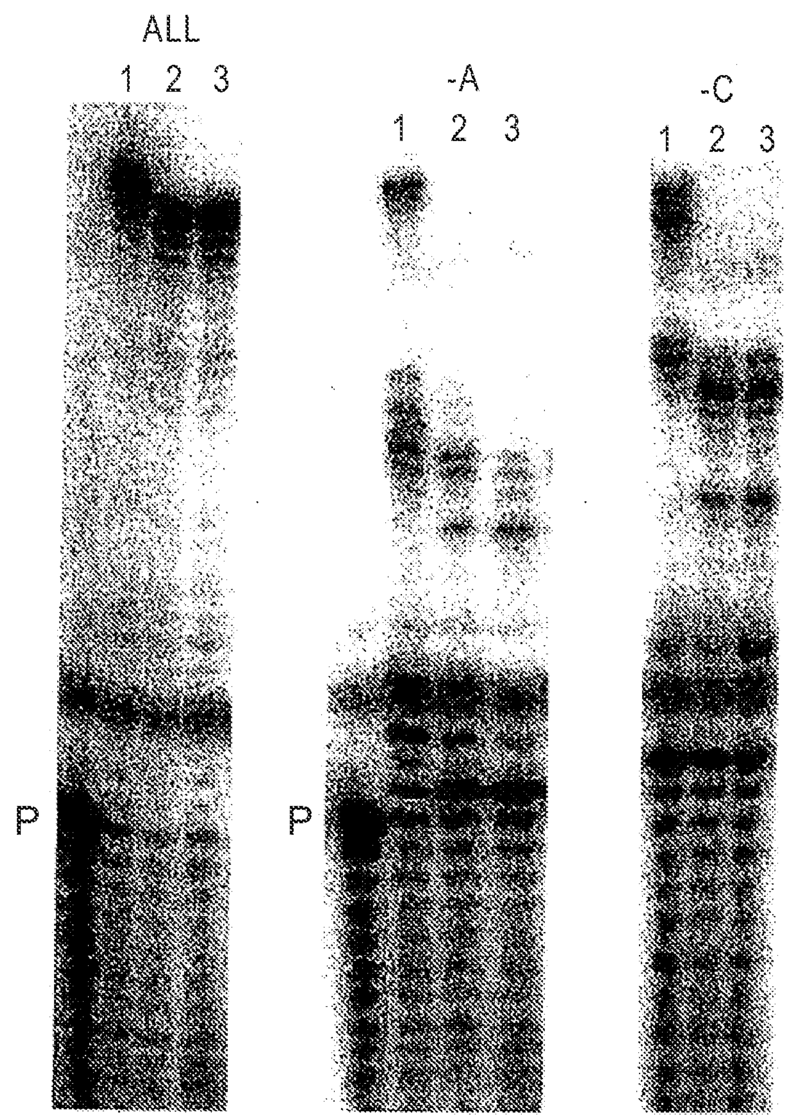

FIG. 6 represents a scanned phosphoimage showing a misinsertion assay of SuperScript™ II reverse transcriptase (1) and mutant protein T197A/F309N reverse transcriptase (2) and V223H/F309N (3) with DNA template. The [$^{32}$P]-labeled 18-mer primer annealed to a 47-mer DNA template (5 nM) was extended by equal units of reverse transcriptase protein at 37° C. for 30 min. as seen in the extension reactions with all four nucleotides. The extension reactions were also performed in the presence of only 3 complementary dNTPs; minus dATP, and minus dCTP. The extension reactions were analyzed by denaturing 6% gel electrophoresis. In this assay, the higher efficiency of elongation of terminated primer with only three nucleotides will reflect the lower fidelity of the SuperScript™ II reverse transcriptase assayed. P, non-extended primer.

Figure 7A:
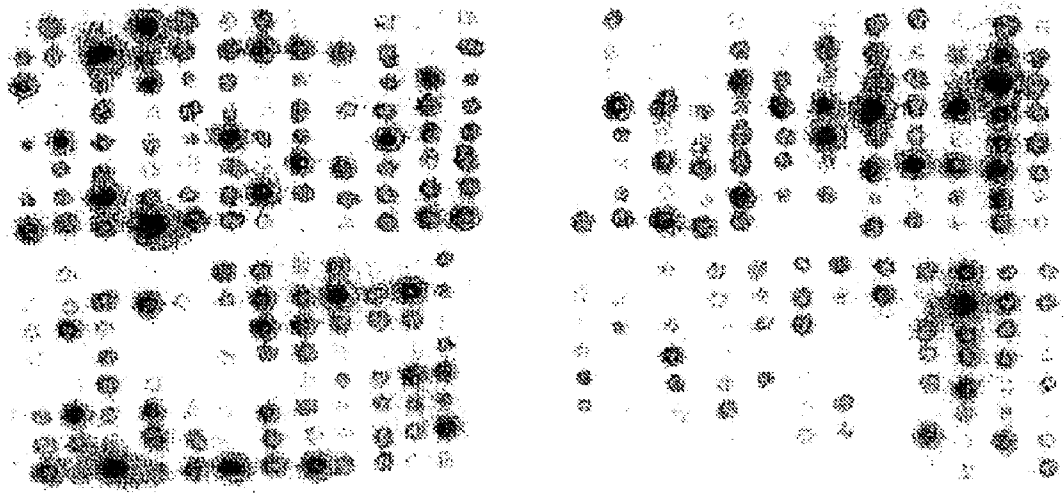
Figure 7B:
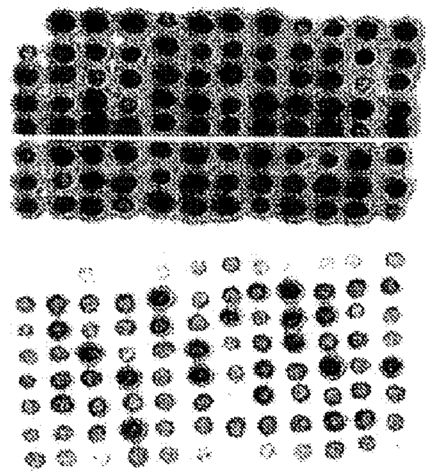
Figure 7C:
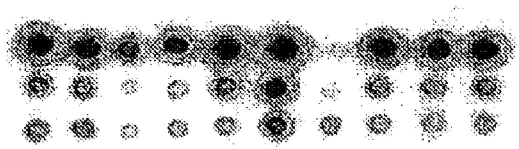

FIGS. 7A-7C show representative results obtained from the screen for thermal stable RT mutants. Lysates of mutants were assayed for RT activity in a 96-well plate format. $^{32}$P-Labeled DNA product was trapped on a membrane and the amount of radioactivity present was quantified with a phosphorimager. FIG. 7A shows the results of an initial screen of RT mutants in 4, 96-well plates. Heat pretreatment of lysates was at 58° C. for 10 min. RT mutants that retained the most activity after heat treatment at 58° C. were selected and lysates were screened again and the results are shown in 7B. A duplicate screen was performed with no heat pretreatment (FIG. 7B upper panel) and heat pretreatment at 58° C. (FIG. 7B lower panel). RT mutants with the highest resistance to heat inactivation in crude extracts were purified by nickel-affinity chromatography and screened again for RT activity and the results are shown in FIG. 7C. The results after heat treatment at 37° C. are shown in FIG. 7C in the upper row, after heat treatment at 53° C. in FIG. 7C middle row, and after heat treatment at 58° C. in 7C bottom row.

Figure 8:
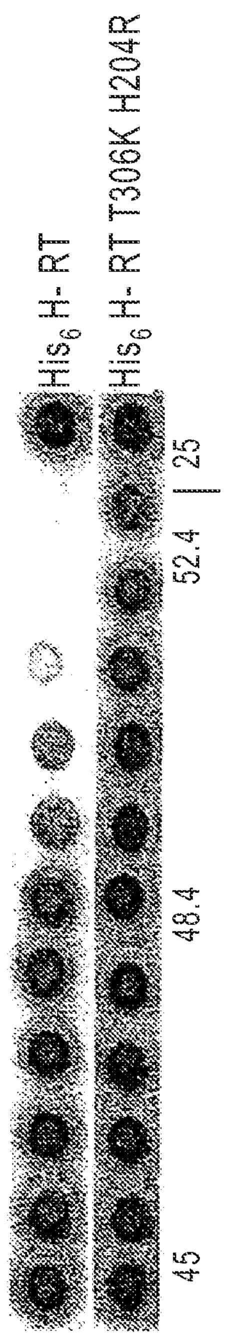

FIG. 8 shows a comparison of the thermal inactivation profiles of $His_6$ H– RT and $His_6$ H– H204R T306K RT in crude extracts. Crude extracts were subjected to a heat treatment in a 96-well plate for 5 min. The temperature of the heat treatment increased from left to right, except that the wells on the far right were not heat treated.

Figure 9:
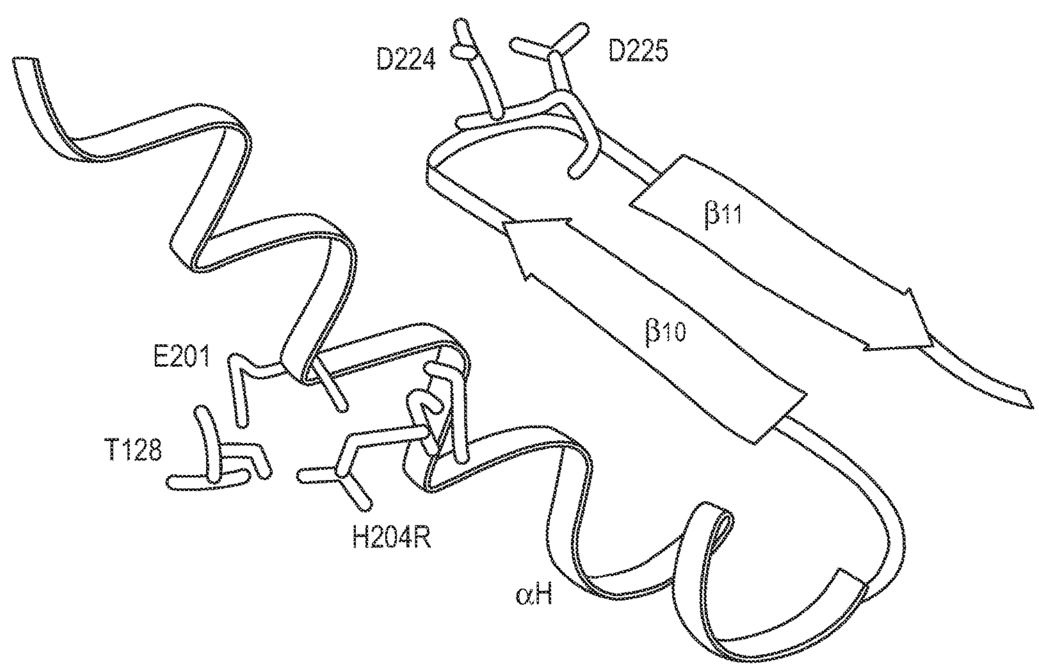

FIG. 9 is a ribbon diagram of the crystal structure of amino acids 193 to 232 of M-MLV RT showing the sites of some of the amino acids identified by the methods of the present invention. Potential interactions of arginine substituted for histidine at M-MLV RT position 204 in α-helix H with E201 or T128. The catalytic site amino acids D224 and D225 in the turn between β10 and β11 are also shown. The three-dimensional structure is taken from Georgiadis, et al., (1995) *Structure* 3, 879-892. Thus, the invention also includes reverse transcriptases having one or more mutations or modifications in various regions including the α-helix H region.

Figure 10A:
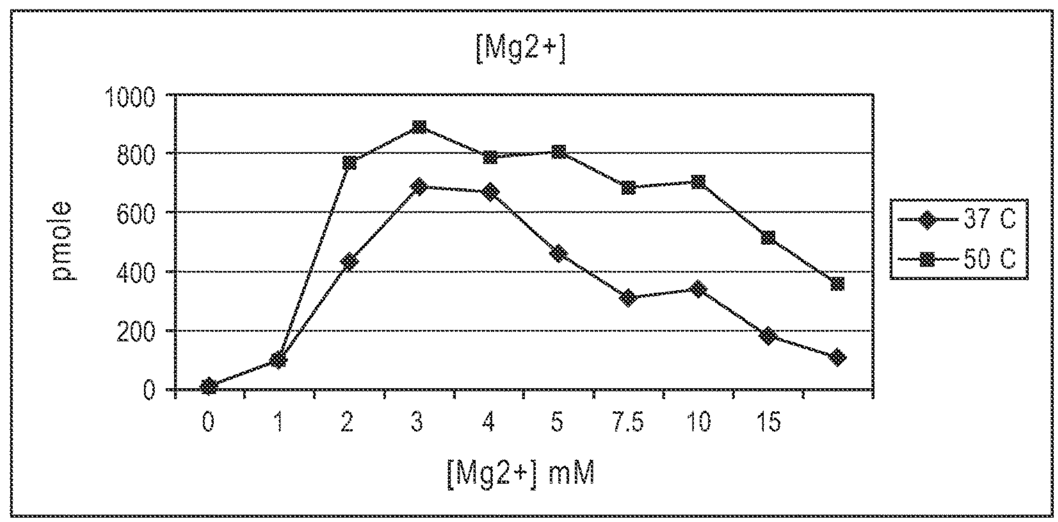
Figure 10B:
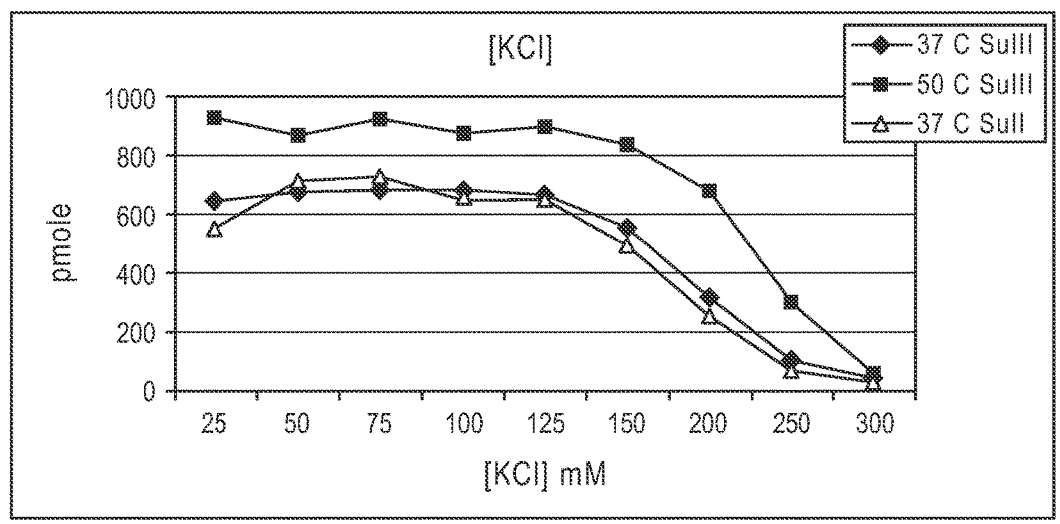

FIGS. 10A and 10B are graphs of reverse transcriptase activity as a function of $Mg^{2+}$ concentration (FIG. 10A) and KCl concentration (FIG. 10B). The DNA polymerase assay for SuperScript™ III (SuIII) RT was conducted at 37° C. or 50° C. for 10 minutes under various concentrations of A) $Mg^{2+}$ or B) KCl. SuperScript™ II (SuII) at 37° C. included for comparison).

Figure 11A:
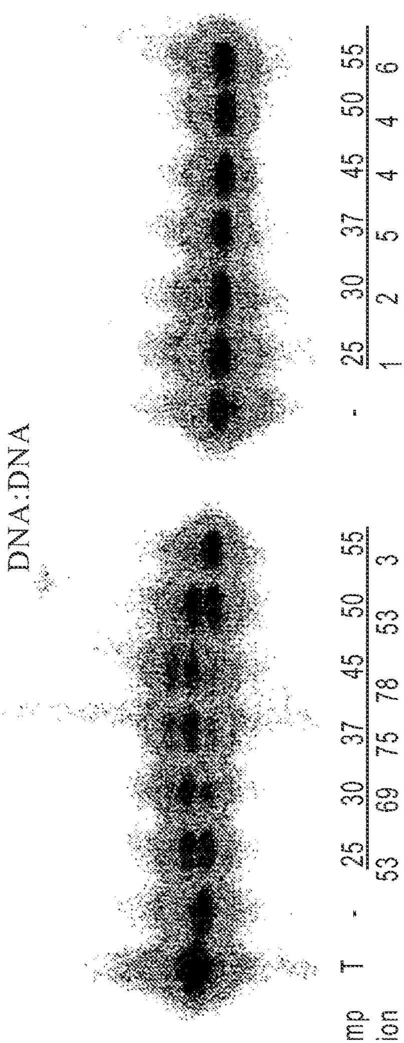
Figure 11B:
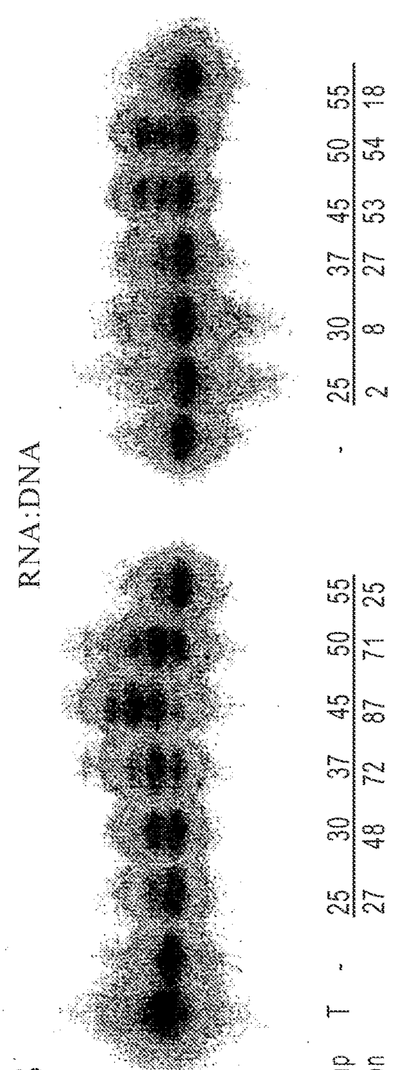

FIGS. 11A and 11B show autoradiograms of TdT activity measure by extension for 60 minutes at various temperatures of a labeled DNA primer on DNA (FIG. 11A) or RNA (FIG. 11B) template forming a blunt end. T is template only, Lanes marked (–) is T-P plus enzyme without dNTPs. Since SuperScript™ III is more thermostable, its TdT activity appears greater at 50 degrees than SuperScript™ II.

Figure 12A:
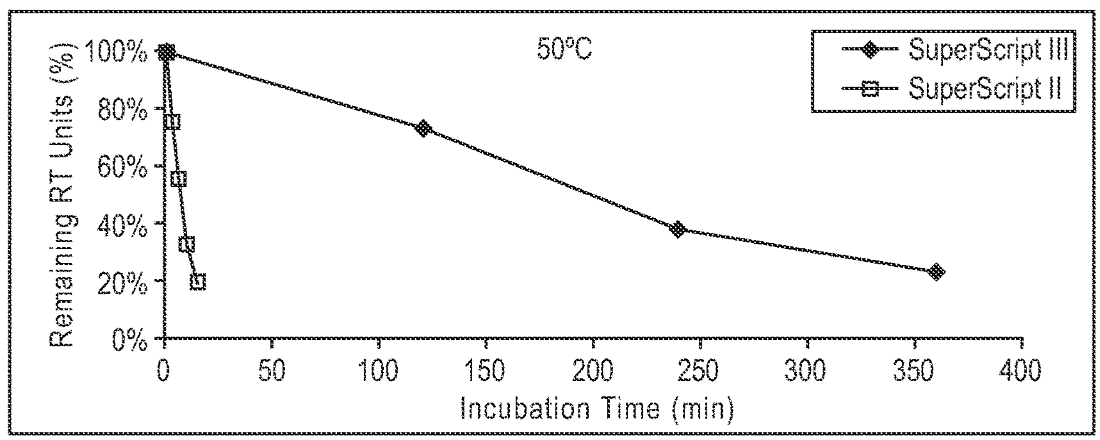
Figure 12B:
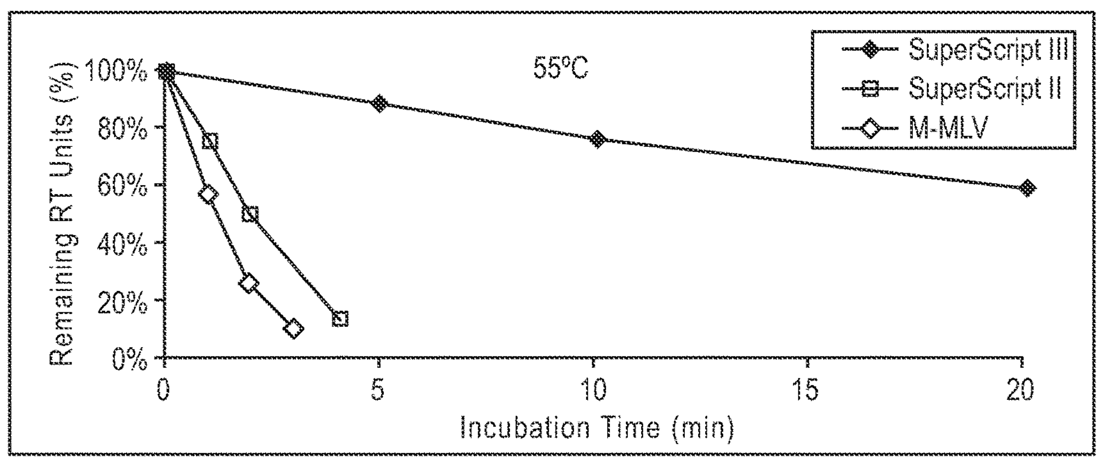
Figure 12C:
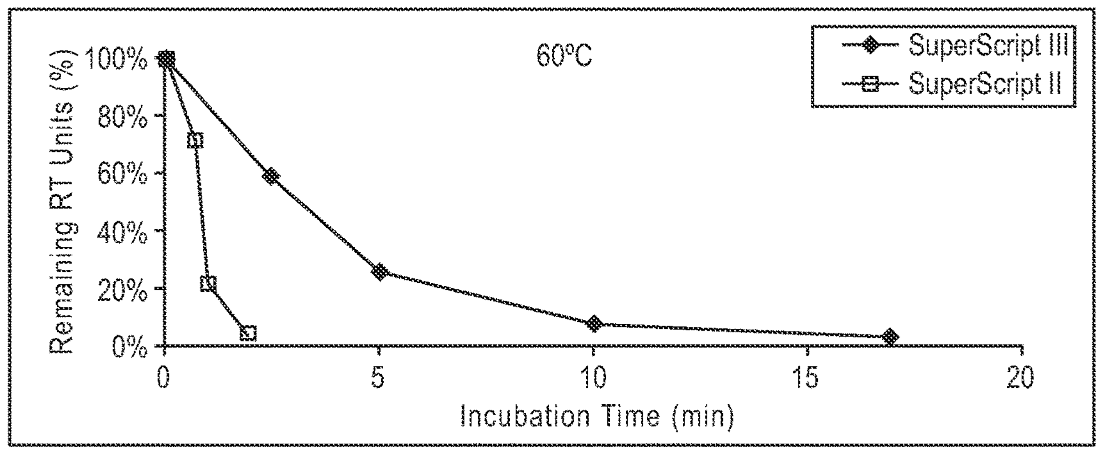

FIGS. 12A, 12B and 12C are graphs of RT activity as a function of incubation time. FIG. 12A shows the data obtained at 50° C., FIG. 12B shows the data obtained at 55° C., and FIG. 12C shows the data obtained at 60° C.

Figure 13:
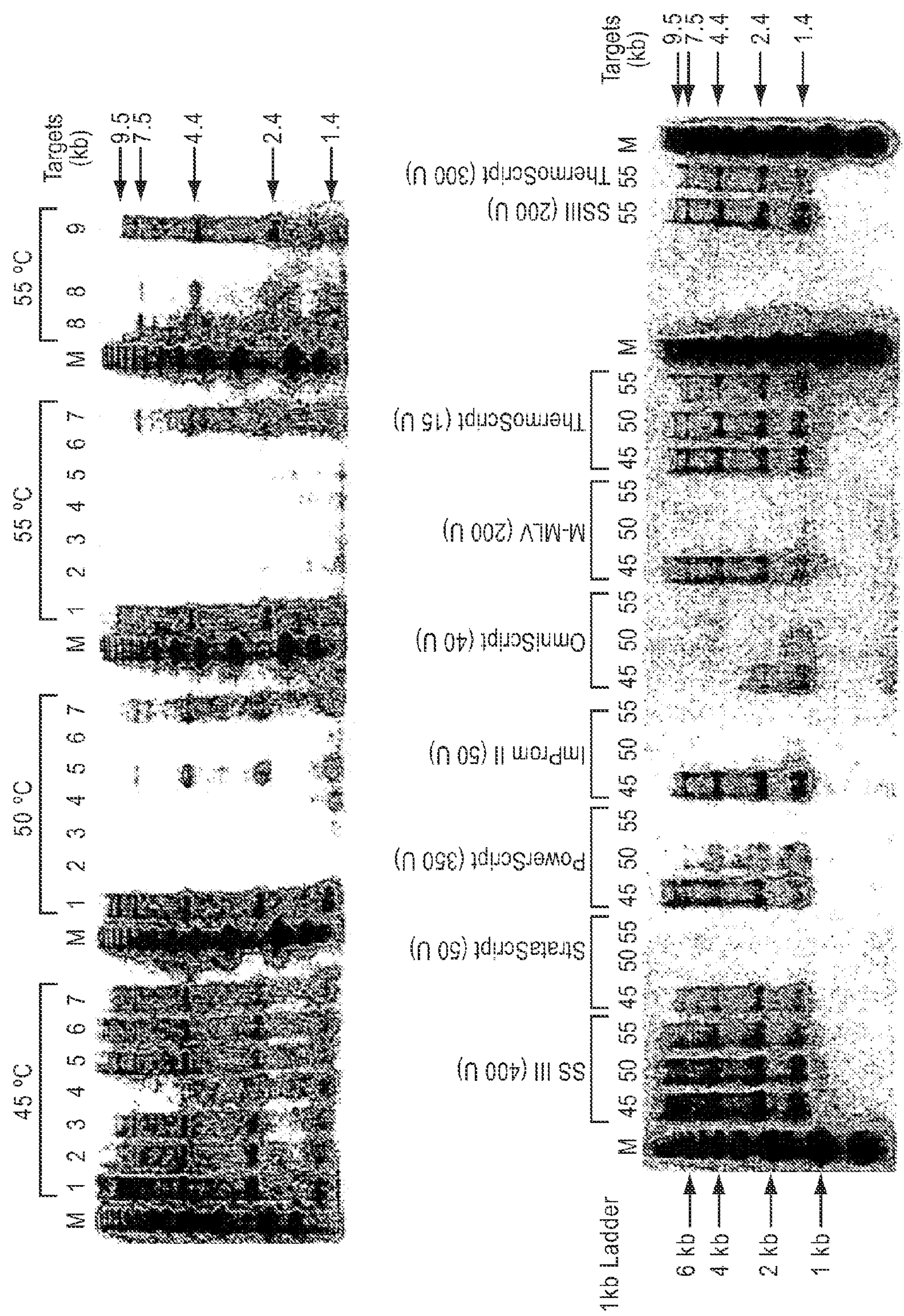

FIG. 13 is an autoradiogram comparing reverse transcriptase activity of a variety of commercially available reverse transcriptase enzymes at 45° C., 50° C., and 55° C. SuperScript™ III is designated SS III and SuperScript™ II is designated SS II.

Figure 14:
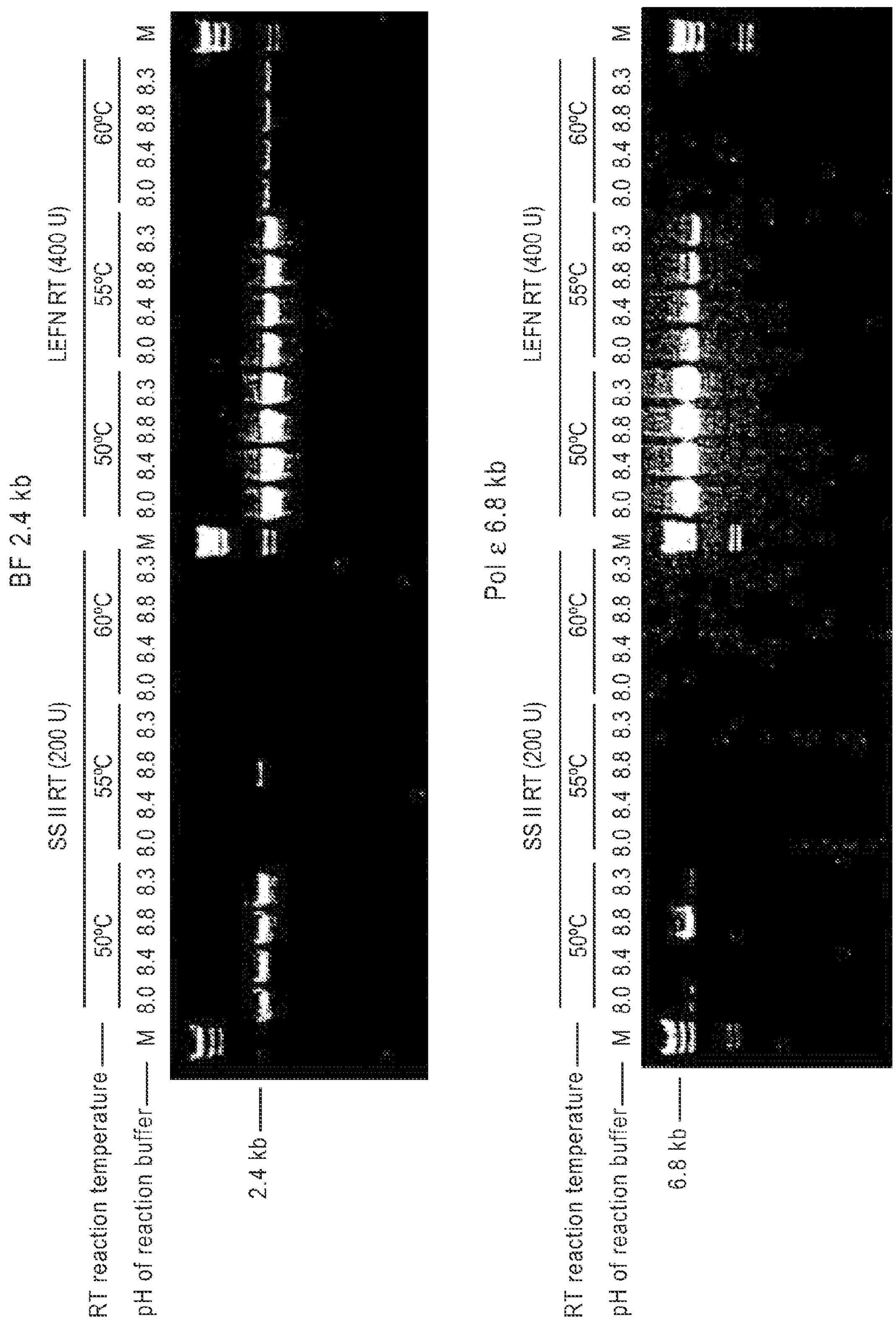

FIG. 14 is a photograph of ethidium bromide stained gels showing the results of the evaluation of the pH of the first strand buffer. RT reactions with first-strand buffers at pHs from 8.0 to 8.8 were performed with 500 ng of total Hela RNA and 200 units of SuperScript™ II (SS II) or 400 units of SuperScript™ III (LEFN RT, which contains an N-terminal tag sequence=MASGTGGQQMGRDLYDDDDKH (SEQ ID NO:3) and the following point mutations H204R, T306K, M289L, and F309N). 2 μl of the resulting cDNA were then added to 50 μl PCR reactions containing the BF 2.4 kb or Pol ϵ 6.8 kb primer set. Resulting PCR products were then run on a 0.8% agarose gel containing 0.4 mg/ml ethidium bromide.

Figure 15:
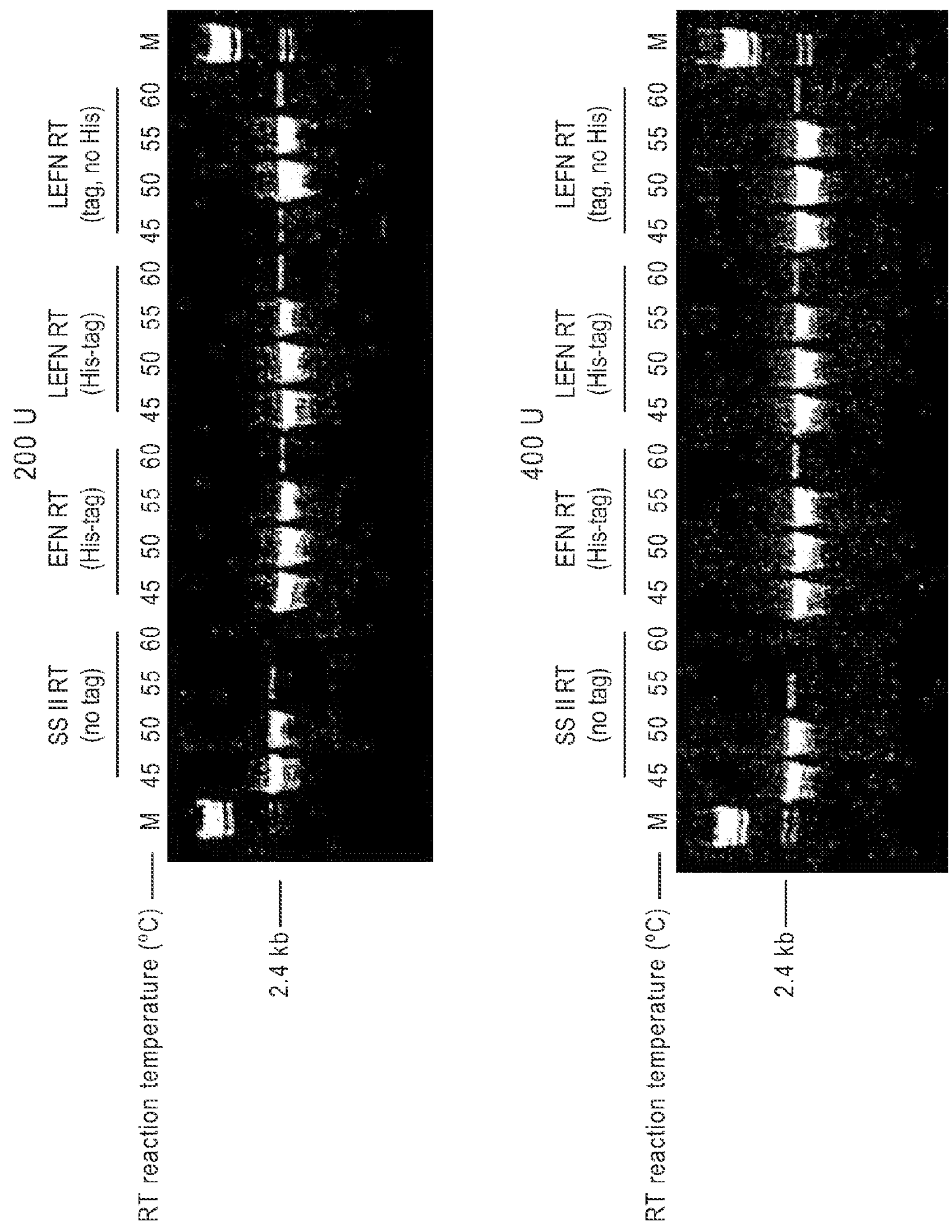

FIG. 15 is a photograph of ethidium bromide stained gels showing the results of the evaluation of the effect of temperature on the reverse transcription reaction with various reverse transcriptases. SuperScript™ II (SS II) was compared to the His-tagged EFN reverse transcriptase (His tag sequence=MGGSHHHHHHGMASMTGGQQMGRDL-YDDDDKH, amino acids 1-32 of SEQ ID NO:2 and Table 3, EFN mutations are H204R, T306K, and F309N), His-tagged LEFN reverse transcriptase (same His tag sequence, LEFN mutations are H204R, T306K, M289L, and F309N), and to SuperScript™ III, which is the tagged, no His LEFN reverse transcriptase (tag sequence=MASGTGGQQMGRDLYDDDDKH (SEQ ID NO:3), LEFN mutations are H204R, T306K, M289L, and F309N).

Figure 16:
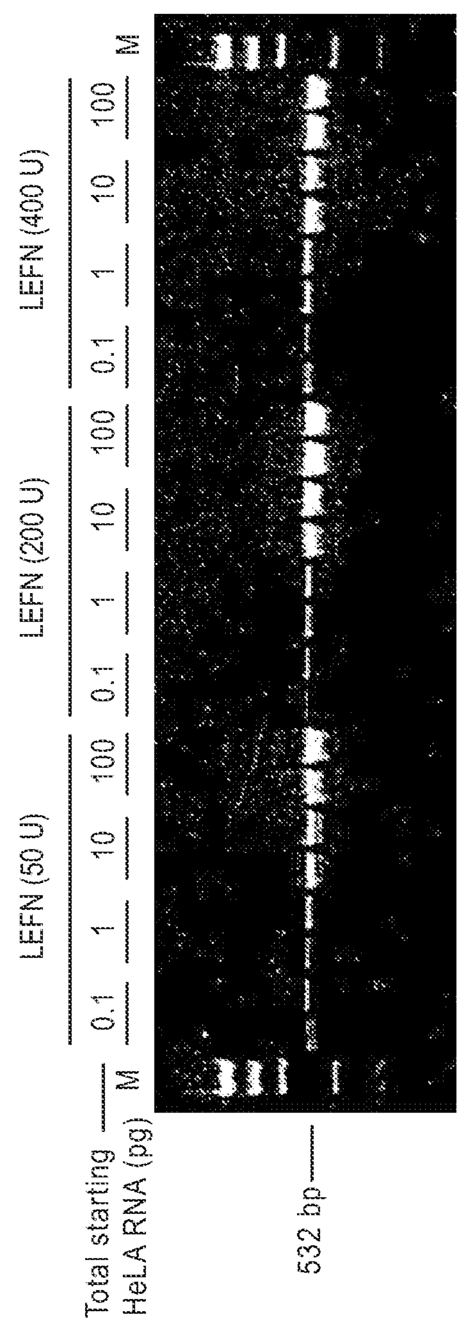

FIG. 16 is a photograph of ethidium bromide stained gels showing the results of the evaluation of the effect of reverse transcriptase concentration on the reverse transcription reaction with SuperScript™ III designated LEFN which contains the tag sequence=MASGTGGQQMGRDLYDDDDKH (SEQ ID NO:1), and LEFN mutations, which are H204R, T306K, M289L, and F309N.

Figure 17:
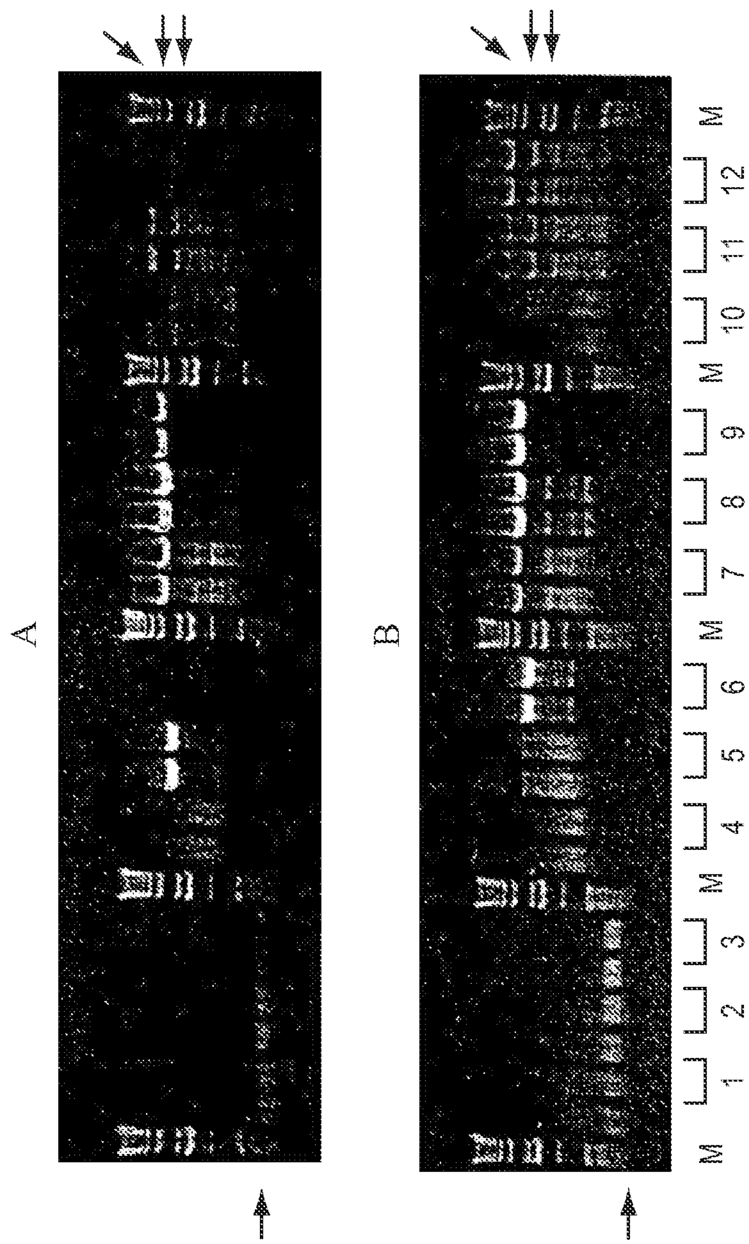

FIG. 17 is a photograph of ethidium bromide stained gels showing the results of the comparison of hot start RT-PCR amplification by SuperScript™ II (Panel A) or SuperScript™ III (Panel B). Lanes (in duplicate) 1, 4, 7, and 10 are products reverse transcribed at 42° C. Lanes 2, 5, 8, and 11 are products reverse transcribed at 50° C. Lanes 3, 6, 9, and 12 are products transcribed at 55° C. Lanes 1-3 are the result of RNAs reverse transcribed by gene-specific priming from FGF, lanes 4-6 CBS 2.4, lanes 7-9 from TOP 3.2, lanes 10-12 VIN 4.6. Arrows indicate expected product sizes of 240 bp, 2390 bp, 3162 bp, and 4641 bp. SuperScript™ III contains the tag sequence=MASGTGGQQMGRDLYDDDDKH (SEQ ID NO:3), and the LEFN mutations, which are H204R, T306K, M289L, and F309N.

Figure 18:
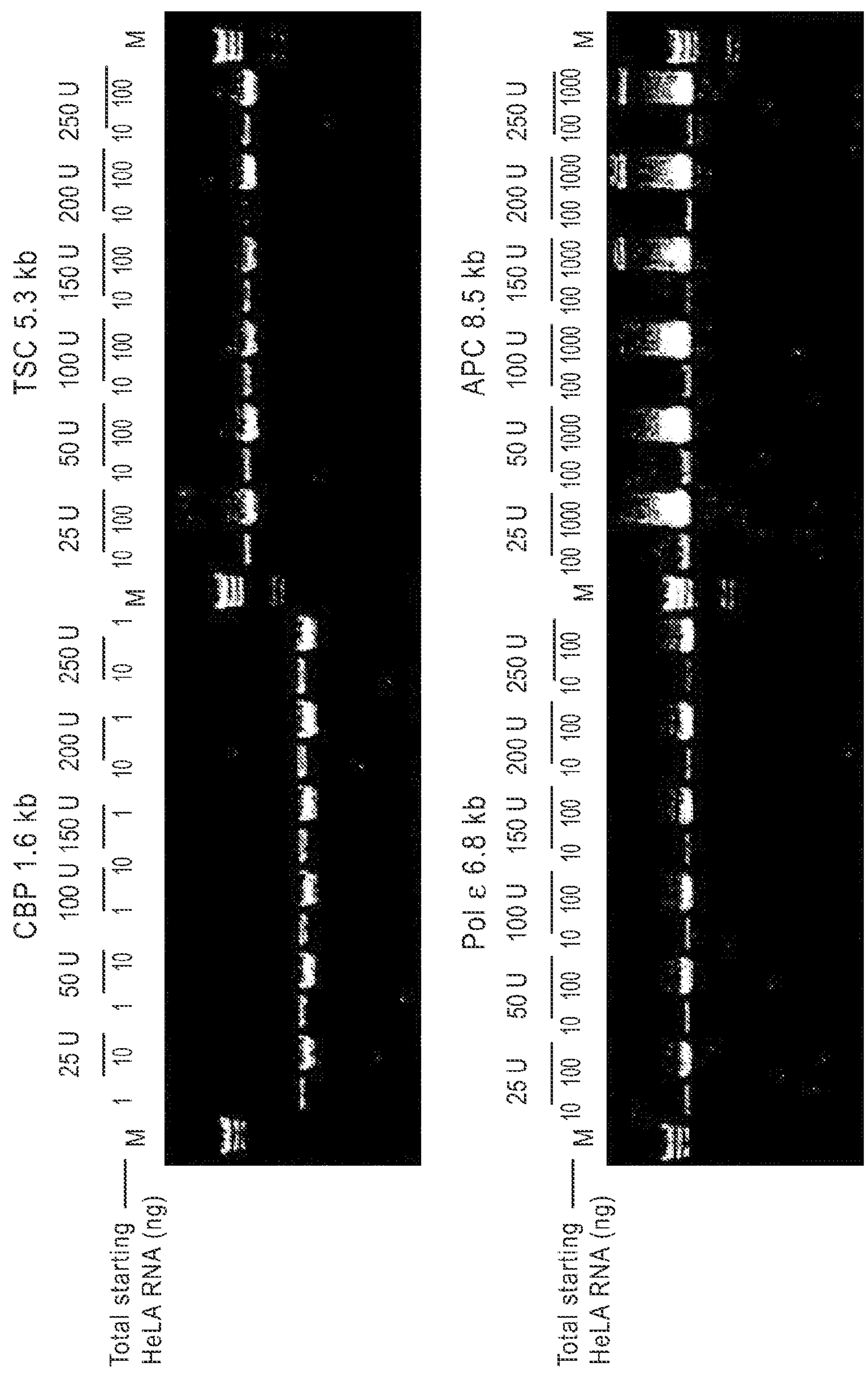

FIG. 18 shows the results of RT-PCR performed with varying amounts SuperScript™ III from 25 units to 250 units per reaction with a variety of primer sets.

Figure 19:
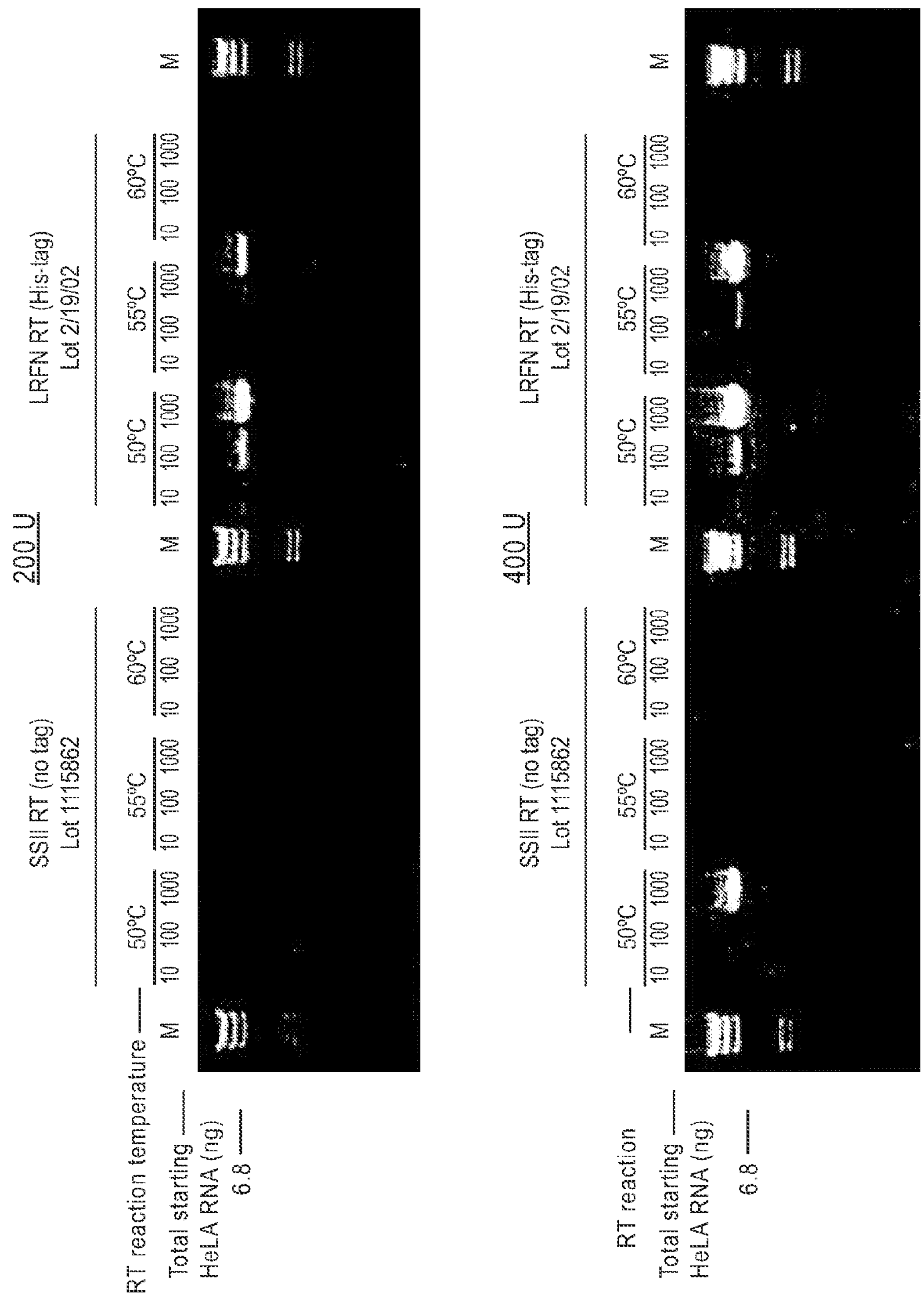

FIG. 19 shows a comparison of SuperScript™ II (SS II) and His tagged LEFN RT in RT-PCR using 200 or 400 units in the first strand reaction. His tagged LEFN has the His tag sequence=MGGSHHHHHHGMASMTGGQQMGR-DLYDDDDKH, amino acids 1-32 of SEQ ID NO:2 and Table 3, and the LEFN mutations, which are H204R, T306K, M289L, and F309N).

Figure 20:
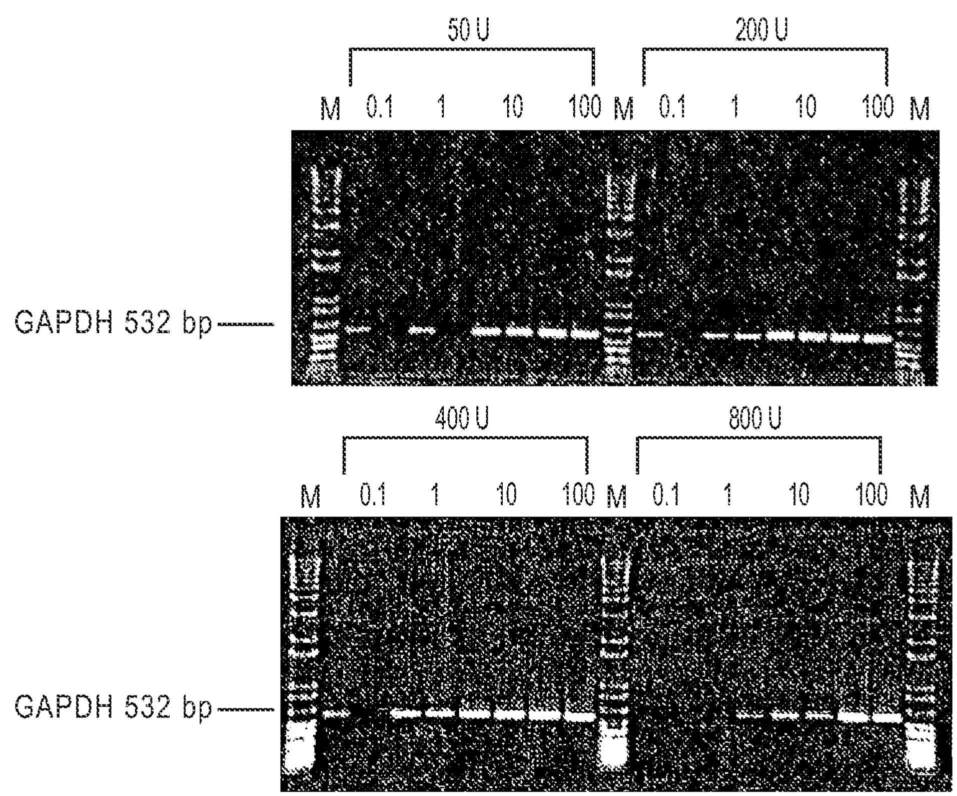

FIG. 20 shows the use of SuperScript™ III (LEFN RT) in RT-PCR with varying amounts of RT in the first strand reaction. SuperScript™ III contains the tag sequence=MASGTGGQQMGRDLYDDDDKH (SEQ ID NO:3), and the LEFN mutations, which are H204R, T306K, M289L, and F309N.

Figure 21:
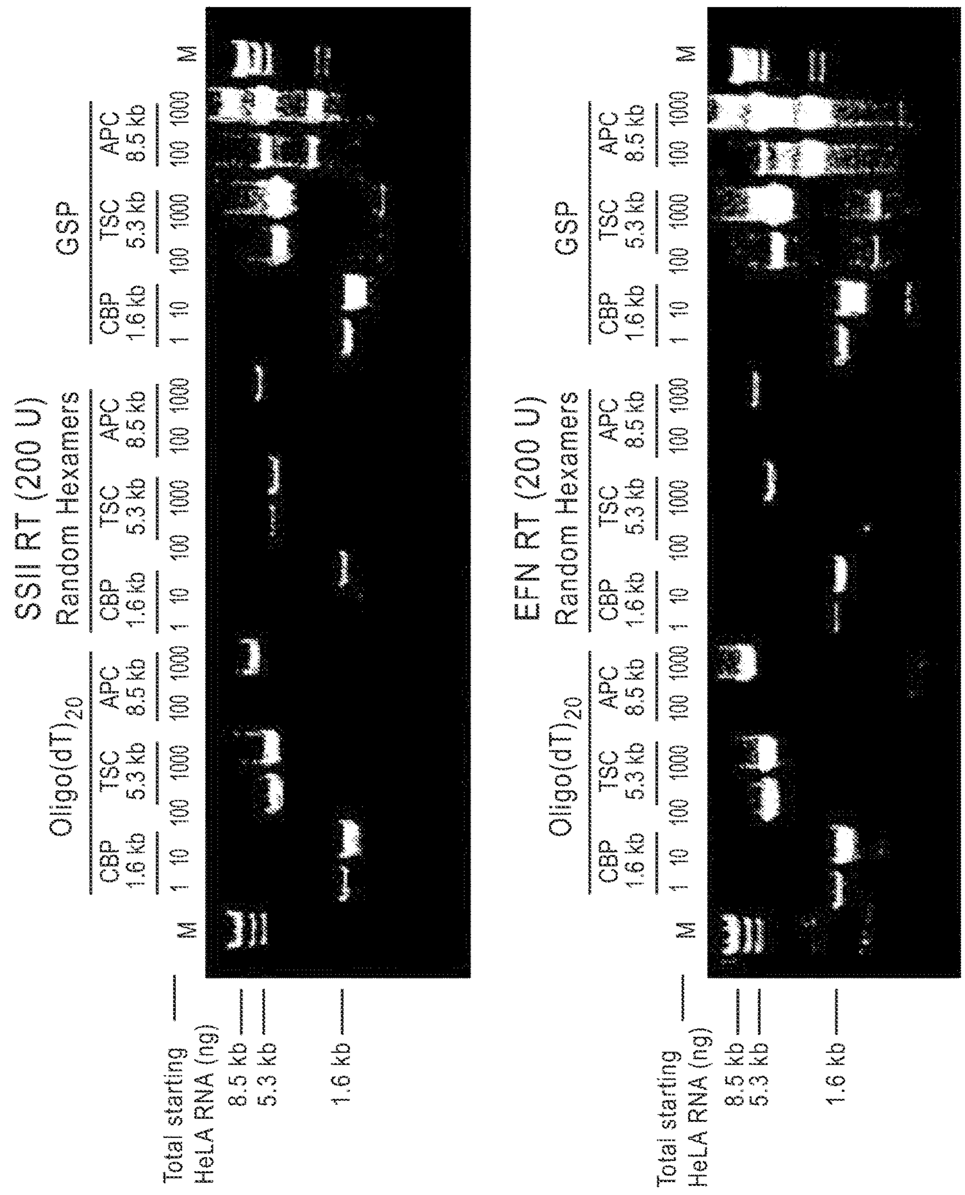

FIG. 21 shows the results of a comparison of various primers in RT-PCR reactions using the polypeptides of the invention. EFN contains the tag sequence=MASGTGGQQMGRDLYDDDDKH (SEQ ID NO:3), and the EFN mutations, which are H204R, T306K, and F309N.

DETAILED DESCRIPTION OF THE INVENTION

In the description that follows, a number of terms used in recombinant DNA, virology and immunology are utilized.

In order to provide a clearer and consistent understanding of the specification and claims, including the scope to be given such terms, the following definitions are provided.

Cloning vector. As used herein "cloning vector" means a nucleic acid molecule such as plasmid, cosmid, phage, phagemid or other nucleic acid molecule which is able to replicate autonomously in a host cell, and which is characterized by one or a small number of recognition sequences, (e.g., restriction endonuclease recognition sites, recombination sites, topoisomerase recognition sites, etc.) at which such nucleic acid sequences may be manipulated in a determinable fashion, and into which a nucleic acid segment of interest may be inserted in order to bring about its replication and cloning. The cloning vector may further contain a marker suitable for use in the identification of cells transformed with the cloning vector. Markers, for example, are genes that confer a recognizable phenotype on host cells in which such markers are expressed. Commonly used markers include, but are not limited to, antibiotic resistance genes such as tetracycline resistance or ampicillin resistance.

Expression vector. As used herein "expression vector" means a nucleic acid molecule similar to a cloning vector but which may additionally comprise nucleic acid sequences capable of enhancing and/or controlling the expression of a gene or other nucleic acid molecule which has been cloned into it, after transformation into a host. The additional nucleic acid sequences may comprise promoter sequences, repressor binding sequences and the like. The cloned gene or nucleic acid molecule is usually operably linked to one or more (e.g., one, two, three, four, etc.) of such control sequences such as promoter sequences.

Recombinant host. As used herein "recombinant" means any prokaryotic or eukaryotic or microorganism which contains the desired cloned genes or nucleic acid molecules, for example, in an expression vector, cloning vector or any nucleic acid molecule. The term "recombinant host" is also meant to include those host cells which have been genetically engineered to contain the desired gene or other nucleic acid molecule on the host chromosome or genome.

Host. As used herein "host" means any prokaryotic or eukaryotic cell or organism that is the recipient of a replicable expression vector, cloning vector or any nucleic acid molecule. The nucleic acid molecule may contain, but is not limited to, a structural gene, a promoter and/or an origin of replication.

Promoter. As used herein "promoter" means a nucleic acid sequence generally described as the 5' region of a gene, located proximal to the start codon which is capable of directing the transcription of a gene or other nucleic acid molecule. At the promoter region, transcription of an adjacent gene(s) or nucleic acid(s) is initiated.

Gene. As used herein "gene" means a nucleic acid sequence that contains information necessary for expression of a polypeptide or protein. It includes the promoter and the structural gene as well as other sequences involved in expression of the protein.

Structural gene. As used herein "structural gene" means a DNA or other nucleic acid sequence that is transcribed into messenger RNA that is then translated into a sequence of amino acids characteristic of a specific polypeptide.

Operably linked. As used herein "operably linked" means that a nucleic acid element is positioned so as to influence the initiation of expression of the polypeptide encoded by the structural gene or other nucleic acid molecule.

Expression. As used herein "expression" refers to the process by which a gene or other nucleic acid molecule produces a polypeptide. It includes transcription of the gene or nucleic acid molecule into messenger RNA (mRNA) and the translation of such mRNA into polypeptide(s).

Substantially Pure. As used herein "substantially pure" means that the desired material is essentially free from contaminating cellular components which are associated with the desired material in nature. In a preferred aspect, a reverse transcriptase of the invention has 25% or less, preferably 15% or less, more preferably 10% or less, more preferably 5% or less, and still more preferably 1% or less contaminating cellular components. In another aspect, the reverse transcriptases of the invention have no detectable protein contaminants when 200 units of reverse transcriptase are run on a protein gel (e.g., SDS-PAGE) and stained with Comassie blue. Contaminating cellular components may include, but are not limited to, enzymatic activities such as phosphatases, exonucleases, endonucleases or undesirable DNA polymerase enzymes. Preferably, reverse transcriptases of the invention are substantially pure.

Substantially isolated. As used herein "substantially isolated" means that the polypeptide of the invention is essentially free from contaminating proteins, which may be associated with the polypeptide of the invention in nature and/or in a recombinant host. In one aspect, a substantially isolated reverse transcriptase of the invention has 25% or less, preferably 15% or less, more preferably 10% or less, more preferably 5% or less, and still more preferably 1% or less contaminating proteins. In another aspect, in a sample of a substantially isolated polypeptide of the invention, 75% or greater (preferably 80%, 85%, 90%, 95%, 98%, or 99% or greater) of the protein in the sample is the desired reverse transcriptase of the invention. The percentage of contaminating protein and/or protein of interest in a sample may be determined using techniques known in the art, for example, by using a protein gel (e.g., SDS-PAGE) and staining the gel with a protein dye (e.g., Coomassie blue, silver stain, amido black, etc.). In another aspect, the reverse transcriptases of the invention have no detectable protein contaminants when 200 units of reverse transcriptase are run on a protein gel (e.g., SDS-PAGE) and stained with Comassie blue.

Primer. As used herein "primer" refers to a single-stranded oligonucleotide that is extended by covalent bonding of nucleotide monomers during amplification or polymerization of a DNA molecule.

Template. The term "template" as used herein refers to a double-stranded or single-stranded nucleic acid molecule which is to be amplified, copied or sequenced. In the case of a double-stranded DNA molecule, denaturation of its strands to form single-stranded first and second strands may be performed before these molecules are amplified, copied or sequenced. A primer complementary to a portion of a nucleic acid template is hybridized under appropriate conditions and a nucleic acid polymerase, such as the reverse transcriptase enzymes of the invention, may then add nucleotide monomers to the primer thereby synthesizing a nucleic acid molecule complementary to said template or a portion thereof. The newly synthesized nucleic acid molecule, according to the invention, may be equal or shorter in length than the original template. Mismatch incorporation during the synthesis or extension of the newly synthesized nucleic acid molecule may result in one or a number of mismatched base pairs. Thus, the synthesized nucleic acid molecule need not be exactly complementary to the template.

Incorporating. The term "incorporating" as used herein means becoming a part of a nucleic acid molecule or primer.

Oligonucleotide. "Oligonucleotide" refers to a synthetic or natural molecule comprising a covalently linked sequence of nucleotides which are joined by a phosphodiester bond between the 3' position of the pentose of one nucleotide and the 5' position of the pentose of the adjacent nucleotide.

Nucleotide. As used herein "nucleotide" refers to a base-sugar-phosphate combination. Nucleotides are monomeric units of a nucleic acid sequence (DNA and RNA). The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP, and nucleotide derivatives that confer nuclease resistance on the nucleic acid molecule containing them. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo)benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides include [R6G]dUTP, [TAMRA]dUTP, [R110]dCTP, [R6G]dCTP, [TAMRA] dCTP, [JOE]ddATP, [R6G]ddATP, [FAM]ddCTP, [R110] ddCTP, [TAMRA]ddGTP, [ROX]ddTTP, [dR6G]ddATP, [dR110]ddCTP, [dTAMRA]ddGTP, and [dROX]ddTTP available from Perkin Elmer, Foster City, Calif. FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham Arlington Heights, Ill.; Fluorescein-15-dATP, Fluorescein-12-dUTP, Tetramethyl-rodamine-6-dUTP, $IR_{770}$-9-dATP, Fluorescein-12-ddUTP, Fluorescein-12-UTP, and Fluorescein-15-2'-dATP available from Boehringer Mannheim Indianapolis, Ind.; and ChromaTide Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg.

Probes. The term probes refer to single or double stranded nucleic acid molecules or oligonucleotides which are detectably labeled by one or more detectable markers or labels. Such labels or markers may be the same or different and may include radioactive labels, fluorescent labels, chemiluminescent labels, bioluminescent labels and enzyme labels, although one or more fluorescent labels (which are the same or different) are preferred in accordance with the invention. Probes have specific utility in the detection of nucleic acid molecules by hybridization and thus may be used in diagnostic assays.

Hybridization. As used herein, hybridization (hybridizing) refers to the pairing of two complementary single-stranded nucleic acid molecules (RNA and/or DNA) to give a double-stranded molecule. As one skilled in the art will recognize, two nucleic acid molecules may be hybridized, although the base pairing is not completely complementary. Accordingly, mismatched bases do not prevent hybridization of two nucleic acid molecules provided that appropriate conditions, well known in the art, are used.

Thermostable Reverse Transcriptase. For the purposes of this disclosure, a thermostable reverse transcriptase includes a reverse transcriptase which retains a greater percentage or amount of its activity after a heat treatment than is retained by a reverse transcriptase that has wild-type thermostability after an identical treatment. Thus, a reverse transcriptase having increased/enhanced thermostability may be defined as a reverse transcriptase having any increase in thermostability, preferably from about 1.2 to about 10,000 fold, from about 1.5 to about 10,000 fold, from about 2 to about 5,000 fold, or from about 2 to about 2000 fold (preferably greater than about 5 fold, more preferably greater than about 10 fold, still more preferably greater than about 50 fold, still more preferably greater than about 100 fold, still more preferably greater than about 500 fold, and most preferably greater than about 1000 fold) retention of activity after a heat treatment sufficient to cause a reduction in the activity of a reverse transcriptase that is wild-type for thermostability. Preferably, the mutant or modified reverse transcriptase of the invention is compared to the corresponding unmodified or wild-type reverse transcriptase to determine the relative enhancement or increase in thermostability. For example, after a heat treatment at 52° C. for 5 minutes, a thermostable reverse transcriptase may retain approximately 90% of the activity present before the heat treatment, whereas a reverse transcriptase that is wild-type for thermostability may retain 10% of its original activity. Likewise, after a heat treatment at 53° C. for five minutes, a thermostable reverse transcriptase may retain approximately 80% of its original activity, whereas a reverse transcriptase that is wild-type for thermostability may have no measurable activity. Similarly, after a heat treatment at 50° C. for five minutes, a thermostable reverse transcriptase may retain approximately 50%, approximately 55%, approximately 60%, approximately 65%, approximately 70%, approximately 75%, approximately 80%, approximately 85%, approximately 90%, or approximately 95% of its original activity, whereas a reverse transcriptase that is wild-type for thermostability may have no measurable activity or may retain 10%, 15% or 20% of its original activity. In the first instance (i.e., after heat treatment at 52° C. for 5 minutes), the thermostable reverse transcriptase would be said to be 9-fold more thermostable than the wild-type reverse transcriptase. Examples of conditions which may be used to measure thermostability of reverse transcriptases are set out below, for example, in the Examples.

The thermostability of a reverse transcriptase can be determined by comparing the residual activity of a sample of the reverse transcriptase that has been subjected to a heat treatment, i.e., incubated at 52° C. for a given period of time, for example, five minutes, to a control sample of the same reverse transcriptase that has been incubated at room temperature for the same length of time as the heat treatment. Typically the residual activity may be measured by following the incorporation of a radiolabled deoxyribonucleotide into an oligodeoxyribonucleotide primer using a complementary oligoribonucleotide template. For example, the ability of the reverse transcriptase to incorporate [α-$^{32}$P]-dGTP into an oligo-dG primer using a poly(riboC) template may be assayed to determine the residual activity of the reverse transcriptase.

In another aspect, thermostable reverse transcriptases of the invention may include any reverse transcriptase which is inactivated at a higher temperature compared to the corresponding wild-type, unmutated, or unmodified reverse transcriptase. Preferably, the inactivation temperature for the thermostable reverse transcriptases of the invention is from about 2° C. to about 50° C. (e.g., about 2° C., about 4° C., about 5° C., about 8° C., about 10° C., about 12° C., about 14° C., about 16° C., about 18° C., about 20° C., about 24° C., about 26° C., about 28° C., about 30° C., about 33° C., about 35° C., about 38° C., about 40° C., about 42° C., about 44° C., about 46° C., about 48° C., or about 50° C.) higher than the inactivation temperature for the corresponding wild-type, unmutated, or unmodified reverse transcriptase. More preferably, the inactivation temperature for the reverse transcriptases of the invention is from about 5° C. to about 50° C., from about 5° C. to about 40° C., from about 5° C. to about 30° C., or from about 5° C. to about 25° C. greater than the inactivation temperature for the corresponding wild-type, unmutated or unmodified reverse transcriptase, when compared under the same conditions.

The difference in inactivation temperature for the reverse transcriptase of the invention compared to its corresponding wild-type, unmutated or unmodified reverse transcriptase can be determined by treating samples of such reverse transcriptases at different temperatures for a defined time period and then measuring residual reverse transcriptase activity, if any, after the samples have been heat treated. Determination of the difference or delta in the inactivation temperature between the test reverse transcriptase compared to the wild-type, unmutated or unmodified control is determined by comparing the difference in temperature at which each reverse transcriptase is inactivated (i.e., no residual reverse transcriptase activity is measurable in the particular assay used). As will be recognized, any number of reverse transcriptase assays may be used to determine the different or delta of inactivation temperatures for any reverse transcriptases tested.

In another aspect, thermostability of a reverse transcriptase of the invention may be determined by measuring the half-life of the reverse transcriptase activity of a reverse transcriptase of interest. Such half-life may be compared to a control or wild-type reverse transcriptase to determine the difference (or delta) in half-life. Half-lifes of the reverse transcriptases of the invention are preferably determined at elevated temperatures (e.g., greater than 37° C.) and preferably at temperatures ranging from 40° C. to 80° C., more preferably at temperatures ranging from 45° C. to 75° C., 50° C. to 70° C., 50° C. to 65° C., and 50° C. to 60° C. Preferred half-lifer of the reverse transcriptases of the invention may range from 4 minutes to 10 hours, 4 minutes to 7.5 hours, 4 minutes to 5 hours, 4 minutes to 2.5 hours, or 4 minutes to 2 hours, depending upon the temperature used. For example, the reverse transcriptase activity of the reverse transcriptases of the invention may have a half-life of at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 20 minute, at least 25 minutes, at least 30 minutes, at least 40 minutes, at least 50 minutes, at least 60 minutes, at least 70 minutes, at least 80 minutes, at least 90 minutes, at least 100 minutes, at least 115 minutes, at least 125 minutes, at least 150 minutes, at least 175 minutes, at least 200 minutes, at least 225 minutes, at least 250 minutes, at least 275 minutes, at least 300 minutes, at least 400 minutes, at least 500 minutes at temperatures of 48° C., 50° C., 52° C., 52.5° C., 55° C., 57° C., 60° C., 62° C., 65° C., 68° C., and/or 70° C.

Terminal extension activity. As used herein, terminal extension activity refers to the ability of a reverse transcriptase (RT) to add additional bases on to the 3' end of a newly synthesized cDNA strand beyond the 5' end of the DNA or mRNA template. Terminal extension activity may add bases specifically (with a nucleotide bias) or randomly.

Terminal extension activity is also known as terminal deoxynucleotidyl transferase (TdT) activity. A reverse transcriptase having reduced TdT activity is defined as any reverse transcriptase having lower TdT specific activity than the TdT specific activity of the corresponding wild-type, unmutated, or unmodified enzyme, for example, less than about 90% of the TdT specific activity of the corresponding wild-type, unmutated, or unmodified enzyme, less than about 85% of the TdT specific activity of the corresponding wild-type, unmutated, or unmodified enzyme, less than about 80% of the TdT specific activity of the corresponding wild-type, unmutated, or unmodified enzyme, less than about 75% of the TdT specific activity of the corresponding wild-type, unmutated, or unmodified enzyme, less than about 50% of the TdT specific activity of the corresponding wild-type, unmutated, or unmodified enzyme, less than about 25% of the TdT specific activity of the corresponding wild-type, unmutated, or unmodified enzyme, less than about 15% of the TdT specific activity of the corresponding wild-type, unmutated, or unmodified enzyme, less than 10% of the TdT specific activity of the corresponding wild-type, unmutated, or unmodified enzyme, less than about 5% of the TdT specific activity of the corresponding wild-type, unmutated, or unmodified enzyme, or less than about 1% of the TdT specific activity of the corresponding wild-type, unmutated, or unmodified enzyme. A reverse transcriptase of the invention having substantially reduced TdT activity refers to a reverse transcriptase having a TdT specific activity level of 30% or less than the TdT specific activity of the corresponding wild-type or $TdT^+$ reverse transcriptase. Eliminated TdT activity is defined as a level of activity that is undetectable by the assay methods set out herein in Example 3.

As noted below in Example 3, reverse transcriptases are known in the art which extend nucleic acid molecules 2-3 nucleotides past the end of templates (e.g., RNA or DNA templates). Further, in any one reaction mixture in which reverse transcription occurs, mixtures of molecules may be present which contain different numbers of nucleotides that extend beyond the end of the template. TdT activity may be determined herein in reference to the number or percentage of molecules which contain one or more nucleotides which extend beyond the end of the template. For example, if a wild-type reverse transcriptase adds 1 or more nucleotides past the end of a template to 90% of the molecules generated during reverse transcription and a modified reverse transcriptase adds 1 or more nucleotides past the end of a template to 45% of the molecules under the same or similar conditions, then the modified reverse transcriptase would be said to exhibit a 50% decrease in TdT activity as compared to the wild-type enzyme. Further, an F309N, T306K, H204R mutant of M-MLV SUPERSCRIPT™ II has been generated which exhibits about 0% of the TdT activity exhibited by SUPERSCRIPT™ II when DNA is used as a template and about 10-20% of the TdT activity exhibited by SUPERSCRIPT™ II when RNA is used as a template.

Fidelity. Fidelity refers to the accuracy of polymerization, or the ability of the reverse transcriptase to discriminate correct from incorrect substrates, (e.g., nucleotides) when synthesizing nucleic acid molecules which are complementary to a template. The higher the fidelity of a reverse transcriptase, the less the reverse transcriptase misincorporates nucleotides in the growing strand during nucleic acid synthesis; that is, an increase or enhancement in fidelity results in a more faithful reverse transcriptase having decreased error rate or decreased misincorporation rate.

A reverse transcriptase having increased/enhanced/higher fidelity is defined as a polymerase having any increase in fidelity, preferably about 1.2 to about 10,000 fold, about 1.5 to about 10,000 fold, about 2 to about 5,000 fold, or about 2 to about 2000 fold (preferably greater than about 5 fold, more preferably greater than about 10 fold, still more preferably greater than about 50 fold, still more preferably greater than about 100 fold, still more preferably greater than about 500 fold and most preferably greater than about 100 fold) reduction in the number of misincorporated nucleotides during synthesis of any given nucleic acid molecule of a given length compared to the control reverse transcriptase. Preferably, the mutant or modified reverse transcriptase of the invention is compared to the corresponding unmodified or wild-type reverse transcriptase to determine the relative enhancement or increase in fidelity. For example, a mutated reverse transcriptase may misincorporate one nucleotide in the synthesis of a nucleic acid molecule segment of 1000 bases compared to an unmutated reverse transcriptase misincorporating 10 nucleotides in the same size segment. Such a mutant reverse transcriptase would be said to have an increase of fidelity of 10 fold.

Fidelity can also be measured by the decrease in the incidence of frame shifting, as described below in Example 5. A reverse transcriptase having increased fidelity may be defined as a polymerase or reverse transcriptase having any increase in fidelity with respect to frame shifting, as compared to a control reverse transcriptase (e.g., a corresponding wild-type and/or a corresponding un-mutated or un-modified reverse transcriptase), for example, a reverse transcriptase having greater than about 1.2 fold increased fidelity with respect to frame shifting, having greater than about 1.5 fold increased fidelity with respect to frame shifting, having greater than about 5 fold increased fidelity with respect to frame shifting, having greater than about 10 fold increased fidelity with respect to frame shifting, having greater than about 20 fold increased fidelity with respect to frame shifting, having greater than about 30 fold increased fidelity with respect to frame shifting, or having greater than about 40 fold increased fidelity with respect to frame shifting.

A reverse transcriptase having increased/enhanced/higher fidelity, with respect to frame shifting, can also be defined as a reverse transcriptase or polymerase having any increase in fidelity, such as from about 1.5 to about 10,000 fold, from about 2 to about 5,000 fold, from about 2 to about 2000 fold, from about 1.5 to about 40 fold, from about 5 to about 40 fold, from about 10 to about 40 fold, from about 20 to about 40 fold, from about 30 to about 40 fold, from about 5 to about 30 fold, from about 10 to about 30 fold, from about 15 to about 30 fold, from about 20 to about 30 fold, from about 5 to about 20 fold, from about 10 to about 20 fold, from about 15 to about 20 fold, from about 10 to about 100 fold, from about 15 to about 100 fold, from about 20 to about 100 fold, from about 30 to about 100 fold, or from about 50 to about 100 fold increased fidelity with respect to frame shifting.

A reverse transcriptase having reduced misincorporation is defined herein as either a mutated or modified reverse transcriptase that has about or less than 90%, has about or less than 85%, has about or less than 75%, has about or less than 70%, has about or less than 60%, or preferably has about or less than 50%, preferably has about or less than 25%, more preferably has about or less than 10%, and most preferably has about or less than 1% of relative misincorporation compared to the corresponding wild-type, unmutated, or unmodified enzyme.

The fidelity or misincorporation rate of a reverse transcriptase can be determined by sequencing or by other methods known in the art (Eckert & Kunkel, 1990*, Nucl. Acids Res.* 18:3739-3744). In one example, the sequence of a DNA molecule synthesized by the unmutated and mutated reverse transcriptases can be compared to the expected (known) sequence. In this way, the number of errors (misincorporation or frame shifts) can be determined for each enzyme and compared. In another example, the unmutated and mutated reverse transcriptases may be used to sequence a DNA molecule having a known sequence. The number of sequencing errors (misincorporation or frame shifts) can be compared to determine the fidelity or misincorporation rate of the enzymes. Other means of determining the fidelity or misincorporation rate include a forward complementation assay using an RNA template as described below and previously in Boyer J. C. et al. *Methods Enzymol.* 275:523 (1996), and are set out in the examples. Other methods of determining the fidelity or misincorporation rate will be recognized by one of skill in the art.

Strand jumping. Strand jumping, as used herein, refers to a type of random mutation caused by an reverse transcriptase "skipping" more than one (e.g., two, five, ten, fifty, one-hundred, etc.) nucleotides on the mRNA template, resulting in a deletion of the corresponding nucleotides in the resulting cDNA. Sequencing the synthesized nucleic acid molecule and comparing to the expected sequence may allow determination of the level or amount of strand jumping for the reverse transcriptases of the invention. This level or amount may then be compared to the level or amount of strand jumping caused by the corresponding wild type and/or un-modified or un-mutated reverse transcriptase.

Hand domain. The hand domain, as used herein, refers to those amino acids which are in the area or areas that control the template, primer, or nucleotide interaction of the reverse transcriptase. This domain is further characterized by a group of three regions of secondary structure in a reverse transcriptase enzyme, the thumb, fingers and palm regions. The thumb region is defined as residing between amino acids 240-315 of HIV reverse transcriptase, or between amino acids 280-355 of M-MLV reverse transcriptase. The fingers region is defined as residing between amino acids 1-85 and 120-154 of HIV reverse transcriptase, or between 1-124 and 161-193 of M-MLV reverse transcriptase. The palm region is defined as residing between amino acids 86-199 and 155-239 of HIV reverse transcriptase, or between amino acids 126-160 and 193-279 of M-MLV reverse transcriptase. These areas are generally defined, and the amino acids defining the N-termini and C-termini are approximate. Corresponding regions may also be defined for other reverse transcriptases. Preferred reverse transcriptases of the invention have one or more modifications or mutations within the hand domain. More particularly, reverse transcriptases of the invention comprise one or more mutations or modifications within one or more regions, including the thumb, finger, and palm regions.

Full length. As used herein, full length when used to describe a product molecule, e.g., a cDNA molecule, indicates that the product molecule is the same length or substantially the same length as the template molecule, e.g., an mRNA molecule, from which it is produced by the activity of polypeptides of the invention. A cDNA molecule may be substantially the same length as the template from which it is copied when it is about 90%, 91%, 92%, 93%, 94%, 95%, 96%, 97%, 98%, 99% or greater of the length of the portion of the template located 3' to the 3' most nucleotide of the primer used to reverse transcribe the template. Thus, if a primer anneals in the center of a template, a full length product would be one that contains a cDNA copy of half of the template. Template molecules may be from about 100 bases to about 50 kb in length, from about 200 bases to about 50 kb in length, from about 300 bases to about 50 kb in length, from about 400 bases to about 50 kb in length, from about 500 bases to about 50 kb in length, from about 600 bases to about 50 kb in length, from about 700 bases to about 50 kb in length, from about 800 bases to about 50 kb in length, from about 900 bases to about 50 kb in length, and from about 1 kb to about 50 kb in length. In some embodiments, template molecules may be from about 500 bases to about 10 kb in length, from about 600 bases to about 10 kb in length, from about 700 bases to about 10 kb in length, from about 800 bases to about 10 kb in length, from about 900 bases to about 10 kb in length, from about 1000 bases to about 10 kb in length, from about 1100 bases to about 10 kb in length, and/or from about 1200 bases to about 10 kb in length. In some embodiments, template molecules may be from about 250 bases to about 5 kb in length, from about 300 bases to about 5 kb in length, and from about 350 bases to about 5 kb in length, from about 400 bases to about 5 kb in length, from about 450 bases to about 5 kb in length, from about 500 bases to about 5 kb in length, from about 550 bases to about 5 kb in length, from about 600 bases to about 5 kb in length, from about 650 bases to about 5 kb in length, from about 700 bases to about 5 kb in length, from about 750 bases to about 5 kb in length, from about 800 bases to about 5 kb in length, and from about 850 bases to about 5 kb in length.

In some embodiments, the ability of a reverse transcriptase to synthesize a full length product may be determined using a defined template and primer, for example, a polyadenylated template corresponding to the chloramphenicol acetyl transferase gene and an oligo(dT) primer, under defined reaction conditions, e.g., pH, salt concentration, divalent metal concentration, template concentration, temperature, etc. In some embodiments, a template molecule is greater than about 500 base pairs in length, and the amount of full length product synthesized may determined by separating full length product from truncated product, for example, by gel electrophoresis, and quantifying the full length product, for example, by incorporating a radiolabel in to the product and using a scintillation counter.

About. The term "about" as used herein, means the recited number plus or minus 10%. Thus, "about 100" includes 90-110.

Overview

In general, the invention provides, in part, compositions for use in reverse transcription of a nucleic acid molecule comprising a reverse transcriptase with one or more (e.g., one, two, three, four, five, ten, twelve, fifteen, twenty, thirty, etc.) mutations or modification which render the reverse transcriptase more thermostable. The invention also provides compositions for use in reverse transcription of a nucleic acid molecule, the compositions comprising a reverse transcriptase with one or more mutations or modification which render the reverse transcriptase more efficient, that is having higher fidelity, and/or has lower TdT activity than a corresponding un-mutated or un-modified reverse transcriptase. The invention further provides compositions comprising a reverse transcriptase with one or more mutations or modification which render the reverse transcriptase more thermostable and/or more efficient than a corresponding un-mutated or un-modified reverse transcriptase.

The enzymes in these compositions are preferably present in working concentrations and are also preferably reduced, substantially reduced, or eliminated in RNase H activity. Alternatively, reverse transcriptases used in the compositions of the invention may have RNase H activity. Preferred reverse transcriptases include retroviral reverse transcriptases such as M-MLV reverse transcriptase, HIV reverse transcriptase, RSV reverse transcriptase, AMV reverse transcriptase, RAV reverse transcriptase, and MAV reverse transcriptase or other ASLV reverse transcriptases or their corresponding RNase H− derivatives. Additional reverse transcriptases which may be used to prepare compositions of the invention include bacterial reverse transcriptases (e.g., *Escherichia coli* reverse transcriptase) (see, e.g., Mao et al., *Biochem. Biophys. Res. Commun.* 227:489-93 (1996)) and reverse transcriptases of *Saccharomyces cerevisiae* (e.g., reverse transcriptases of the Ty1 or Ty3 retrotransposons) (see, e.g., Cristofari et al., *Jour. Biol. Chem.* 274:36643-36648 (1999); Mules et al., *Jour. Virol.* 72:6490-6503 (1998)).

In accordance with the invention, any number of mutations can be made to the reverse transcriptases and, in a preferred aspect, multiple mutations can be made to result in an increased thermostability and/or to confer other desired properties on reverse transcriptases of the invention. Such mutations include point mutations, frame shift mutations, deletions and insertions, with one or more (e.g., one, two, three, four, five, ten, twelve, fifteen, twenty, thirty, etc.) point mutations preferred. Mutations may be introduced into reverse transcriptases of the present invention using any methodology known to those of skill in the art. Mutations may be introduced randomly by, for example, conducting a PCR reaction in the presence of manganese as a divalent metal ion cofactor. Alternatively, oligonucleotide directed mutagenesis may be used to create the mutant polymerases which allows for all possible classes of base pair changes at any determined site along the encoding DNA molecule. In general, this technique involves annealing an oligonucleotide complementary (except for one or more mismatches) to a single stranded nucleotide sequence coding for the reverse transcriptase of interest. The mismatched oligonucleotide is then extended by DNA polymerase, generating a double-stranded DNA molecule which contains the desired change in sequence in one strand. The changes in sequence can, for example, result in the deletion, substitution, or insertion of an amino acid. The double-stranded polynucleotide can then be inserted into an appropriate expression vector, and a mutant or modified polypeptide can thus be produced. The above-described oligonucleotide directed mutagenesis can, for example, be carried out via PCR.

The invention is also directed to methods for reverse transcription of one or more (e.g., one, two, three, four, five, ten, twelve, fifteen, twenty, etc.) nucleic acid molecules comprising mixing one or more (e.g., one, two, three, four, five, ten, twelve, fifteen, twenty, etc.) nucleic acid templates, which are preferably RNA or messenger RNA (mRNA) and more preferably a population of mRNA molecules, with one or more reverse transcriptase of the present invention and incubating the mixture under conditions sufficient to make a nucleic acid molecule or molecules complementary to all or a portion of the one or more (e.g., one, two, three, four, five, ten, twelve, fifteen, twenty, thirty, etc.) templates. To make the nucleic acid molecule or molecules complementary to the one or more templates, a primer (e.g., an oligo(dT) primer) and one or more nucleotides are preferably used for nucleic acid synthesis in the 5' to 3' direction. Nucleic acid molecules suitable for reverse transcription according to this aspect of the invention include any nucleic acid molecule, particularly those derived from a prokaryotic or eukaryotic cell. Such cells may include normal cells, diseased cells, transformed cells, established cells, progenitor cells, precursor cells, fetal cells, embryonic cells, bacterial cells, yeast cells, animal cells (including human cells), avian cells, plant cells and the like, or tissue isolated from a plant or an animal (e.g., human, cow, pig, mouse, sheep, horse, monkey, canine, feline, rat, rabbit, bird, fish, insect, etc.). Nucleic acid molecules suitable for reverse transcription may also be isolated and/or obtained from viruses and/or virally infected cells.

The invention further provides methods for amplifying or sequencing a nucleic acid molecule comprising contacting the nucleic acid molecule with a reverse transcriptase of the present invention. Preferred such methods comprise one or more polymerase chain reactions (PCRs).

Sources of Reverse Transcriptases

Enzymes for use in compositions, methods and kits of the invention include any enzyme having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, R. K., et al., *Science* 239:487-491 (1988); U.S. Pat. Nos. 4,889,818 and 4,965,188), Tne DNA polymerase (PCT Publication No. WO 96/10640), Tma DNA polymerase (U.S. Pat. No. 5,374,553) and mutants, fragments, variants or derivatives thereof (see, e.g., commonly owned U.S. Pat. Nos. 5,948,614 and 6,015,668, which are incorporated by reference herein in their entireties). Preferably, reverse transcriptases for use in the invention include retroviral reverse transcriptases such as M-MLV reverse transcriptase, AMV reverse transcriptase, RSV reverse transcriptase, RAV reverse transcriptase, MAV reverse transcriptase, and generally ASLV reverse transcriptases. As will be understood by one of ordinary skill in the art, modified reverse transcriptases may be obtained by recombinant or genetic engineering techniques that are routine and well-known in the art. Mutant reverse transcriptases can, for example, be obtained by mutating the gene or genes encoding the reverse transcriptase of interest by site-directed or random mutagenesis. Such mutations may include point mutations, deletion mutations and insertional mutations. For example, one or more point mutations (e.g., substitution of one or more amino acids with one or more different amino acids) may be used to construct mutant reverse transcriptases of the invention.

The invention further includes reverse transcriptases which are 70%, 75%, 80%, 85%, 90%, 95%, 96%, 97%, 98%, or 99% identical at the amino acid level to a wild-type reverse transcriptase (e.g., M-MLV reverse transcriptase, AMV reverse transcriptase, RSV reverse transcriptase, HIV reverse transcriptase, etc.) and exhibit increased thermostability and/or other desired properties of the invention. Also included within the invention are reverse transcriptases which are 70%, 75%, 80%, 85%, 90%, 95%, 96%, 97%, 98%, or 99% identical at the amino acid level to a reverse transcriptase comprising the amino acid sequence set out below in Table 3 (SEQ ID NO:2) and exhibit increased thermostability and/or more efficient (e.g., having higher fidelity and/or having lower TdT activity). The invention also includes nucleic acid molecules which encode the above described reverse transcriptases.

The invention also includes fragments of reverse transcriptases which comprise at least 200, 250, 300, 350, 400, 450, 500, 550, 600, 650, or 700 amino acid residues and retain one or more activities associated with reverse transcriptases. Such fragments may be obtained by deletion mutation, by recombinant techniques that are routine and well-known in the art, or by enzymatic digestion of the reverse transcriptase(s) of interest using any of a number of well-known proteolytic enzymes. The invention further includes nucleic acid molecules which encode the above described mutant reverse transcriptases and reverse transcriptase fragments.

Reverse transcriptase fragments of the invention also comprise amino acids 1-10, 11-20, 21-30, 31-40, 41-50, 51-60, 61-70, 71-80, 81-90, 91-100, 101-110, 111-120, 121-130, 131-140, 141-150, 151-160, 161-170, 171-180, 181-190, 191-200, 201-210, 211-220, 221-230, 231-240, 241-250, 251-260, 261-270, 271-280, 281-290, 291-300, 301-310, 311-320, 321-330, 331-340, 341-350, 351-360, 361-370, 371-380, 381-390, 391-400, 401-410, 411-420, 421-430, 431-440, 441-450, 451-460, 461-470, 471-480, 481-490, 491-500, 501-510, 511-520, 521-530, 531-540, and/or 541-550 and/or amino acids 1-355, 1-498, 1-500, and/or 1-550 of M-MLV reverse transcriptase (and more preferably the sequence shown in Table 3, which may further contain one or more of the modifications or mutations discussed herein), as well as corresponding fragments of other reverse transcriptases. Reverse transcriptase fragments of the invention further comprise polypeptides which are 70%, 75%, 80%, 85%, 90%, 95%, 96%, 97%, 98%, or 99% identical to one or more of the fragments set out above. The invention also concerns various combinations of any number of these fragments.

By a protein or protein fragment having an amino acid sequence at least, for example, 70% "identical" to a reference amino acid sequence it is intended that the amino acid sequence of the protein is identical to the reference sequence except that the protein sequence may include up to 30 amino acid alterations per each 100 amino acids of the amino acid sequence of the reference protein. In other words, to obtain a protein having an amino acid sequence at least 70% identical to a reference amino acid sequence, up to 30% of the amino acid residues in the reference sequence may be deleted or substituted with another amino acid, or a number of amino acids up to 30% of the total amino acid residues in the reference sequence may be inserted into the reference sequence. These alterations of the reference sequence may occur at the amino (N-) and/or carboxy (C-) terminal positions of the reference amino acid sequence and/or anywhere between those terminal positions, interspersed either individually among residues in the reference sequence and/or in one or more contiguous groups within the reference sequence. As a practical matter, whether a given amino acid sequence is, for example, at least 70% identical to the amino acid sequence of a reference protein can be determined conventionally using known computer programs such as those described above for nucleic acid sequence identity determinations, or using the CLUSTAL W program (Thompson, J. D., et al., *Nucleic Acids Res.* 22:4673-4680 (1994)).

Sequence identity may be determined by comparing a reference sequence or a subsequence of the reference sequence to a test sequence. The reference sequence and the test sequence are optimally aligned over an arbitrary number of residues termed a comparison window. In order to obtain optimal alignment, additions or deletions, such as gaps, may be introduced into the test sequence. The percent sequence identity is determined by determining the number of positions at which the same residue is present in both sequences and dividing the number of matching positions by the total length of the sequences in the comparison window and multiplying by 100 to give the percentage. In addition to the number of matching positions, the number and size of gaps is also considered in calculating the percentage sequence identity.

Sequence identity is typically determined using computer programs. A representative program is the BLAST (Basic Local Alignment Search Tool) program publicly accessible at the National Center for Biotechnology Information (NCBI, http://www.ncbi.nlm.nih.gov/). This program compares segments in a test sequence to sequences in a database to determine the statistical significance of the matches, then identifies and reports only those matches that that are more significant than a threshold level. A suitable version of the BLAST program is one that allows gaps, for example, version 2.X (Altschul, et al., *Nucleic Acids Res.* 25(17): 3389-402, 1997). Standard BLAST programs for searching nucleotide sequences (blastn) or protein (blastp) may be used. Translated query searches in which the query sequence is translated, i.e., from nucleotide sequence to protein (blastx) or from protein to nucleic acid sequence (tbblastn) may also be used as well as queries in which a nucleotide query sequence is translated into protein sequences in all 6 reading frames and then compared to an NCBI nucleotide database which has been translated in all six reading frames (tbblastx).

Additional suitable programs for identifying proteins with sequence identity to the proteins of the invention include, but are not limited to, PHI-BLAST (Pattern Hit Initiated BLAST, Zhang, et al., *Nucleic Acids Res.* 26(17):3986-90, 1998) and PSI-BLAST (Position-Specific Iterated BLAST, Altschul, et al., *Nucleic Acids Res.* 25(17):3389-402, 1997).

Programs may be used with default searching parameters. Alternatively, one or more search parameter may be adjusted. Selecting suitable search parameter values is within the abilities of one of ordinary skill in the art.

Preferred enzymes for use in the invention include those that are reduced, substantially reduced, or lacking in RNase H activity. Such enzymes that are reduced or substantially reduced in RNase H activity may be obtained by mutating, for example, the RNase H domain within the reverse transcriptase of interest, for example, by introducing one or more (e.g., one, two, three, four, five, ten, twelve, fifteen, twenty, thirty, etc.) point mutations, one or more (e.g., one, two, three, four, five, ten, twelve, fifteen, twenty, thirty, etc.) deletion mutations, and/or one or more (e.g., one, two, three, four, five, ten, twelve, fifteen, twenty, thirty, etc.) insertion mutations as described above. In some embodiments, the reverse transcriptase of the invention does not contain a modification or mutation in the RNase H domain and preferably does not contain a modification which reduces RNase H activity. In one aspect, the reverse transcriptase of the invention has 90%, 95%, or 100% of the RNase H activity compared to the corresponding wildtype reverse transcriptase.

By an enzyme "substantially reduced in RNase H activity" is meant that the enzyme has less than about 30%, less than about 25%, less than about 20%, more preferably less than about 15%, less than about 10%, less than about 7.5%, or less than about 5%, and most preferably less than about 5% or less than about 2%, of the RNase H activity of the corresponding wild-type or RNase $H^+$ enzyme, such as wild-type Moloney Murine Leukemia Virus (M-MLV), Avian Myeloblastosis Virus (AMV) or Rous Sarcoma Virus (RSV) reverse transcriptases. A reduction in RNase H activity means any reduction in the activity compared, for example, to the corresponding wild type or un-mutated or un-modified reverse transcriptase.

Reverse transcriptases having reduced, substantially reduced, undetectable or lacking RNase H activity have been previously described (see U.S. Pat. No. 5,668,005, U.S. Pat. No. 6,063,608, and PCT Publication No. WO 98/47912). The RNase H activity of any enzyme may be determined by a variety of assays, such as those described, for example, in U.S. Pat. No. 5,244,797, in Kotewicz, M. L., et al., *Nucl. Acids Res.* 16:265 (1988), in Gerard, G. F., et al., *FOCUS* 14(5):91 (1992), in PCT publication number WO 98/47912, and in U.S. Pat. No. 5,668,005, the disclosures of all of which are fully incorporated herein by reference. Reverse transcriptases having no detectable RNase H activity or lacking RNase H activity by one or more of the described assays are particularly preferred.

Particularly preferred enzymes for use in the invention include, but are not limited to, M-MLV RNase H− reverse transcriptase, RSV RNase H− reverse transcriptase, AMV RNase H− reverse transcriptase, RAV RNase H− reverse transcriptase, MAV RNase H− reverse transcriptase and HIV RNase H− reverse transcriptase. It will be understood by one of ordinary skill, however, that any enzyme capable of producing a DNA molecule from a ribonucleic acid molecule (i.e., an enzyme having reverse transcriptase activity) that is reduced, substantially reduced, or lacking in RNase H activity may be equivalently used in the compositions, methods and kits of the invention.

Enzymes for use in the invention also include those in which terminal deoxynucleotidyl transferase (TdT) activity has been reduced, substantially reduced, or eliminated. Such enzymes that are reduced or substantially reduced in terminal deoxynucleotidyl transferase activity, or in which TdT activity has been eliminated, may be obtained by mutating, for example, amino acid residues within the reverse transcriptase of interest which are in close proximity or in contact with the template-primer, for example, by introducing one or more (e.g., one, two, three, four, five, ten, twelve, fifteen, twenty, thirty, etc.) point mutations, one or more deletion mutations, and/or one or more insertion mutations. Reverse transcriptases which exhibit decreased TdT activity are described in U.S. application Ser. No. 09/808,124, filed Mar. 15, 2001 (the entire disclosure of which is incorporated herein by reference), and include reverse transcriptases with one or more alterations at amino acid positions equivalent or corresponding to Y64, M289, F309, T197 and/or Y133 of M-MLV reverse transcriptase.

In one aspect, amino acid substitutions are made at one or more of the above identified positions (i.e., amino acid positions equivalent or corresponding to Y64, M289, F309, T197 or Y133 of M-MLV reverse transcriptase). Thus, the amino acids at these positions may be substituted with any other amino acid including Ala, Arg, Asn, Asp, Cys, Gln, Glu, Gly, His, Ile, Leu, Lys, Met, Phe, Pro, Ser, Thr, Trp, Tyr, and Val. Specific example of reverse transcriptases which exhibit reduced, substantially reduced, or eliminated TdT activity include M-MLV reverse transcriptases (e.g., SUPERSCRIPT™ II) in which (1) the phenylalanine residue at position 309 has been replaced with asparagine, (2) the threonine residue at position 197 has been replaced with either alanine or glutamic acid, and/or (3) the tyrosine residue at position 133 has been replaced with alanine.

Enzymes for use in the invention also include those that exhibit increased fidelity. Reverse transcriptases which exhibit increased fidelity are described in U.S. Appl. No. 60/189,454, filed Mar. 15, 2000, and U.S. application Ser. No. 09/808,124, filed Mar. 15, 2001 (the entire disclosures of each of which are incorporated herein by reference), and include reverse transcriptases with one or more alterations at positions equivalent or corresponding to those set out below in Table 2.

TABLE 2

| RT | Amino Acid |
|---|---|
| M-MLV | Y64 (e.g., Y64W, Y64R), R116 (e.g., R116M), K152 (e.g., K152R), Q190 (e.g., Q190F), T197 (e.g., T197A, T197E), V223 (e.g., V223H, V223I, V223F), D124, H126, Y133 (e.g., Y133A, Y133H), F309 (e.g., F309N, F309R) |
| AMV | W25, R76, K110, Q149, T156, M182 |
| RSV | W25, R76, K110, Q149, T156, M182 |
| HIV | W24, R78, G112, Q151, A158, M184 |

In some embodiments of the invention, amino acid substitutions are made at one or more of the above identified positions. Thus, the amino acids at these positions may be substituted with any other amino acid including Ala, Arg, Asn, Arg, Asp, Cys, Gln, Glu, Gly, His, Ile, Leu, Lys, Met, Phe, Pro, Ser, Thr, Trp, Tyr, and Val. Specific example of reverse transcriptases which exhibit increased fidelity include M-MLV reverse transcriptase in which (1) the valine residue at position 223 has been replaced with histidine, phenylalanine or isoleucine, (2) the arginine residue at position 116 has been replaced with methionine, (3) the lysine residue at position 152 has been replaced with arginine, (4) the glutamic acid residue at position 190 has been replaced with phenylalanine, (5) the threonine residue at position 197 has been replaced with alanine or glutamic acid, (6) the phenylalanine residue at position 309 has been replaced with asparagine or arginine, (7) the tyrosine residue at position 133 has been replaced with histidine or alanine, and/or (8) the tyrosine residue at position 64 has been replaced with tryptophan or arginine.

Thus, in specific embodiments, the invention includes reverse transcriptases which exhibit increased thermostability and, optionally, also exhibit one or more of the following characteristics: (1) reduced or substantially reduced RNase H activity, (2) reduced or substantially reduced TdT activity, and/or (3) increased fidelity.

The invention also relates to reverse transcriptase mutants, where the mutations or substitutions have been made in a recognized region of the reverse transcriptase enzyme. Such regions include, but are not limited to, the fingers, palm, thumb, α-helix H, β-sheet 10, and/or β-sheet 11 regions. Thus, the invention includes reverse transcriptases which exhibit increased thermostability (as well as other properties), as described elsewhere herein, and have one or more (e.g., one, two, three, four, five, ten, fifteen, etc.) mutations or modification in the hand domain and, more specifically, in one or more regions including the fingers, palm and/or thumb regions.

Polypeptides having reverse transcriptase activity for use in the invention may be isolated from their natural viral or bacterial sources according to standard procedures for isolating and purifying natural proteins that are well-known to one of ordinary skill in the art (see, e.g., Houts, G. E., et al., *J. Virol.* 29:517 (1979); U.S. Pat. No. 5,668,005; and PCT publication number WO 98/47912). In addition, polypeptides having reverse transcriptase activity may be prepared by recombinant DNA techniques that are familiar to one of ordinary skill in the art (see, e.g., Kotewicz, M. L., et al., *Nucl. Acids Res.* 16:265 (1988); Soltis, D. A., and Skalka, A. M., *Proc. Natl. Acad. Sci. USA* 85:3372-3376 (1988)); U.S. Pat. No. 5,668,005; and PCT publication no. WO 98/47912.

In one aspect of the invention, mutant or modified reverse transcriptases are made by recombinant techniques. A number of cloned reverse transcriptase genes are available or may be obtained using standard recombinant techniques (see U.S. Pat. No. 5,668,005 and PCT Publication No. WO 98/47912).

To clone a gene or other nucleic acid molecule encoding a reverse transcriptase which will be modified in accordance with the invention, isolated, DNA which contains the reverse transcriptase gene or open reading frame may be used to construct a recombinant DNA library. Any vector, well known in the art, can be used to clone the reverse transcriptase of interest. However, the vector used must be compatible with the host in which the recombinant vector will be transformed.

Prokaryotic vectors for constructing the plasmid library include plasmids such as those capable of replication in *E. coli* such as, for example, pBR322, ColE1, pSC101, pUC-vectors (pUC18, pUC19, etc.: In: *Molecular Cloning, A Laboratory Manual*, Cold Spring Harbor Laboratory Press, Cold Spring Harbor, N.Y. (1982); and Sambrook et al., In: Molecular Cloning A Laboratory Manual (2d ed.) Cold Spring Harbor Laboratory Press, Cold Spring Harbor, N.Y. (1989)). *Bacillus* plasmids include pC194, pUB110, pE194, pC221, pC217, etc. Such plasmids are disclosed by Glyczan, T. In: *The Molecular Biology Bacilli*, Academic Press, York (1982), 307-329. Suitable *Streptomyces* plasmids include pIJ101 (Kendall et al., *J. Bacteriol.* 169:4177-4183 (1987)). *Pseudomonas* plasmids are reviewed by John et al., (*Rad. Insec. Dis.* 8:693-704 (1986)), and Igaki, (*Jpn. J. Bacteriol.* 33:729-742 (1978)). Broad-host range plasmids or cosmids, such as pCP13 (Darzins and Chakrabarty, *J. Bacteria* 159: 9-18 (1984)) can also be used for the present invention. Preferred vectors for cloning the genes and nucleic acid molecules of the present invention are prokaryotic vectors. Preferably, pBAD, pCP13 and pUC vectors are used to clone the genes of the present invention. Other suitable vectors are known to those skilled in the art and are commercially available, for example, from Invitrogen Corporation, Carlsbad, Calif.

Suitable host for cloning the reverse transcriptase genes and nucleic acid molecules of interest are prokaryotic hosts. One example of a prokaryotic host is *E. coli*. However, the desired reverse transcriptase genes and nucleic acid molecules of the present invention may be cloned in other prokaryotic hosts including, but not limited to, hosts in the genera *Escherichia, Bacillus, Streptomyces, Pseudomonas, Salmonella, Serratia*, and *Proteus*. Bacterial hosts of particular interest include *E. coli* DH10B, which may be obtained from Invitrogen Corporation (Carlsbad, Calif.).

Eukaryotic hosts for cloning and expression of the reverse transcriptase of interest include yeast, fungal, and mammalian cells. Expression of the desired reverse transcriptase in such eukaryotic cells may require the use of eukaryotic regulatory regions which include eukaryotic promoters. Cloning and expressing the reverse transcriptase gene or nucleic acid molecule in eukaryotic cells may be accomplished by well known techniques using well known eukaryotic vector systems.

Once a DNA library has been constructed in a particular vector, an appropriate host is transformed by well known techniques. Transformed cells are plated at a density to produce approximately 200-300 transformed colonies per petri dish. For selection of reverse transcriptase, colonies are then screened for the expression of a reverse transcriptase or a thermostable reverse transcriptase as described in the Examples below. Briefly, overnight cultures of individual transformant colonies are assayed directly for reverse transcriptase or thermostable reverse transcriptase activity and/or other desirable activities using a labeled deoxynucleotide and analyzed for the presence of labeled product. If thermostable reverse transcriptase activity and/or other desirable activity is detected, the mutant is sequenced to determine which amino acids maintained reverse transcriptase activity. The gene or nucleic acid molecule encoding a reverse transcriptase of the present invention can be cloned using techniques known to those in the art.

Modifications or Mutations of Polymerases

In accordance with the invention, one or more mutations may be made in any reverse transcriptase in order to increase the thermostability of the enzyme, or confer other properties described herein upon the enzyme, in accordance with the invention. Such mutations include point mutations, frame shift mutations, deletions and insertions. Preferably, one or more point mutations, resulting in one or more amino acid substitutions, are used to produce reverse transcriptases having enhanced or increased thermostability. In a preferred aspect of the invention, one or more mutations at positions equivalent or corresponding to position H204 (e.g., H204R) and/or T306 (e.g., T306K or T306R) of M-MLV reverse transcriptase may be made to produced the desired result in other reverse transcriptases of interest.

In specific embodiments, one or more mutations at positions equivalent or corresponding to position L52, Y64, R116, Y133, K152 Q190, T197, H204, V223, M289, T306 and/or F309 of M-MLV reverse transcriptase may be made to produced a desired result (e.g., increased thermostability, increased fidelity, decreased TdT activity, etc.). Thus, in specific embodiments, using amino acid positions of M-MLV reverse transcriptase as a frame of reference, proteins of the invention include reverse transcriptases (e.g., M-MLV reverse transcriptase, AMV reverse transcriptase, HIV reverse transcriptase, RSV reverse transcriptase, etc.) having one or more of the following alterations: L52P, Y64S, Y64W, Y64R, R116M, Y133A, Y133H, K152R, K152M, Q190F, T197R, T197E, T197A, T197K, H204R, V223H, V223F, V223I, M289L, T306K, T306R, F309R, and/or F309N, as well as compositions containing these proteins, nucleic acid molecules which encode these proteins, and host cells which contain these nucleic acid molecules.

Mutations in reverse transcriptases which alter thermostability properties of these proteins may be present in conjunction with alterations which either have little or no effect on activities normally associated with reverse transcriptases (e.g., RNase H activity, reverse transcriptase or polymerase activity, terminal deoxynucleotidyl transferase (TdTase) activity, etc.) or substantially alter one or more activities normally associated with reverse transcriptases. One example of a reverse transcriptase which has such a combination of mutations is a M-MLV reverse transcriptase which has the following alterations: K152M, V223H.

One mutation which has been shown to enhanced the fidelity of SuperScript™ II (Invitrogen Corporation (Carlsbad, Calif.) Catalog No. 18064-022) is V223H (see U.S. Appl. No. 60/189,454, filed Mar. 15, 2000, U.S. application Ser. No. 09/808,124, filed Mar. 15, 2001, and PCT publication number WO 01/68895, the entire disclosures of each of which are incorporated herein by reference). However, the V223H alteration decreases the thermostability of this enzyme. One mutant was identified, K152M, which suppress the destabilizing effect of enzymes having the V223H mutation. Thus, the invention includes M-MLV reverse transcriptase which contain alterations at positions K152 and V223 and exhibit both increased fidelity and increased thermostability. Specific examples of such reverse transcriptases are those in which K152 is replaced with methionine and V223 is replaced with histidine. Other reverse transcriptases (e.g., AMV reverse transcriptase, HIV reverse transcriptase, RSV reverse transcriptase, etc.) with corresponding alterations are also included within the scope of the invention.

SuperScript™ II is an RNase H− reverse transcriptase from M-MLV which has the following substitutions: D524G, E562Q, and D583N (see U.S. Pat. Nos. 5,017,492, 5,244,797, 5,405,776, 5,668,005, and 6,063,608, the entire disclosures of which are incorporated herein by reference). The invention includes reverse transcriptases that contain alterations, such as those reference positions (i.e., 524, 562, and/or 583) or equivalent positions.

One or more amino acid substitutions are made at one or more selected positions for any reverse transcriptase of interest. Thus, the amino acids at the selected positions may be substituted with any other amino acid including Ala, Arg, Asn, Asp, Cys, Gln, Glu, Gly, His, Ile, Leu, Lys, Met, Phe, Pro, Ser, Thr, Trp, Tyr, and Val. In some preferred embodiments, the selected amino acid will be a non-charged surface residue and will be replaced by a charged residue. In some preferred embodiments, the non-charged surface residue may be replaced by a positively charged amino acid (e.g., lysine or arginine). In one aspect, a charged residue will be replaced with an un-charged residue. In one aspect, a non-charged residue will be replaced with a negatively charged residue. In another aspect, a negatively charged residue will be replaced with a positively charged residue and/or a positively charged residue will be replaced with a negatively charged residue.

The corresponding positions of M-MLV reverse transcriptase identified above may be readily identified for other reverse transcriptases by one with skill in the art. Thus, given the defined region and the assays described in the present application, one with skill in the art can make one or a number of modifications which would result in increased thermostability and/or other desired features of any reverse transcriptase of interest. Residues to be modified in accordance with the present invention may include those listed in Table 1 above.

The nucleotide sequences for M-MLV reverse transcriptase (Shinnick et al., 1981, *Nature* 293:543-548; Georgiadis et al., 1995, *Structure* 3:879-892), AMV reverse transcriptase (Joliot et al., 1993, *Virology* 195:812-819), RSV reverse transcriptase (Schwartz et al., 1983, *Cell* 32:853-859), and HIV reverse transcriptase (Wong-Staal et al., 1985, *Nature* 313:277-284) are known and are incorporated herein by reference in their entirety.

Preferably, oligonucleotide directed mutagenesis is used to create the mutant reverse transcriptases which allows for all possible classes of base pair changes at any determined site along the encoding DNA molecule.

Enhancing Expression of Reverse Transcriptases

To optimize expression of reverse transcriptases of the present invention, inducible or constitutive promoters are well known and may be used to express high levels of a reverse transcriptase structural gene in a recombinant host. Similarly, high copy number vectors, well known in the art, may be used to achieve high levels of expression. Vectors having an inducible high copy number may also be useful to enhance expression of the reverse transcriptases of the invention in a recombinant host.

To express the desired structural gene in a prokaryotic cell (such as *E. coli, B. subtilis, Pseudomonas*, etc.), it is preferable to operably link the desired structural gene to a functional prokaryotic promoter. However, the natural promoter of the reverse transcriptase gene may function in prokaryotic hosts allowing expression of the reverse transcriptase gene. Thus, the natural promoter or other promoters may be used to express the reverse transcriptase gene. Such other promoters that may be used to enhance expression include constitutive or regulatable (i.e., inducible or derepressible) promoters. Examples of constitutive promoters include the int promoter of bacteriophage λ, and the bla promoter of the β-lactamase gene of pBR322. Examples of inducible prokaryotic promoters include the major right and left promoters of bacteriophage λ ($P_R$ and $P_L$), trp, recA, lacZ, lacI, tet, gal, trc, ara BAD (Guzman, et al., 1995, *J. Bacteriol.* 177(14):4121-4130) and tac promoters of *E. coli*. The *B. subtilis* promoters include α-amylase (Ulmanen et al., *J. Bacteriol* 162:176-182 (1985)) and *Bacillus* bacteriophage promoters (Gryczan, T., In: *The Molecular Biology Of Bacilli*, Academic Press, New York (1982)). *Streptomyces* promoters are described by Ward et al., *Mol. Gen. Genet.* 203:468478 (1986)). Prokaryotic promoters are also reviewed by Glick, *J. Ind. Microbiol.* 1:277-282 (1987); Cenatiempto, Y., *Biochimie* 68:505-516 (1986); and Gottesman, *Ann. Rev. Genet.* 18:415-442 (1984). Expression in a prokaryotic cell also requires the presence of a ribosomal binding site upstream of the gene-encoding sequence. Such ribosomal binding sites are disclosed, for example, by Gold et al., *Ann. Rev. Microbiol.* 35:365404 (1981).

To enhance the expression of polymerases of the invention in a eukaryotic cell, well known eukaryotic promoters and hosts may be used. Enhanced expression of the polymerases may be accomplished in a prokaryotic host. One example of a prokaryotic host suitable for use with the present invention is *Escherichia coli.*

Isolation and Purification of Reverse Transcriptases

The enzyme(s) of the present invention is preferably produced by growth in culture of the recombinant host containing and expressing the desired reverse transcriptase gene. However, the reverse transcriptase of the present invention may be isolated from any strain, organism, or tissue which produces the reverse transcriptase of the present invention. Fragments of the reverse transcriptase are also included in the present invention. Such fragments include proteolytic fragments and fragments having reverse transcriptase activity. Such fragments may also be produced by cloning and expressing portions of the reverse transcriptase gene of interest, creating frame shift mutations and/or by adding one or more stop codons in the gene of interest for expression of a truncated protein or polypeptide. Preferably, polypeptides of the invention may be purified and/or isolated from a cell or organism expressing them, which may be a wild type cell or organism or a recombinant cell or organism. In some embodiments, such polypeptides may be substantially isolated from the cell or organism in which they are expressed.

Any nutrient that can be assimilated by a host containing the cloned reverse transcriptase gene may be added to the culture medium. Optimal culture conditions should be selected case by case according to the strain used and the composition of the culture medium. Antibiotics may also be added to the growth media to insure maintenance of vector DNA containing the desired gene to be expressed. Media formulations have been described in DSM or ATCC Catalogs and Sambrook et al., *In: Molecular Cloning, a Laboratory Manual* (2nd ed.), Cold Spring Harbor Laboratory Press, Cold Spring Harbor, N.Y. (1989).

Recombinant host cells producing the reverse transcriptases of this invention can be separated from liquid culture, for example, by centrifugation. In general, the collected microbial cells are dispersed in a suitable buffer, and then broken open by ultrasonic treatment or by other well known procedures to allow extraction of the enzymes by the buffer solution. After removal of cell debris by ultracentrifugation or centrifugation, the reverse transcriptases can be purified by standard protein purification techniques such as extraction, precipitation, chromatography, affinity chromatography, electrophoresis or the like. Assays to detect the presence of the reverse transcriptase during purification are well known in the art and can be used during conventional biochemical purification methods to determine the presence of these enzymes.

In some embodiments, reverse transcriptases of the present invention may be modified to contain an affinity tag in order to facilitate the purification of the reverse transcriptase. Suitable affinity tags are well known to those skilled in the art and include, but are not limited to, repeated sequences of amino acids such as six histidines, epitopes such as the hemagglutinin epitope and the myc epitope, and other amino acid sequences that permit the simplified purification of the reverse transcriptase.

The invention further relates to fusion proteins comprising (1) a protein, or fragment thereof, having one or more activity associated with a reverse transcriptase and (2) a tag (e.g., an affinity tag). In particular embodiments, the invention includes a reverse transcriptase (e.g., a thermostable reverse transcriptase) described herein having one or more (e.g., one, two, three, four, five, six, seven, eight, etc.) tags. These tags may be located, for example, (1) at the N-terminus, (2) at the C-terminus, or (3) at both the N-terminus and C-terminus of the protein, or a fragment thereof having one or more activities associated with a reverse transcriptase. A tag may also be located internally (e.g., between regions of amino acid sequence derived from a reverse transcriptase and/or attached to an amino acid side chain). For example, Ferguson et al., *Protein Sci.* 7:1636-1638 (1998), describe a siderophore receptor, FhuA, from *Escherichia coli* into which an affinity tag (i.e., a hexahistidine sequence) was inserted. This tag was shown to function in purification protocols employing metal chelate affinity chromatography. Additional fusion proteins with internal tags are described in U.S. Pat. No. 6,143,524, the entire disclosure of which is incorporated herein by reference.

Tags used to prepare compositions of the invention may vary in length but will typically be from about 5 to about 500, from about 5 to about 100, from about 10 to about 100, from about 15 to about 100, from about 20 to about 100, from about 25 to about 100, from about 30 to about 100 from about 35 to about 100, from about 40 to about 100, from about 45 to about 100, from about 50 to about 100, from about 55 to about 100, from about 60 to about 100, from about 65 to about 100, from about 70 to about 100, from about 75 to about 100, from about 80 to about 100, from about 85 to about 100, from about 90 to about 100, from about 95 to about 100, from about 5 to about 80, from about 10 to about 80, from about 20 to about 80, from about 30 to about 80, from about 40 to about 80, from about 50 to about 80, from about 60 to about 80, from about 70 to about 80, from about 5 to about 60, from about 10 to about 60, from about 20 to about 60, from about 30 to about 60, from about 40 to about 60, from about 50 to about 60, from about 5 to about 40, from about 10 to about 40, from about 20 to about 40, from about 30 to about 40, from about 5 to about 30, from about 10 to about 30, from about 20 to about 30, from about 5 to about 25, from about 10 to about 25, or from about 15 to about 25 amino acid residues in length.

Tags used to prepare compositions of the invention include those which contribute to the thermostability of the fusion protein. Thus, these tags may be at least partly responsible, for example, for a particular protein (e.g., a protein having one or more activities of a reverse transcriptase activity) having increased thermostability. Examples of tags that enhance the thermostability of a reverse transcriptase (i.e., M-MLV reverse transcriptase) include, but are not limited to, tags having the following amino acid sequences: MGGSHHHHHHGMASMTGGQQMGRDLYDDDDKH, which corresponds to amino acids 1-32 of the sequence set forth in SEQ ID NO:2 and Table 3, and MASGTGGQQMGRDLYDDDDKH, (SEQ ID NO:3). Fragments of these tags may also be used in accordance with the invention (preferably those having 3 or more, 5 or more, 10 or more, or 15 or more amino acids) Thus, the invention includes, in part, reverse transcriptases, or fragments thereof that comprise tags and demonstrate enhanced thermostability. Using well known methods, one of skill in the art can attach one or more of above-mentioned tags to one or more RT enzymes, or fragments thereof having reverse transcriptase activity, to produce a thermostable RT enzyme or fragment thereof. Suitable RT enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, R. K., et al., *Science* 239:487-491 (1988); U.S. Pat. Nos. 4,889,818 and 4,965,188), Tne DNA polymerase (PCT Publication No. WO 96/10640), Tma DNA polymerase (U.S. Pat. No. 5,374,553) and mutants, fragments, variants or derivatives thereof (see, e.g., commonly owned U.S. Pat. Nos. 5,948,614 and 6,015,668, which are incorporated by reference herein in their entireties). Reverse transcriptases for use in the invention also include retroviral reverse transcriptases such as M-MLV reverse transcriptase, AMV reverse transcriptase, RSV reverse transcriptase, RAV reverse transcriptase, MAV reverse transcriptase, and generally ASLV reverse transcriptases.

Tags used in the practice of the invention may serve any number of purposes and a number of tags may be added to impart one or more different functions to the reverse transcriptase of the invention. For example, tags may (1) contribute to protein-protein interactions both internally within a protein and with other protein molecules, (2) make the protein amenable to particular purification methods, (3) enable one to identify whether the protein is present in a composition; or (4) give the protein other functional characteristics.

Examples of tags which may be used in the practice of the invention include metal binding domains (e.g., a polyhistidine segments such as a three, four, five, six, or seven histidine region), immunoglobulin binding domains (e.g., (1) Protein A; (2) Protein G; (3) T cell, B cell, and/or Fc receptors; and/or (4) complement protein antibody-binding domain); sugar binding domains (e.g., a maltose binding domain, chitin-binding domain); and detectable domains (e.g., at least a portion of beta-galactosidase). Fusion proteins may contain one or more tags such as those described above. Typically, fusion proteins that contain more than one tag will contain these tags at one terminus or both termini (i.e., the N-terminus and the C-terminus) of the reverse transcriptase, although one or more tags may be located internally instead of or in addition to those present at termini. Further, more than one tag may be present at one terminus, internally and/or at both termini of the reverse transcriptase. For example, three consecutive tags could be linked end-to-end at the N-terminus of the reverse transcriptase. The invention further include compositions and reaction mixture which contain the above fusion proteins, as well as methods for preparing these fusion proteins, nucleic acid molecules (e.g., vectors) which encode these fusion proteins and recombinant host cells which contain these nucleic acid molecules. The invention also includes methods for using these fusion proteins as described elsewhere herein (e.g., methods for reverse transcribing nucleic acid molecules).

Tags which enable one to identify whether the fusion protein is present in a composition include, for example, tags which can be used to identify the protein in an electrophoretic gel. A number of such tags are known in the art and include epitopes and antibody binding domains which can be used for Western blots.

The amino acid composition of the tags for use in the present invention may vary. In some embodiments, a tag may contain from about 1% to about 5% amino acids that have a positive charge at physiological pH, e.g., lysine, arginine, and histidine, or from about 5% to about 10% amino acids that have a positive charge at physiological pH, or from about 10% to about 20% amino acids that have a positive charge at physiological pH, or from about 10% to about 30% amino acids that have a positive charge at physiological pH, or from about 10% to about 50% amino acids that have a positive charge at physiological pH, or from about 10% to about 75% amino acids that have a positive charge at physiological pH. In some embodiments, a tag may contain from about 1% to about 5% amino acids that have a negative charge at physiological pH, e.g., aspartic acid and glutamic acid, or from about 5% to about 10% amino acids that have a negative charge at physiological pH, or from about 10% to about 20% amino acids that have a negative charge at physiological pH, or from about 10% to about 30% amino acids that have a negative charge at physiological pH, or from about 10% to about 50% amino acids that have a negative charge at physiological pH, or from about 10% to about 75% amino acids that have a negative charge at physiological pH. In some embodiments, a tag may comprise a sequence of amino acids that contains two or more contiguous charged amino acids that may be the same or different and may be of the same or different charge. For example, a tag may contain a series (e.g., two, three, four, five, six, ten etc.) of positively charged amino acids that may be the same or different. A tag may contain a series (e.g., two, three, four, five, six, ten etc.) of negatively charged amino acids that may be the same or different. In some embodiments, a tag may contain a series (e.g., two, three, four, five, six, ten etc.) of alternating positively charged and negatively charged amino acids that may be the same or different (e.g., positive, negative, positive, negative, etc.). Any of the above-described series of amino acids (e.g., positively charged, negatively charged or alternating charge) may comprise one or more neutral polar or non-polar amino acids (e.g., two, three, four, five, six, ten etc.) spaced between the charged amino acids. Such neutral amino acids may be evenly distributed through out the series of charged amino acids (e.g., charged, neutral, charged, neutral) or may be unevenly distributed throughout the series (e.g., charged, a plurality of neutral, charged, neutral, a plurality of charged, etc.). In some embodiments, tags to be attached to the polypeptides of the invention may have an overall charge at physiological pH (e.g., positive charge or negative charge). The size of the overall charge may vary, for example, the tag may contain a net plus one, two, three, four, five, etc. or may possess a net negative one, two, three, four, five, etc. The present invention also relates to reverse transcriptases (e.g., thermostable reverse transcriptases) comprising one or more of the above-described tag sequences, vectors encoding such reverse transcriptases, host cells reaction mixture, compositions and reaction mixtures comprising such reverse transcriptases, as well as kits comprising containers containing such reverse transcriptases.

In some embodiments, it may be desirable to remove all or a portion of a tag sequence from a fusion protein comprising a tag sequence and a sequence having reverse transcriptase (RT) activity. In embodiments of this type, one or more amino acids forming a cleavage site, e.g., for a protease enzyme, may be incorporated into the primary sequence of the fusion protein. The cleavage site may be located such that cleavage at the site may remove all or a portion of the tag sequence from the fusion protein. In some embodiments, the cleavage site may be located between the tag sequence and the sequence having RT activity such that all of the tag sequence is removed by cleavage with a protease enzyme that recognizes the cleavage site. Examples of suitable cleavage sites include, but are not limited to, the Factor Xa cleavage site having the sequence Ile-Glu-Gly-Arg (SEQ ID NO:4), which is recognized and cleaved by blood coagulation factor Xa, and the thrombin cleavage site having the sequence Leu-Val-Pro-Arg (SEQ ID NO:5), which is recognized and cleaved by thrombin. Other suitable cleavage sites are known to those skilled in the art and may be used in conjunction with the present invention.

The reverse transcriptases of the invention preferably have specific activities (e.g., RNA-directed DNA polymerase activity and/or RNase H activity) greater than about 5 units/mg, more preferably greater than about 50 units/mg, still more preferably greater than about 100 units/mg, 250 units/mg, 500 units/mg, 1000 units/mg, 5000 units/mg or 10,000 units/mg, and most preferably greater than about 15,000 units/mg, greater than about 16,000 units/mg, greater than about 17,000 units/mg, greater than about 18,000 units/mg, greater than about 19,000 units/mg and greater than about 20,000 units/mg. In some embodiments, the reverse transcriptases of the present invention may have specific activities greater than about 50,000 units/mg, greater than about 100,000 units/mg, greater than about 150,000 units/mg, greater than about 200,000 units/mg, greater than about 250,000 units/mg and greater than about 300,000 units/mg. Preferred ranges of specific activities for the reverse transcriptases of the invention include a specific activity from about 5 units/mg to about 750,000 units/mg, a specific activity from about 5 units/mg to about 500,000 units/mg, from about 5 units/mg to about 300,000 units/mg, a specific activity of from about 50 units/mg to about 750,000 units/mg, a specific activity from about 100 units/mg to about 750,000 units/mg, a specific activity from about 250 units/mg to about 750,000 units/mg, a specific activity from about 500 units/mg to about 750,000 units/mg, a specific activity from about 1000 units/mg to about 750,000 units/mg, a specific activity from about 5000 units/mg to about 750,000 units/mg, a specific activity from about 10,000 units/mg to about 750,000 units/mg, a specific activity from about 25,000 units/mg to about 750,000 units/mg, a specific activity from about 100 units/mg to about 500 units/mg, a specific activity from about 100 units/mg to about 400 units/mg, and a specific activity from about 200 units/mg to about 500 units/mg. Other preferred ranges of specific activities include a specific activity of from about 200,000 units/mg to about 350,000 units/mg, a specific activity from about 225,000 units/mg to about 300,000 units/mg, a specific activity from about 250,000 units/mg to about 300,000 units/mg, a specific activity of from about 200,000 units/mg to about 750,000 units/mg, a specific activity of from about 200,000 units/mg to about 500,000 units/mg, a specific activity of from about 200,000 units/mg to about 400,000 units/mg, a specific activity of from about 250,000 units/mg to about 750,000 units/mg, a specific activity of from about 250,000 units/mg to about 500,000 units/mg, and a specific activity of from about 250,000 units/mg to about 400,000 units/mg. Preferably, the lower end of the specific activity range may vary from 50, 100, 200, 300, 400, 500, 700, 900, 1,000, 5,000, 10,000, 20,000, 30,000, 35,000, 40,000, 45,000, 50,000, 55,000, 60,000, 65,000, 70,000, 75,000, and 80,000 units/mg, while the upper end of the range may vary from 750,000, 650,000, 600,000, 550,000, 500,000, 450,000, 400,000, 350,000, 300,000, 250,000, 200,000, 150,000, 140,000, 130,000, 120,000, 110,000, 100,000, and 90,000 units/mg. Specific activity may be determined using enzyme assays and protein assays well known in the art. DNA polymerase assays and RNase H assays are described, for example, in U.S. Pat. No. 5,244,797 and WO 98/47912. In some embodiments of the present invention, the specific activity of the thermostable reverse transcriptase prepared in accordance with the present invention may be higher than the specific activity of a non-thermostable reverse transcriptase. In some embodiments, the specific activity of the thermostable reverse transcriptase may be 5%, 10,%, 15%, 20%, 25%, 30%, 40%, 50%, 60%, 70%, 80%, 90%, 100% or more higher than the specific activity of a corresponding non-thermostable reverse transcriptase. In some preferred embodiments, the specific activity of the thermostable reverse transcriptase according to the present invention may be 30% or more higher than the specific activity of a corresponding non-thermostable reverse transcriptase. In accordance with the invention, specific activity is a measurement of the enzymatic activity (in units) of the protein or enzyme relative to the total amount of protein or enzyme used in a reaction. The measurement of a specific activity may be determined by standard techniques well-known to one of ordinary skill in the art.

The reverse transcriptases of the invention may be used to make nucleic acid molecules from one or more templates. Such methods comprise mixing one or more nucleic acid templates (e.g., mRNA, and more preferably a population of mRNA molecules) with one or more of the reverse transcriptases of the invention and incubating the mixture under conditions sufficient to make one or more nucleic acid molecules complementary to all or a portion of the one or more nucleic acid templates.

The invention also relates to methods for the amplification of one or more nucleic acid molecules comprising mixing one or more nucleic acid templates with one of the reverse transcriptases of the invention, and incubating the mixture under conditions sufficient to amplify one or more nucleic acid molecules complementary to all or a portion of the one or more nucleic acid templates. Such amplification methods may further comprise the use of one or more DNA polymerases and may be employed as in standard RT-PCR reactions.

The invention also concerns methods for the sequencing of one or more nucleic acid molecules comprising (a) mixing one or more nucleic acid molecules to be sequenced with one or more primer nucleic acid molecules, one or more reverse transcriptases of the invention, one or more nucleotides and one or more terminating agents; (b) incubating the mixture under conditions sufficient to synthesize a population of nucleic acid molecules complementary to all or a portion of the one or more nucleic acid molecules to be sequenced; and (c) separating the population of nucleic acid molecules to determine the nucleotide sequence of all or a portion of the one or more nucleic acid molecules to be sequenced.

The invention also concerns nucleic acid molecules produced by such methods (which may be full-length cDNA molecules), vectors (particularly expression vectors) comprising these nucleic acid molecules and host cells comprising these vectors and nucleic acid molecules.

Sources of DNA Polymerase

A variety of DNA polymerases are useful in accordance with the present invention. Such polymerases include, but are not limited to, *Thermus thermophilus* (Tth) DNA polymerase, *Thermus aquaticus* (Taq) DNA polymerase, *Thermotoga neapolitana* (Tne) DNA polymerase, *Thermotoga maritima* (Tma) DNA polymerase, *Thermococcus litoralis* (Tli or VENT™) DNA polymerase, *Thermococcus kodakaraensis* KOD1 DNA Polymerase, *Pyrococcus furiosis* (Pfu) DNA polymerase, *Pyrococcus* species GB-D (DEEPVENT™) DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, *Mycobacterium* spp. DNA polymerase (Mtb, Mlep), and mutants, variants and derivatives thereof.

DNA polymerases used in accordance with the invention may be any enzyme that can synthesize a DNA molecule from a nucleic acid template, typically in the 5' to 3' direction. Such polymerases may be mesophilic or thermophilic, but are preferably thermophilic. Mesophilic polymerases include T5 DNA polymerase, T7 DNA polymerase, Klenow fragment DNA polymerase, DNA polymerase III, and the like. Preferred DNA polymerases are thermostable DNA polymerases such as Taq, Tne, Tma, Pfu, VENT™, DEEPVENT™, Tth and mutants, variants and derivatives thereof (U.S. Pat. No. 5,436,149; U.S. Pat. No. 5,512,462; PCT Publication No. WO 92/06188; PCT Publication No. WO 92/06200; PCT Publication No. WO 96/10640; Barnes, W. M., *Gene* 112:29-35 (1992); Lawyer, F. C., et al., *PCR Meth. Appl.* 2:275-287 (1993); Flaman, J.-M., et al., *Nucl. Acids Res.* 22(15):3259-3260 (1994)). For amplification of long nucleic acid molecules (e.g., nucleic acid molecules longer than about 3-5 Kb in length), at least two DNA polymerases (one substantially lacking 3' exonuclease activity and the other having 3' exonuclease activity) are typically used. See U.S. Pat. No. 5,436,149; U.S. Pat. No. 5,512,462; Barnes, W. M., *Gene* 112:29-35 (1992); PCT Publication No. WO 98/06736; and commonly owned, co-pending U.S. patent application Ser. No. 08/801,720, filed Feb. 14, 1997, the disclosures of all of which are incorporated herein in their entireties. Examples of DNA polymerases substantially lacking in 3' exonuclease activity include, but are not limited to, Taq, Tne($exo^-$), Tma, Pfu($exo^-$), Pwo and Tth DNA polymerases, and mutants, variants and derivatives thereof. Nonlimiting examples of DNA polymerases having 3' exonuclease activity include Pfu, DEEPVENT™ and Tli/VENT™ and mutants, variants and derivatives thereof.

Formulation of Compositions and Reaction Mixtures

To form the compositions of the present invention, one or more reverse transcriptases are preferably admixed in a buffered salt solution. One or more DNA polymerases and/or one or more nucleotides, and/or one or more primers may optionally be added to make the compositions of the invention. More preferably, the enzymes are provided at working concentrations in stable buffered salt solutions. The terms "stable" and "stability" as used herein generally mean the retention by a composition, such as an enzyme composition, of at least 70%, preferably at least 80%, and most preferably at least 90%, of the original enzymatic activity (in units) after the enzyme or composition containing the enzyme has been stored for about one week at a temperature of about 4° C., about two to six months at a temperature of about −20° C., and about six months or longer at a temperature of about −80° C. As used herein, the term "working concentration" means the concentration of an enzyme that is at or near the optimal concentration used in a solution to perform a particular function (such as reverse transcription of nucleic acids).

The water used in forming the compositions of the present invention is preferably distilled, deionized and sterile filtered (through a 0.1-0.2 micrometer filter), and is free of contamination by DNase and RNase enzymes. Such water is available commercially, for example from Sigma Chemical Company (Saint Louis, Mo.), or may be made as needed according to methods well known to those skilled in the art.

In addition to the enzyme components, the present compositions preferably comprise one or more buffers and cofactors necessary for synthesis of a nucleic acid molecule such as a cDNA molecule. Particularly preferred buffers for use in forming the present compositions are the acetate, sulfate, hydrochloride, phosphate or free acid forms of Tris-(hydroxymethyl)aminomethane (TRIS®), although alternative buffers of the same approximate ionic strength and pKa as TRIS® may be used with equivalent results. In addition to the buffer salts, cofactor salts such as those of potassium (preferably potassium chloride or potassium acetate) and magnesium (preferably magnesium chloride or magnesium acetate) are included in the compositions. Addition of one or more carbohydrates and/or sugars to the compositions and/or synthesis reaction mixtures may also be advantageous, to support enhanced stability of the compositions and/or reaction mixtures upon storage. Preferred such carbohydrates or sugars for inclusion in the compositions and/or synthesis reaction mixtures of the invention include, but are not limited to, sucrose, trehalose, glycerol, and the like. Furthermore, such carbohydrates and/or sugars may be added to the storage buffers for the enzymes used in the production of the enzyme compositions and kits of the invention. Such carbohydrates and/or sugars are commercially available from a number of sources, including Sigma (St. Louis, Mo.).

It is often preferable to first dissolve the buffer salts, cofactor salts and carbohydrates or sugars at working concentrations in water and to adjust the pH of the solution prior to addition of the enzymes. In this way, the pH-sensitive enzymes will be less subject to acid- or alkaline-mediated inactivation during formulation of the present compositions.

To formulate the buffered salts solution, a buffer salt which is preferably a salt of Tris(hydroxymethyl)aminomethane (TRIS®), and most preferably the hydrochloride salt thereof, is combined with a sufficient quantity of water to yield a solution having a TRIS® concentration of 5-150 millimolar, preferably 10-60 millimolar, and most preferably about 20-60 millimolar. To this solution, a salt of magnesium (preferably either the chloride or acetate salt thereof) or other divalent cation, may be added to provide a working concentration thereof of 1-10 millimolar, preferably 1.5-8.0 millimolar, and most preferably about 3-7.5 millimolar. A salt of potassium (preferably a chloride or acetate salt of potassium), or other monovalent cation (e.g., Na), may also be added to the solution, at a working concentration of 10-100 millimolar and most preferably about 75 millimolar. A reducing agent, such as dithiothreitol, may be added to the solution, preferably at a final concentration of about 1-100 mM, more preferably a concentration of about 5-50 mM or about 7.5-20 mM, and most preferably at a concentration of about 10 mM. Preferred concentrations of carbohydrates and/or sugars for inclusion in the compositions of the invention range from about 5% (w/v) to about 30% (w/v), from about 7.5% (w/v) to about 25% (w/v), from about 10% (w/v) to about 25% (w/v), from about 10% (w/v) to about 20% (w/v), and preferably from about 10% (w/v) to about 15% (w/v). A small amount of a salt of ethylenediaminetetraacetate (EDTA), such as disodium EDTA, may also be added (preferably about 0.1 millimolar), although inclusion of EDTA does not appear to be essential to the function or stability of the compositions of the present invention. After addition of all buffers and salts, this buffered salt solution is mixed well until all salts are dissolved, and the pH is adjusted using methods known in the art to a pH value of from about 7.4 to about 9.2, preferably from about 8.0 to about 9.0, and most preferably to about 8.4.

To these buffered salt solutions, the enzymes (reverse transcriptases and/or DNA polymerases) are added to produce the compositions of the present invention. M-MLV reverse transcriptases are preferably added at a working concentration in the solution of from about 1,000 to about 50,000 units per milliliter, from about 2,000 to about 30,000 units per milliliter, from about 2,500 to about 25,000 units per milliliter, from about 3,000 to about 22,500 units per milliliter, from about 4,000 to about 20,000 units per milliliter, and most preferably at a working concentration of from about 5,000 to about 20,000 units per milliliter. In some embodiments, a reverse transcriptases of the invention (e.g., an M-MLV reverse transcriptase) may be added at a working concentration described above in a first strand reaction mixture (e.g., a reaction to reverse transcribe an mRNA molecule) and/or in a couple RT/PCR. A suitable concentration of a reverse transcriptase of the invention for these reactions may be from about 5,000 units/ml to about 50,000 units/ml, from about 5,000 units/ml to about 40,000 units/ml, from about 5,000 units/ml to about 30,000 units/ml, or from about 5,000 units/ml to about 20,000 units/ml of reverse transcriptase. A reaction may be conducted in a volume of 20 μl to 50 μl and such a reaction may contain 50 units, 100, units, 200 units, 300 units, 400 units or more of a reverse transcriptase of the invention. Those skilled in the art will appreciate that adding additional reverse transcriptase may allow increased synthesis of the first strand (e.g., the DNA strand complementary to the mRNA strand) at the expense of increased enzyme usage. The skilled artisan can determine without undue experimentation the amount of a reverse transcriptase of the invention to add to a reaction in order to produce a desired amount of product at an acceptable expense.

AMV reverse transcriptases, RSV reverse transcriptases and HIV reverse transcriptases, including those of the invention described above, are preferably added at a working concentration in the solution of from about 100 to about 5000 units per milliliter, from about 125 to about 4000 units per milliliter, from about 150 to about 3000 units per milliliter, from about 200 to about 2500 units per milliliter, from about 225 to about 2000 units per milliliter, and most preferably at a working concentration of from about 250 to about 1000 units per milliliter. The enzymes in the thermophilic DNA polymerase group (Taq, Tne, Tma, Pfu, VENT, DEEPVENT, Tth and mutants, variants and derivatives thereof) are preferably added at a working concentration in the solution of from about 100 to about 1000 units per milliliter, from about 125 to about 750 units per milliliter, from about 150 to about 700 units per milliliter, from about 200 to about 650 units per milliliter, from about 225 to about 550 units per milliliter, and most preferably at a working concentration of from about 250 to about 500 units per milliliter. The enzymes may be added to the solution in any order, or may be added simultaneously.

The compositions of the invention may further comprise one or more nucleotides, which are preferably deoxynucleoside triphosphates (dNTPs) or dideoxynucleoside triphosphates (ddNTPs). The dNTP components of the present compositions serve as the "building blocks" for newly synthesized nucleic acids, being incorporated therein by the action of the polymerases, and the ddNTPs may be used in sequencing methods according to the invention. Examples of nucleotides suitable for use in the present compositions include, but are not limited to, dUTP, dATP, dTTP, dCTP, dGTP, dITP, 7-deaza-dGTP, α-thio-dATP, α-thio-dTTP, α-thio-dGTP, α-thio-dCTP, ddUTP, ddATP, ddTTP, ddCTP, ddGTP, ddITP, 7-deaza-ddGTP, α-thio-ddATP, α-thio-ddTTP, α-thio-ddGTP, α-thio-ddCTP or derivatives thereof, all of which are available commercially from sources including Invitrogen Corporation (Carlsbad, Calif.), New England BioLabs (Beverly, Mass.) and Sigma Chemical Company (Saint Louis, Mo.). The nucleotides may be unlabeled, or they may be detectably labeled by coupling them by methods known in the art with radioisotopes (e.g., 3H, $^{14}C$, $^{32}P$ or $^{35}S$), vitamins (e.g., biotin), fluorescent moieties (e.g., fluorescein, rhodamine, Texas Red, or phycoerythrin), chemiluminescent labels (e.g., using the PHOTO-GENE™ or ACES™ chemiluminescence systems, available commercially from Invitrogen Corporation (Carlsbad, Calif.)), dioxigenin and the like. Labeled nucleotides may also be obtained commercially, for example from Invitrogen Corporation (Carlsbad, Calif.) or Sigma Chemical Company (Saint Louis, Mo.). In the present compositions, the nucleotides are added to give a working concentration of each nucleotide of about 10-4000 micromolar, about 50-2000 micromolar, about 100-1500 micromolar, or about 200-1200 micromolar, and most preferably a concentration of about 1000 micromolar.

To reduce component deterioration, storage of the reagent compositions is preferably at about 4° C. for up to one day, or most preferably at −20° C. for up to one year.

In another aspect, the compositions and reverse transcriptases of the invention may be prepared and stored in dry form in the presence of one or more carbohydrates, sugars, or synthetic polymers. Preferred carbohydrates, sugars or polymers for the preparation of dried compositions or reverse transcriptases include, but are not limited to, sucrose, trehalose, and polyvinylpyrrolidone (PVP) or combinations thereof. See, e.g., U.S. Pat. Nos. 5,098,893, 4,891,319, and 5,556,771, the disclosures of which are entirely incorporated herein by reference. Such dried compositions and enzymes may be stored at various temperatures for extended times without significant deterioration of enzymes or components of the compositions of the invention. Preferably, the dried reverse transcriptases or compositions are stored at 4° C. or at −20° C.

The invention further includes reaction solutions for reverse transcribing nucleic acid molecules, as well as reverse transcription methods employing such reaction solutions and product nucleic acid molecules produced using such methods. In many instances, reaction solutions of the invention will contain one or more of the following components: (1) one or more buffering agent (e.g., sodium phosphate, sodium acetate, 2-(N-moropholino)-ethanesulfonic acid (MES), tris-(hydroxymethyl)aminomethane (Tris), 3-(cyclohexylamino)-2-hydroxy-1-propanesulfonic acid (CAPS), citrate, N-2-hydroxyethylpiperazine-N'-2-ethanesulfonic acid (HEPES), acetate, 3-(N-morpholino)prpoanesulfonic acid (MOPS), N-tris(hydroxymethyl)methyl-3-aminopropanesulfonio acid (TAPS), etc.), (2) one or more monovalent cationic salt (e.g., NaCl, KCl, etc.), (3) one or more divalent cationic salt (e.g., $MnCl_2$, $MgCl_2$, $MgSO_4$, $CaCl_2$, etc.), (4) one or more reducing agent (e.g., dithiothreitol, β-mercaptoethanol, etc.), (5) one or more ionic or non-ionic detergent (e.g., Triton X-100™, Nonidet P40™, sodium dodecyl sulphate, etc.), (6) one or more DNA polymerase inhibitor (e.g., Actinomycin D, etc.), (7) nucleotides (e.g., dNTPs, such as dGTP, dATP, dCTP, dTTP, etc.), (8) RNA to be reverse transcribed and/or amplified, (9) one or more RNase inhibitor (e.g., RNaseOut™, Invitrogen Corporation, Carlsbad, Calif., catalog number 10777-019 etc.), (10) a reverse transcriptase (e.g., a reverse transcriptase of the invention, and/or (11) one or more diluent (e.g., water). Other components and/or constituents (e.g., primers, DNA polymerases, etc.) may also be present in reaction solutions.

The concentration of the buffering agent in the reaction solutions of the invention will vary with the particular buffering agent used. Typically, the working concentration (i.e., the concentration in the reaction mixture) of the buffering agent will be from about 5 mM to about 500 mM (e.g., about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, from about 5 mM to about 500 mM, from about 10 mM to about 500 mM, from about 20 mM to about 500 mM, from about 25 mM to about 500 mM, from about 30 mM to about 500 mM, from about 40 mM to about 500 mM, from about 50 mM to about 500 mM, from about 75 mM to about 500 mM, from about 100 mM to about 500 mM, from about 25 mM to about 50 mM, from about 25 mM to about 75 mM, from about 25 mM to about 100 mM, from about 25 mM to about 200 mM, from about 25 mM to about 300 mM, etc.). When Tris (e.g., Tris-HCl) is used, the Tris working concentration will typically be from about 5 mM to about 100 mM, from about 5 mM to about 75 mM, from about 10 mM to about 75 mM, from about 10 mM to about 60 mM, from about 10 mM to about 50 mM, from about 25 mM to about 50 mM, etc.

The final pH of solutions of the invention will generally be set and maintained by buffering agents present in reaction solutions of the invention. The pH of reaction solutions of the invention, and hence reaction mixtures of the invention, will vary with the particular use and the buffering agent present but will often be from about pH 5.5 to about pH 9.0 (e.g., about pH 6.0, about pH 6.5, about pH 7.0, about pH 7.1, about pH 7.2, about pH 7.3, about pH 7.4, about pH 7.5, about pH 7.6, about pH 7.7, about pH 7.8, about pH 7.9, about pH 8.0, about pH 8.1, about pH 8.2, about pH 8.3, about pH 8.4, about pH 8.5, about pH 8.6, about pH 8.7, about pH 8.8, about pH 8.9, about pH 9.0, from about pH 6.0 to about pH 8.5, from about pH 6.5 to about pH 8.5, from about pH 7.0 to about pH 8.5, from about pH 7.5 to about pH 8.5, from about pH 6.0 to about pH 8.0, from about pH 6.0 to about pH 7.7, from about pH 6.0 to about pH 7.5, from about pH 6.0 to about pH 7.0, from about pH 7.2 to about pH 7.7, from about pH 7.3 to about pH 7.7, from about pH 7.4 to about pH 7.6, from about pH 7.0 to about pH 7.4, from about pH 7.6 to about pH 8.0, from about pH 7.6 to about pH 8.5, from about pH 7.7 to about pH 8.5, from about pH 7.9 to about pH 8.5, from about pH 8.0 to about pH 8.5, from about pH 8.2 to about pH 8.5, from about pH 8.3 to about pH 8.5, from about pH 8.4 to about pH 8.5, from about pH 8.4 to about pH 9.0, from about pH 8.5 to about pH 9.0, etc.)

As indicated, one or more monovalent cationic salts (e.g., NaCl, KCl, etc.) may be included in reaction solutions of the invention. In many instances, salts used in reaction solutions of the invention will dissociate in solution to generate at least one species which is monovalent (e.g., Na+, K+, etc.) When included in reaction solutions of the invention, salts will often be present either individually or in a combined concentration of from about 0.5 mM to about 500 mM (e.g., about 1 mM, about 2 mM, about 3 mM, about 5 mM, about 10 mM, about 12 mM, about 15 mM, about 17 mM, about 20 mM, about 22 mM, about 23 mM, about 24 mM, about 25 mM, about 27 mM, about 30 mM, about 35 mM, about 40 mM, about 45 mM, about 50 mM, about 55 mM, about 60 mM, about 64 mM, about 65 mM, about 70 mM, about 75 mM, about 80 mM, about 85 mM, about 90 mM, about 95 mM, about 100 mM, about 120 mM, about 140 mM, about 150 mM, about 175 mM, about 200 mM, about 225 mM, about 250 mM, about 275 mM, about 300 mM, about 325 mM, about 350 mM, about 375 mM, about 400 mM, from about 1 mM to about 500 mM, from about 5 mM to about 500 mM, from about 10 mM to about 500 mM, from about 20 mM to about 500 mM, from about 30 mM to about 500 mM, from about 40 mM to about 500 mM, from about 50 mM to about 500 mM, from about 60 mM to about 500 mM, from about 65 mM to about 500 mM, from about 75 mM to about 500 mM, from about 85 mM to about 500 mM, from about 90 mM to about 500 mM, from about 100 mM to about 500 mM, from about 125 mM to about 500 mM, from about 150 mM to about 500 mM, from about 200 mM to about 500 mM, from about 10 mM to about 100 mM, from about 10 mM to about 75 mM, from about 10 mM to about 50 mM, from about 20 mM to about 200 mM, from about 20 mM to about 150 mM, from about 20 mM to about 125 mM, from about 20 mM to about 100 mM, from about 20 mM to about 80 mM, from about 20 mM to about 75 mM, from about 20 mM to about 60 mM, from about 20 mM to about 50 mM, from about 30 mM to about 500 mM, from about 30 mM to about 100 mM, from about 30 mM to about 70 mM, from about 30 mM to about 50 mM, etc.).

As indicated, one or more divalent cationic salts (e.g., $MnCl_2$, $MgCl_2$, $MgSO_4$, $CaCl_2$, etc.) may be included in reaction solutions of the invention. In many instances, salts used in reaction solutions of the invention will dissociate in solution to generate at least one species which is monovalent (e.g., $Mg^{++}$, $Mn^{++}$, $Ca^{++}$, etc.) When included in reaction solutions of the invention, salts will often be present either individually or in a combined concentration of from about 0.5 mM to about 500 mM (e.g., about 1 mM, about 2 mM, about 3 mM, about 4 mM, about 5 mM, about 6 mM, about 7 mM, about 8 mM, about 9 mM, about 10 mM, about 12 mM, about 15 mM, about 17 mM, about 20 mM, about 22 mM, about 23 mM, about 24 mM, about 25 mM, about 27 mM, about 30 mM, about 35 mM, about 40 mM, about 45 mM, about 50 mM, about 55 mM, about 60 mM, about 64 mM, about 65 mM, about 70 mM, about 75 mM, about 80 mM, about 85 mM, about 90 mM, about 95 mM, about 100 mM, about 120 mM, about 140 mM, about 150 mM, about 175 mM, about 200 mM, about 225 mM, about 250 mM, about 275 mM, about 300 mM, about 325 mM, about 350 mM, about 375 mM, about 400 mM, from about 1 mM to about 500 mM, from about 5 mM to about 500 mM, from about 10 mM to about 500 mM, from about 20 mM to about 500 mM, from about 30 mM to about 500 mM, from about 40 mM to about 500 mM, from about 50 mM to about 500 mM, from about 60 mM to about 500 mM, from about 65 mM to about 500 mM, from about 75 mM to about 500 mM, from about 85 mM to about 500 mM, from about 90 mM to about 500 mM, from about 100 mM to about 500 mM, from about 125 mM to about 500 mM, from about 150 mM to about 500 mM, from about 200 mM to about 500 mM, from about 10 mM to about 100 mM, from about 10 mM to about 75 mM, from about 10 mM to about 50 mM, from about 20 mM to about 200 mM, from about 20 mM to about 150 mM, from about 20 mM to about 125 mM, from about 20 mM to about 100 mM, from about 20 mM to about 80 mM, from about 20 mM to about 75 mM, from about 20 mM to about 60 mM, from about 20 mM to about 50 mM, from about 30 mM to about 500 mM, from about 30 mM to about 100 mM, from about 30 mM to about 70 mM, from about 30 mM to about 50 mM, etc.).

When included in reaction solutions of the invention, reducing agents (e.g., dithiothreitol, β-mercaptoethanol, etc.) will often be present either individually or in a combined concentration of from about 0.1 mM to about 50 mM (e.g., about 0.2 mM, about 0.3 mM, about 0.5 mM, about 0.7 mM, about 0.9 mM, about 1 mM, about 2 mM, about 3 mM, about 4 mM, about 5 mM, about 6 mM, about 10 mM, about 12 mM, about 15 mM, about 17 mM, about 20 mM, about 22 mM, about 23 mM, about 24 mM, about 25 mM, about 27 mM, about 30 mM, about 35 mM, about 40 mM, about 45 mM, about 50 mM, from about 0.1 mM to about 50 mM, from about 0.5 mM to about 50 mM, from about 1 mM to about 50 mM, from about 2 mM to about 50 mM, from about 3 mM to about 50 mM, from about 0.5 mM to about 20 mM, from about 0.5 mM to about 10 mM, from about 0.5 mM to about 5 mM, from about 0.5 mM to about 2.5 mM, from about 1 mM to about 20 mM, from about 1 mM to about 10 mM, from about 1 mM to about 5 mM, from about 1 mM to about 3.4 mM, from about 0.5 mM to about 3.0 mM, from about 1 mM to about 3.0 mM, from about 1.5 mM to about 3.0 mM, from about 2 mM to about 3.0 mM, from about 0.5 mM to about 2.5 mM, from about 1 mM to about 2.5 mM, from about 1.5 mM to about 2.5 mM, from about 2 mM to about 3.0 mM, from about 2.5 mM to about 3.0 mM, from about 0.5 mM to about 2 mM, from about 0.5 mM to about 1.5 mM, from about 0.5 mM to about 1.1 mM, from about 5.0 mM to about 10 mM, from about 5.0 mM to about 15 mM, from about 5.0 mM to about 20 mM, from about 10 mM to about 15 mM, from about 10 mM to about 20 mM, etc.).

Reaction solutions of the invention may also contain one or more ionic or non-ionic detergent (e.g., Triton X-100™, Nonidet P40™, sodium dodecyl sulphate, etc.). When included in reaction solutions of the invention, detergents will often be present either individually or in a combined concentration of from about 0.01% to about 5.0% (e.g., about 0.01%, about 0.02%, about 0.03%, about 0.04%, about 0.05%, about 0.06%, about 0.07%, about 0.08%, about 0.09%, about 0.1%, about 0.15%, about 0.2%, about 0.3%, about 0.5%, about 0.7%, about 0.9%, about 1%, about 2%, about 3%, about 4%, about 5%, from about 0.01% to about 5.0%, from about 0.01% to about 4.0%, from about 0.01% to about 3.0%, from about 0.01% to about 2.0%, from about 0.01% to about 1.0%, from about 0.05% to about 5.0%, from about 0.05% to about 3.0%, from about 0.05% to about 2.0%, from about 0.05% to about 1.0%, from about 0.1% to about 5.0%, from about 0.1% to about 4.0%, from about 0.1% to about 3.0%, from about 0.1% to about 2.0%, from about 0.1% to about 1.0%, from about 0.1% to about 0.5%, etc.). For example, reaction solutions of the invention may contain Triton X-100™ at a concentration of from about 0.01% to about 2.0%, from about 0.03% to about 1.0%, from about 0.04% to about 1.0%, from about 0.05% to about 0.5%, from about 0.04% to about 0.6%, from about 0.04% to about 0.3%, etc.

Reaction solutions of the invention may also contain one or more DNA polymerase inhibitor (e.g., Actinomycin D, etc.). When included in reaction solutions of the invention, such inhibitors will often be present either individually or in a combined concentration of from about 0.1 μg/ml to about 100 μg/ml (e.g., about 0.1 μg/ml, about 0.2 μg/ml, about 0.3 μg/ml, about 0.4 μg/ml, about 0.5 μg/ml, about 0.6 μg/ml, about 0.7 μg/ml, about 0.8 μg/ml, about 0.9 μg/ml, about 1.0 μg/ml, about 1.1 μg/ml, about 1.3 μg/ml, about 1.5 μg/ml, about 1.7 μg/ml, about 2.0 μg/ml, about 2.5 μg/ml, about 3.5 μg/ml, about 5.0 μg/ml, about 7.5 μg/ml, about 10 μg/ml, about 15 μg/ml, about 20 μg/ml, about 25 μg/ml, about 30 μg/ml, about 35 μg/ml, about 40 μg/ml, about 50 μg/ml, about 60 μg/ml, about 70 μg/ml, about 80 μg/ml, about 90 μg/ml, about 100 μg/ml, from about 0.5 μg/ml to about 30 μg/ml, from about 0.75 μg/ml to about 30 μg/ml, from about 1.0 μg/ml to about 30 μg/ml, from about 2.0 μg/ml to about 30 μg/ml, from about 3.0 μg/ml to about 30 μg/ml, from about 4.0 μg/ml to about 30 μg/ml, from about 5.0 μg/ml to about 30 μg/ml, from about 7.5 μg/ml to about 30 μg/ml, from about 10 μg/ml to about 30 μg/ml, from about 15 μg/ml to about 30 μg/ml, from about 0.5 μg/ml to about 20 μg/ml, from about 0.5 μg/ml to about 10 μg/ml, from about 0.5 μg/ml to about 5 μg/ml, from about 0.5 μg/ml to about 2 μg/ml, from about 0.5 μg/ml to about 1 μg/ml, from about 1 μg/ml to about 10 μg/ml, from about 1 μg/ml to about 5 μg/ml, from about 1 μg/ml to about 2 μg/ml, from about 1 μg/ml to about 100 μg/ml, from about 10 μg/ml to about 100 μg/ml, from about 20 μg/ml to about 100 μg/ml, from about 40 μg/ml to about 100 μg/ml, from about 30 μg/ml to about 80 μg/ml, from about 30 μg/ml to about 70 μg/ml, from about 40 μg/ml to about 60 μg/ml, from about 40 μg/ml to about 70 μg/ml, from about 40 μg/ml to about 80 μg/ml, etc.).

In many instances, nucleotides (e.g., dNTPs, such as dGTP, dATP, dCTP, dTTP, etc.) will be present in reaction mixtures of the invention. Typically, individually nucleotides will be present in concentrations of from about 0.05 mM to about 50 mM (e.g., about 0.07 mM, about 0.1 mM, about 0.15 mM, about 0.18 mM, about 0.2 mM, about 0.3 mM, about 0.5 mM, about 0.7 mM, about 0.9 mM, about 1 mM, about 2 mM, about 3 mM, about 4 mM, about 5 mM, about 6 mM, about 10 mM, about 12 mM, about 15 mM, about 17 mM, about 20 mM, about 22 mM, about 23 mM, about 24 mM, about 25 mM, about 27 mM, about 30 mM, about 35 mM, about 40 mM, about 45 mM, about 50 mM, from about 0.1 mM to about 50 mM, from about 0.5 mM to about 50 mM, from about 1 mM to about 50 mM, from about 2 mM to about 50 mM, from about 3 mM to about 50 mM, from about 0.5 mM to about 20 mM, from about 0.5 mM to about 10 mM, from about 0.5 mM to about 5 mM, from about 0.5 mM to about 2.5 mM, from about 1 mM to about 20 mM, from about 1 mM to about 10 mM, from about 1 mM to about 5 mM, from about 1 mM to about 3.4 mM, from about 0.5 mM to about 3.0 mM, from about 1 mM to about 3.0 mM, from about 1.5 mM to about 3.0 mM, from about 2 mM to about 3.0 mM, from about 0.5 mM to about 2.5 mM, from about 1 mM to about 2.5 mM, from about 1.5 mM to about 2.5 mM, from about 2 mM to about 3.0 mM, from about 2.5 mM to about 3.0 mM, from about 0.5 mM to about 2 mM, from about 0.5 mM to about 1.5 mM, from about 0.5 mM to about 1.1 mM, from about 5.0 mM to about 10 mM, from about 5.0 mM to about 15 mM, from about 5.0 mM to about 20 mM, from about 10 mM to about 15 mM, from about 10 mM to about 20 mM, etc.). The combined nucleotide concentration, when more than one nucleotides is present, can be determined by adding the concentrations of the individual nucleotides together. When more than one nucleotide is present in reaction solutions of the invention, the individual nucleotides may not be present in equimolar amounts. Thus, a reaction solution may contain, for example, 1 mM dGTP, 1 mM dATP, 0.5 mM dCTP, and 1 mM dTTP.

RNA will typically be present in reaction solutions of the invention. In most instances, RNA will be added to the reaction solution shortly prior to reverse transcription. Thus, reaction solutions may be provided without RNA. This will typically be the case when reaction solutions are provided in kits. RNA, when present in reaction solutions will often be present in a concentration of 1 picogram to 100 μg/20 μl reaction mixture (e.g., about 1 picogram/20 μl, about 10 picograms/20 μl, about 50 picograms/20 about 100 picograms/20 μl, about 200 picograms/20 μl, about 10 picograms/20 μl, about 500 picograms/20 about 800 picograms/20 μl, about 1.0 nanogram/20 about 5.0 nanograms/20 about 10 nanograms/20 about 25 nanograms/20 μl, about 50 nanograms/20 about 75 nanograms/20 μl, about 100 nanograms/20 about 150 nanograms/20 about 250 nanograms/20 μl, about 400 nanograms/20 μl, about 500 nanograms/20 μl, about 750 nanograms/20 μl, about 1.0 μg/20 about 5.0 μg/20 μl, about 10 μg/20 μl, about 20 μg/20 about 30 μg/20 about 40 μg/20 μl, about 50 μg/20 about 70 μg/20 μl, about 85 μg/20 μl, about 100 μg/20 μl, from about 10 picograms/20 μl to about 100 μg/20 μl, from about 10 picograms/20 μl to about 100 μg/20 μl, from about 100 picograms/20 μl to about 100 μg/20 μl, from about 1.0 nanograms/20 μl to about 100 μg/20 μl, from about 100 nanograms/20 μl to about 100 μg/20 μl, from about 10 picograms/20 μl to about 10 μg/20 μl, from about 10 picograms/20 μl to about 5 μg/20 μl, from about 100 nanograms/20 μl to about 5 μg/20 μl, from about 1 μg/20 μl to about 10 μg/20 μl, from about 1 μg/20 μl to about 5 μg/20 μl, from about 100 nanograms/20 μl to about 1 μg/20 μl, from about 500 nanograms/20 μl to about 5 μg/20 etc.). As one skilled in the art would recognize, different reverse transcription reactions may be performed in volumes other than 20 μl. In such instances, the total amount of RNA present will vary with the volume used. Thus, the above amounts are provided as examples of the amount of RNA/20 μl of reaction solution.

Reverse transcriptases (e.g., reverse transcriptases of the invention) may also be present in reaction solutions. When present, reverse transcriptases, will often be present in a concentration which results in about 0.01 to about 1,000 units of reverse transcriptase activity/μl (e.g., about 0.01 unit/μl, about 0.05 unit/μl, about 0.1 unit/μl, about 0.2 unit/μl, about 0.3 unit/μl, about 0.4 unit/μl, about 0.5 unit/μl, about 0.7 unit/μl, about 1.0 unit/μl, about 1.5 unit/μl, about 2.0 unit/μl, about 2.5 unit/μl, about 5.0 unit/μl, about 7.5 unit/μl, about 10 unit/μl, about 20 unit/μl, about 25 unit/μl, about 50 unit/μl, about 100 unit/μl, about 150 unit/μl, about 200 unit/μl, about 250 unit/μl, about 350 unit/μl, about 500 unit/μl, about 750 unit/μl, about 1,000 unit/μl, from about 0.1 unit/μl to about 1,000 unit/μl, from about 0.2 unit/μl to about 1,000 unit/μl, from about 1.0 unit/μl to about 1,000 unit/μl, from about 5.0 unit/μl to about 1,000 unit/μl, from about 10 unit/μl to about 1,000 unit/μl, from about 20 unit/μl to about 1,000 unit/μl, from about 50 unit/μl to about 1,000 unit/μl, from about 100 unit/μl to about 1,000 unit/μl, from about 200 unit/μl to about 1,000 unit/μl, from about 400 unit/μl to about 1,000 unit/μl, from about 500 unit/μl to about 1,000 unit/μl, from about 0.1 unit/μl to about 300 unit/μl, from about 0.1 unit/μl to about 200 unit/μl, from about 0.1 unit/μl to about 100 unit/μl, from about 0.1 unit/μl to about 50 unit/μl, from about 0.1 unit/μl to about 10 unit/μl, from about 0.1 unit/μl to about 5.0 unit/μl, from about 0.1 unit/μl to about 1.0 unit/μl, from about 0.2 unit/μl to about 0.5 unit/μl, etc.

Reaction solutions of the invention may be prepared as concentrated solutions (e.g., 5× solutions) which are diluted to a working concentration for final use. With respect to a 5× reaction solution, a 5:1 dilution is required to bring such a 5× solution to a working concentration. Reaction solutions of the invention may be prepared, for examples, as a 2×, a 3×, a 4×, a 5×, a 6×, a 7×, a 8×, a 9×, a 10×, etc. solutions. One major limitation on the fold concentration of such solutions is that, when compounds reach particular concentrations in solution, precipitation occurs. Thus, concentrated reaction solutions will generally be prepared such that the concentrations of the various components are low enough so that precipitation of buffer components will not occur. As one skilled in the art would recognize, the upper limit of concentration which is feasible for each solution will vary with the particular solution and the components present.

In many instances, reaction solutions of the invention will be provided in sterile form. Sterilization may be performed on the individual components of reaction solutions prior to mixing or on reaction solutions after they are prepared. Sterilization of such solutions may be performed by any suitable means including autoclaving or ultrafiltration.

Labeling Nucleic Acids

In general, the invention provides, in part, compositions for use in reverse transcription of a nucleic acid molecule to produce labeled nucleic acid molecules. Such compositions may comprise one or more reverse transcriptases (e.g., single subunit and/or multi-subunit RTs). The enzymes in these compositions are preferably present in working concentrations and have RNase H activity or are reduced or substantially reduced or lacking in RNase H activity, although mixtures of enzymes, some having RNase H activity and some reduced or substantially reduced or lacking in RNase H activity, may be used in the compositions of the invention. Preferred reverse transcriptases include M-MLV reverse transcriptase, RSV reverse transcriptase, AMV reverse transcriptase, RAV reverse transcriptase, MAV reverse transcriptase and HIV reverse transcriptase or other ASLV reverse transcriptases.

The invention is also directed to methods for reverse transcription of one or more nucleic acid molecules comprising mixing one or more nucleic acid templates, which is preferably RNA or messenger RNA (mRNA) and more preferably a population of mRNA molecules, with one or more polypeptides having reverse transcriptase activity and incubating the mixture under conditions sufficient to make one or more labeled nucleic acid molecules complementary to all or a portion of the one or more templates. To make the nucleic acid molecule or molecules complementary to the one or more templates, at least one primer (e.g., an oligo(dT) primer) and one or more nucleotides (a portion of which are preferably labeled, most preferably fluorescently labeled) are used for nucleic acid synthesis. Nucleic acid templates suitable for reverse transcription according to this aspect of the invention include any nucleic acid molecule, particularly those derived from a prokaryotic or eukaryotic cell. Such cells may include normal cells, diseased cells, transformed cells, established cells, progenitor cells, precursor cells, fetal cells, embryonic cells, bacterial cells, yeast cells, animal cells (including human cells), avian cells, plant cells and the like, or tissue isolated from a plant or an animal (e.g., human, cow, pig, mouse, sheep, horse, monkey, canine, feline, rat, rabbit, bird, fish, insect, etc.). Such nucleic acid molecules may also be isolated from viruses. In some embodiments, methods of the invention result in the direct labeling of a nucleic acid molecule by incorporation of a labeled nucleotide (e.g., a nucleotide containing a fluorescent label). In other methods, nucleic acid molecules are indirectly labeled by first, incorporating a nucleotide analog containing a reactive functionality to produce a nucleic acid containing one or more reactive functionalities. The nucleic acid containing reactive functionalities may subsequently be reacted with a molecule containing a label that reacts with the functionality to attach the label to the nucleic acid molecule. The reaction may be result in covalent attachment of all or a portion of the label-containing molecule to the nucleic acid molecule (e.g., chemical coupling). In some embodiments, amine-modified NTPs (e.g., amino allyl-dUTP/UTP) are incorporated during reverse transcription. Amino allyl-NTPs are incorporated with similar efficiency as unmodified NTPs during enzymatic reactions such as reverse transcription. The amine functionality is then coupled with a dye using standard techniques. Kits for indirect labeling of cDNA are commercially available from, for example, Ambion, Inc., Austin, Tex. In some embodiments, the label-containing molecule may be non-covalently bound to the reactive functionality. For example, the reactive functionality may be a biotin moiety and the label-containing molecule may be a labeled (e.g., fluorescently labeled) avidin or streptavidin molecule.

The invention also provides labeled nucleic acid molecules produced according to the above-described methods. Such labeled nucleic acid molecules may be single or double stranded and are useful as detection probes. Depending on the labeled nucleotide(s) used during synthesis, the labeled molecules may contain one or a number of labels. Where multiple labels are used, the molecules may comprise a number of the same or different labels. Thus, one type or multiple different labeled nucleotides may be used during synthesis of nucleic acid molecules to provide for the labeled nucleic acid molecules of the invention. Such labeled nucleic acid molecules will thus comprise one or more (e.g., two, three, four, five, six, seven, eight, nine, ten, etc.) labeled nucleotides (which may be the same or different).

Labeled nucleic acid molecules produced by methods of the invention may either (1) comprise a particular numbers of labeled nucleotides or (2) a particular percentage of the nucleotides present in the nucleic acid molecule may be labeled. In either instance, the concentration of labeled nucleotides present in the reaction mixture may be adjusted, with respect to un-labeled nucleotides, such that product nucleic acid molecules are produced which contain (1) a particular number of labeled nucleotides or (2) a particular percentage of label nucleotides as compared to un-labeled nucleotides. In particular instances, from about 0.1% to about 20%, from about 0.1% to about 15%, from about 0.1% to about 10%, from about 0.1% to about 5.0%, from about 0.1% to about 2.5%, from about 0.1% to about 1.5%, from about 0.1% to about 1.0%, from about 0.1% to about 0.5%, from about 2.0% to about 20%, from about 4.0% to about 20%, from about 0.5% to about 10%, from about 0.5% to about 5%, from about 0.5% to about 2.0%, or from about 0.5% to about 1.0% of the total nucleotides present in product nucleic acid molecules are labeled. As one skilled in the art would recognize, the actual number of labeled nucleotides, and thus the percentage of nucleotides which are labeled, present in individual molecules of a population will typically differ. In other words, different members of populations of nucleic acid molecules will typically contain different numbers of labeled nucleotides with the overall average of labeled nucleotides present in each product molecule varying with a number of factors (e.g., the ratio of labeled to un-labeled nucleotides present in the reaction mixture). In most instances, at least 85%, at least 90%, at least 95%, or at least 99% of the individual product nucleic acid molecules in the population will contain labeled nucleotides which fall within a range set out above.

In accordance with the invention, the amount of labeled product is preferably measured based on percent incorporation of the label of interest into synthesized product as may be determined by one skilled in the art, although other means of measuring the amount or efficiency of labeling of product will be recognized by one of ordinary skill in the art. The invention provides for enhanced or increased percent incorporation of labeled nucleotide during synthesis of a nucleic acid molecule from a template, preferably during synthesis of one or more cDNA molecules from RNA. According to the invention, such enhancement or increase in percent incorporation is preferably about equal to or greater than a 2-fold, a 5-fold, a 10-fold, a 15-fold, a 20-fold, a 25-fold, a 30-fold, a 40-fold or a 50-fold increase or enhancement in percent incorporation compared to a standard reverse transcriptase.

The invention also provides kits for use in accordance with the invention. Such kits comprise a carrier means, such as a box or carton, having in close confinement therein one or more container means, such as vials, tubes, bottles and the like, wherein the kit comprises, in the same or different containers, one or more reverse transcriptases. The kits of the invention may also comprise, in the same or different containers, one or more DNA polymerases, one or more primers, one or more suitable buffers and/or one or more nucleotides (such as deoxynucleoside triphosphates (dNTPs) and preferably labeled dNTPs (e.g., fluorescently labeled dNTPs)).

In some embodiments, the RTs used in the invention comprise two or more subunits (or derivatives, variants, fragments or mutants thereof) and preferably comprise two subunits (e.g., a dimer or heterodimer). Two subunit reverse transcriptases typically have an $\alpha$ and a $\beta$ subunit forming a dimer, although any form or combination of subunits (and derivatives, variants or mutants of such subunits) may be used. Such combinations may include $\alpha\beta$, $\beta\beta$, $\alpha\alpha$ and the like. Preferred two subunit RTs for use in the invention include RSV RT, AMV RT, AEV RT, RAV RT, HIV RT and MAV RT, or other ASLV RTs, or mutants, variants or derivatives thereof. In a particular embodiment, AMV RT and/or RSV RT is used in accordance with the invention. Preferred single subunit RTs include M-MLV reverse transcriptase.

Production/Sources of cDNA Molecules

In accordance with the invention, cDNA molecules (single-stranded or double-stranded) may be prepared from a variety of nucleic acid template molecules. Preferred nucleic acid molecules for use in the present invention include single-stranded or double-stranded DNA and RNA molecules, as well as double-stranded DNA:RNA hybrids. More preferred nucleic acid molecules include messenger RNA (mRNA), transfer RNA (tRNA) and ribosomal RNA (rRNA) molecules, although mRNA molecules are the preferred template according to the invention.

The nucleic acid molecules that are used to prepare cDNA molecules according to the methods of the present invention may be prepared synthetically according to standard organic chemical synthesis methods that will be familiar to one of ordinary skill. More preferably, the nucleic acid molecules may be obtained from natural sources, such as a variety of cells, tissues, organs or organisms. Cells that may be used as sources of nucleic acid molecules may be prokaryotic (bacterial cells, including but not limited to those of species of the genera *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium, Xanthomonas* and *Streptomyces*) or eukaryotic (including fungi (especially yeasts), plants, protozoans and other parasites, and animals including insects (particularly *Drosophila* spp. cells), nematodes (particularly *Caenorhabditis elegans* cells), and mammals (particularly human cells)).

Mammalian somatic cells that may be used as sources of nucleic acids include blood cells (reticulocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, Schwann cells). Mammalian germ cells (spermatocytes and oocytes) may also be used as sources of nucleic acids for use in the invention, as may the progenitors, precursors and stem cells that give rise to the above somatic and germ cells. Also suitable for use as nucleic acid sources are mammalian tissues or organs such as those derived from brain, kidney, liver, pancreas, blood, bone marrow, muscle, nervous, skin, genitourinary, circulatory, lymphoid, gastrointestinal and connective tissue sources, as well as those derived from a mammalian (including human) embryo or fetus.

Any of the above prokaryotic or eukaryotic cells, tissues and organs may be normal, diseased, transformed, established, progenitors, precursors, fetal or embryonic. Diseased cells may, for example, include those involved in infectious diseases (caused by bacteria, fungi or yeast, viruses (including AIDS, HIV, HTLV, herpes, hepatitis and the like) or parasites), in genetic or biochemical pathologies (e.g., cystic fibrosis, hemophilia, Alzheimer's disease, muscular dystrophy or multiple sclerosis) or in cancerous processes. Transformed or established animal cell lines may include, for example, COS cells, CHO cells, VERO cells, BHK cells, HeLa cells, HepG2 cells, K562 cells, 293 cells, L929 cells, F9 cells, and the like. Other cells, cell lines, tissues, organs and organisms suitable as sources of nucleic acids for use in the present invention will be apparent to one of ordinary skill in the art.

Once the starting cells, tissues, organs or other samples are obtained, nucleic acid molecules (such as mRNA) may be isolated therefrom by methods that are well-known in the art (See, e.g., Maniatis, T., et al., *Cell* 15:687-701 (1978); Okayama, H., and Berg, P., *Mol. Cell. Biol.* 2:161-170 (1982); Gubler, U., and Hoffman, B. J., *Gene* 25:263-269 (1983)). The nucleic acid molecules thus isolated may then be used to prepare cDNA molecules and cDNA libraries in accordance with the present invention.

In the practice of the invention, cDNA molecules or cDNA libraries are produced by mixing one or more nucleic acid molecules obtained as described above, which is preferably one or more mRNA molecules such as a population of mRNA molecules, with a polypeptide having reverse transcriptase activity of the present invention, or with one or more of the compositions of the invention, under conditions favoring the reverse transcription of the nucleic acid molecule by the action of the enzymes or the compositions to form one or more cDNA molecules (single-stranded or double-stranded). Thus, the method of the invention comprises (a) mixing one or more nucleic acid templates (preferably one or more RNA or mRNA templates, such as a population of mRNA molecules) with one or more reverse transcriptases of the invention and (b) incubating the mixture under conditions sufficient to make one or more nucleic acid molecules complementary to all or a portion of the one or more templates. Such methods may include the use of one or more DNA polymerases, one or more nucleotides, one or more primers, one or more buffers, and the like. The invention may be used in conjunction with methods of cDNA synthesis such as those described in the Examples below, or others that are well-known in the art (see, e.g., Gubler, U., and Hoffman, B. J., *Gene* 25:263-269 (1983); Krug, M. S., and Berger, S. L., *Meth. Enzymol.* 152:316-325 (1987); Sambrook, J., et al., *Molecular Cloning: A Laboratory Manual,* 2nd ed., Cold Spring Harbor, N.Y.: Cold Spring Harbor Laboratory Press, pp. 8.60-8.63 (1989); PCT Publication No. WO 99/15702; PCT Publication No. WO 98/47912; and PCT Publication No. WO 98/51699), to produce cDNA molecules or libraries.

Other methods of cDNA synthesis which may advantageously use the present invention will be readily apparent to one of ordinary skill in the art.

Having obtained cDNA molecules or libraries according to the present methods, these cDNAs may be isolated for further analysis or manipulation. Detailed methodologies for purification of cDNAs are taught in the GENETRAPPER™ manual (Invitrogen Corporation (Carlsbad, Calif.)), which is incorporated herein by reference in its entirety, although alternative standard techniques of cDNA isolation that are known in the art (see, e.g., Sambrook, J., et al., *Molecular Cloning: A Laboratory Manual,* 2nd ed., Cold Spring Harbor, N.Y.: Cold Spring Harbor Laboratory Press, pp. 8.60-8.63 (1989)) may also be used.

In other aspects of the invention, the invention may be used in methods for amplifying and sequencing nucleic acid molecules. Nucleic acid amplification methods according to this aspect of the invention may be one-step (e.g., one-step RT-PCR) or two-step (e.g., two-step RT-PCR) reactions. According to the invention, one-step RT-PCR type reactions may be accomplished in one tube thereby lowering the possibility of contamination. Such one-step reactions comprise (a) mixing a nucleic acid template (e.g., mRNA) with one or more reverse transcriptases of the present invention and with one or more DNA polymerases and (b) incubating the mixture under conditions sufficient to amplify a nucleic acid molecule complementary to all or a portion of the template. Such amplification may be accomplished by the reverse transcriptase activity alone or in combination with the DNA polymerase activity. Two-step RT-PCR reactions may be accomplished in two separate steps. Such a method comprises (a) mixing a nucleic acid template (e.g., mRNA) with a reverse transcriptase of the present invention, (b) incubating the mixture under conditions sufficient to make a nucleic acid molecule (e.g., a DNA molecule) complementary to all or a portion of the template, (c) mixing the nucleic acid molecule with one or more DNA polymerases, and (d) incubating the mixture of step (c) under conditions sufficient to amplify the nucleic acid molecule. For amplification of long nucleic acid molecules (i.e., greater than about 3-5 Kb in length), a combination of DNA polymerases may be used, such as one DNA polymerase having 3' exonuclease activity and another DNA polymerase being substantially reduced in 3' exonuclease activity.

Nucleic acid sequencing methods according to this aspect of the invention may comprise both cycle sequencing (sequencing in combination with amplification) and standard sequencing reactions. The sequencing method of the invention thus comprises (a) mixing a nucleic acid molecule to be sequenced with one or more primers, one or more reverse transcriptases of the invention, one or more nucleotides and one or more terminating agents, (b) incubating the mixture under conditions sufficient to synthesize a population of nucleic acid molecules complementary to all or a portion of the molecule to be sequenced, and (c) separating the population to determine the nucleotide sequence of all or a portion of the molecule to be sequenced. According to the invention, one or more DNA polymerases (preferably thermostable DNA polymerases) may be used in combination with or separate from the reverse transcriptases of the invention.

Amplification methods which may be used in accordance with the present invention include PCR (U.S. Pat. Nos. 4,683,195 and 4,683,202), Strand Displacement Amplification (SDA; U.S. Pat. No. 5,455,166; EP 0 684 315), and Nucleic Acid Sequence-Based Amplification (NASBA; U.S. Pat. No. 5,409,818; EP 0 329 822), as well as more complex PCR-based nucleic acid fingerprinting techniques such as Random Amplified Polymorphic DNA (RAPD) analysis (Williams, J. G. K., et al., *Nucl. Acids Res.* 18(22):6531-6535, 1990), Arbitrarily Primed PCR (AP-PCR; Welsh, J., and McClelland, M., *Nucl. Acids Res.* 18(24):7213-7218, 1990), DNA Amplification Fingerprinting (DAF; Caetano-Anollés et al., *Bio/Technology* 9:553-557, 1991), microsatellite PCR or Directed Amplification of Minisatellite-region DNA (DAMD; Heath, D. D., et al., *Nucl. Acids Res.* 21(24): 5782-5785, 1993), and Amplification Fragment Length Polymorphism (AFLP) analysis (EP 0 534 858; Vos, P., et al., *Nucl. Acids Res.* 23(21):44407-4414, 1995; Lin, J. J., and Kuo, J., *FOCUS* 17(2):66-70, 1995). Nucleic acid sequencing techniques which may employ the present compositions include dideoxy sequencing methods such as those disclosed in U.S. Pat. Nos. 4,962,022 and 5,498,523. In a particularly preferred aspects, the invention may be used in methods of amplifying or sequencing a nucleic acid molecule comprising one or more polymerase chain reactions (PCRs), such as any of the PCR-based methods described above.

Kits

In another embodiment, the present invention may be assembled into kits, which may be used in reverse transcription or amplification of a nucleic acid molecule, or into kits for use in sequencing of a nucleic acid molecule. Kits according to this aspect of the invention comprise a carrier means, such as a box, carton, tube or the like, having in close confinement therein one or more container means, such as vials, tubes, ampoules, bottles and the like, wherein a first container means contains one or more polypeptides of the present invention having reverse transcriptase activity. When more than one polypeptide having reverse transcriptase activity is used, they may be in a single container as mixtures of two or more polypeptides, or in separate containers. The kits of the invention may also comprise (in the same or separate containers) one or more DNA polymerases, a suitable buffer, one or more nucleotides and/or one or more primers. The kits of the invention may also comprise one or more hosts or cells including those that are competent to take up nucleic acids (e.g., DNA molecules including vectors). Preferred hosts may include chemically competent or electrocompetent bacteria such as *E. coli* (including DH5, DH5α, DH10B, HB101, Top 10, and other K-12 strains as well as *E. coli* B and *E. coli* W strains).

In a specific aspect of the invention, the kits of the invention (e.g., reverse transcription and amplification kits) may comprise one or more components (in mixtures or separately) including one or more polypeptides having reverse transcriptase activity of the invention, one or more nucleotides (one or more of which may be labeled, e.g., fluorescently labeled) used for synthesis of a nucleic acid molecule, and/or one or more primers (e.g., oligo(dT) for reverse transcription). Such kits (including the reverse transcription and amplification kits) may further comprise one or more DNA polymerases. Sequencing kits of the invention may comprise one or more polypeptides having reverse transcriptase activity of the invention, and optionally one or more DNA polymerases, one or more terminating agents (e.g., dideoxynucleoside triphosphate molecules) used for sequencing of a nucleic acid molecule, one or more nucleotides and/or one or more primers. Preferred polypeptides having reverse transcriptase activity, DNA polymerases, nucleotides, primers and other components suitable for use in the reverse transcription, amplification and sequencing kits of the invention include those described above. The kits encompassed by this aspect of the present invention may further comprise additional reagents and compounds necessary for carrying out standard nucleic acid reverse transcription, amplification or sequencing protocols. Such polypeptides having reverse transcriptase activity of the invention, DNA polymerases, nucleotides, primers, and additional reagents, components or compounds may be contained in one or more containers, and may be contained in such containers in a mixture of two or more of the above-noted components or may be contained in the kits of the invention in separate containers. Such kits may also comprise instructions (e.g., for performing the methods of the invention such as for labeling nucleic acid molecules in accordance with the invention).

Use of Nucleic Acid Molecules

The nucleic acid molecules or cDNA libraries prepared by the methods of the present invention may be further characterized, for example by cloning and sequencing (i.e., determining the nucleotide sequence of the nucleic acid molecule), by the sequencing methods of the invention or by others that are standard in the art (see, e.g. U.S. Pat. Nos. 4,962,022 and 5,498,523, which are directed to methods of DNA sequencing). Alternatively, these nucleic acid molecules may be used for the manufacture of various materials in industrial processes, such as hybridization probes by methods that are well-known in the art. Production of hybridization probes from cDNAs will, for example, provide the ability for those in the medical field to examine a patient's cells or tissues for the presence of a particular genetic marker such as a marker of cancer, of an infectious or genetic disease, or a marker of embryonic development.

Furthermore, such hybridization probes can be used to isolate DNA fragments from genomic DNA or cDNA libraries prepared from a different cell, tissue or organism for further characterization.

The nucleic acid molecules of the present invention may also be used to prepare compositions for use in recombinant DNA methodologies. Accordingly, the present invention relates to recombinant vectors which comprise the cDNA or amplified nucleic acid molecules of the present invention, to host cells which are genetically engineered with the recombinant vectors, to methods for the production of a recombinant polypeptide using these vectors and host cells, and to recombinant polypeptides produced using these methods.

Recombinant vectors may be produced according to this aspect of the invention by inserting, using methods that are well-known in the art, one or more of the cDNA molecules or amplified nucleic acid molecules prepared according to the present methods into a vector. The vector used in this aspect of the invention may be, for example, a phage or a plasmid, and is preferably a plasmid. Preferred are vectors comprising cis-acting control regions to the nucleic acid encoding the polypeptide of interest. Appropriate trans-acting factors may be supplied by the host, supplied by a complementing vector or supplied by the vector itself upon introduction into the host.

In certain preferred embodiments in this regard, the vectors provide for specific expression (and are therefore termed "expression vectors"), which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids or bacteriophages, and vectors derived from combinations thereof, such as cosmids and phagemids, and will preferably include at least one selectable marker such as a tetracycline or ampicillin resistance gene for culturing in a bacterial host cell. Prior to insertion into such an expression vector, the cDNA or amplified nucleic acid molecules of the invention should be operatively linked to an appropriate promoter, such as the phage lambda $P_L$ promoter, the *E. coli* lac, trp and tac promoters. Other suitable promoters will be known to the skilled artisan.

Among vectors preferred for use in the present invention include pQE70, pQE60 and pQE-9, available from Qiagen; pBS vectors, Phagescript vectors, Bluescript vectors, pNH8A, pNH16a, pNH18A, pNH46A, available from Stratagene; pcDNA3 available from Invitrogen; pGEX, pTrxfus, pTrc99a, pET-5, pET-9, pKK223-3, pKK233-3, pDR540, pRIT5 available from Pharmacia; and pSPORT1, pSPORT2 and pSV•SPORT1, available from Invitrogen Corporation (Carlsbad, Calif.). Other suitable vectors will be readily apparent to the skilled artisan.

The invention also provides methods of producing a recombinant host cell comprising the cDNA molecules, amplified nucleic acid molecules or recombinant vectors of the invention, as well as host cells produced by such methods. Representative host cells (prokaryotic or eukaryotic) that may be produced according to the invention include, but are not limited to, bacterial cells, yeast cells, plant cells and animal cells. Preferred bacterial host cells include *Escherichia coli* cells (most particularly *E. coli* strains DH10B and Stbl2, which are available commercially (Invitrogen Corporation (Carlsbad, Calif.)), *Bacillus subtilis cells, Bacillus megaterium cells, Streptomyces* spp. cells, *Erwinia* spp. cells, *Klebsiella* spp. cells and *Salmonella typhimurium* cells. Preferred animal host cells include insect cells (most particularly *Spodoptera frugiperda* Sf9 and Sf21 cells and *Trichoplusa* HigH-Five cells) and mammalian cells (most particularly CHO, COS, VERO, BHK and human cells). Such host cells may be prepared by well-known transformation, electroporation or transfection techniques that will be familiar to one of ordinary skill in the art.

In addition, the invention provides methods for producing a recombinant polypeptide, and polypeptides produced by these methods. According to this aspect of the invention, a recombinant polypeptide may be produced by culturing any of the above recombinant host cells under conditions favoring production of a polypeptide therefrom, and isolation of the polypeptide. Methods for culturing recombinant host cells, and for production and isolation of polypeptides therefrom, are well-known to one of ordinary skill in the art.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1: Preparation of Mutant Reverse Transcriptases

Figure 1:
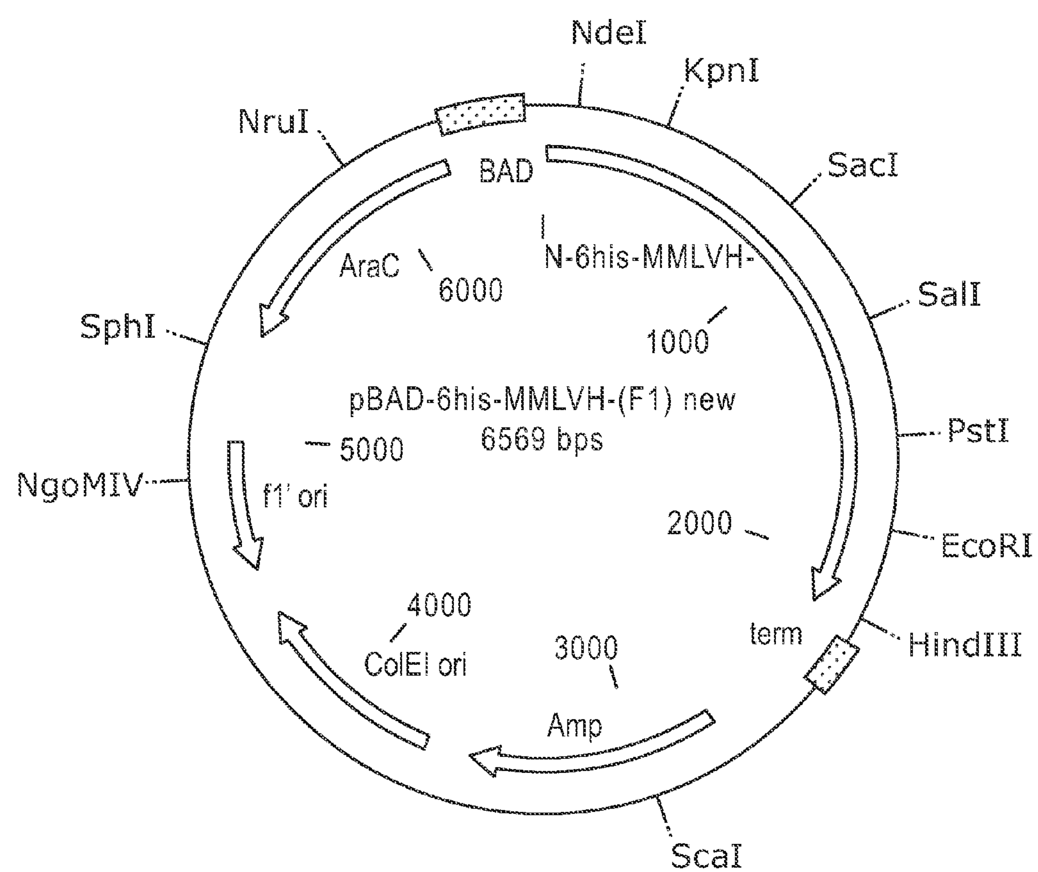
FIG. 1 is a map of plasmid pBAD-6-His-M-MLV H− (F1).

Plasmid pBAD was obtained from Invitrogen Corporation, Carlsbad, Calif. and the coding sequence of M-MLV reverse transcriptase was inserted to produce plasmid pBAD-6-His-M-MLV H− (F1). Plasmid pBAD-6-His-M-MLV H− (F1) was used as both a cloning vector and as a target for PCR mutagenesis (FIG. 1). pBAD-6-His-M-MLV H− (F1) replicates in *E. coli* and confers ampicillin resistance to transformed cells. The M-MLV reverse transcriptase gene is expressed from the ara BAD promoter which is induced by the presence of arabinose. The promoter is repressed by the product of the araC gene, which is present on the plasmid. The host used, *E. coli* strain DH10B, is an araD mutant and cannot metabolize arabinose, making arabinose a gratuitous inducer in DH10B cells transformed with pBAD-6-His-M-MLV H− (F1). The plasmid contains a 6 histidine containing leader sequence in frame with the coding sequence of the M-MLV reverse transcriptase gene. The gene starting at nucleotide 2598 and ending at nucleotide 4628 (Shinnick, et al., (1981) *Nature* 293, 543-548.) was cloned under control of an araD promoter into plasmid pBAD/HisA (Invitrogen). The M-MLV gene was further modified by site-directed mutagenesis without changing amino acid coding to include several unique restriction endonuclease sites that divided the gene into five segments (FIG. 2). The amino end of the protein contained a $His_6$ tag to simplify purification that included the following amino acids: MGGSHHHHHHGMASMTGGQQMGRDLYDDDDKH corresponding to amino acids 1-32 of SEQ ID NO:2. The carboxy end of the protein contained the additional amino acids NSRLIN, corresponding to amino acids 711-716 of SEQ ID NO:2, present as the result of subcloning from pRT601. In addition, the M-MLV RT gene was mutated (D524G, E562Q, D583N) to eliminate RNase H activity. The final construct was designated pBAD-HSS2 (FIG. 1), and the gene and gene product were designated $His_6$ H− RT. In addition to this construct, other constructs having different N-terminal sequences are contemplated in the present invention. For example, a construct beginning at methionine 12 of SEQ ID NO:6 and Table 3 and containing a mutation changing methionine 15 to glycine (M15G) to produce a protein with an N-terminal sequence MASGTGGQQMGRDLYDDDDKH (SEQ ID NO:1) followed by the remaining sequence of M-MLV RT from Table 3 has been produced as well as a construct beginning with methionine 33 of SEQ ID NO:6 and Table 3.

With reference to the sequence of this plasmid provided in Table 3 (SEQ ID NOs:1 and 2), nucleotides 1-96 encode the leader sequence and nucleotides 97-99 encode a methionine. Those skilled in the art will appreciate that the wild-type M-MLV reverse transcriptase is derived by proteolysis from a precursor polyprotein and thus the wild-type M-MLV reverse transcriptase does not start with a methionine. Therefore, amino acid number 1 of the M-MLV reverse transcriptase is the threonine (amino acid 34 in SEQ ID NO:2 and Table 3) following the methionine encoded by nucleotides 97-99 (amino acid 33 in SEQ ID NO:2 and Table 3).

The sequence of the M-MLV reverse transcriptase gene in pBAD-6-His-M-MLV H− (F1) which was used in these experiments was derived from the sequence of plasmid pRT601. pRT601 is described in Kotewicz, et al., (1988) *Nuc. Acids Res.* 16, 265-277, Gerard, et al., (1986) DNA 5, 271-279, U.S. Pat. Nos. 5,668,005 and 5,017,492, which are incorporated herein by reference in their entireties.

TABLE 3

(SEQ ID NOs: 1 and 2).

```
   1 atgggggtt ctcatcatca tcatcatcat ggtatggcta gcatgactgg tggacagcaa
      m  g  g   s  h  h   h  h  h  h   g  m  a   s  m  t   g  g  q  q

  61 atgggtcggg atctgtacga cgatgacgat aagcatatga ccctaaatat agaagatgag
      m  g  r   d  l  y   d  d  d  d   k  h  m   t  l  n   i  e  d  e

 121 tatcggctac atgagacctc aaaagagcca gatgtttctc tagggtccac atggctgtct
      y  r  l   h  e  t   s  k  e  p   d  v  s   l  g  s   t  w  l  s

 181 gattttcctc aggcctgggc ggaaaccggg ggcatgggac tggcagttcg ccaagctcct
      d  f  p   q  a  w   a  e  t  g   g  m  g   l  a  v   r  q  a  p

 241 ctgatcatac ttctgaaagc aacctctacc cccgtgtcca taaaacaata ccccatgtca
      l  i  i   l  l  k   a  t  s  t   p  v  s   i  k  q   y  p  m  s

 301 caagaagcca gactggggat caagccccac atacagagac tgttggacca gggaatactg
      q  e  a   r  l  g   i  k  p  h   i  q  r   l  l  d   q  g  i  l

 361 gtaccctgcc agtccccctg gaacacgccc ctgctacccg tcaagaaacc cgggactaat
      v  p  c   q  s  p   w  n  t  p   l  l  p   v  k  k   p  g  t  n

 421 gattacaggc ctgtccaaga tctgagagag gtcaacaaac gcgtagaaga catccacccc
      d  y  r   p  v  q   d  l  r  e   v  n  k   r  v  e   d  i  h  p

 481 accgtaccca acccctacaa cctcttgagt gggctcccac cgtcccacca gtggtacact
      t  v  p   n  p  y   n  l  l  s   g  l  p   p  s  h   q  w  y  t

 541 gttctagact taaaagatgc ctttttctgc ctgagactcc acccgacgtc tcagcctctc
      v  l  d   l  k  d   a  f  f  c   l  r  l   h  p  t   s  q  p  l

 601 ttcgcctttg aatggagaga cccagagatg ggaatctctg gccaactaac ctggaccaga
      f  a  f   e  w  r   d  p  e  m   g  i  s   g  q  l   t  w  t  r

 661 ctcccacagg gattcaaaaa cagtcccacc ctgtttgatg aggcactgcg cagagaccta
      l  p  q   g  f  k   n  s  p  t   l  f  d   e  a  l   r  r  d  l

 721 gcagacttcc ggatccagca cccagacttg atcctgctac agtacgtaga tgacttactg
      a  d  f   r  i  q   h  p  d  l   i  l  l   q  y  v   d  d  l  l

 781 ctggccgcca cttctgagct cgactgccaa caaggtactc gggccctgtt acaaacccta
      l  a  a   t  s  e   l  d  c  q   q  g  t   r  a  l   l  q  t  l

 841 ggagacctcg ggtatcgggc ctcggccaag aaagcccaaa tttgccagaa acaggtcaag
      g  d  l   g  y  r   a  s  a  k   k  a  q   i  c  q   k  q  v  k

 901 tatctggggt atcttctaaa agagggtcag agatggctga ctgaggccag aaaagagact
      y  l  g   y  l  l   k  e  g  q   r  w  l   t  e  a   r  k  e  t

 961 gtgatggggc agcctactcc gaagaccccg cggcaactaa gggagttcct agggacggca
      v  m  g   q  p  t   p  k  t  p   r  q  l   r  e  f   l  g  t  a

1021 ggcttctgtc gcctctggat ccctgggttt gcagaaatgg cagcccccctt gtaccctctc
      g  f  c   r  l  w   i  p  g  f   a  e  m   a  a  p   l  y  p  l

1081 accaaaacgg ggactctgtt taattggggc ccagaccaac aaaaggccta tcaagaaatc
      t  k  t   g  t  l   f  n  w  g   p  d  q   q  k  a   y  q  e  i

1141 aagcaagctc ttctaactgc cccagccctg gggttgccag atttgactaa gccctttgaa
      k  q  a   l  l  t   a  p  a  l   g  l  p   d  l  t   k  p  f  e
```

TABLE 3 -continued (SEQ ID NOs: 1 and 2).

```
1201 ctctttgtcg acgagaagca gggctacgcc aaaggtgtcc taacgcaaaa actgggacct
       l  f  v   d  e  k   q  g  y  a   k  g  v   l  t  q   k  l  g  p

1261 tggcgtcggc cggtggccta cctgtccaaa aagctagacc cagtagcagc tgggtggccc
       w  r  r   p  v  a   y  l  s  k   k  l  d   p  v  a   a  g  w  p

1321 ccttgcctac ggatggtagc agccattgcc gtactgacaa aggatgcagg caagctaacc
       p  c  l   r  m  v   a  a  i  a   v  l  t   k  d  a   g  k  l  t

1381 atgggacagc cactagtcat tctggccccc catgcagtag aggcactagt caaacaaccc
       m  g  q   p  l  v   i  l  a  p   h  a  v   e  a  l   v  k  q  p

1441 cccgatcgat ggctttccaa cgcccggatg actcactatc aggccttgct tttggacacg
       p  d  r   w  l  s   n  a  r  m   t  h  y   q  a  l   l  l  d  t

1501 gaccgggtcc agttcggacc ggtggtagcc ctgaacccgg ctacactgct cccactgcct
       d  r  v   q  f  g   p  v  v  a   l  n  p   a  t  l   l  p  l  p

1561 gaggaagggc tgcagcacaa ctgccttgat atcctggccg aagcccacgg aacccgaccc
       e  e  g   l  q  h   n  c  l  d   i  l  a   e  a  h   g  t  r  p

1621 gacctaacgg accagccgct cccagacgcc gaccacacct ggtacacggg tggatccagt
       d  l  t   d  q  p   l  p  d  a   d  h  t   w  y  t   g  g  s  s

1681 ctcttgcaag agggacagcg taaggcggga gctgcggtga ccaccgagac cgaggtaatc
       l  l  q   e  g  q   r  k  a  g   a  a  v   t  t  e   t  e  v  i

1741 tgggctaaag ccctgccagc cgggacatcc gctcagcggg ctcagctgat agcactcacc
       w  a  k   a  l  p   a  g  t  s   a  q  r   a  q  l   i  a  l  t

1801 caggccctaa ggatggcaga aggtaagaag ctaaatgttt atacgaattc ccgttatgct
       q  a  l   r  m  a   e  g  k  k   l  n  v   y  t  n   s  r  y  a

1861 tttgctactg cccatatcca tggagaaata tacagaaggc gtgggttgct cacatcagaa
       f  a  t   a  h  i   h  g  e  i   y  r  r   r  g  l   l  t  s  e

1921 ggcaaagaga tcaaaaataa ggacgagata ttggccctac taaaagccct ctttctgccc
       g  k  e   i  k  n   k  d  e  i   l  a  l   l  k  a   l  f  l  p

1981 aaaagactta gcataatcca ttgtccagga catcaaaagg gacacagcgc cgaggctaga
       k  r  l   s  i  i   h  c  p  g   h  q  k   g  h  s   a  e  a  r

2041 ggcaaccgga tggctgacca agcggcccga aaggcagcca tcacagagaa tccagacacc
       g  n  r   m  a  d   q  a  a  r   k  a  a   i  t  e   n  p  d  t

2101 tctaccctcc tcatagaaaa ttcatcaccc aattcccgct taattaatta a
       s  t  l   l  i  e   n  s  s  p   n  s  r   l  i  n   -
```

Table 4 provides a list of the point mutations introduced in the M-MLV reverse transcriptase coding sequence of pRT601 to produce the plasmid used. The numbering of the point mutations corresponds to the nucleotide sequence presented in Table 3.

TABLE 4

| Nucleotide # in Table 3 | change |
|---|---|
| 411 | a→c |
| 459 | g→a |
| 462 | g→c |
| 543 | g→t |
| 546 | t→a |
| 585 | c→g |
| 588 | c→g |
| 589 | a→t |
| 590 | g→c |
| 639 | a→t |
| 642 | a→c |
| 710 | a→g |
| 801 | a→c |
| 990 | t→g |

TABLE 4-continued

| Nucleotide # in Table 3 | change |
|---|---|
| 993 | a→g |
| 1446 | c→t |
| 1449 | c→a |
| 1670 | a→g |
| 1675 | a→t |
| 1676 | g→c |
| 1783 | g→c |
| 1785 | a→g |
| 1845 | t→g |
| 1846 | g→a |
| 1849 | a→t |
| 1850 | g→c |
| 1950 | c→a |

The mutations which were introduced to make RNase H− mutants of M-MLV reverse transcriptase are D524G, D583N, and E562Q. The remaining mutations were introduced to insert or remove restriction enzyme sites to facilitate the production of appropriately sized segments for the random PCR mutagenesis. This RNase H− mutant is referred to herein as SuperScript™ II or SuperScript™ II gene.

The sequence of the M-MLV reverse transcriptase was engineered to introduce restriction enzyme cleavage sites as shown schematically in FIG. 2 without changing the amino acids encoded by the sequence. The sequence was divided into 5 segments and oligonucleotides were designed so that each segment could be amplified. The segments roughly corresponded to the coding sequences of the five separate structural subdomains of RT (Kohlstaedt, et al., (1992) *Science* 256, 1783-1789, Jacobo-Molina, et al., (1993) *Proc. Natl. Acad. Sci. USA* 90, 6320-6324). Segments one through four corresponded to the polymerase subdomain of fingers, palm, thumb, and connection, respectively, and segment five corresponded to the RNase H domain (FIG. 2). An upper limit cut-off of 1 to 2 mutations per segment was set as the target for mutation frequency to suppress accumulation of deleterious mutations, and to minimize the amount of screening required to find active mutants. Mutation frequencies of >5 mutations/segment in segment one, two, or three produced only about 5% active mutants with all the mutants having less than wild-type activity. At the mutation frequency used of 1 to 2 mutations per segment, approximately one-third of the mutants had little or no activity, one-third had less than 50% of $His_6$ H− RT activity, and one-third had up to 100% of $His_6$ H− RT activity.

Segments were prepared from pBAD-6-His-M-MLV H− (F1) by restriction enzyme digests and the segments were gel purified away from the vector backbone. Each segment was randomly mutagenized by PCR in the presence of manganese. The PCR conditions were standard except that 0.25 mM $MnCl_2$ was present, and the nucleotide triphosphate concentration was limited to 20 μM of each dNTP (50 mM Tris.HCl pH 8.3, 50 mM KCl, 3 mM $MgCl_2$, 20 μM dGTP, 20 μM dCTP, 20 μM dATP, 20 μM dTTP, 1 unit Taq DNA polymerase per 100 μl reaction). The PCR product was extracted with phenol-chloroform, precipitated with ethanol and the mutated segments were cloned into a vector from which the given segment had been removed.

In some random mutagenesis experiments, mutagenic PCR was performed in a reaction mixture (100 μl) containing 20 mM Tris-HCl (pH 8.4), 0.50 mM KCl, 1.8 mM $MgCl_2$, 0.3 mM $MnSO_4$, 200 μM each of dCTP, dGTP, dTTP, and dATP, and 0.5 units of Taq DNA polymerase (Invitrogen Corporation, Carlsbad, Calif.). After a 1 min denaturation step at 94° C., the cycling protocol was 15 sec at 94° C., 15 sec at 55° C., and 30 sec at 72° C. for 20 cycles. Amplification was 100 fold from 50 ng of target to 5 μg of amplified product. PCR primers included appropriate restriction endonuclease cut sites. An amplified DNA segment was cleaved with appropriate restriction endonucleases, gel purified, and cloned into gel purified vector DNA cut with the corresponding restriction enzymes. The vectors containing the mutated segments were transformed into appropriate host cells to produce a library.

Libraries were sampled by DNA sequencing of the mutagenized H− RT gene segment of a small number of clones to determine the mutation frequency. The goal was to achieve rates of PCR random mutagenesis that produced 1 to 2 mutations per segment. It was found that random mutagenesis that produced greater than 2 mutations per segment tended to produce a large proportion of inactive RT mutants. If the library met this criterion, further screening by heat treatment was carried out to identify mutants that showed greater RT activity in lysates than H− RT after a heat treatment step. Those mutants with the highest apparent thermal stability were screened again in duplicate by pretreatment at 24° C. (to normalize for activity) and at 52 to 58° C. to confirm the presence of enhanced thermal stability. In all, about 15,000 clones were screened by heat treatment in the 96-well format for each segment or a total of about 100,000 mutants. Libraries of transformants for each mutated segment were screened for thermostable variants.

Example 2: Screening for Thermostable Reverse Transcriptases

In this example the following solutions were used:

EG—per liter: 20 g bacto-tryptone, 10 g bacto yeast extract, 2 ml glycerol, 0.54 g NaCl, 0.194 g KCl EG-arabinose—150 ml EG plus 1.5 ml of 10 mg/ml ampicillin and 1.5 ml of 20% (w/v) arabinose (if plates are to have arabinose)

20×PEB-I Buffer—18% (w/v) glucose, 500 mM Tris-HCl (pH 8.0), 200 mM EDTA

Kinase Storage Buffer-50% (v/v) glycerol, 20 mM Tris-HCl (pH 8.0), 100 mM KCl, 5 mM βME 100 mg/ml lysozyme—made in Kinase Storage Buffer and stored at −20° C.

2×PLD—5 ml of 20×PEB-I, 1 ml of 1 M DTT, 5 ml of 10% (v/v) Triton X-100, 1 ml of 100 mg/ml lysozyme and 38 ml of water 2×PZD—0.5 ml of 20×PEB-I, 100 μl of 1 M DTT, 0.5 ml of 10% (v/v) Triton X-100, 10 μl of zymolase and 3.9 ml of water 10× Poly(C) Reaction Buffer—500 mM Tris-HCl (pH 8.4), 500 mM KCl, 100 mM $MgCl_2$ 1.25× Reaction Mix-1 ml of 10× Poly(C) Reaction Buffer, 100 μl of 1 M DTT, 1 ml of poly(C)/oligo(dG) (30 mM/12 mM in nucleotide), 10 μl of 100 mM dGTP, 5.87 ml of water and 20 μl of [α-$^{32}$P] dGTP at 10 μCi/μl

*E. coli* DH10B (Invitrogen Corporation, Carlsbad, Calif.) was used in all experiments. Bacterial liquid cultures were grown at 37° C. in EG: 2% tryptone, 1% yeast extract, 0.5% glycerol, 10 mM NaCl, and 1 mM KCl. Solid medium was LB (1% bacto-tryptone, 0.5% yeast extract, and 86 mM NaCl)+1.5% agar. Selective media included 100 μg/ml ampicillin. For induction of cultures, cells were inoculated into selective EG+0.2% arabinose and grown for 18 hr.

Mutant populations were plated on selective agar. Individual transformant colonies were inoculated into single wells of a 96 well culture plate. Each well contained 120 μl of EG-Ap medium (EG medium with 100 μg/ml ampicillin). Although colonies from the selective agar may be grown in media containing 0.2% arabinose, it is preferable to first inoculate a 96 well plate with selective medium without the inducer, to grow that master plate overnight, and then to make a replica of the master plate into a 96-well plate with the inducer and grow that plate overnight.

An aliquot of the un-induced culture from each well was transferred into a new 96-well plate containing 120 μl per well of selective media+0.2% arabinose. The cultures containing the inducer were grown overnight (e.g., 15-20 hours) at 37° C. without shaking to induce RT production. An aliquot (5 μl) of culture from each well was then transferred into another 96-well plate containing 5 μl per well of 2×PLD (50 mM Tris-HCl, pH 8.0, 20 mM EDTA, 1.8% (w/v) sucrose, 1% (v/v) Triton X-100, 10 mM DTT, and 2 mg/ml lysozyme) at room temperature. These extracts were sometimes assayed directly for reverse transcriptase before the heating step. The amount of RT activity in a 5-μl aliquot of extract was within the linear range of the assay. Lysates were stable at room temperature for at least 1 hr.

The extracts were heated, for example, using a water bath or thermocycler, for 5 or 10 minutes at temperatures that ranged from 50° C. to 60° C. Preferably, the cultures were heated for 5 minutes at 52° C. After heating and cooling to room temperature, RT activity in a 5-μl aliquot from the lysate in each well was assayed with $(rC)_n \cdot (dG)_{15}$ in another 96-well plate. An aliquot (5 to 10 μl) of the extract was mixed with 1.25×RT reaction mix. This reaction was placed in a 37° C. water bath for 10 minutes. A small aliquot of the reaction mixture (5 μl) was spotted onto a charged nylon membrane (Genescreen+, NEN). The membrane was washed twice with 10% TCA+1% sodium pyrophosphate, rinsed with ethanol, dried, and placed next to a phosphor screen. As an alternative, the membrane may be washed twice with 4% sodium pyrophosphate (pH 8.0), rinsed with ethanol, dried, and then placed next to a phosphor screen. Radioactive product that had been trapped on the filter was detected by analyzing the screen in a Posphorimager, using ImageQuant software (Molecular Devices).

Candidates were selected if they showed more reverse transcriptase activity (radioactivity) after the heat inactivation step. These candidates were screened a second time to confirm the phenotype. Candidates which appeared to be thermostable after the second screen were grown in small cultures and tested a third time for thermostable reverse transcriptase activity. Candidates that were reproducibly heat resistant were sequenced and the mutation in each clone was determined.

Plasmid DNA was prepared from an over night *E. coli* culture bearing an RT mutant using a Concert High Purity Miniprep Kit (Invitrogen Corporation, Carlsbad, Calif.) following the manufacturer's instructions. Each DNA was sequenced using a forward and reverse primer bordering the segment that had been mutagenized to generate the mutant. The sequencing reactions were carried out as specified for plasmid DNA using the ABI Big Dye Terminator Sequencing Ready Reaction Kit. The reactions were analyzed using an ABI PRISM 377 DNA Sequencer.

An oligonucleotide corresponding to the mutagenized site was designed in which the codon for the mutagenized amino acid was randomized (NNK or NNN). Oligonucleotide site-directed mutagenesis was carried out by established procedures. Saturation of an amino acid coding site in the H− RT gene with all possible amino acids was performed by introducing the sequence NNK (N=A, C, G or T and K=G or T) at the codon site into the mutagenic oligonucleotide. These oligonucleotides were used in site-directed mutagenesis to generate a library in which all possible substitutions at the mutagenized site were made. This library was screened for thermostable reverse transcriptase activity, and the most promising clones were sequenced.

Screening of mutants in Segment 2 (see FIG. 2) resulted in the identification of one mutant, H204R. Screening of a library mutagenized at site H204 resulted in several mutants, but the only one that was more thermostable than M-MLV reverse transcriptase was another H204R mutant. H204R mutants of M-MLV reverse transcriptase have enhanced thermostability. Screening of mutants in segment 3 (see FIG. 2) resulted in one mutant, T306K. Randomization of the T306 position produced thermostable mutants which, when sequenced, were T306R. Both T306K and T306R mutants of M-MLV reverse transcriptase have about 1.5 fold enhanced thermostability.

Example 3: TdT Reverse Transcriptase Mutants

In checking fidelity mutants of reverse transcriptase (RT) for misextension in a 3 dNTP assay, it was observed that SUPERSCRIPT™ II reverse transcriptase extended 2-3 bases past the end of the template in the presence of 3 and 4 dNTPs. This non-template directed extension or TdT activity is reduced in many mutants, but in a few such as F309N and T197E it appears that this activity is severely reduced or eliminated. These mutants are probably in close proximity or in contact with the template-primer as determined by homology to HIV reverse transcriptase and its crystal structure with bound template-primer.

Methods

Mutagenesis

For F309N:

Primers were designed corresponding to the mutant position F309 with the silent insertion of a NgoMIV restriction site at amino acid positions 310-311. The primers encoded a random NNK sequence for this position generating a random library of F309 mutants, where N is any of the four bases and K is T or G. The primers along with internal SUPERSCRIPT™ II reverse transcriptase primers at an upstream SstI restriction site and a downstream SalI restriction site were used in a standard PCR reaction (10 ng SUPERSCRIPT™ II reverse transcriptase template, 2 μM of each primer, 48 μl SuperMix (Invitrogen Corporation (Carlsbad, Calif.)) for 20 cycles of 94° C. 15 sec, 55° C. 15 sec, 72° C. 30 sec) to generate two PCR fragments. These were a 240 base pair SstI-NgoMIV fragment and a 200 base pair NgoMIV-SalI fragment. The fragments were isolated and digested and ligated together and then inserted into the original SUPERSCRIPT™ II reverse transcriptase clone cut with SstI and SalI. The resulting ligation product was transformed in Max Efficiency DH10B (Invitrogen Corporation (Carlsbad, Calif.)) competent cells to create the library of mutants at site F309. This library was then plated overnight for selection.

For T197E and Y133A:

The mutants T197E and Y133A were made by oligo-directed mutagenesis as described in Kunkel, T. A. et al. *Methods Enzymol.* 204:125 (1991). Briefly, the SUPERSCRIPT™ II reverse transcriptase gene was inserted into pBADhisA (Invitrogen Corporation) vector and named pBAD-SSII. This plasmid was transformed into DH11S cells and the cells were infected with M13K07 helper phage from which single strand DNA was isolated. Oligos were designed corresponding to each mutation: T197E and Y133A. Each oligo (100 μM) was kinased with T4 polynucleotide kinase (Invitrogen Corporation (Carlsbad, Calif.)) using the Forward Reaction Buffer (Invitrogen Corporation (Carlsbad, Calif.)). The oligo was annealed to single stranded pBAD-SSII DNA. Native T7 DNA polymerase (USB) and T4 DNA ligase (Invitrogen Corporation (Carlsbad, Calif.)) were added with synthesis buffer (0.4 mM dNTPs, 17.5 mM Tris-HCl, pH 7.5, 5 mM $MgCl_2$, 2.5 mM DTT, and 1 mM ATP) to the annealed reaction on ice. The reactions were incubated at 37° C. for 30 minutes and terminated by adding 1 μl of 0.5 M EDTA. The reactions were transformed and plated with DH10B cells. Colonies were picked and mutants were determined by restriction enzyme analysis and sequenced for confirmation using an ABI 377 instrument and ABI Big Dye Terminator Cycle Sequencing Ready Reaction kit.

Selecting Colonies Containing Active Reverse Transcriptase.

Individual transformant colonies were inoculated into single wells of a 96 well culture plate. Each well contained 120 μl of media (EG-Ap) containing 0.2% arabinose. It is preferable to first inoculate a 96 well plate with selective medium without the inducer, to grow that master plate overnight, and then to make a replica of the master plate into a 96-well plate with the inducer and grow that plate overnight. The cultures were grown overnight at 37° C. without shaking. Overnight cultures were mixed with an equal volume of 2×PLD (1.8% glucose, 50 mM Tris-HCl, pH 8.0, 20 mM EDTA, 20 mM DTT, 1% Triton X-100, 2 mg/mL lysozyme) at room temperature. These extracts were assayed directly for reverse transcriptase activity by mixing 10 μl of the extract with 40 μl of 1.25×RT reaction mix (62.5 mM Tris-HCl, pH 8.4, 62.5 mM KCl, 12.5 mM $MgCl_2$, 12.5 mM DTT, 1.25 mM dGTP, polyC/oligo dG (3.75 mM/1.5 mM in nucleotide), [$^{32}$P] dGTP). This reaction was placed in a 37° C. water bath for 10 minutes. A small aliquot of the reaction mixture (5 μl) was spotted onto a charged nylon membrane (Genescreen+, NEN). The membrane was washed twice with 10% TCA+1% sodium pyrophosphate, rinsed with ethanol, dried, and placed next to a phosphor screen. Radioactive product that had been trapped on the filter was detected by analyzing the screen in a Phosphorimager, using ImageQuant software (Molecular Devices). Candidates were selected if they showed reverse transcriptase activity (radioactivity). These candidates were screened a second time to confirm the phenotype. The confirmed candidates were then sequenced to determine which amino acids maintained detectable reverse transcriptase activity.

Purification of Reverse Transcriptase Mutants.

The cell pellet containing induced reverse transcriptase was suspended in a ratio of 2 mL Lysis buffer (40 mM Tris-HCl, pH 8.0, 0.1 M KCl, 1 mM PMSF)/1 gram of cell pellet. The suspension was sonicated on ice and then centrifuged at 27,000 g for 30 minutes. The cell-free extract was filtered through a 0.45μ syringe filter. The cell-free extract was applied to a 5 mL $Ni^{2+}$ HI-TRAP column (Pharmacia) pre-equilibrated with 5 volumes 5 mM imidazole in buffer A (40 mM Tris HCl, pH 8.0, 10% glycerol, 0.01% Triton X-100, 0.1 M KCl) at 1 mL/min. The column was washed with 10 volumes 5 mM imidazole in buffer A. The reverse transcriptase was eluted by washing with 20 volumes of a gradient of 5 mM to 1M imidazole in buffer A. The eluate containing reverse transcriptase protein was applied to a 1 mL Mono-S column (Pharmacia) pre-equilibrated with 10 column volumes 50 mM KCl in buffer B (40 mM Tris-HCl, pH 8.0, 10% glycerol, 0.01% Triton X-100, 0.1 mM EDTA, 1 mM DTT) at a flow rate of 1.0 mL/min. The column was washed with 10 volumes of 50 mM KCl in buffer B. Reverse transcriptase was eluted with 20 volumes of a gradient from 50 mM to 1 M KCl in buffer B. The individual fractions were analyzed for RT activity. The fraction containing peak RT activity was dialyzed against storage buffer (40 mM Tris-HCl, pH 8.0, 50% glycerol, 0.01% Triton X-100, 0.1 mM EDTA, 1 mM DTT, 0.1 M KCl). The purified reverse transcriptases were more than 95% pure, as judged by SDS-PAGE. The protein concentrations were determined by using the Biorad colorimetric kit.

3 dNTP Assay Method.

Procedures were modified from those of Preston, B. D., et al. *Science* 242:1168 (1988). The DNA template-primer was prepared by annealing a 47-mer template (5'-GAGTTACA-GTGTTTTTGTTCCAGTCTGTAGCAGTGTGTGAATG-GAA G-3') (SEQ ID NO:6) to an 18-mer primer (5'-CTTCCATTCACACACTGC-3') (SEQ ID NO:7) [$^{32}$P]-labeled at the 5'-end with T4 polynucleotide kinase (template:primer, 3:1). Assay mixture (10 μl) contained 5 nM template-primer, 50-200 nM reverse transcriptase as specified in figure legends, 3 or 4 dNTPs (250 μM each), 50 mM Tris-HCl (pH 8.3), 75 mM KCl, 3 mM $MgCl_2$, 10 mM DTT. Reactions were incubated at 37° C. for 30 minutes and terminated by the addition of 5 μl of 40 mM EDTA, 99% formamide. Reaction products were denatured by incubating at 95° C. for 5 minutes and analyzed by electrophoresis on urea 6% polyacrylamide gels.

To determine if any TdT activity was occurring in the control reaction of the 3 dNTP assay, which uses all 4 dNTPs, the control reaction was repeated with varying amounts of enzyme, >600 units to 20 units, at 37° C. for 30 minutes. For SUPERSCRIPT™ II, T197E, and Y133A, 200, 100, 50, and 20 units were used. For F309N, 646, 200, 50, and 20 units were used.

Results

We carried out a misinsertion assay of F309N(H204R, T306K) SUPERSCRIPT™ II reverse transcriptase, hereafter referred to as F309N, with DNA template. This assay was employed to compare the misincorporation capability of the mutant to SUPERSCRIPT™ II. The assay is a primer extension assay using synthetic DNA template-primer and biased dNTP pools containing only three of four dNTPs. The reactions are displayed on a gel in FIG. 3. While conducting this procedure to screen for mutants with lower misinsertion/misextension rates it was observed that SUPERSCRIPT™ II reverse transcriptase extended 2-3 nucleotides past the template end and that some mutations reduced or appeared to eliminate this non-template directed extension or TdT activity. As shown in FIG. 4, in the presence of all 4 dNTPs, SUPERSCRIPT™ II reverse transcriptase and the mutant F309N were able to extend the primer approximately equally, with SUPERSCRIPT™ II reverse transcriptase adding 2 nucleotides past the template, and F309N adding none beyond the end of the template. To further evaluate this non-templated directed extension the control reaction for the 3 dNTP misextension assay containing all 4 dNTPs was carried out with SUPERSCRIPT™ II, F309N, T197E, and Y133A reverse transcriptase for 30 minutes with varying amounts of enzyme. The three mutants had shown very reduced levels of TdT activity in prior screens. Since it had been observed that 5 minutes with 20 units of enzyme was more than enough time for the primer extension to be completed, a 30 minute incubation and 200 to 646 units of reverse transcriptase were both in large excess over what was necessary for the reaction to be completed. As seen in FIG. 4, all the reverse transcriptase reactions at the lowest amount tested had similar extension products to the reactions at the highest unit concentrations demonstrating that the reaction had gone to completion. SUPERSCRIPT™ II reverse transcriptase added 2 nucleotides past the end of the template, F309N and T197E did not extend past the end of the template, and Y133A appears to have a small amount of product that is 1 nucleotide past the end of the template.

Example 4: Dual Thermostable and TdT Mutants

The F309 amino acid position in M-MLV reverse transcriptase (RT) aligns with the W266 position in HIV reverse transcriptase. This position is at the base of the thumb domain and is considered part of the minor groove binding tract which interacts with the minor groove of the template-primer. The mutations H204R and T306K have been shown to increase the thermostability of the enzyme. The F309N mutation in an H204R/T306K clone displays 2.3× lower mutation frequency in a lacZ forward assay (Table 5) on RNA template and shorter extension products in a 3 dNTP extension assay than SuperScript™ II reverse transcriptase or H204R/T306K in SuperScript™ II reverse transcriptase. Both findings support the claim of an enzyme with higher fidelity (Table 6).

TABLE 5

Mutation Frequency of M-MLV Reverse Transcriptase High Fidelity Mutants

| Construct | total plaques | mutant plaques | MF ($\times 10^{-4}$) |
|---|---|---|---|
| SUPERSCRIPT ™ II | 15689 | 87 | 39 |
| SUPERSCRIPT ™ II (H204R, T306K) | 14410 | 83 | 41 |
| SUPERSCRIPT ™ II (H204R, T306K, F309N) | 11623 | 39 | 17 |
| SUPERSCRIPT ™ II (H204R, T306K, F309N, V223H) | 11415 | 39 | 14 |

Table 5. The mutation frequency of SUPERSCRIPT ™ II reverse transcriptase and point mutants. Mutation frequency (MF) was determined by dividing the number of mutant plaques (light blue or white) by the total number of plaques. The background mutant frequency of the starting DNA was $17 \times 10^{-4}$ for the first 3 constructs and $20 \times 10^{-4}$ for the last construct.

TABLE 6

Error Rates of M-MLV Reverse Transcriptase High Fidelity Mutants

| | M-MLV | SUPER-SCRIPT ™ II | F309N | V223H/ F309N |
|---|---|---|---|---|
| Overall ER (oER) | 1/17,000 | 1/15,000 | 1/34,000 | 1/41,000 |
| Mismatch | | | | |
| % of total | 46 | 35 | 68 72 | |
| ER (mER) | 1/37,000 | 1/42,000 | 1/50,000 | 1/58,000 |
| Frameshift | | | | |
| % of total | 46 | 60 | 21 22 | |
| ER (rER) | 1/37,000 | 1/25,000 | 1/162,000 | 1/188,000 |
| Strand Jump | | | | |
| % of total | 8 | 5 | 11 6 | |
| ER (jER) | 1/213,000 | 1/297,000 | 1/324,000 | 1/690,000 |

Methods

Mutagenesis. Using a standard site directed mutagenesis protocol, as described in Example 3, a primer containing the V223H mutation was annealed to single strand DNA of SuperScript™ H with the following mutations: H204R, T306K, F309N. The colonies were sequenced to confirm the new combination of V223H, H204R, T306K, and F309N.

Selecting Colonies Containing Active Reverse Transcriptase. Colony selection was performed as in Example 3.

Purification of RT mutants. Purification was performed as in Example 3.

Sequencing of plaques. The plaques from the lacZ forward assay were transferred from the soft agar plate to Whatmann 3 MM paper and allowed to dry for at least 1 hour. The plaque was then punched out and the plaque/paper disk was added directly to a sequencing reaction mix containing 4-8 μl ABI PRISM Dye Terminator Cycle Sequencing Ready Reaction (Perkin Elmer), 1 μl primer (GAAGATCGCACTCCAGCCAGC) (SEQ ID NO:8), and distilled water to 20 μl total volume. The ABI cycle sequencing protocol was used for 96° C. 10 seconds, 50° C. 5 seconds, 60° C. 4 minutes for 25 cycles. The paper disks were removed and the reactions were precipitated, then resuspended in loading dye and run on an ABI 377 sequencing machine.

The sequences were compared to wild type lacZ alpha sequence and then classified as frameshift (either 1 nucleotide insertion or deletion), mismatch, or strand jump (an insertion or deletion between repeated sequences). The overall error rate for each class was determined by dividing the mutation frequency by the number of detectable sites (i.e., sites the alteration of which results in a phenotypic change) (116) multiplied by 0.5 (to exclude the original single strand contribution) and then multiplied by the percentage of mutants observed to be in each class. ER=MF/(detectable sites*0.5)*(% in each class).

3dNTP assay method. 3dNTP assays were performed as in Example 3.

Results

We carried out a misinsertion assay of F309N(H204R T306K) SuperScript™ II reverse transcriptase, hereafter referred to as F309N, and V223H F309N(H204R T306K), hereafter referred to as V223H/F309N with DNA template. This assay was employed to compare the misincorporation capability of the mutant to SuperScript™ II. The assay is a primer extension assay using synthetic DNA template-primer and biased dNTP pools containing only three of the four dNTPs. The reactions are displayed on a gel in FIG. 5 and FIG. 6. In this assay, higher efficiency of primer extension denotes lower fidelity. As shown in FIGS. 5 and 6, in the presence of all 4 dNTPs, SuperScript™ II reverse transcriptase and the mutants F309N and V223H/F309N were able to extend the primer approximately equally, with some variance in the addition of non-template directed nucleotides at the end of the primer. However when incubated with biased pools of nucleotides, SuperScript™ II reverse transcriptase was able to catalyze substantial extension past template nucleotides for which a complementary dNTP was missing, indicating use of incorrect nucleotides and lower fidelity. In FIG. 5, the F309N (2) mutant showed shorter extension products than SuperScript™ II reverse transcriptase in each of the biased pools of three dNTPs, indicating less ability to incorporate incorrect nucleotides and thus higher fidelity. In FIG. 6, the V223H/F309N mutant was extended with just the dATP and dCTP pools. In each case V223H/F309N also had lower extension products than SuperScript™ II. This corresponds with the results of the lacZα assay where the F309N and V223H/F309N mutants had a lower mutation frequency than SuperScript™ II reverse transcriptase ($17\times10^{-4}$ and $14\times10^{-4}$ to $39\times10^{-4}$). The reverse transcriptase with just the H204R T306K mutations without F309N has a mutation frequency similar to SuperScript™ II reverse transcriptase ($41\times10^{-4}$ to $39\times10^{-4}$), suggesting that these mutations do not influence fidelity. This data shows a correlation between the misinsertion assay on DNA and the lacZα assay on RNA wherein higher fidelity mutants had both shorter extension products with biased pools of dNTPs and lower mutation frequencies in the lacZα assay.

Example 5: Error Rate Determination

To determine Error Rates, mutant plaques from the lacZ forward assay were sequenced using known methods. The mutations were then classified into one of the following categories: mismatches for misinsertion events, frameshifts for single insertion or deletion events, or jumps for large insertions or deletions caused by jumping between similar sequences. An overall Error Rate was then determined for nucleic acid encoding the lacZ alpha peptide using the following equation:

ER (error rate)=MF (mutation frequency)/(number of detectable sites×0.5), where the number of detectable sites is 116.

Not all bases mutated in lacZ forward assays result in a detectable phenotypic change. To determine specific error rates for mismatch, frameshift and jumps, the mutation frequency was modified by multiplying by the percent of the total of each mutant category, and then used to determine the specific error rate. The following is a sequence map of the lacZα peptide in M13 mp19 from SUPERSCRIPT™ II reverse transcriptase and the high fidelity SUPERSCRIPT™ II H203R T306K F309N reverse transcriptase assays. Underlining indicates deletions; "^" indicates insertions of the base A, T, C, or G shown above; A, T, C, or G shown above the complete sequence indicates mismatches.

Map of Mutations Introduced by SUPERSCRIPT™ II (SEQ ID NO: 9)

```
                                                     T C
       T                      T                     TC C
AGCGCAACGC AATTAATGTG AGTTAGCTCA CTCATTAGGC ACCCCAGGCT TTACACTTTA
                  1                  1               4

              CG                                  C      CC
TGCTTCCGGC TCGTATGTTG TGTGGAATTG TGAGCGGATA ACAATTTCAC ACAGGAAACA
     1

    C
    CC                CG       C
GCTATG ACC ATG ATT ACG^CCA AGC TTG CAT GCC TGC AGG TCG ACT CTA GAG GAT CCC CGG
                                                   1

                                       T                          AAAA
                                       T A                        AAA
                     T                 T A                         A
                     T       T         T A               T         A    C
GTA CCG AGC TCG AAT TCA CTG GCC GTC GTT^TTA CAA CGT CGT GAC TGG GAA AAC CCT GGC
                                     7                       1   1      1

                                               TTTTT
                                               TTTTT
                                           C   TTTTT
                                           C   TTT
                                           A T T
        TC   C            C       T  TC  T C T T   C    G       T
GTT ACC CAA CTT AAT CGC CTT GCA GCA CAT CCC^CCT^TTC^GCC AGC TGG CGT
                                        1     4

AAT AGC G
```

Example 6: Analysis of Enzymatic Activity in Mutant RTs

Reverse transcriptase (RT) (e.g., retroviral RT) is one of the most intensely studied DNA polymerases, both because of its use as an essential tool for the synthesis and cloning of cDNA and because of its importance as a target for inhibition of HIV (Skalka, A. M. and Goff, S. P., *Reverse Transcriptase*, Cold Spring Harbor Laboratory Press, Cold Spring, N.Y. (1993)). A dichotomy exists however in that HIV RT, the focus of much of recent study (Le Grice, S. F. J. in *Reverse Transcriptase* (Skalka, A. M. and Goff, S. P., eds) Cold Spring Harbor Laboratory Press, Cold Spring, N.Y., pp. 163-191, (1993)), has not been used widely as a tool for cDNA synthesis. This is because HIV RT has a relatively high error rate (Bebenek, K. and Kunkel, T. A. in *Reverse Transcriptase* (Skalka, A. M. and Goff, S. P., eds) Cold Spring Harbor Laboratory Press, Cold Spring, N.Y., pp. 85-102 (1993), and because it does not synthesize efficiently full-length copies of long mRNAs in vitro. Other forms of retroviral RT used widely to synthesize cDNA, M-MLV RT and AMV RT, also suffer from these limitations, but to a lesser extent (Bebenek, K. and Kunkel, T. A. in *Reverse Transcriptase* (Skalka, A. M. and Goff, S. P., eds) Cold Spring Harbor Laboratory Press, Cold Spring, N.Y., pp. 85-102 (1993); Krug, M. S, and Berger, S. L. *Methods in Enzymol.* 152:316-325 (1987); Gerard, G. F. and D'Alessio, J. M. (1993) in *Methods in Molecular Biology, Vol* 16*: Enzymes of Molecular Biology* (Burrell, M. M., ed) pp. 73-93, Humana Press, Totowa, N.J. (1993); Gerard, G. F., et al., *Molecular Biotechnology* 8:61-77 (1997)). In addition to polymerase activity, retroviral RT possesses RNase H activity that degrades the RNA in an RNA-DNA hybrid (Moelling, K., et al., *Nature New Biology* 234:240-244 (1971)). The presence of this degradative activity is responsible in part for the limitation on efficient synthesis of long cDNA (Krug, M. S, and Berger, S. L. *Methods in Enzymol.* 152:316-325 (1987), Berger, S. L., et al., *Biochem.*

TABLE 7

| | | | |
|---|---|---|---|
| Insertions | 40 | 38% | 60% frameshift (insertion or deletion) |
| Deletions | 23 | 22% | |
| Mismatches | 36 | 35% | 35% mismatch |
| Jumps | 5 | 5% | 5% Jumps |

TABLE 8

| | | |
|---|---|---|
| Overall Error Rate (oER) | 1/15,000 | $(39 \times 10^{-4})/(116 \times 0.5)$ |
| Mismatch Error Rate (mER) | 1/42,500 | $(0.35 \times 39 \times 10^{-4})/(116 \times 0.5)$ |
| Frameshift Error Rate (fER) | 1/25,000 | $(0.60 \times 39 \times 10^{-4})/(116 \times 0.5)$ |
| Jumps Error Rate (jER) | 1/297,000 | $(0.05 \times 39 \times 10^{-4})/(116 \times 0.5)$ |

22:2365-2372 (1983)). The RNase H domain of RT can be mutated to reduce or eliminate RNase H activity while maintaining mRNA-directed DNA polymerase activity (Kotewicz, M. L., et al., *Nuc. Acids Res.* 16:265-277 (1988), DeStefano, J. J., et al., *Biochim. Biophys. Acta* 1219:380-388 (1994)), improving the efficiency of cDNA synthesis (Kotewicz, M. L., et al., *Nuc. Acids Res.* 16:265-277 (1988)).

A second significant drawback to copying mRNA is the tendency of RT to pause during cDNA synthesis resulting in the generation of truncated products (Harrison, G. P., et al., *Nuc. Acids Res.* 26:3433-3442 (1998), DeStefano, J. J., et al., *J. Biol. Chem.* 266:7423-7431 (1991)). This pausing is due in part to the secondary structure of RNA (Harrison, G. P., et al., *Nuc. Acids Res.* 26:3433-3442 (1998), Wu, W., et al., *J. Virol.* 70:7132-7142 (1996)). Performing cDNA synthesis at reaction temperatures that melt the secondary structure of mRNA helps to alleviate this problem (Myers, T. W. and Gelfand, D. H., *Biochem.* 30:7661-7666 (1991)). In addition, the oligo$(dT)_n$ primer often used to initiate cDNA synthesis tends to prime at internal stretches of A residues in mRNA at lower temperatures, resulting in the synthesis of 3'-end truncated cDNA products. M-MLV RT does not efficiently synthesize cDNA from mRNA above 43° C. (Tosh, C., et al., *Acta Virol.* 41:153-155 (1997)). RNase H− minus (H−) M-MLV RT can be used up to 48° C. because in the absence of RNase H activity the mRNA template-DNA product complex is maintained during cDNA synthesis in a structural form that protects RT from thermal inactivation.

In an effort to raise the temperature at which M-MLV RT can be used to synthesize cDNA, we have randomly mutagenized the H− M-MLV RT gene and screened for thermal stable mutants. Several thermal stable mutants of H− M-MLV RT were identified and purified enzymes were characterized. We show that when the mutations are present together they increase RT thermal activity by increasing its intrinsic thermal stability without altering catalytic activity.

Experimental Procedures

Bacterial Strains and Plasmids—*E. coli* DH10B (Invitrogen) was used in all experiments. Bacterial liquid cultures were grown at 37° C. in EG: 2% tryptone, 1% yeast extract, 0.5% glycerol, 10 mM NaCl, and 1 mM KCl. Solid medium was LB (1% bactotryptone, 0.5% yeast extract, and 86 mM NaCl)+1.5% agar. Selective media included 100 μg/ml ampicillin. For induction of cultures, cells were inoculated into selective EG+0.2% arabinose and grown for 18 hr.

RNA and DNA—Chloramphenicol acetyl transferase (CAT) cRNA (~900 nt) with a 40-nucleotide poly(A) tail at the 3'-end was synthesized by T7 RNA polymerase run-off transcription from linearized plasmid DNA (D'Alessio, J. M. and Gerard, G. F., *Nuc. Acids Res.* 16:1999-2014 (1988)). The cRNA was selected on oligo(dT)-cellulose to ensure the presence of a poly(A) tail. For labeling, the 5' end of CAT cRNA was dephosphorylated with alkaline phosphatase. $(rC)_n$, $p(dT)_{12-18}$, and $p(dT)_{25-30}$ were purchased from Amersham Pharmacia. $(rA)_{630}$ was purchased from Miles. $(dG)_{15}$ and $(dT)_{20}$ were from Invitrogen. A DNA 24-mer complementary to CAT cRNA that annealed between nucleotides 679 and 692 with its 5' end 146 nucleotides distant from the first base at the 5' end of the CAT cRNA poly(A) tail was from Invitrogen. Oligonucleotides to prime PCR and perform site-directed mutagenesis were from Invitrogen.

Figure 2A:
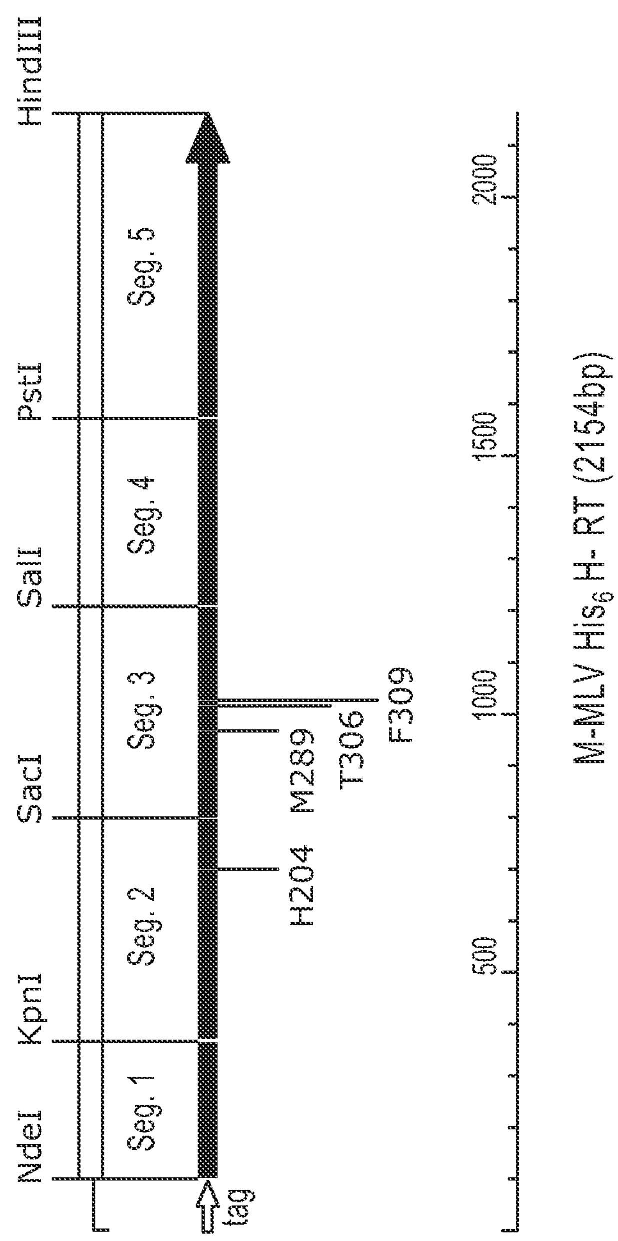
FIG. 2A is a linear representation of the coding sequence of the M-MLV reverse transcriptase showing the locations of the restriction enzyme cleavage sites used to generate the segments of the gene used to generate mutations.

M-MLV RT Gene—The M-MLV RT gene used in these studies was derived from pRT601 (Kotewicz, M. L., et al., *Nuc. Acids Res.* 16:265-277 (1988), Gerard, G. F., et al., *DNA* 5:271-279 (1986)). The gene starting at nucleotide 2598 and ending at nucleotide 4628 (Shinnick, T. M., et al., *Nature* 293:543-548 (1981)) was cloned under control of an araD promoter into plasmid pBAD/HisA (Invitrogen). The M-MLV gene was further modified by site-directed mutagenesis without changing amino acid coding to include several unique restriction endonuclease sites that divided the gene into five segments (FIG. 2A). The amino end of the protein contained a $His_6$ tag to simplify purification that included the following amino acids: MGGSHHHHHHG-MASMTGGQQMGRDLYDDDDKH (amino acids 1-32 of SEQ ID NO:2). The carboxy end of the protein contained the additional amino acids NSRLIN present as the result of subcloning from pRT601 (17). In addition, the M-MLV RT gene was mutated (D524G, E562Q, D583N) to eliminate RNase H activity. The final construct was designated pBAD-HSS2 (FIG. 2B), and the gene and gene product were designated $His_6$ H− RT.

DNA Sequencing—Plasmid DNA was prepared from an over night *E. coli* culture bearing an RT mutant using a Concert High Purity Miniprep Kit (Invitrogen) following the manufacturer's instructions. Each DNA was sequenced using a forward and reverse primer bordering the segment that had been mutagenized to generate the mutant. The sequencing reactions were carried out as specified for plasmid DNA using the ABI Big Dye Terminator Sequencing Ready Reaction Kit. The reactions were analyzed using an ABI PRISM 377 DNA Sequencer.

Random Mutagenesis—Mutagenic PCR was performed in a reaction mixture (100 μl) containing 20 mM Tris-HCl (pH 8.4), 50 mM KCl, 1.8 mM $MgCl_2$, 0.3 mM $MnSO_4$, 200 μM each of dCTP, dGTP, dTTP, and dATP, and 0.5 units of Taq DNA polymerase (Invitrogen Corporation, Carlsbad, Calif.). After a 1 mM denaturation step at 94° C., the cycling protocol was 15 sec at 94° C., 15 sec at 55° C., and 30 sec at 72° C. for 20 cycles. Amplification was 100 fold from 50 ng of target to 5 μg of amplified product. PCR primers included appropriate restriction endonuclease cut sites. An amplified DNA segment was cleaved with appropriate restriction endonucleases, gel purified, and cloned into gel purified vector DNA cut with the corresponding restriction enzymes.

Site-directed Mutagenesis—Oligonucleotide site-directed mutagenesis was carried out by established procedures (Kunkel, T. A., et al., *Methods Enzymol.* 154:812-819 (1987), Kunkel, T. A., et al., *Methods Enzymol.* 204:125-139 (1991)). Saturation of an amino acid coding site in the H− RT gene with all possible amino acids was performed by introducing the sequence NNK (N=A, C, G or T and K=G or T) at the codon site into the mutagenic oligonucleotide.

DNA Polymerase Assays—During screening of RT mutants, RT RNA-directed DNA polymerase activity was assayed with $(rC)_n \bullet (dG)_{15}$, which is specific for RT under the reaction conditions used (Gerard, G. F., et al., *Biochem.* 13:1632-1641 (1974)). Reaction mixtures (50 μl) containing 50 mM Tris-HCl (pH 8.4), 50 mM KCl, 10 mM $MgCl_2$, 300 μM $(rC)_n$, 120 μM $(dG)_{15}$, 0.01% (v/v) Triton X-100, and 100 μM [α-$^{32}$P]dGTP (1,000 cpm/pmole), were incubated at 37° C. for 10 min in the wells of a 96-well plate. An aliquot (5 μl) from each well was spotted onto a Genescreen+(NEN) filter and the filter was washed twice for 10 min with 4% (w/v) sodium pyrophosphate (pH 8.0). Radioactivity bound to the dried filter was quantified in a phosphorimager (Molecular Dynamics).

RT DNA polymerase unit activity was assayed with $(rA)_{630}$•$p(dT)_{12-18}$ (Houts, G. E., et al., *J. Virol.* 29:517-522 (1979)). One unit of DNA polymerase activity is the amount of RT that incorporates one nmole of deoxynucleoside triphosphate into acid insoluble product at 37° C. in 10 min.

cDNA synthesis from CAT cRNA was carried out in reaction mixtures (20 μl) containing 50 mM Tris-HCl (pH 8.4), 75 mM KCl, 3 mM $MgCl_2$, 10 mM dithiotreitol (DTT), 500 μM each of dATP, dTTP, dGTP, and [α-$^{32}$P]dCTP (300 cpm/pmole), 1,750 units/ml RNase Inhibitor, 130 μg/ml (465 nM) CAT cRNA, 20 μg/ml (2,300 nM) $p(DT)_{25-30}$, and 3,250 units/ml (100 nM) RT. Incubation was at various temperatures for 60, min in individual tubes. An aliquot of the reaction mixture was precipitated with TCA to determine yield of cDNA synthesized, and the remaining cDNA product was size fractionated on an alkaline 1.2% agarose gel (McDonell, M. W., et al., *J. Mol. Biol.* 110:199-146 (1977)).

To establish mono- and divalent metal reaction optima, initial reaction rates were determined under conditions of limiting RT concentration during a 10-min incubation at 37 or 50° C. Reaction mixtures (20 μl) contained 50 mM Tris-HCl (pH 8.4), 10 mM DTT, 500 μM each of dTTP, dATP, dCTP, and [$^3$H]dGTP (100 cpm/pmole), 10 pmoles (2.8 μg) CAT cRNA, 50 pmoles DNA 24-mer, 0.5 pmoles RT, and KCl and $MgCl_2$, varied in concentration one at a time.

Steady-state Kinetic Measurements—The steady-state kinetic parameters $K_{m(dTTP)}$ and $k_{cat}$ were determined as described (Polesky, A. H., et al., *J. Biol. Chem.* 265:14579-14591 (1990)), using $(A)_n$•$(dT)_{30}$. A range of five [$^{32}$P]dTTP concentrations, which bracketed the $K_{m(dTTP)}$ value, was used for each determination of the kinetic parameters. The concentration of the template-primer and enzyme in the reaction were 2 μM (in primer termini) and 4 μM, respectively. Reaction mixtures (50 μl) also contained 50 mM Tris-HCl, pH 8.4, 75 mM KCl, 3 mM $MgCl_2$, and 10 mM DTT and were incubated at 37° C.

Mutant Screening—Mutant populations were plated on selective agar. Individual colonies were inoculated into 120 μl of selective EG in 96 well plates and grown overnight at 37° C. The cell density of the cultures was ~$10^9$ cfu/ml. An aliquot of the culture from each well was transferred into a new 96-well plate containing 120 μl per well of selective media+0.2% arabinose. This plate was incubated at 37° C. for 20 hr to induce expression of RT. An aliquot (5 μl) of culture from each well was then transferred into another 96-well plate containing 5 μl per well of 2×PLD (50 mM Tris-HCl, pH 8.0, 20 mM EDTA, 1.8% (w/v) sucrose, 1% (v/v) Triton X-100, 10 mM DTT, and 2 mg/ml lysozyme). After heating for 5 to 10 min at various temperatures (52 to 58° C.) in a thermocycler and cooling to room temperature, RT activity in a 5-μl aliquot from the lysate in each well was assayed with $(rC)_n$•$(dG)_{15}$ in another 96-well plate as described above. The amount of RT activity in a 5-μl aliquot of extract was within the linear range of the assay. Lysates were stable at room temperature for at least 1 hr.

Purification of RTs—All operations were at 4° C. Induced *E. coli* cells (5 g) bearing pBAD-HSS2 or a derivative were suspended in 10 mL of buffer (20 mM Tris-HCl, pH 8.0, 100 mM KCl, and 1 mM PMSF) and were sonicated for disruption. After clarification by centrifugation at 20,000×g for 30 min, RT was purified by sequential chromatography on a 5-ml Chelating Sepharose column charged with $Ni^{2+}$ and a Mono S HR 5/5 column (Amersham Pharmacia). In some cases the RT was fractionated on a third column (AF-Heparin-650 from TosoHaas) to eliminate traces of RNase contamination. The purified RT was dialyzed against storage buffer (40 mM Tris-HCl, pH 8.0, 100 mM KCl, 0.01% (v/v) Triton X-100, 0.1 mM EDTA, 1 mM DTT, and 50% v/v glycerol) and stored at −20° C. RT purified by this procedure was >90% homogeneous as judged by SDS PAGE and was free of detectable contaminating DNA endonuclease, DNA exonuclease, and RNA endonuclease.

Thermal Inactivation Profile of RT in Extracts—Cell lysates prepared in PLD as described already were heated in a 96-well plate in a thermocycler in which a temperature gradient exists through the rows, but the temperature in each column is the same. After incubation for 5 min at temperatures ranging from 25° C. to 56° C., RT activity was assayed with $(rC)_n$•$(dG)_{15}$ as described already.

Half Life Determination—Mixtures (20 μl) were incubated for various times in 0.5-ml tubes in a thermocycler at 50 or 55° C. and contained 50 mM Tris-HCl (pH 8.4), 75 mM KCl, 3 mM $MgCl_2$, 10 mM DTT, 0.1% (v/v) Triton X-100, and 3-7 μg/ml purified RT. Incubation was stopped by placing the tube in ice. An aliquot (5 μl) was assayed for residual activity with $(rA)_{630}$•$p(dT)_{12-18}$.

Measurement of $K_D$ by Filter Binding—A nitrocellulose filter-binding assay (Bailey, J. M., *Anal. Biochem.* 93:204-206 (1979), Strauss, H. S., et al., *Gene* 13:75-87 (1981)) was used to determine the nucleic acid binding constants ($K_D$) of RTs for CAT cRNA•$(dT)_{20}$. Dephosphorylated CAT cRNA was labeled at the 5' end with [γ-$^{32}$P]ATP and T4 polynucleotide kinase (Boehringer). Oligo$(dT)_{20}$ was annealed to the poly(A)-tailed CAT cRNA in a buffer containing 10 mM Tris-HCl, pH 7.5, and 80 mM KCl at 65° C. for 5 mM followed by chilling on ice. Reaction mixtures (100 μl) containing binding buffer (50 mM Tris-HCl, pH 8.4, 75 mM KCl, 3 mM $MgCl_2$, and 10 mM DTT), 0.05 nM $^{32}$P-labeled CAT cRNA, 1 nM $(dT)_{20}$, and 1 to 50 nM RT were incubated at 23° C. for 5 min. After incubation, the mixture was filtered through a nitrocelullose filter (Millipore, HA 0.45 mm) soaked in binding buffer, which was then washed with binding buffer. The $K_D$ is equal to that enzyme concentration at which 50% of the labeled CAT cRNA is bound. For this method of analysis to be valid, the CAT cRNA concentration in the reaction must be substantially below $K_D$, so that the total enzyme concentration approximates the concentration of free unbound enzyme.

Results

Figure 2B:
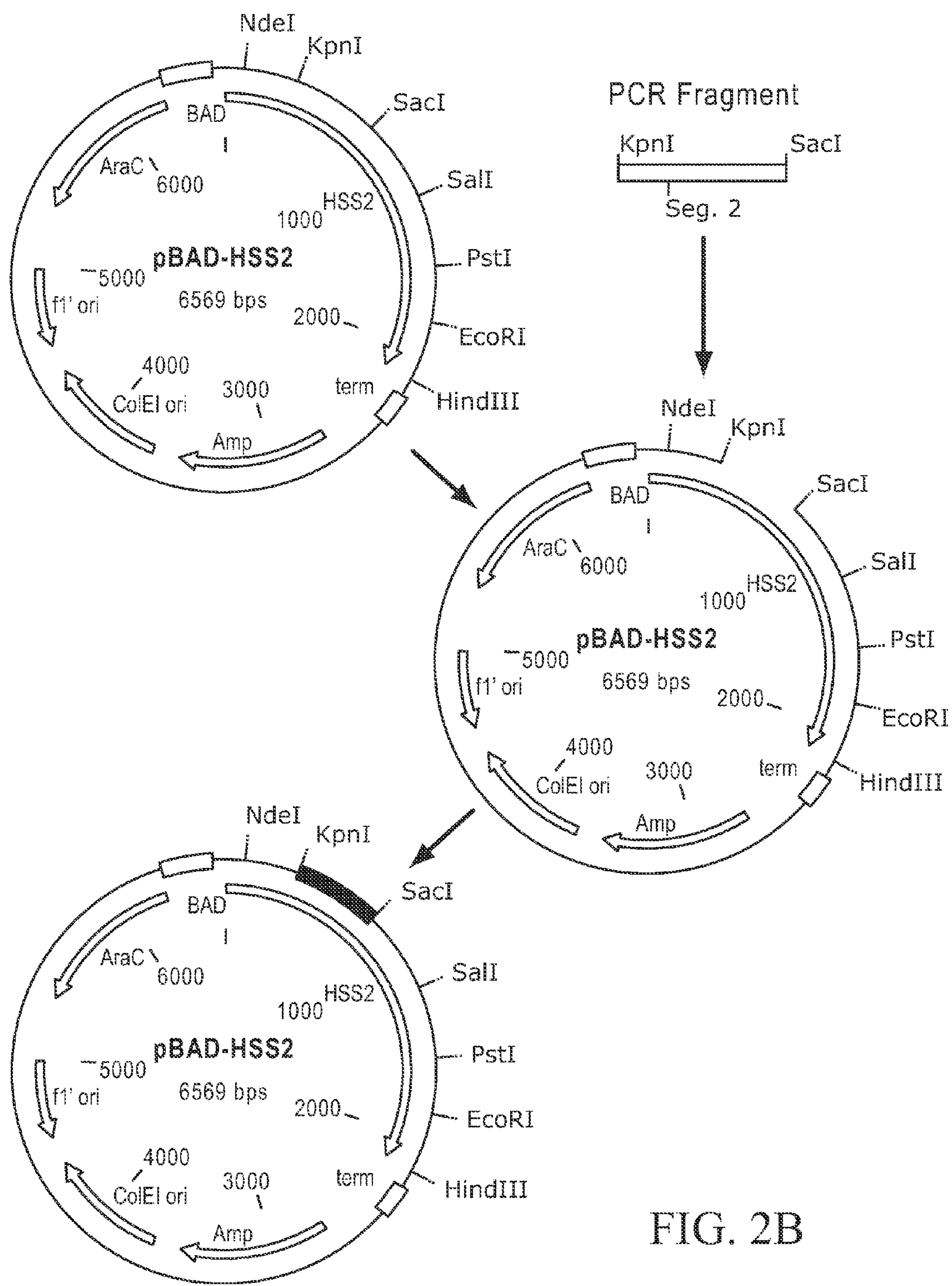
FIG. 2B is a schematic representation showing the insertion of a mutagenized PCR fragment into the coding sequence of the remaining portion of the reverse transcriptase gene.

Mutants Generated by Random Mutagenesis—PCR primers were designed to amplify each of five segments of the M-MLV $His_6$ H− RT gene (FIG. 2A) and to contain appropriate restriction endonuclease cut sites. Each segment was randomly mutagenized by PCR mutagenesis (Experimental Procedures), digested with the appropriate restriction endonucleases, and cloned into a similarly digested pBAD-HSS2 plasmid in such a way as to replace the corresponding segment in the H− RT gene with the mutagenized segment (FIG. 2B). Libraries were sampled by DNA sequencing of the mutagenized H− RT gene segment of a small number of clones to determine the mutation frequency. The goal was to achieve rates of PCR random mutagenesis that produced 1 to 2 mutations per segment. We found that random mutagenesis that produced greater than 2 mutations per segment tended to produce a large proportion of inactive RT mutants. If the library met this criterion, further screening by heat treatment was carried out to identify mutants that showed greater RT activity in lysates than H− RT after a heat treatment step (Experimental Procedures; FIG. 7A). Those mutants with the highest apparent thermal stability were screened again in duplicate by pretreatment at 24° C. (to normalize for activity) and at 52 to 58° C. to confirm the presence of enhanced thermal stability (FIG. 7B). In all, about 15,000 clones were screened by heat treatment in the 96-well format for each segment or a total of about 100,000 mutants.

Two mutants were found that produced RT with greater thermal stability than H− RT. DNA sequencing of their genes revealed them to be H204R in segment 2 and T306R in segment 3. Having identified two amino acid locations that influence RT thermal stability, we wished to establish if the particular mutant amino acid selected gave the greatest possible increase in thermal stability. The two sites in the H− RT gene were independently subjected to site-directed mutagenesis in which the sequence NNK was substituted for the existing codon in the mutagenic oligonucleotide (Experimental Procedures). Eighty-four members from each of these libraries were screened for thermal stable mutants. The results showed that T306K and T306R were the most thermal stable variants at T306, with T306K being somewhat more thermal stable, and H204R was the most thermal stable variant at H204.

The mutations were combined in one clone by sequential site-directed mutagenesis. Assay of heat-treated extracts showed that the double mutant $His_6$ H− H204R T306K RT was more thermal stable than either mutant alone and much more thermal stable than $His_6$ H− RT (FIG. 8).

Utilizing plasmid pBAD-HSS2 that contained the H204R and T306K mutations as a starting point, RT gene segments 1 through 5 were again randomly mutagenized and libraries were screened for additional mutations that rendered $His_6$ H− H204R T306K RT more thermal stable. One additional mutation, M289L, in segment 3 was identified that increased the thermal stability of the RT double mutant in crude extracts.

Mutants from Single-Site Mutagenesis—$His_6$ H− T306K RT was mutated at position F309 to F309N by site-directed mutagenesis as part of a study of the fidelity of H− RT. The F309N mutation increased the thermal stability of $His_6$ H− T306K RT in crude extracts.

Thermal Stability of Purified Mutant RTs—A number of RT mutants were purified to near homogeneity (Experimental Procedures) in order to establish their intrinsic thermal stability in the absence of contaminants and to characterize their enzymatic properties. The intrinsic thermal stability of purified forms of single mutants of $His_6$ H− RT at each of the 4 positions were established and compared with that of the starting enzyme. Mutations T306K, M289L, or F309N increased the half-life of $His_6$ H− RT a small amount at 50° C. from 8 min to between 10 and 13 min (Table 9).

TABLE 9

Half-lives of purified RT mutants at 50° C.

| Enzyme | Half-life at 50° C. (min)[a] |
|---|---|
| H-RT (SUPERSCRIPT ™ II) | 3.2 ± 0.2 |
| $His_6$ H-RT | 8 ± 1.2 (1.6 ± 0.3)[b] |
| $His_6$ H-H204R RT | 43 ± 9 |
| $His_6$ H-T306K RT | 10 ± 0.4 |
| $His_6$ H-F309N RT | 13 ± 3 |
| $His_6$ H-M289L RT | 13 ± 1 |
| $His_6$ H-H204R T306K RT | 78 ± 8 |
| H-H204R T306K F309N RT | 30 |
| $His_6$ H-H204R T306K F309N RT | 105 ± 11 |
| $His_6$ H-H204R M289L T306K F309N RT | 240 ± 10 (8.1 ± 0.3) |

[a]Mean ± standard deviation of two or three determinations

[b]Half-lives at 55° C. are in parentheses

The single mutation with the greatest impact was H204R, which increased the half-life of RT at 50° C. 5-fold (Table 9). However, combining the mutations had at a minimum a positive additive effect upon thermal stability. Combining H204R and T306K increased the half-life at 50° C. 10-fold, and combining M289L and F309N with these two mutations increased the half-life at 50° C. another 3-fold to 240 min (a 30-fold increase relative to the half-life of the starting enzyme; Table 9).

The half-lives of $His_6$ H− RT and all its mutants dropped off at 55° C. relative to 50° C. (Table 9). The magnitude of the relative increase in intrinsic half-life observed at 50° C. for the quadruple mutant was maintained partially at 55° C. (Table 9). The half-life of $His_6$ H− RT of 1.6 min at 55° C. was increased 5-fold by H204R M289L T306K F309N to 8.1 min (Table 9).

The presence of an N-terminal tag was seen to increase thermal stability of the RTs examined. A comparison of an RT with no N-terminal tag (SUPERSCRIPT™ II) with an RT having the same point mutations and having an N-terminal tag with the sequence MGGSHHHHHHGMASMTGGQQMGRDLYDDDDKH corresponding to amino acids 1-32 of SEQ ID NO:2 ($His_6$ H− RT) shows that the presence of the tag increases the thermal stability of the RT. The presence of the tag increased the half-life of the RT at 50° C. by a factor of 2.5-fold (from 3.2 minutes to 8 minutes). A comparison of the triple mutant H204R T306K F309N with and without tag showed an increase in the half-life of the enzyme at 50° C. by a factor of 3.5-fold (30 minutes to 105 minutes). Thus, the present invention contemplates RTs with an increased thermal stability that comprise one or more amino acids added to the N-terminal of the RT. In addition, the invention contemplates RTs with enhanced thermal stability that comprise one or more amino acids added to the C-terminal of the RT.

Enzymatic Characterization of Purified Mutant RTs—A number of catalytic properties of the purified RT mutants were compared to ascertain if introduction of all four point mutations in RT altered its DNA synthetic activity. With one exception, all of the thermal stable mutants characterized had RNA-directed DNA polymerase specific activities greater than that of starting $His_6$ H− RT, but within a factor of 1.5-fold (Table 10).

TABLE 10

RNA-directed DNA polymerase specific activity of purified RT mutants

| Enzyme | DNA Polymerase Specific Activity (units/μg) |
|---|---|
| $His_6$ H-RT | 281 (1.0)[a] |
| $His_6$ H-H204R RT | 325 (1.16) |
| $His_6$ H-T306K RT | 402 (1.43) |
| $His_6$ H-F309N RT | 257 (0.91) |
| $His_6$ H-M289L RT | 339 (1.21) |
| $His_6$ H-H204R T306K RT | 385 (1.37) |
| $His_6$ H-H204R T306K F309N RT | 391 (1.39) |
| $His_6$ H-H204R M289L T306K F309N RT | 410 (1.46) |

[a]Ratio of specific activity setting that of $His_6$ H-RT at 1.0.

$His_6$ H− F309N RT had a slightly reduced DNA polymerase specific activity (Table 10). The catalytic efficiency ($k_{cat}/K_m$) of $His_6$ H− RT and $His_6$ H− H204R M289L T306K F309N were within a factor of two of each other and their Kms for nucleotide substrate were similar (Table 11).

TABLE 11

Catalytic constants of purified RT mutants[a]

| Enzyme | $K_m$ (μM) | $k_{cat}$ ($sec^{-1}$) | $k_{cat}/K_m$ |
|---|---|---|---|
| $His_6$ H-RT | 390 ± 98 | 45 ± 18 | 0.115 |
| $His_6$ H-H204R M289L T306K F309N RT | 274 ± 92 | 46 ± 11 | 0.17 |

[a]Mean ± standard deviation of three determinations

The monovalent and divalent metal ion optima of $His_6$ H− RT and $His_6$ H− H204R M289L T306K F309N RT were determined. CAT cRNA•DNA 24-mer in excess over enzyme was used as template-primer (Experimental Procedures). The optima were the same: 75 mM KCl and 3 mM $MgCl_2$ at 37° C. for $His_6$ H− RT and $His_6$ H− H204R M289L T306K F309N and at 50° C. for the quadruple point mutant. Taken together these results indicate that the four mutations identified that substantially increased the thermal stability of H− RT did not appreciably affect its DNA polymerase catalytic capability.

In the presence of a template-primer, the half-life of M-MLV H− RT at 50° C. is increased by a factor of 3 to 4 relative to the half-life in the absence of nucleic acids. This is the result of the enzyme being more resistant to heat inactivation when bound to template-primer than when unbound in solution. Mutations that impact the affinity of RT for template-primer will affect the apparent thermal stability of RT when it is engaged in cDNA synthesis. Therefore the affinities ($K_D$) of $His_6$ H− RT and several of its mutants for CAT cRNA•$(dT)_{20}$ were determined (Table 12).

TABLE 12

Nucleic acid dissociation constants of purified RT mutants

| Enzyme | $K_D$ (nM)[a,b] |
|---|---|
| $His_6$ H-RT | 8 ± 0.5 |
| $His_6$ H-H204R RT | 35 ± 0.5 |
| $His_6$ H-T306K RT | 6.6 ± 0.4 |
| $His_6$ H-F309N RT | 28 ± 2.5 |
| $His_6$ H-M289L RT | 4.7 ± 0.7 |
| $His_6$ H-H204R T306K RT | 6.1 ± 1.5 |
| $His_6$ H-H204R T306K F309N RT | 7.3 ± 2.4 |
| $His_6$ H-H204R M289L T306K F309N RT | 11 ± 1.0 |

[a]Mean ± standard deviation of two or three determinations

[b]The nucleic acid was CAT cRNA•$(dT)_{20}$

The $K_D$ of the $His_6$ H− RT quadruple mutant was increased somewhat from 8 nM to 11 nM, indicating that nucleic acid binding affinity was reduced slightly by the four point mutations together. Interestingly two of the point mutations when present alone, H204R and F309N, reduced the binding affinity of $His_6$ H− RT substantially more, having a $K_D$ of 35 and 28, respectively. The effects of these mutations on binding were apparently counter balanced by mutation T306K ($K_D$=6.6 nM), since the triple mutant H204R T306K F309N had a $K_D$ of 7.3 nM. We conclude that when the triple (H204R T306K F309N) or quadruple mutant of $His_6$ H− RT is engaged in cDNA synthesis, any increase in apparent thermal stability observed relative to $His_6$ H− RT is not due to increased protection by virtue of binding more tightly to template-primer.

Practical Implication of Higher RT Thermal Stability—To assess the practical impact of the increases in thermal stability imparted by the H− RT mutations selected in this study, we measured the ability of some of the mutants to synthesize full-length CAT cDNA between 40 and 55° C. (Table 13).

TABLE 13

Synthesis of full-length cDNA product from CAT cRNA by purified RT mutants at elevated temperatures[a]

| | Amount of Full Length Product (ng) Synthesized at | | | | |
|---|---|---|---|---|---|
| Enzyme | 40° C. | 45° C. | 50° C. | 52.5° C. | 55° C. |
| $His_6$ H-RT | 517 | 523 | 229 | 40 | 2 |
| $His_6$ H-H204R RT | 521 | 446 | 146 | 36 | 17 |
| $His_6$ H-T306K RT | 456 | 512 | 338 | 122 | 28 |
| $His_6$ H-H204R T306K RT | 664 | 528 | 330 | 202 | 43 |
| $His_6$ H-H204R T306K F309N RT | 488 | 556 | 396 | 209 | 53 |
| $His_6$ H-H204R M289L T306K F309N RT | 540 | 547 | 539 | 376 | 120 |

[a]cDNA synthesis reaction mixtures (as described above) contained 9.3 pmoles (2.6 μg) of CAT cRNA. The amounts of full-length products were established by cutting the region corresponding to the size of each full-length band from a dried alkaline 1.2% agarose gel and counting it in a scintillation counter.

Reaction mixtures contained 2 pmoles of RT and were incubated at the temperatures indicated for 60 min. The results of a single experiment are shown. Similar results were obtained in one other experiment.

The amount of RT relative to template-primer was limiting in these reactions. In the presence of limiting RT, failure to achieve full-length cDNA synthesis as the temperature is increased is an indicator of thermal inactivation of the enzyme under cDNA synthesis conditions. With one exception at temperatures above 50° C., the amount of full-length CAT cDNA synthesized by a particular RT mutant (Table 13) correlated well with the thermal stability (half-life) of the enzyme at 50° C. (Table 9). The one exception is mutant H204R. It produced less fun-length cDNA than $His_6$ H− RT at 50 and 52.5° C., in spite of having a 5-fold greater half-life at 50° C. This is probably due to the weaker binding of H204R than H− RT to CAT cRNA•DNA, diminishing thermal protection by template-primer. All the RTs tested maintained activity at 45° C. relative to 40° C., but with the exception of the quadruple mutant, all RTs synthesized less full-length CAT cDNA at 50° C. and above. The $His_6$ H− RT quadruple mutant was fully active at 50° C. and at 55° C. synthesized 60 times more full-length CAT cDNA than $His_6$ H− RT. This was 22% of the amount synthesized by both enzymes at 40° C.

The methods of the present invention can be used to engineer a polypeptide to have a desired characteristic, for example, a desired level of thermostability. The nucleic acid sequence of the polypeptide may be sub-divided into segments and the segments individually mutagenized, for example, using PCR random mutagenesis. The individual segments may then be re-assembled and used to express a mutated polypeptide that is screened for the desired activity. The Examples above provide working embodiments of the invention in which the rather large RT gene (2154 bases) was randomly mutated in segments by PCR random mutagenesis (Leung, et al., (1989) *Technique* 1, 11-15. Cadwell, et al., (1992) *PCR Methods and Applications* 2, 28-33). It may be desirable to sub-divide the sequence of the polypeptide of interest into fragments that correspond to functional or structural domains of the polypeptide of interest if such domains are known. In the working embodiments above, the segments roughly corresponded to the coding sequences of the five separate structural subdomains of RT (Kohlstaedt, et al., (1992) *Science* 256, 1783-1789. Jacobo-Molina, et al., (1993) *Proc. Natl. Acad. Sci. USA* 90, 6320-6324). Segments one through four corresponded to the polymerase subdomain of fingers, palm, thumb, and connection, respectively, and segment five corresponded to the RNase H domain (FIG. 2A).

Using the materials and methods of the present invention, one skilled in the art can construct a modified RT enzyme having a desired level of thermostability. In the examples presented above, the operating temperature of H− M-MLV RT was increased to at least 10° C. above 45° C. This target temperature was selected as a compromise: high enough to help reduce RNA secondary structure and low enough to avoid RNA breakdown. Although, the rate of chemical RNA breakdown catalyzed by $Mg^{++}$ increases dramatically as the temperature is increased above 55 to 60° C. under cDNA synthesis reaction conditions, it may be desirable in certain instances (e.g., RNA with pronounced secondary structure) to conduct a reverse transcription reaction at a temperature higher than 55° C., for example, at about 60° C., or at about 65° C., or at about 70° C. Using the methods described above a suitable RT can be constructed using routine experimentation.

Reaction conditions for the mutagenesis reaction may be adjusted to introduce the desired number of mutations in each segment. In the present study, an upper limit cut-off of 1 to 2 mutations per segment was set as the target for mutation frequency to suppress accumulation of deleterious mutations (Lehmann, et al., (2001) *Current Opinion in Biotechnology* 12, 371-375), and to minimize the amount of screening required to find active mutants. Those skilled in the art will appreciate that conditions may be adjusted in order to induce a greater mutation frequency, for example, by adjusting the concentration of $Mn^{2+}$, pH, salt concentration etc. Mutation frequencies of >5 mutations/segment in segment one, two, or three produced only about 5% active mutants with all the mutants having less thin wild-type activity. At the mutation frequency used of 1 to 2 mutations per segment, approximately one-third of the mutants had little or no activity, one-third had less than 50% of $His_6$ H− RT activity, and one-third had up to 100% of $His_6$ H− RT activity.

Polypeptides produced from the mutated sequences are screened for a desired activity. The polypeptides may be screened from crude extracts, partially purified extracts or from purified polypeptide preparations. In the Examples above, crude extracts of mutants were screened in a 96-well plate format with template-primer specific for RT activity (Gerard, et al., (1974) *Biochem.* 13, 1632-1641). The procedure used to produce *E. coli* cell crude extracts permeabilized rather the lysed the cells, releasing proteins and small RNAs to the outside of the cell matrix, while keeping DNA inside. This made representative sampling and assay with an exogenous template-primer of the cell suspension feasible. The signal-to-noise ratio of the assay was such that to differentiate starting from mutant cells at least a two-fold difference in activity was required. Those skilled in the art will appreciate that other methods of screening, for example, by first purifying the mutated polypeptides of interest (e.g., RTs) will permit detection of smaller changes in activity level.

Utilizing this approach, two mutations were found in segment three (thumb) and one in segment two (fingers). A rational sequence homology approach combined with site-directed mutagenesis was used to identify a fourth mutation located in the fingers subdomain. The small number of mutations found and the failure to identify mutations in segments one and four were probably due to limitations of both the random mutagenesis approach and the screen. The mutation frequency cut off of 1 to 2 mutations per segment imposed on the random mutagenesis limited the mutant space available in the mutant population. The inability of the assay to detect less than a two-fold difference in activity probably made many active and slightly more thermal stable mutants undetectable. Since the RNase H domain of wild-type M-MLV RT is already substantially more thermal stable than the polymerase domain (Verma, I. (1975) *J. Virol.* 15, 843-854), it was unlikely that stabilizing mutations introduced in segment five would be picked up in a screen for more thermal stable polymerase activity.

In spite of the limited number of mutations found with the approach used, those that were identified had a significant positive impact on RT thermal stability. The thermal stability of $His_6$ H− M-MLV H204R M289L T306K F309N RT was increased 30 fold at 50° C. The RT operating temperature was increased 7° C. to 55° C. Three of the four mutations alone increased the RT half-life 1.2 to 1.6-fold and the fourth mutation gave a 5-fold increase. A well established operating principle in protein stabilization is that the total stabilization obtained by multiple mutations is the sum of the effects of individual mutations, assuming each mutation exerts its effect independent of the other mutations (Wells, J. A. (1990) *Biochem.* 29, 8509-8517). The thermal stabilizing effects of the four mutations appear to be additive, but an additional contribution to increased thermal stability due to cooperative interaction between mutations cannot be excluded.

Discussion of the mechanisms whereby each of these four mutations affect the thermal stability and template-primer binding affinity of M-MLV RT requires a 3-dimensional structural framework. In the case of the mutation at H204 in the M-MLV RT palm subdomain, this is easily accomplished because the structure of a fingers-palm fragment of M-MLV RT is known (Georgiadis, et al., (1995) *Structure* 3, 879-892). For T306K and F309N located in the thumb, we must rely on 3-dimensional structural data taken from HIV RT (Kohlstaedt, et al., Jacobo-Molina, et al., Ding, et al., (1998) *J. Mol. Biol.* 284, 1095-1111, and Huang, et al., (1998) *Science* 282, 1669-1675). Fortunately in this region of the thumb subdomain of HIV RT (T253 to P272) and the corresponding region of M-MLV RT (T296 to P315), the amino acid sequence is reasonably well conserved. M-MLV RT can be predicted to have an α-helix in this region that resembles the structure of HIV RT α-helix H (Kohlstaedt, et al., Jacobo-Molina, et al., Kneller, et al., (1990) *J. Mol. Biol.* 214, 171-182, and Rost, B. (1996) *Methods Enzymol.* 266, 525-539.)

Together the four RT amino acid changes exerted their stabilizing effect without significantly altering the DNA synthesizing catalytic activity of the enzyme. However two mutations, H204R and F309N, did significantly reduce RT binding to template-primer (Table 12). M-MLV RT H204R is located in the middle of the long α-helix H (αH) on the backside of the palm subdomain, directly below p3-sheets 10-11 (β310-β11) (FIG. 9, Georgiadis, et al., supra). Beta-sheets 10-11 contain the M-MLV RT polymerase catalytic site (YVDD) at residues 222 to 225 on the inside of the palm that contact the template-primer (Georgiadis, et al., supra). Changes in H204R could directly affect packing of amino acid residues near it in αH and β10-β11, thus influencing how β10-β11 interact with template-primer. Or its effect could be translated along the polypeptide backbone since the α-helix containing H204 and the β-sheet containing Y222 are separated by a single short turn (FIG. 9). As discussed above based upon an amino acid homology comparison of M-MLV and HIV RT and from crystal structures of HIV RT (Kohlstaedt, et al., supra, Jacobo-Molina, et al., supra, Ding, et al., supra, Huang, et al., supra, Kneller, et al., supra, Rost, Bebenek, et al., (1997) *Nature Structural Biology* 4, 194-197, and Beard, et al., (1998) *J. Biol. Chem.* 273, 30435-30442), F309 in M-MLV RT can be predicted to be part of a minor groove binding track in an α-helix of the RT thumb subdomain. In HIV RT this structure contributes significantly to RT binding to template-primer (Bebenek, et al., supra). The aromatic phenylalanine at position 309 in M-MLV RT corresponds to tryptophan 266 in HIV RT (Bebenek, et al., supra). Extensive amino acid substitution studies of HIV RT W266 show that any substitution at this position reduces the binding affinity of RT for template-primer (Beard, et al., supra). We postulate that alteration of M-MLV RT F309 to asparagine impacts the structure of a putative M-MLV RT minor groove binding track resulting in a reduction in binding affinity for template-primer. Interestingly T306K was able to compensate for the reduced binding produced by H204R or H204R and F309N together, restoring template-primer binding affinity to the original level (Table 12). Again based upon amino acid homology in this region, T306 in M-MLV RT corresponds to a lysine in position 263 in the α-helix of HIV RT that contains the minor groove binding track. The crystal structure of HIV RT complexed with double-stranded DNA shows that K263 contacts the n-2 phosphate of the DNA primer (Ding, et al., supra, Huang, et al., supra). Introduction into M-MLV RT of a positively charged lysine in place of phenylalanine at position 306 compensates for the reduced binding of H204R and F309N, perhaps by enhancing RT binding at the n-2 primer phosphate position.

H204R had the greatest individual thermal stabilizing effect on H− M-MLV RT. At position 204 histidine has been replaced with a more highly charged arginine in α-helix H at the underside of the palm subdomain (Georgiadis, et al., supra). Examination of the 3-dimensional structural model of the fingers-palm fragment of M-MLV RT (Georgiadis, et al., supra) reveals this substitution places arginine at a proper distance to form a salt bridge with E201 in α-helix H or a hydrogen bond with T128 in the loop between β-sheet 6 and α-helix E (FIG. 9). Either event would help stabilize the RT molecule (Kumar, et al., (2001) *Cell. Mol. Life. Sci.* 58, 1216-1233).

The mutation at position 306 from threonine to lysine probably contributes to the thermal stability of M-MLV RT by making an electrostatic contribution to stabilizing the polypeptide backbone. Saturation of this site with all possible amino acids showed that only substitution of arginine or lysine increased M-MLV RT thermal stability. Both of these amino acids could allow for hydrogen bonding to main chain carbonyl groups and amino acid side chains in a loop adjacent to the putative α-helix containing residue 306.

Predictions about the mechanism whereby F309N increases M-MLV RT thermal stability are complicated by its proposed role in template-primer binding (see discussion above). M-MLV RT position 309 was also examined by saturation with all possible amino acid changes. Only serine and asparagine increased thermal stability. Substitution of charged amino acids for the exposed hydrophobic phenylalanine, which in other protein families correlates well with amino acid changes observed in transitioning from mesophilic to thermophilic family representatives (Kumar, et al., supra, Cambillau, et al., (2000) *J. Biol. Chem.* 275, 32383-32386), reduced or eliminated polymerase activity. Correlation of increased thermal stability with substitution of polar for exposed hydrophobic amino acids is observed much less frequently in protein families (Kumar, et al., supra, Cambillau, et al., supra), so that the structural basis for the stabilizing effect of F→N at position 309 is not clear.

In the absence of both 3-dimensional structural information and reasonable sequence homology between HIV RT and M-MLV RT in the region of M-MLV RT M289, it is difficult to predict the structural basis for the contribution of M289L to M-MLV RT thermal stability. As a general tendency, thermally stable proteins have more and larger hydrophobic amino acids than their mesophilic counterparts that are better able to exclude water from the protein core (Cambillau, et al., supra). It is possible that M→L at position 289 increases M-MLV RT thermal stability through allowing better hydrophobic packing by replacing an unbranched methionine with a β-branched leucine (Cambillau, et al., supra).

Consistent with the results of other studies focused on identifying mutations that increase protein thermal stability (Arnold, et al., (2001) *Trends in Biochemical Sciences* 26, 100-106), the mutations identified in this study probably reside on the RT surface and influence thermal stability without decreasing catalytic activity. In the case of two of the stabilizing amino acids, T306 and F309, they probably reside on a protein surface that contacts template-primer and they bind in such a way that their effects on binding are off setting.

The present invention provides materials and methods for engineering a polypeptide to contain a desired characteristic. As an example, the M-MLV RT gene was mutated to increase the thermostability of the enzyme. The goal of this research was to increase the temperature at which M-MLV RT efficiently catalyzes cDNA synthesis from 48° C. to about 55° C. to about 60° C. by increasing the intrinsic thermal stability of RT. The ability to use retroviral RT at 55 to 60° C. increases both the efficiency and specificity of priming of cDNA synthesis. With the mutagenesis and screening approaches used, mutations were identified that increased the M-MLV RT operating temperature limit to at least about 55° C. These mutations created a dramatic increase in intrinsic thermal stability measured as a half-life increase at 50° C. (30-fold), that was maintained partially at 55° C. (5-fold increase in half-life). There are alternative approaches that could potentially build on the four mutants already identified. For example, the target mutation frequency could be set much higher (5-10 mutations/segment) during random mutagenesis of several larger segments of the H− M-MLV RT quadruple mutant polymerase domain, giving a much smaller proportion of active mutants but a much broader mutant spectrum. Several libraries generated in this fashion could then be shuffled by recombination (Stemmer, W. P. C. (1994) *Nature* 370, 389-391), which would tend to eliminate deleterious mutations (Lehmann, et al., supra). When combined with a 96-well DNA polymerase activity screen made more sensitive and a sampling procedure used to assay multiple mutants per well to increase the number of mutations screened, such an approach should yield additional mutations that further increase the thermal stability of M-MLV RT.

Example 7: Engineering of SuperScript™ III RT, Thermal Stability, cDNA Synthesis The gene for Moloney murine leukemia virus (M-MLV) RNase H− minus (H−) reverse transcriptase (RT), also known as SuperScript™ II was randomly mutagenized and mutants were screened for increased thermal stability. Four mutations were identified that together increased the half-life of M-MLV H− RT at 50° C. 35-fold and raised the RT cDNA synthesis operating temperature from 42° C. to 55° C. This increase in thermal stability was achieved by increasing the intrinsic thermal stability of M-MLV H− RT and without diminishing the DNA polymerase catalytic activity of the enzyme.

Reverse transcriptase (RT, e.g., retroviral RT) is an essential tool for the synthesis and cloning of cDNA. Forms of retroviral RT used widely to synthesize cDNA are M-MLV RT and AMV RT. In addition to polymerase activity, retroviral RT possesses RNase H activity that degrades the RNA in an RNA-DNA hybrid (Moelling, et al., (1971) *Nature New Biology* 234, 240-244). The presence of this degradative activity is responsible in part for the limitation on efficient synthesis of long cDNA (Krug and Berger (1987) *Methods in Enzymol.* 152, 316-325; Berger, et al., (1983) *Biochem.* 22, 2365-2372). The RNase H domain of RT can be mutated to reduce or eliminate RNase H activity while maintaining mRNA-directed DNA polymerase activity (Kotewicz, et al., (1988) *Nuc. Acids Res.* 16, 265-277; DeStefano, et al., (1994) *Biochim. Biophys. Acta* 1219, 380-388), improving the efficiency of cDNA synthesis (Kotewicz, et al., supra). This has been done in SUPERSCRIPT™ II and ThermoScript.

A second significant drawback to copying mRNA is the tendency of RT to pause during cDNA synthesis resulting in the generation of truncated products (Harrison, et al., (1998) *Nuc. Acids Res.* 26, 3433-3442; DeStefano, et al., (1991) *J. Biol. Chem.* 266, 7423-7431). This pausing is due in part to the secondary structure of RNA (Harrison, et al., supra, Wu, et al., (1996) *J. Virol.* 70, 7132-7142). Performing cDNA synthesis at reaction temperatures that melt the secondary structure of mRNA helps to alleviate this problem (Myers and Gelfand, (1991) *Biochem.* 30, 7661-7666). In addition, the oligo(dT)n primer often used to initiate cDNA synthesis tends to prime at internal stretches of A residues in mRNA at lower temperatures, resulting in the synthesis of 3'-end truncated cDNA products. M-MLV RT does not efficiently synthesize cDNA from mRNA above 43° C. (Tosh, et al., (1997) *Acta Virol.* 41, 153-155).

In an effort to raise the temperature at which SUPERSCRIPT™ II RT can be used to synthesize cDNA, we have randomly mutagenized the SUPERSCRIPT™ II RT gene and screened for thermal stable mutants. Several thermal stable mutants of SUPERSCRIPT™ II RT were identified and purified enzymes were characterized. We show that when the mutations are present together they increase RT thermal activity by increasing its intrinsic thermal stability without altering catalytic activity.

SUPERSCRIPT™ III RT Purification: The SUPERSCRIPT™ III RT gene was derived from SUPERSCRIPT™ II RT. Four mutations, in addition to the 3 RNase H mutations present in SUPERSCRIPT™ II, were included along with modifications to the N-terminus to increase the thermostability. The gene was cloned into plasmid pBAD (Invitrogen Corporation, Carlsbad, Calif.) under control of an araD promoter. The purified protein has an apparent molecular weight of 78 kDa. The plasmid was transformed into *E. coli* DH10B (Invitrogen Corporation, Carlsbad, Calif.) cells and a seed stock was grown up to an O.D. of 1.0 in EG (2% Tryptone, 1% yeast extract, 0.5% glycerol, 10 mM NaCl, and 1 mM KCl) and frozen in 60% S.O.B./40% glycerol at −80° C.

For purification, a stab from the frozen seed was used to inoculate a starter culture of 500 ml. The media used for the R&D prep was either EG or CircleGrow (Bio101), supplemented with 100 μg/ml Ampicillin. The starter culture was incubated overnight at 37° C. and used to inoculate 10 liters EG+ Amp media. The culture was incubated at 37° C. to an $OD_{600}$ of 1.0 (3-4 hours), induced with 0.2% arabinose, and incubation continued another 3 hours. Cells were pelleted by centrifugation at 5,000 g for 20 minutes at 4° C. The supernatant was removed and cells were either frozen at −80° C. or processed.

Purification of SUPERSCRIPT™ III was done the same as SUPERSCRIPT™ II and is outlined as follows, with the exception of using an AF-Heparin 650M resin (TosoHaas) in place of Heparin Agarose as the third column. All buffers must be autoclaved and columns thoroughly cleaned to prevent RNase contamination. The procedure is done at 4° C. unless otherwise indicated.

Purification Method A. Thaw 50 grams of cells in 100 ml Buffer A (2 ml per g of cell pellet: 20 mM Tris-HCL pH 7.5, 25 mM NaCl, 1 mM EDTA, 1 mM DTT, 1.3 mM PMSF), stirring at 4° C. until homogenous. Add another 0.78 ml 0.1 M PMSF and mix well (5 minutes). Strain cells through 6 layers of cheesecloth. Filter the sample through gaulin pre-equilibrated with 1 volume Buffer A (avoid bubbles and particulates in gaulin) at 4-6° C. with pressure at 8000 psi. Repeat and check sample for >80% lysis. Determine volume of cells and add 0.053 V of 5M NaCl to lysate. Stir at 4° C. till mixed. Add 0.111 V of 5% polymin P (pH 7.9) over 30 minutes while mixing and then mix for another 30 minutes. Centrifuge at 18,100 g for 60 min at 4° C., keep the supernatant. Add 226 g/L $(NH_4)_2SO_4$ to supernatant over 30 minutes while stirring and mix for another 30 minutes. Centrifuge at 18,100 g for 60 min at 4° C., keep the supernatant. Resuspend the pellet in Buffer B (20 mM Tris-HCL pH 7.5, 100 mM NaCl, 1 mM EDTA, 1 mM DTT, 0.01% NOG, 5% glycerol) at 0.52 ml/g original pellet weight (26 ml) while stirring for 1 hour.

A G-25 F column (AP-Biotech, 270 ml resin volume) was equilibrated with Buffer B and then the sample was loaded. The column was washed and the sample eluted with 2 column volumes of Buffer B at a flow rate of 3.3 ml/min and fraction volume of 6 ml/tube. Fractions were pooled based on UV absorbance and a clear amber color. If precipitation formed, the pool was centrifuged at 18,100 g for 30 min at 4° C.

The fraction pool was loaded onto a P-11 column (Whatman: 2× cycled, 25 ml resin volume) pre-equilibrated with Buffer B at a flow rate of 1.0 ml/min. The column was washed with 10 column volumes of Buffer C (20 mM Tris-HCL pH 7.5, 100 mM NaCl, 1 mM EDTA, 1 mM DTT, 0.01% NP-40, 5% glycerol) and eluted with 12 column volumes of a 100 to 500 mM NaCl gradient (Buffer C and 0 to 100% of Buffer D: 20 mM Tris-HCL pH 7.5, 500 mM NaCl, 1 mM EDTA, 1 mM DTT, 0.01% NP-40, 5% glycerol) at a flow rate of 1.6 mL/min and fraction volume of 4 ml. Fractions were pooled by either $OD_{280}$>50% peak height or >50% peak RT activity. The fraction pool was then diluted with one volume of Buffer E (20 mM Tris-HCL pH 7.5, 1 mM EDTA, 1 mM DTT, 0.01% NP-40, 5% glycerol).

The diluted pool was then loaded onto an AF-Heparin 650M column (TosoHaas, 12.5 ml resin volume) pre-equilibrated with Buffer F (20 mM Tris-HCL pH 7.5, 160 mM NaCl, 1 mM EDTA, 1 mM DTT, 0.01% NP-40, 5% glycerol) at a flow rate of 0.7 mL/min.

The column was washed with 10 column volumes of Buffer F (20 mM Tris-HCL pH 7.5, 160 mM NaCl, 1 mM EDTA, 1 mM DTT, 0.01% NP-40, 5% glycerol) and eluted with 10 column volumes of a 160 to 700 mM NaCl gradient (Buffer F and 0 to 100% of Buffer G: 20 mM Tris-HCL pH 7.5, 700 mM NaCl, 1 mM EDTA, 1 mM DTT, 0.01% NP-40, 5% glycerol) at a flow rate of 0.5 mL/min and fraction volume of 2 ml. Fractions were pooled by either $OD_{280}$>50% peak height or >50% peak RT activity. The fraction pool was then diluted with three volumes of Buffer H (20 mM Tris-HCL pH 7.5, 100 mM NaCl 1 mM EDTA, 1 mM DTT, 0.03% NP-40, 5% glycerol).

The diluted pool was then loaded onto an SP Sepharose HP column (Ap Biotech, 12.5 ml resin volume) pre-equilibrated with Buffer I (20 mM Tris-HCl pH 7.5, 100 mM NaCl, 1 mM EDTA, 1 mM DTT, 0.01% NP-40, 5% glycerol) at a flow rate of 1.2 ml/min. The column was washed with 10 column volumes of Buffer I (20 mM Tris-HCL pH 7.5, 100 mM NaCl, 1 mM EDTA, 1 mM DTT, 0.01% NP-40, 5% glycerol) and eluted with 10 column volumes of a 100 to 280 mM NaCl gradient (Buffer 1 and 0 to 40% of Buffer G) at a flow rate of 0.6 mL/min and fraction volume of 2 ml. Fractions were pooled by either $OD_{280}$>50% peak height or >50% peak RT activity.

The RT containing fractions from the Sepharose column were dialyzed against 20 volumes Buffer J (20 mM Tris-HCL pH 7.5, 100 mM NaCl, 0.1 mM EDTA, 1 mM DTT, 0.01% NP-40, 50% glycerol) overnight at 4° C.

Purification Method B. One hundred grams of cells is suspended in 80 ml of permeabilization buffer (500 mM Bis-Tris, pH 7.0 at 4° C./50 mM EDTA/5 mM DTT). (Note: The DTT can be added as a separate component and the volume of water added adjusted accordingly.) 79.6 ml of $H_2O$ is added and the cell suspension is stirred with an overhead stirrer at ~700 rpm with a Heidolph mixer or at 6+ with a StirPak mixer using the three blade mixer shaft. The suspension is checked to ensure that it is homogeneous by stopping the mixer and pouring the suspension into a glass beaker slowly while looking for clumps. Once thoroughly mixed, 80 ml 25% Triton X-100/10% deoxycholic acid (at ambient temperature) is added while mixing vigorously (as above). 400 ul of 100 mM PMSF is added and the suspension is allowed to stand with mixing for 30 mM at 4° C. 60 ml of 2 M $(NH_4)_2SO_4$ is added and mixing is continued for an additional 15 min at 4° C. Samples can now be taken or proceed to the filtration stage.

Volumes:

| | |
|---|---|
| Cells | 100 ml |
| Buffer | 80 ml |
| $H_2O$ | 79.6 ml |
| Detergent | 80 ml |
| PMSF | 0.400 ml |
| $(NH_4)_2SO_4$ | 60 ml |
| | 400 ml |

Filtration. The cell slurry is poured into a circulation vessel and a flow rate of 1.5 L/min/ft2 through a 0.2 um Spectrum mixed ester cellulose hollow fiber filter with a 1.0 mm lumen is established. Extraction is performed with seven volumes of 100 mM TRIS, pH 8.0/300 mM ammonium sulfate/10 mM EDTA/1 mM DTT/10% glycerol (v/v) while maintaining 4-6° C. and a TMP of 5-10 psi.

Once enough filtrate has been collected, the second stage filtration using an AG/Tech 30,000 MWCO hollow fiber with a maximum inlet pressure of 50 psi. (all operations chilled to 4-6° C.) is initiated. Once all seven volumes of extraction have been collected, the solution is concentrate to 600 ml and diafiltered against five volumes of 100 mM Tris, pH 8.0/100 mM NaCl/10 mM EDTA/1 mM DTT.

The diafiltered retentate is collected and 50 ml previously equilibrated DEAE cellulose is added. The suspension is mixed gently for 15 min at 4° C. The resulting solution is clarified by filtration through a CUNO 30 SP depth filter.

Chromatography. The above solution is applied to a previously equilibrated 120 ml column of Macroprep High S (20 mM Tris, pH 8.0/150 mM NaCl/10% glycerol/1 mM EDTA/1 mM DTT/0.01% Triton X-100). The column is washed with 10 column volumes of equilibration buffer and eluted with a linear gradient of equilibration buffer to the same buffer at 800 mM NaCl. 50 fractions are collected and the major uv peak is pooled.

The pool is applied to a previously equilibrated 120 ml column of Ceramic hydroxy apatite (20 mM Kpi, pH 7.0/100 mM KCl/10% glycerol/1 mM DTT/0.01% Triton X-100) at 20 cm/h. Elution is with this same buffer and 10 ml fractions are collected. The uv peak is pooled and an equal volume of solubilization buffer (100 mM Tris, pH7.5/300 mM NaCl/0.2 mM EDTA/30% glycerol/1 mM DTT) is added.

The pool is applied to a previously equilibrated 16 ml column of EM COO— (20 mM Tris, pH 7.5/100 mM NaCl/0.1 mM EDTA/20% glycerol/1 mM DTT/0.01% Triton X-100) at 20 cm/h. The column is washed with two column volecules of equilibration buffer. Elution is with a linear gradient of equilibration buffer to the same buffer with 200 mM NaCl. The uv peak is pooled and dialyzed against 20 volumes of 20 mM Tris, pH 7.5/100 mM NaCl/0.1 mM/1 mM DTT/0.01% Triton X-100/50% glycerol.

DNA Polymerase Assays: RT DNA polymerase unit activity was assayed with $(rA)_{630}$•$p(dT)_{12-18}$. One unit of DNA polymerase activity is the amount of RT that incorporates one nmole of deoxynucleoside triphosphate into acid insoluble product at 37° C. in 10 min. Specific Activity is determined by dividing the Units/μl by the protein concentration to get units/mg.

cDNA synthesis from CAT cRNA was carried out in reaction mixtures (20 μl) containing 50 mM Tris-HCl (pH 8.4), 75 mM KCl, 3 mM $MgCl_2$, 10 mM dithiotreitol (DTT), 500 μM each of dATP, dTTP, dGTP, and [α-$^{32}$P]dCTP (300 cpm/pmole), 1,750 units/ml RNase Inhibitor, 130 μg/ml (465 nM) CAT cRNA, 20 μg/ml (2,300 nM) $p(dT)_{25-30}$, and 3,250 units/ml (100 nM) RT. Incubation was at various temperatures for 60 min individual tubes. An aliquot of the reaction mixture was precipitated with TCA to determine yield of cDNA synthesized, and the remaining cDNA product was size fractionated on an alkaline 1.2% agarose gel. To establish mono- and divalent metal reaction optima, initial reaction rates were determined under conditions of limiting RT concentration during 10 min incubation at 37° C. or 50° C. Reaction mixtures (20 μl) contained 50 mM Tris-HCl (pH 8.4), 10 mM DTT, 500 μM each of dTTP, dATP, dCTP, and [$^3$H]dGTP (100 cpm/pmole), 10 pmoles (2.8 μg) CAT cRNA, 50 pmoles DNA 24-mer, 0.5 pmoles RT, and KCl and $MgCl_2$, varied in concentration one at a time.

Half Life Determination:

Mixtures (20 μl) were incubated for various times in 0.5-ml tubes in a thermocycler at 50° C. or 55° C. and contained 50 mM Tris-HCl (pH 8.4), 75 mM KCl, 3 mM $MgCl_2$, 10 mM DTT, OA % (v/v) Triton X-100, and 3-7 μg/ml purified RT. Incubation was stopped by placing the tube in ice. An aliquot (5 μl) was assayed for residual activity with $(rA)_{630}$•$p(dT)_{12-18}$.

Measurement of $K_D$ by Filter Binding:

A nitrocellulose filter-binding assay was used to determine the nucleic acid binding constants ($K_D$) of RTs for CAT cRNA•$(dT)_{20}$. Dephosphorylated CAT cRNA was labeled at the 5' end with [γ-$^{32}$P]ATP and T4 polynucleotide kinase (Boehringer). Oligo$(dT)_{20}$ was annealed to the poly(A)-tailed CAT cRNA in a buffer containing 10 mM Tris-HCl, pH 7.5, and 80 mM KCl at 65° C. for 5 min followed by chilling on ice. Reaction mixtures (100 μl) containing binding buffer (50 mM Tris-HCl, pH 8.4, 75 mM KCl, 3 mM $MgCl_2$, and 10 mM DTT), 0.05 nM $^{32}$P-labeled CAT cRNA, 1 nM $(dT)_{20}$, and 1 to 50 nM RT were incubated at 23° C. for 5 min. After incubation, the mixture was filtered through a nitrocellulose filter (Millipore, HA 0.45 mm) soaked in binding buffer, which was then washed with binding buffer. The $K_D$ is equal to that enzyme concentration at which 50% of the labeled CAT cRNA is bound. For this method of analysis to be valid, the CAT cRNA concentration in the reaction must be substantially below $K_D$, so that the total enzyme concentration approximates the concentration of free unbound enzyme.

LacZα Fidelity Measurements:

Fidelity measurement were conducted using a modified lacZα gapped procedure from Boyer, J. C. et al., (*Methods in Enzymology*, Vol 275, p 523-537). Briefly, a modified pUC19 plasmid containing the promoter for T7 RNA polymerase between nucleotides −112 and −113 (where position +1 is the first transcribed nucleotide of the lacZα gene) was used. The plasmid was linearized with FspI, and transcription by T7 RNA polymerase produces a 344 nucleotide transcript. Using this RNA as template, cDNA synthesis under desired conditions (200 units SuperScript™ III RT or 15 units AMV H+ RT in their respective buffers) was initiated from a 15-mer DNA primer. After heat denaturation, the RNA was digested and an excess of cDNA was used for hybridization to a circular DNA substrate containing a complementary single-stranded gap. This substrate was made by cutting M13mp19 RF with PvuI and PvuII in the appropriate buffer and isolating the large linear fragment. This fragment is then denatured and reannealed to a 2-fold excess of single-strand M13mp19. The resulting DNA product is transfected into competent DH12S cells, plated onto LB indicator plates containing X-gal and IPTG and plaques are scored for color. Mutation frequency was determined by dividing the number of mutant plaques (light blue or white) by the total. The enzyme's mutation frequency is corrected by subtracting the mutation frequency of the starting DNA. The error rate is determined by dividing the mutation frequency by the number of known detectable sites (116) and then dividing by the probability of expressing the minus strand (50%).

rpsL Fidelity Assay:

Fidelity assay was performed based on the streptomycin resistance that rpsL mutatants exhibit (Fujii, et al., (1999) *J Mol Biol.* 289(4):835-50). Briefly, pMOL 21 plasmid DNA (4 kb), containing the ampicillin ($Ap^r$) and (rpsL) genes, was modified with the insertion of a T7 RNA promoter sequence downstream of the rpsL gene. The plasmid was linearized with ScaI and this template was used for in vitro transcription of a 1.4 kb RNA containing the rpsL gene. A first strand cDNA reaction using the desired RT and reaction conditions was carried out, followed by second strand synthesis using pol I, RNase H and ligase. This double-strand DNA was then cut with HindIII and EcoRI and cloned back into the original pMOL 21 plasmid and transformed into MF101 competent cells. Cells were plated on ampicillin plates to determine the total number of transformed cells. Cells were plated on ampicillin and streptomycin plates to determine the total number of rpsL mutants. Mutation frequency was determined by dividing the total number of mutations by the total number of transformed cells. The error rate was determined by dividing the mutation frequency by 130 (the number of amino acids that cause phenotypic changes for rpsL) and the template doubling. In addition rpsL was further modified by altering the sequence prone to mutations to remove template bias.

TDT Activity:

The template-primer was prepared by annealing a 47-mer template (either RNA or DNA):

5'-GAGTTACAGTGTTTTTGTTCCAGTCTGTAGCA-GTGTGTGAATGG

AAG-3' (SEQ ID NO:6) to a 18-mer DNA primer (5'-GAACAAAAACACTGTAACTC-3' (SEQ ID NO:10)) [$^{32}$P]-labeled at the 5'-end with T4 polynucleotide kinase (template:primer, 3:1). Assay mixture (10 μl) contained 5 nM template-primer, 200 units each of either SuperScript™ II or SuperScript™ III, all 4 dNTPs, none or dCTP, dATP, dTTP, dGTP (250 uM each) as shown in the figure legends, 50 mM Tris-HCl (pH 8.3), 75 mM KCl, 3 mM $MgCl_2$, 10 mM DTT. Reactions were incubated at various temperatures for 10 or 60 min and terminated by the addition of 5 μl of 40 mM EDTA, 99% formamide. Reaction products were denatured by incubating at 95° C. for 5 min and analyzed by electrophoresis on urea 6% polyacrylamide gels.

Half Life Determination:

Mixtures (20 μl) were incubated for various times in 0.5-ml tubes in a thermocycler at 50° C., 55° C., or 60° C. and contained 1× First Strand Buffer (50 mM Tris-HCl (pH 8.3), 75 mM KCl, 3 mM $MgCl_2$), 10 mM DTT, 3 mM $MgCl_2$ (total to 6 mM), 0.5 mM dTTP, 0.05% (v/v) NP-40, [methyl-$^3$H]dTTP (20 μCi/ml), and 5 μl of RT. Incubation was stopped by placing the tube in ice. An aliquot (5 μl) was assayed for residual Unit activity with 5 mM poly(A)/3 mM oligo$(dT)_{25}$. One unit of RT DNA polymerase activity is the amount of RT that incorporates 1 nmol of deoxynucleoside triphosphate into acid-insoluble product at 37° C. in 10 min.

Full-Length cDNA Profiling:

cDNA synthesis from cRNA by SuperScript™ III was carried out in reaction mixtures (20 μl) containing 1× First Strand Buffer (50 mM Tris-HCl (pH 8.3), 75 mM KCl, 3 mM $MgCl_2$), 10 mM dithiotreitol (DTT), 500 μM each of dATP, dTTP, dGTP, and dCTP, [α-$^{32}$P]-dCTP (300 cpm/pmole), 2 units/μl RNaseOUT, different amounts of RNA, and 0.5 μg oligo$(dT)_{25}$. The mix is prewarmed at various temperatures for 2 minutes. After warming, 200 or 400 units of SuperScript™ III RT are added. The mixtures were incubated at the same temperature for another 50 min in individual tubes. The reactions were stopped by adding 10 μl of 0.5 M EDTA. An aliquot (5 μl) of the reaction mixture was precipitated with TCA to determine yield of cDNA synthesized, and the remaining cDNA product was size fractionated on an alkaline 1.2% agarose gel (McDonell, et al., *J. Mol. Biol.* 110, 199-146, 1977). For the RTs from other vendors, each was assayed following the manufacturer's suggestion.

Results and Discussion

Designation of polypeptides. Unless otherwise indicated, the following designations will be used to describe various polypeptides of the invention. SuperScript™ II is M-MLV reverse transcriptase with a methionine added as a start codon (as discussed earlier, wild type M-MLV RT is a cleavage product that does not contain a methionine) and having three point mutations that reduce RNase H activity. EFN indicates a polypeptide having the SuperScript™ II sequence with an N-terminal six histidine tag sequence MGGSHHHHHHGMASMTGGQQMGRDLYDDDDKH (amino acids 1-32 of SEQ ID NO:2 and Table 3) and containing the EFN mutations, which are H204R, T306K, and F309N of the SuperScript™ II sequence. Tagged, no His EFN has the tag sequence MASGTGGQQMGRDLYDDDDKH (SEQ ID NO:3) and the EFN mutations, no tag EFN contains the EFN mutations. SuperScript™ III, which may be designated LEFN, has the SuperScript™ II sequence and an N-terminal tag sequence MASGTGGQQMGRDLYDDDDK (SEQ ID NO:11) and the LEFN mutations, which are H204R, M289L, T306K, and F309N of the SuperScript™ II sequence. His tagged LEFN indicates a polypeptide having an N-terminal six histidine tag sequence MGGSHHHHHHGMASMTGGQQMGRDLYDDDDKH (amino acids 1-32 of SEQ ID NO:2 and Table 3) and containing the LEFN mutations.

Purification:

The protein expresses well and appears to not be toxic. Varying levels of arabinose induction were used with 0.2% being optimal but not very different from 2.0%. Induction times longer than 3 hours can be done, however there is a 70 kDa product that is generated over longer incubation periods. It appears to be a proteolysis product removing the C-terminus as purified N-terminal Histidine-tagged clones also had this protein co-purify.

The purification protocol is essentially the same as was used for SuperScript™ II and the SuperScript™ III enzyme behaves almost the same throughout the purification. SuperScript™ III may be prepared at concentrations of 2,000-4,000 units/μl after dialysis with no precipitation problems.

Fidelity:

Initial results have shown no difference between SuperScript™ II and SuperScript™ III using either the rpsL or lacZα fidelity assay. RTs have sequence dependant mutation hotspots in homopolymeric runs of nucleotides, primarily runs of A or T. These most common mutations at these runs are one nucleotide insertion or deletion which is caused by the template or primer breathing and re-annealing with an overlap. The resulting frameshift mutation usually results in premature termination of the gene product. The modified EFN polypeptide, which contains the H204R, T306K, and F309N mutations, had improved frameshift error rates compared to SuperScript™ II and MMLV H+. Experiments are ongoing to determine if SuperScript™ III, which contains the M289L mutation in addition to the H204R, T306K, and F309N mutations, also has this improvement.

Specific Activity:

The specific activity for SuperScript™ III is about 25% higher than SuperScript™ II. RT DNA polymerase unit activity was assayed with $(rA)_{630}•p(dT)_{12-18}$ at 37° C. and protein concentration was determined by Bradford assay. Table 14 shows the RNA-directed DNA polymerase specific activity of SuperScript™ II and SuperScript™ III using $(rA)_{630}•p(dT)_{12-18}$ at 37° C. for 10 min.

TABLE 14

| Enzyme | DNA Polymerase Specific Activity (units/mg) |
|---|---|
| SUPERSCRIPT ™ II | 330,000 |
| SUPERSCRIPT ™ III | 410,000 |

Mono- and Divalent Metal Reaction Optima:

Using primed CAT RNA as substrate, the $Mg^{2+}$ and KCl concentration optima were determined and are shown in FIGS. 10A and 10B. The DNA polymerase assay for SuperScript™ III RT was conducted at 37° C. or 50° C. for 10 minutes under various concentrations of $Mg^{2+}$ (FIG. 10A) or KCl (FIG. 10B). SuperScript™ II at 37° C. is included for comparison. The $Mg^{2+}$ concentration optima is at 3 mM at both 37° C. and 50° C. Though at 50° C. there appears to be a broader working range of 2-5 mM without much difference. For KCl, the optima is at 75 mM at both temperatures, but the working range is from 25-125 mM without much difference. Again at the higher temperature a broader range is allowed (25-200 mM). Since there is no change in optima between SuperScript™ II and III, the 5× First Strand Buffer from SuperScript™ II can be used as SuperScript™ III's reaction buffer.

TdT Activity:

TdT or non-template directed nucleotide addition to the 3' primer end is a well known property of many polymerases including RTs (Chen, D. et al., *Biotechniques* 2001; 30(3): 574-582). Using a DNA template (FIG. 11A), SuperScript™ II adds 1-3 additional nucleotides to the end of the transcript. SuperScript™ III however has a greatly reduced TdT and on a DNA template will not add any detectable nucleotides. On an RNA template (FIG. 11B), SuperScript™ II adds 1-2 bases with 69% of the primer extended after 10 minutes and 90% extended after an hour. SuperScript™ III does have some TdT activity on RNA template, but it is reduced with about 14% extended after 10 minutes and 50% extended after an hour at 45° C. as shown in FIG. 11B. This TdT activity is biased with the addition of dATP being strongly favored followed by dGTP, dCTP and dTTP for both SuperScript™ II and III. TdT activity is temperature and time dependant. The optimal temperature for SuperScript™ III is 45° C. to 50° C. while SuperScript™ II is at 45° C. (FIG. 11). To further minimize TdT activity in any RT one must shorten the extension time or lower the temperature.

Fidelity assays. The results of the fidelity assays are shown in Tables 15 and 16.

TABLE 15

| rpsL Fidelity Assay | | | |
|---|---|---|---|
| RT | Temp | Wt rpsL | Mutated rpsL |
| SUPERSCRIPT ™ III | 45° C. | $3.9 \times 10^{-4}$ | $3.4 \times 10^{-5}$ |
| SUPERSCRIPT ™ II | 45° C. | $3.5 \times 10^{-4}$ | $3.1 \times 10^{-5}$ |
| MMLV H+ | 37° C. | $3.9 \times 10^{-4}$ | NA |

TABLE 16

| lacZα Fidelity Assay | | |
|---|---|---|
| RT | Temp | Error Rate |
| SUPERSCRIPT ™ III | 45° C. | $2.9 \times 10^{-5}$ |
| | 50° C. | $2.7 \times 10^{-5}$ |
| | 55° C. | $1.8 \times 10^{-5}$ |
| SUPERSCRIPT ™ II | 45° C. | $2.9 \times 10^{-5}$ |
| MMLV H+ | 45° C. | $4.8 \times 10^{-5}$ |

Fidelity assays for SuperScript™ III, SuperScript™ II and MMLV Rnase H+ RTs. rpsL assay was conducted with either WT rpsL gene or rpsL gene with mutation hotspots removed. A wt rpsL DNA fragment was used as control to see the spontaneously mutation. The error rate is about $10^{-6}$ to $10^{-7}$. The lacZα assay was conducted with gapped DNA starting substrate used as a control with a background error rate of $2.2\times10^{-5}$.

Thermal Stability of Purified Mutant RTs: The rate of chemical RNA breakdown catalyzed by $Mg^{2+}$ increases dramatically as the temperature is increased above 55° C. to 60° C. under cDNA synthesis reaction conditions. In order to characterize their intrinsic thermal stability, the half lives of M-MLV, SuperScript™ II and SuperScript™ III were measured at elevated temperatures. The RT enzymes were first diluted to 0.2-0.5 Unit/μl in the 1× first strand buffer in the presence of 0.05% of NP-40. If diluted in absence of detergent, the RT activity is reduced to more than 90% without incubation (data not shown). FIGS. 12A, 12B, and 12C and Table 17 show the half-lives of M-MLV, SuperScript™ II, and SuperScript™ III at various temperatures. The RT half-lives were detected in 1× First strand reaction buffer in presence of 0.05% NP-40. Mixtures (20 μl) were incubated for various times in 0.5-ml tubes in a thermocycler at 50° C., 55° C., or 60° C. and contained 1× First Strand Buffer (50 mM Tris-HCl (pH 8.3), 75 mM KCl, 3 mM $MgCl_2$), 10 mM DTT, 3 mM $MgCl_2$ (total to 6 mM), 0.5 mM dTTP, 0.05% (v/v) NP-40, [methyl-$^3$H]dTTP (20 μCi/ml), and 5 μl of RT. Incubation was stopped by placing the tube in ice. An aliquot (5 μl) was assayed for remaining units with 5 mM poly(A)/3 mM oligo$(dT)_{25}$. The half live of SuperScript™ III at 50° C. was 220 minutes, about 35 fold longer than that of SuperScript™ II. The half live of SuperScript™ III at 55° C. was 24 min, ~10 fold longer than that of SuperScript™ II.

TABLE 17

Summary of RT Half lives at 50° C., 55° C., and 60° C.

| | M-MLV (min) | SUPERSCRIPT ™ II (min) | SUPERSCRIPT ™ III (min) |
|---|---|---|---|
| 50° C. | ND | 6.1 | 220 |
| 55° C. | 1.5 | 2.2 | 24 |
| 60° C. | 0.6 | ND | 2.5 |

Full-Length cDNA Profiling of RT:

A practical method for judging the useful higher temperature of the DNA polymerase activity of RT is an assessment of the effect of increasing reaction temperature on the amounts of full-length cDNA products synthesized by RT from mixture of cRNA of various lengths. The labeled full-length cDNA products can be separated and quantified on an alkaline agarose gel. As the reaction temperate is increased, full-length cDNA products disappear starting with those derived from longer cRNA until a temperature is reached where no discernible full-length product of any length is synthesized. For comparison, we included Clontech's PowerScript RT, Stratagene's StrataScript RT, Promega's ImProm II RT, and SuperScript™ II (Invitrogen Corporation, Carlsbad, Calif., catalog #18064022). Only SuperScript™ III could produce a clear 9.5 kb full-length product at 50° C., and SuperScript™ II can get a very faint 9.5 kb band.

To compare RT from different companies, the same number of units of RT were used for comparison. PowerScript RT is ~350 unit/μl, StrataScript RT is 50 unit/μl, ImProm II is 50 unit/μl. SuperScript™ II, SuperScript™ III and PowerScript RT were diluted to 50 unit/μl in RT dilution buffer. 100 units (2 μl) of RT enzyme were used. The amounts of full-length products generated were determined and are shown in Tables 17 and 18 for various length templates. SuperScript™ III RT shows improved performance at 50° C. and 55° C. compared to the other RTs.

TABLE 17

Comparison of full length cDNA produced by various RTs.

| Temp. | RT | Total cDNA Pmol | Amount of Full-Length cDNA 7.5 kb (ng) | 2.4 kb (ng) |
|---|---|---|---|---|
| 45° C. | PowerScript | 293 | 75 | 64 |
| | StrataScript | 199 | 47 | 35 |
| | ImProm II | 256 | 41 | 44 |
| | SUPERSCRIPT ™ III | 345 | 99 | 72 |
| | SUPERSCRIPT ™ II | 300 | 100 | 59 |
| 50° C. | PowerScript | 180 | 54 | 31 |
| | StrataScript | 9 | <2 | <2 |
| | ImProm II | 42 | <2 | <2 |
| | SUPERSCRIPT ™ III | 323 | 97 | 68 |
| | SUPERSCRIPT ™ II | 170 | 46 | 22 |
| 55° C. | PowerScript | 5 | <2 | <2 |
| | StrataScript | 5 | <2 | <2 |
| | ImProm II | 3 | <2 | <2 |
| | SUPERSCRIPT ™ III | 37 | 3 | 22 |
| | SUPERSCRIPT ™ II | 3 | <2 | <2 |

The amounts of full-length product were established by cutting the region in a dried 1.2% alkaline agarose gel corresponding to the size of each full-length band and counting it in a scintillation counter. Only amounts of full-length products >2 ng could be seen as discernible bands on the gel autoradiograph. The cDNA synthesis reactions were performed in 20 μl with 0.25 μg of 2.4 kb, 0.5 mg of 7.5 kb cRNA, and 0.1 μg of oligo $(dT)_{25}$. If provided, buffers and other components were used from their own kits plus 0.1 μl of α-$^{32}$P-dCTP (10 μCi/μl). All the reactions were "hot start." In "hot start" reactions, tubes were incubated at reaction temperature for 2 minutes before adding enzyme. 2 μl of RT (50 u/μl) was added and incubated at 45° C. or 50° C. or 55° C. for 50 min. The reactions were stopped by adding 10 μl of 0.5 M EDTA. After ethanol precipitation, the products were loaded on 1.2% agarose gel. The dried gel was exposed on the film for 1 hour.

TABLE 18

Comparison of full length cDNA produced by various RTs.

| RT | Temp (° C.) | Amount of full length cDNA (ng) 9.5 kb | 7.5 kb |
|---|---|---|---|
| SUPERSCRIPT ™ III | 45 | 19 | 54 |
| | 50 | 26 | 78 |
| | 55 | 13 | 53 |
| StratScript | 45 | 4 | 10 |
| | 50 | 0 | 0 |
| | 55 | 0 | 0 |
| ImProm II | 45 | 3 | 9 |
| | 50 | 0 | 0 |
| | 55 | 0 | 0 |
| OmniScript | 45 | 0 | 0 |
| | 50 | 0 | 0 |
| | 55 | 0 | 0 |
| PowerScript | 45 | 19 | 38 |
| | 50 | 3 | 25 |
| | 55 | 0 | 0 |
| M-MLV | 45 | 10 | 39 |
| | 50 | 0 | 3 |
| | 55 | 0 | 0 |
| ThermoScript | 45 | 16 | 38 |
| | 50 | 29 | 56 |
| | 55 | 3 | 13 |

cDNA synthesis reaction mixtures contained 9.5 kb (1.1 μg) and 7.5 kb (0.8 μg) cRNA. The cDNA synthesis reactions were performed in 20 μl with 20 μg of Hela total RNA, and 0.5 μg of oligo $(dT)_{25}$. If provided, buffers and other components used were from their own kits plus 0.1 μl of $\alpha$-$^{32}$P-dCTP (10 μCi/μl). All the reactions were "hot start," 1 μl of RT was added and incubated at 45° C. or 55° C. for 50 min. 400 or 200 units of SuperScript™ III were used for comparison. The reactions were stopped by adding 10 μl of 0.5 M EDTA. After ethanol precipitation, the products were loaded on 1.2% agarose gel. The dried gel was exposed on the film for 1 hour.

In an alternate procedure for comparing RTs from various sources, a comparison of cDNA synthesis from Hela total RNA was performed. The cDNA size synthesized by SuperScript™ III RT at 55° C. is from 0.5-10 kb. cDNA synthesis reactions were performed in 20 μl with 20 μg of Hela total RNA, and 0.5 μg of oligo$(dT)_{25}$. If provided, buffers and other components used were from their own kits plus 0.1 μl of $\alpha$-$^{32}$P-dCTP (10 μCi/μl). All the reactions were "hot start," 1 μl of RT was added and incubated at 45° C. or 55° C. for 50 min. 400 or 200 units of SuperScript™ III were used for comparison. The reactions were stopped by adding 10 μl of 0.5 M EDTA. Total cDNA synthesis was obtained by TCA-precipitation of 5 μl of mixtures. After ethanol precipitation of the rest of the mixture, the products were loaded on 1.2% agarose gel. The dried gel was exposed on the film for 1 hour.

Each reaction was performed according to each vendor's recommendation. In these experiments, we used the buffers provided with the RTs. DTT, RNase inhibitor, dNTP were used at the recommended concentration and from the kit if provided. Otherwise, Invitrogen's reagents were used. 1 μl of RT was used in these competitive audit. Table 18 shows the result when using 9.5 kb and 7.5 kb cRNA. FIG. 13 shows the results of a competitive audit for cDNA profiling using poly (A)-tailed RNA ladder. The cDNA synthesis reactions were performed in 20 μl with 2 μg of RNA Ladder and 0.5 μg of oligo$(dT)_{25}$. If provided, buffers and other components were used from their own kits plus 0.1 μl of $\alpha$-$^{32}$P-dCTP (10 μCi/μl). All the reactions were "hot start," 1 μl of RT was added and incubated at 45° C. or 50° C. or 55° C. for 50 min. 400 or 200 units of SuperScript™ III were used for comparison. The reactions were stopped by adding 10 μl of 0.5 M EDTA. After ethanol precipitation, the products were loaded in different order on two 1.2% agarose gels. The dried gels were exposed on the film for 1 hour.

Example 8: RT-PCR Applications

RT-PCR has become an effective tool in such applications as detecting RNA, gene expression, profiling, gene quantitation, and cloning full-length genes. An RNase H minus mutant of MMLV RT, SuperScript™ II RT, is widely accepted as the RT choice since it has already proven that it produces higher cDNA yield and longer target capacity than MMLV RT.

Recently we have engineered a new generation RT—SuperScript™ III™ RT. In addition to all the premier features of SuperScript™ II RT, it also provides a high temperature RT capacity up to 55 degrees, which is approximately 5 degrees or more higher than SuperScript™ II RT. The enzyme half-life of SuperScript™ II RT and SuperScript™ III RT at 50° C. is 6 minutes and 220 minutes respectively. Efficient full-length cDNA synthesis activity occurs with SuperScript™ III even at 55 degrees RT temperature. High yield and more specific RT-PCR products were also produced by this enzyme at elevated RT temperatures. SuperScript™ III provides a tool for efficient cDNA synthesis for difficult RNA targets such as high GC and secondary structured templates.

The enzyme has also been optimized for RT-PCR for both sensitivity and long targets. We have demonstrated that SuperScript™ III RT is able to amplify as little as 1 pg of starting HeLa RNA and amplify targets up to 12.3 kb in length. This enzyme, when used with the accompanying buffers and conditions, provides performance better than that of other MMLV derivative reverse transcriptases.

Materials and Methods

Kit Components:

SuperScript™ III RT (200 U/μl), 5× First-Strand Buffer, 0.1M DTT.

SuperScript™ III RT=H204R, M289L, T306K, and F309N mutations and may be referred to as the LEFN RT.

5× First-Strand Buffer: 250 mM Tris-HCl (pH 8.3), 375 mM potassium chloride, and 15 mM magnesium chloride.

SuperScript™ III RT Storage Buffer: 20 mM Tris-HCl, pH 7.5, 100 mM NaCl, 1 mM EDTA, 1 mM DTT, 0.01% NP-40, 50% (v/v) glycerol.

RNA: Total HeLa RNA and total rat brain RNA were isolated using TRIZOL® Reagent.

Gel Electrophoresis: RT-PCR products (10 μl) were analyzed by electrophoresis on 0.8% to 1.5% (w/v) agarose gels in 0.5×TBE with 0.4 μg/ml ethidium bromide.

RT-PCR Procedure: First-Strand cDNA Synthesis for RT-PCR: A 20-μl reaction volume can be used for 10 pg-5 μg of total RNA or 10 pg-500 ng of mRNA. Add the following components to a nuclease-free microfuge tube: 1 μl Oligo$(dT)_{20}$ (500 μg/ml), 10 pg to 5 μg total RNA, 1 μl 10 mM dNTP mix (10 mM each dATP, dTTP, dGTP, and dCTP at neutral pH), and sterile, distilled water to 12 μl. Alternatively, 50-250 ng random primers or 2 pmole of a gene specific primer may be used. Use of random primers requires incubation at 25° C. for 10 min before the 50° C. incubation.

Heat the mixture at 65° C. for 5 min and then place on ice. Collect the contents of the tube by brief centrifugation and add: 4 μl 5× First-Strand Buffer, 2 μl 0.1 M DTT, 1 μl RNaseOUT Recombinant Ribonuclease Inhibitor (40 units/μl, when using less than 50 ng of starting RNA, the addition of an RNase inhibitor (e.g., RNaseOUT, Invitrogen Corporation, Carlsbad, Calif., catalog #10777019) is essential).

Mix the contents of the tube gently and incubate at 50° C. for 2 minutes. Add 1 μl (200-400 units) of SuperScript™ III RT, mix by pipetting gently up and down. Incubate 50 min at 50° C. (cDNA synthesis can be performed at 42° C.-60° C. for oligo$(dT)_{20}$ or gene specific primers). Inactivate the reaction by heating at 70° C. for 15 min. The cDNA can now be used as a template for amplification in PCR or can be stored at −20° C. until use. However, amplification of some PCR targets (those >1 kb) may require removal of RNA complementary to the cDNA. To remove RNA complementary to the cDNA, add 1 μl (2 units) of *E. coli* RNase H and incubate at 37° C. for 20 min.

RT-PCR Optimization

For the following experiments, either EFN (His-tag), EFN (no tag), LEFN (His-tag), or LEFN (tag, no His) were used in finding the optimal conditions for LEFN (tag, no His). These 4 reverse transcriptases differ in their thermal-stability profiles. The modified version of SuperScript™ III, EFN, contains the H204R, T306K, and F309N mutations. LEFN, otherwise known as SuperScript™ III RT, contains the M289L mutation in addition to the H204R, T306K, and F309N mutations.

Unless otherwise noted, 20 μl RT reactions were typically done using 2.5 μM Oligo(dT)$_{20}$ (500 ng Oligo(dT)$_{12-18}$ for SuperScript™ II RT), 0.5 mM dNTPs, 1× First-Strand Buffer, 10 mM DTT, and 40 units of RNaseOUT. In "hot start" reactions, tubes were incubated at reaction temperature for 2 minutes before adding enzyme. Reactions were treated with 2 units of RNase H at 37° C. for 20 min after cDNA synthesis.

For the evaluation of these RTs in RT-PCR, standard 50 μl PCR reactions were performed. For primer sets deigned to amplify <4 kb, PCR reactions consisted of 0.2 μM primers, 200 μM each dNTP, 1×PCR Buffer, 1.5 mM $MgCl_2$, 2 μl of the cDNA reaction, and 2 units of PLATINUM® Taq DNA Polymerase. For primer sets designed to amplify >4 kb, PCR reactions consisted of 0.2 μM primers, 200 μM each dNTP, 1× High Fidelity PCR Buffer, 2 mM $MgSO_4$, 2 μl of the cDNA reaction, and 1 unit of PLATINUM® Taq DNA Polymerase High Fidelity. After an incubation of 94° C. for 2 min, amplification was 35 to 40 cycles of 94° C. for 15 s, 55° C.-60° C. for 30 s, and 68° C. for 1 min/kb. 10 μl of the PCR reactions were analyzed on agarose gels containing 0.4 μg/ml EtBr. Primers used in PCR are found in Table 19.

cDNA synthesis buffer: Reactions with 50 or 200 units of SuperScript™ II RT or EFN (His-tag) were assembled using the reagent systems of SuperScript™ II RT (stand-alone), SuperScript™ II First-Strand Synthesis System for RT-PCR, and ThermoScript RT-PCR System. The conditions for each are as follows:

1) SuperScript™ II RT stand-alone: 50 mM Tris-HCl (pH 8.3), 75 mM KCl, 3 mM $MgCl_2$, 0.5 mM dNTPs
2) SuperScript™ II First-Strand Synthesis System for RT-PCR: 20 mM Tris-HCl (pH 8.4), 50 mM KCl, 5 mM $MgCl_2$, 0.5 mM dNTPs
3) ThermoScript RT-PCR System: 50 mM Tris-acetate (pH 8.4), 75 mM potassium acetate, 8 mM magnesium acetate, 1 mM dNTPs 20 μl RT reactions containing 1 pg to 100 ng of starting total HeLa RNA were performed at 45° C. for 50 min followed by 85° C. for 5 min. 2 μl of the resulting cDNA were added to 50 μl PCR reactions containing the β-actin 353 bp, BF 2.4 kb, Pol ε 6.8 kb, or APC 8.5 kb primer set (see Table 19).

Magnesium chloride was titrated into cDNA synthesis buffers in final reaction concentrations of 1 to 10 mM, with dNTP concentrations of 0.5 mM and 1 mM tested concurrently. These buffers were used in 20 μl RT reactions performed at 45° C. for 50 min followed by 85° C. for 5 min with 1 pg, 100 ng, or 5 μg of total HeLa RNA and 50 units or 200 units of EFN (His-tag). 2 μl of the resulting cDNA were added to 50 μl PCR reactions containing the β-actin 353 bp or Pol ε 6.8 kb target (the 5 μg cDNA samples were diluted 100 fold before addition).

5× First-Strand Buffer containing Tris-HCl at pH 8.0, 8.4, 8.8 and 8.3 were prepared to determine the ideal pH for the enzyme to function at higher reaction temperatures. 20 μl RT reactions containing 100 ng to 500 ng of total HeLa RNA and 200 units of SuperScript™ II or 400 units of LEFN (His-tag) were performed at 50° C.-60° C. for 50 min (hot start) followed by 70° C. for 15 min using these different buffers. 2 μl of the resulting cDNA were added to 50 μl PCR reactions containing the BF 2.4 kb or Pol ε 6.8 kb primer set.

RT reaction temperature: SuperScript™ II RT (50 units), EFN (His-tag) (50 and 200 units), and ThermoScript RT (15 units) were compared in RT reactions from 42° C. to 60° C. 20 μl RT reactions containing 1 pg to 100 ng of starting total HeLa RNA were performed at the given temperatures for 50 min (hot start) followed by 85° C. for 5 min. 2 μl of the resulting cDNA were added to 50 μl PCR reactions containing the β-actin 353 bp, TSC 5.3 kb, or Pol ε 6.8 kb primer set.

SuperScript™ II RT and EFN (no tag) were compared at 200 units in RT reactions at 45° C. and 50° C. 20 μl RT reactions containing 1 ng to 1 μg of total HeLa RNA were performed at the given temperatures for 50 min (hot start) followed by 70° C. for 15 min. 2 μl of the resulting cDNA were added to 50 μl PCR reactions containing primer sets from 2.4 kb to 9.3 kb.

SuperScript™ II RT, EFN (His-tag), and EFN (no tag) were compared at 200 units in RT reactions from 45° C. to 55° C. 20 μl RT reactions containing 1 pg to 100 ng of total HeLa RNA were performed at the given temperatures for 50 min (hot start) followed by 70° C. for 15 min. 2 μl of the resulting cDNA were added to 50 μl PCR reactions containing either the β-actin 353 bp or Pol ε 6.8 kb primer set.

SuperScript™ II RT, EFN (His-tag), EFN (no tag), and LEFN (His-tag) were compared at 200 units in RT reactions from 45° C. to 55° C. 20 μl RT reactions containing 1 pg to 1 μg of total HeLa RNA were performed at the given temperatures for 50 min (hot start) followed by 70° C. for 15 min. 2 μl of the resulting cDNA were added to 50 μl PCR reactions containing either the β-actin 353 bp or Pol ε 6.8 kb primer set.

SuperScript™ II RT, EFN (His-tag), EFN (no tag), and LEFN (His-tag) were compared at 200 units in RT reactions from 45° C. to 55° C. with a gene-specific primer (CBP 1.6 kb) instead of Oligo(dT). 20 μl RT reactions containing 1 ng or 10 ng of total HeLa RNA were performed at the given temperatures for 50 min (hot start) followed by 70° C. for 15 min. 2 μl of the resulting cDNA were added to 50 μl PCR reactions containing the CBP 1.6 kb primer set.

SuperScript™ II RT, EFN (no tag), EFN (His-tag), and LEFN (His-tag) were compared at 200 and 400 units in RT reactions from 45° C. to 60° C. 20 μl RT reactions containing 500 ng of total HeLa RNA were performed at the given temperatures for 50 min (hot start) followed by 70° C. for 15 min. 2 μl of the resulting cDNA were added to 50 μl PCR reactions containing either the BF 2.4 kb or Pol ε 6.8 kb primer set.

SuperScript™ II RT, EFN (His-tag), LEFN (His-tag), and LEFN (tag, no His) were compared at 200 and 400 units in RT reactions from 45° C. to 60° C. 20 μl RT reactions containing 500 ng of total HeLa RNA were performed at the given temperatures for 50 min (hot start) followed by 70° C. for 15 min. 2 μl of the resulting cDNA were added to 50 μl PCR reactions containing either the BF 2.4 kb or Pol ε 6.8 kb primer set.

RT enzyme concentration: 20 μl RT reactions containing 0.1 pg to 1 μg of starting total HeLa RNA and 25 units to 250 units of EFN (His-tag) were performed at 45° C. for 50 min followed by 85° C. for 5 min. 2 μl of the resulting cDNA were added to 50 μl PCR reactions containing either the β-actin 353 bp, CBP 1.6 kb, TSC 5.3 kb, Pol ε 6.8 kb, or APC 8.5 kb primer set.

SuperScript™ II RT and LEFN (His-tag) were compared at 200 units and 400 units in RT reactions from 50° C. to 60° C. 20 μl RT reactions containing 10 ng to 1 μg of total HeLa RNA were performed at the given temperatures for 50 min (hot start) followed by 70° C. for 15 min. 2 μl of the resulting cDNA were added to 50 μl PCR reactions containing either BF 2.4 kb or Pol ε 6.8 kb primer set.

SuperScript™ II RT and LEFN (His-tag) were compared at 200 units and 400 units (LEFN was also used at 800 units) in RT reactions (with or without 0.05% Triton X-100) from 50° C. to 60° C. 20 μl RT reactions containing 500 ng of total HeLa RNA were performed at the given temperatures for 50 min (hot start) followed by 70° C. for 15 min. 2 μl of the resulting cDNA were added to 50 μl PCR reactions containing either BF 2.4 kb or Pol ϵ 6.8 kb primer set. Triton did not improve the yield of the reaction and actually reduced the yield slightly.

LEFN (tag, no His) was compared at 50, 200, and 400 units to determine the effect on sensitivity. 20 μl RT reactions containing 0.1 pg to 100 pg of total HeLa RNA were performed at 50° C. under both hot start and cold start conditions followed by 70° C. for 15 min. 2 μl of the resulting cDNA were added to 50 μl PCR reactions containing either the β-actin 353 bp or GAPDH 532 bp primer set.

Comparison of 85° C., 5 min and 70° C., 15 min Inactivation Steps. SUPERSCRIPT™ II RT and EFN (no tag) were compared in RT reactions with either a 70° C., 15 min or an 85°, 5 min inactivation step. 20 μl RT reactions containing 1 pg to 100 ng of starting total HeLa RNA and 200 units of RT were performed at 45° C. for 50 min followed by one of the inactivation steps. 2 μl of the resulting cDNA were added to 50 μl PCR reactions containing either the β-actin 353 bp, CBP 1.6 kb, Pol ϵ 3.5 kb, TSC 5.3 kb, or Pol ϵ 6.8 kb primer set.

Priming with Oligo$(dT)_{20}$, Random Hexamers, and Gene-Specific Primers (GSP). EFN (no tag) and SUPERSCRIPT™ II RT were used in RT reactions containing either 2.5 μM oligo$(dT)_{20}$, 50 ng random hexamers, or 0.1 μM GSP. 20 μl RT reactions containing 1 ng to 1 μg of starting total HeLa RNA and 200 units of RT were performed at 45° C. for 50 min followed by 70° C. for 15 min. 2 μl of the resulting cDNA were added to 50 μl PCR reactions containing either the CBP 1.6 kb, TSC 5.3 kb, or APC 8.5 kb primer set (FIG. 21).

Comparison of reverse transcriptases from various sources. LEFN (tag, no His) was compared to Clontech PowerScript™ RT, Stratagene StrataScript™ RT, Qiagen SensiScript™ RT, Qiagen OmniScript™ RT, and Promega ImProm-II™ RT System. RT reactions containing 0.1 pg to 1 μg of starting total HeLa RNA or 1 μg of rat brain RNA were performed in duplicate with each of the reverse transcriptases using the procedure and conditions recommended by each supplier. 10% of the cDNA reactions were added to 50 μl PCR reactions containing either the β-actin 353 bp, GAPDH 532 bp, CBP 1.6 kb, BF 2.4 kb, VIN 4.6 kb, FIB 9.4 kb, or Dynein 12.3 kb primer set.

TABLE 19

| Primer list |
|---|
| Human β-actin-353 bp<br>sense GCTCGTCGTCGACAACGGCTC (SEQ ID NO: 12)<br>antisense CAAACATGATCTGGGTCATCTTCTC (SEQ ID NO: 13) |
| Human GAPDH-532 bp<br>sense GTGAAGGTCGGAGTCAACGGATTT (SEQ ID NO: 14)<br>antisense CACAGTCTTCTGGGTGGCAGTGAT (SEQ ID NO: 15) |
| Human Cap Binding Protein (CBP)-1.6 kb<br>sense ATGGCGATCGTCGAACCGGA (SEQ ID NO: 16)<br>antisense CACTGTCTTAATATGAATGGGACCTACTGAG (SEQ ID NO: 17) |
| Human B-factor properdin (BF)-2.4 kb<br>sense GAGCCAAGCAGACAAGCAAAGCAAGC (SEQ ID NO: 18)<br>antisense TGTTTTAATTCAATCCCACGCCCCTGT (SEQ ID NO: 19) |
| Human DNA Polymerase ϵ (Pol ϵ)-3.5 kb<br>sense AAGGCTGGCGGATTACTGCC (SEQ ID NO: 20)<br>antisense GATGCTGCTGGTGATGTACTC (SEQ ID NO: 21) |
| Human Vinculin (VIN)-4.6 kb<br>sense GAGGAGGGCGAGGTGGACGGC (SEQ ID NO: 22)<br>antisense GAACTAACACACAGCGATGGGTGGGAA (SEQ ID NO: 23) |
| Human Tuberous Sclerosis 2 (TSC-2)-5.3 kb<br>sense GGAGTTTATCATCACCGCGGAAATACTGAGAG (SEQ ID NO: 24)<br>antisense TATTTCACTGACAGGCAATACCGTCCAAGG (SEQ ID NO: 25) |
| Human DNA Polymerase ϵ (Pol ϵ)-6.8 kb<br>sense CGCCAAATTTCTCCCCTGAA (SEQ ID NO: 26)<br>antisense CCGTAGTGCTGGGCAATGTTC (SEQ ID NO: 27) |
| Human Adenomatous Polyposis coli (APC)-8.5 kb<br>sense GCTGCAGCTTCATATGATCAGTTGTTA (SEQ ID NO: 28)<br>antisense AATGGCGCTTAGGACTTTGG (SEQ ID NO: 29) |
| Human Fibrillin (FIB)-9.4 kb<br>sense TGGAGGCTGGGAACGTGAAGGAAA (SEQ ID NO: 30)<br>antisense ACAGGAATGACCGAGGGTAATCTTGGC (SEQ ID NO: 31) |
| Rat Dynein-12.3 kb<br>sense GCGGCGCTGGAGGAGAA (SEQ ID NO: 32)<br>antisense AGGTGGCGGCTCAAACACAAAG (SEQ ID NO: 33) |
| H-fibroblast growth factor 11 (FGF)-240 bp; 97° C. denaturing, 60° C. annealing temp.<br>sense (f1-60)-CGGGTGGTAACTGGCTGCTGTGGA (SEQ ID NO: 34)<br>antisense TGGAGGCTGGGAACGTGAAGGAAA (SEQ ID NO: 35)<br>antisense (r2-299)-GCGGACCTCCCGCTTCTGCCGGA (SEQ ID NO: 36) |

TABLE 19 -continued

| Primer list |
|---|
| H-cystathionine-beta-synthase (CBS 2.4)-2390 bp; 64° C. annealing temperature<br>sense (f2-71)-CCAAGTAAAACAGCATCGGAACACCAGG (SEQ ID NO: 37)<br>antisense (r2-2460)-AAAGTCGATCAGCAGTTGCCAGGGG (SEQ ID NO: 38) |
| H-topoisomerase I (TOP3.2)-3162 bp; 60° C. annealing temperature<br>sense (f2-80)- CCCACAGTCACCGCCGCTTACCT (SEQ ID NO: 39)<br>antisense (r1-3241)-CTTCATCCCTCCCCAACCCCAATCT (SEQ ID NO: 40) |
| H-vinculin (VIN4.6)-4641 bp; 66° C. annealing temperature<br>sense (f1-132)- GAGGAGGGCGAGGTGGACGGC (SEQ ID NO: 41)<br>antisense (r2-4772)-GAACTAACACACAGCGATGGGTGGGAA (SEQ ID NO: 42) |
| H-PolE (PolE 6.8)-6800 bp; 60° C. annealing temperature<br>sense-CGCCAAATTTCTCCCCTGAA (SEQ ID NO: 43)<br>antisense-CCGTAGTGCTGGGCAATGTTC (SEQ ID NO: 44) |
| H-β-actin (βact353)-353 bp; 55° C. annealing temperature<br>sense-5' GCTCGTCGTCGACAACGGCTC (SEQ ID NO: 45)<br>antisense-ACCACATGATCTGGGTCATCTTCTC (SEQ ID NO: 46) |

Comparison of SuperScript™ III to SuperScript™ II

A comparison of SuperScript™ III to SuperScript™ II was made using the following assay. Total HeLa RNA (1 μg) was combined with 10 pmol gene specific primer (antisense primer, Table 19) and hybridized at 65 C for 5 min. Transcription with 200 U of each enzyme was carried out at 42° C., 50° C., or 55° C. for 50 min. Reverse transcription for comparison of enzyme preparations were performed using 1 pg, 10 pg, 100 ng or 1 μg of total RNA from HeLa cells with 50 pmol OligodT$_{(20)}$ at 55° C. 50 min. Reaction components included 0.5 mM dNTPs, 0.01 M DTT, 40 U RNase OUT™, 50 mM Tris-KCl (pH 8.3), 75 mM KCl, 3 mM $MgCl_2$. After reverse transcription, the enzyme was heat inactivated by incubation at 70° C. for 15 min. After a 20 min. incubation with 2 U RnaseH at 37° C., 2 μL of the 20 μL reaction was amplified by PCR using Platinum Taq hi-fidelity. The amplification reaction contained 60 mM Tris-$SO_4$ (pH 8.9), 18 mM $NH_4SO_4$, 2 mM $MgSO_4$, 0.2 mM each dNTP, 0.2 μM each primer (Table 19), and 1 U Platinum Taq high fidelity. The amplification was carried out by an initial 94° C. denaturation step for two min., followed by 35 cycles of the following steps: 94° C. 15 sec., X° C. 30 sec., 68° C. 1 min/kb, where X indicates the annealing temperature of the primer set listed in Table 19 (55° C.-66° C.). High G/C content products were amplified with the following cycling beginning with a 94° C. denaturation step for two min. followed by 35 cycles of the following: 97° C., 15 sec.; 60° C. 30 sec.; 68° C. one min. The reactions were combined with 5 μL 10× BlueJuice® and 20% (11 μL) of each reaction was electrophorsed through 0.8% or 1.5% agarose gels stained with 0.5 μg/ml ethidium bromide.

Results

RT-PCR Optimization: cDNA synthesis buffer. SuperScript™ III RT was used with the SuperScript™ II RT stand-alone conditions. These conditions were found to be optimal for SuperScript™ III RT in first-strand synthesis. No significant difference in performance in RT-PCR was seen with SuperScript™ III RT using the reaction conditions of SuperScript™ II RT stand-alone, SuperScript™ II First-Strand Synthesis System for RT-PCR, or ThermoScript RT-PCR System with a β-actin 353 bp target or with larger targets.

A magnesium concentration of 3 mM was chosen for SuperScript™ III RT as this the minimum concentration needed in the RT reaction and it was the same concentration found with the SuperScript™ II RT stand-alone. With 0.5 mM dNTPs, optimal performance was seen with magnesium concentrations from 3 mM to 7 mM with both low RNA concentrations of 1 pg, 100 ng, and 5 μg.

The pH of the 5× First-Strand Buffer will remain at 8.3 as this is the pH found in the SuperScript™ II RT buffer and little difference was seen with different pHs at higher temperatures (FIG. 14).

RT reaction temperature. 200 units of LEFN (SuperScript™ III RT) showed little reduction in product up to 50° C., which is 5° C. higher than the capabilities of SuperScript™ II RT (50 U), and 5° C. lower than that of ThermoScript RT (15 U). Results were similar with both low levels of RNA and the β-actin 353 bp primer set, and higher levels of RNA and the TSC 5.3 kb primer set.

When a His-tag is part of the RT, slightly higher thermalstability is noted. RT reactions containing 10 to 1000 ng of total HeLa RNA and 200 units of SuperScript™ II or LEFN RT were run at 45° C. to 55° C. for 50 minutes in a hot start reaction. 2 μl of the resulting cDNA products were then added to 50 μl PCR reactions containing the Pol ϵ 6.8 kb primer set. Resulting PCR products were then run on a 0.8% agarose gel containing 0.4 mg/ml ethidium bromide. Not much difference was seen between 200 units of EFN (His-tag), EFN (no tag), and LEFN (His-tag) with the β-actin 353 bp primer set with all three showing product up to 55° C. However, with the Pol ϵ 6.8 kb target, product was also seen up to 55° C. with all three mutants, except EFN (no tag) showed less product at this temperature than either of the mutants with His-tags.

The same temperature profile as found with oligo$(dT)_{20}$ and the advantage of the His-tag was also seen with a gene-specific primer. RT reactions containing 1 to 10 ng of total HeLa RNA and 200 units of SuperScript™ II, EFN, or LEFN RT were run at 45° C. to 65° C. for 50 minutes in a hot start reaction. 2 μl of the resulting cDNA products were then added to 50 μl PCR reactions containing the CBP 1.6 kb primer set. Resulting PCR products were then run on a 0.8% agarose gel containing 0.4 mg/ml ethidium bromide. Using a gene-specific primer in the RT reaction, 200 units of EFN (His-tag), EFN (no tag), and LEFN (His-tag) all still showed CBP 1.6 kb product up to 55° C., but EFN (no tag) showed slightly less than the others at 55° C.

In order to exploit the stability provided by the His-tag, LEFN with a tag minus the 6×His was designed. RT reactions containing 500 ng of total HeLa RNA and 200 or 400 units of SuperScript™ II, EFN, or LEFN RT were run at 45° C. to 65° C. for 50 minutes in a hot start reaction. 2 μl of the resulting cDNA products were then added to 50 μl PCR reactions containing the BF 2.4 kb primer set. Resulting PCR products were then run on a 0.8% agarose gel containing 0.4 mg/ml ethidium bromide. Little difference was seen with the mutant when compared to both EFN (His-tag) and LEFN (His-tag), product was seen up to 60° C. with all three with the BF 2.4 kb primer set (FIG. 15).

RT enzyme concentration. An experiment comparing units of EFN (His-tag) from 25 units to 250 units showed little difference in performance over the entire range, when looking at both sensitivity with the β-actin 353 primer set or with longer targets. RT reactions containing 0.1 to 1000 ng of total HeLa RNA and 25 to 250 units of EFN were run at 45° C. for 50 minutes in a hot start reaction. 2 μl of the resulting cDNA products were then added to 50 μl PCR reactions containing the β-actin 353 bp, CBP 1.6 kb, TSC 5.3 kb, Pol ϵ 6.8 kb, or APC 8.5 kb primer set. Resulting PCR products were then run on a 0.8% agarose gel containing 0.4 mg/ml ethidium bromide.

200 and 400 units of LEFN (tag, no His) showed slightly better performance than 50 units with low concentrations of RNA. RT reactions containing 0.1 to 100 pg of total HeLa RNA and 50 to 400 units of LEFN RT were run at 50° C. for 50 minutes in a hot start reaction. 2 μl of the resulting cDNA products were then added to 50 μl PCR reactions containing the β-actin 353 bp primer (not shown) or the GAPDH 532 primer set. Resulting PCR products were then run on a 1.5% agarose gel containing 0.4 mg/ml ethidium bromide. The higher RT units yielded slightly more PCR product under hot start conditions with both β-actin 353 bp (data not shown) and GAPDH 532 bp (FIG. 16).

Priming with Oligo$(dT)_{20}$, Random Hexamers, and Gene-Specific Primers (GSP). SuperScript™ III RT performed similarly to SuperScript™ II RT when RT reactions were run with different priming methods. Oligo(dT) yielded the cleanest product and highest specific yield with GSP having high levels on non-specific products (at 55 degrees RT temperature) and random hexamers having high specificity but low yield.

Comparison of reverse transcriptases from various sources. Using β-actin 353 bp primer set, SuperScript™ III RT was again able to detect down to 1 pg of starting HeLa RNA. RT reactions containing 1 to 100 pg of total HeLa RNA were run with each RT using the reagents and conditions specified in each protocol. 2 μl of the resulting cDNA products were then added to 50 μl PCR reactions containing the β-actin 353 bp primer set. Resulting PCR products were then run on a 1.5% agarose gel containing 0.4 mg/ml ethidium bromide. ImProm II RT and SensiScript were also able to detect down to 1 pg, but StrataScript and OmniScript could only detect down to 10 pg, and PowerScript was unable to even detect 100 pg of starting HeLa RNA.

With larger targets and higher concentrations of total HeLa RNA, SuperScript™ III RT (LEFN tag, no His) performed significantly better than most of the competitors in relation to the RT-PCR product yield and length. RT reactions containing 10 to 1000 ng of total HeLa RNA were run with each RT using the reagents and conditions specified in each protocol. 2 μl of the resulting cDNA products were then added to 50 μl PCR reactions containing the CBP 1.6 kb, BF 2.4 kb, VIN 4.6 kb or 9.4 kb primer set. Resulting PCR products were then run on a 0.8% agarose gel containing 0.4 mg/ml ethidium bromide. CLONTECH PowerScript only showed product when the total HeLa RNA was 1000 ng, and the yield of specific products was not as high as with SuperScript™ III RT. Qiagen SensiScript and OmniScript RT showed sufficient product yield with the smaller targets (CBP 1.6 kb and BF 2.4 kb), but were not able to detect the longer targets. Stratagene StrataScript was able to detect all the targets but with lower yields than SuperScript™ III RT. Promega ImProm-II RT System showed performance similar to SuperScript™ III RT, but did not have as high a yield with the longest target (FIB 9.4 kb).

Additional reactions with lower starting HeLa RNA concentrations showed a similar pattern. RT reactions containing 10 to 100 ng of total HeLa RNA were run with each RT using the reagents and conditions specified in each protocol. 2 μl of the resulting cDNA products were then added to 50 μl PCR reactions containing the CBP 1.6 kb, BF 2.4 kb, VIN 4.6 kb or 9.4 kb primer set. Resulting PCR products were then run on a 0.8% agarose gel containing 0.4 mg/ml ethidium bromide. CLONTECH PowerScript was unable to detect any of the targets with 100 ng or less of starting total HeLa RNA. Qiagen SensiScript was able to detect the VIN 4.6 kb target with this lower concentration of RNA when it had not been able to detect this target previously with 1 μg of starting total HeLa RNA. Promega ImProm-II did not perform as well as SuperScript™ III RT with lower concentrations of RNA. SuperScript™ III RT was the only RT that was able to detect the FIB 9.4 kb target with 100 ng starting total HeLa RNA.

RT-PCR analysis. SuperScript™ II and SuperScript™ III performance in hot start RT-PCR amplification at 42° C., 50° C., or 55° C. were compared and the results are shown in FIG. 17 SuperScript™ II (Panel A) or SuperScript™ III (Panel B). Lanes (in duplicate) 1, 4, 7, and 10 are products reverse transcribed at 42° C. Lanes 2, 5, 8, and 11 are products reverse transcribed at 50° C. Lanes 3, 6, 9, and 12 are products transcribed at 55° C. Lanes 1-3 are the result of RNAs reverse transcribed by gene-specific priming from FGF, lanes 4-6 CBS 2.4, lanes 7-9 from TOP 3.2, lanes 10-12 VIN 4.6. Arrows indicate expected product sizes of 240 bp, 2390 bp, 3162 bp, and 4641 bp. SuperScript™ II transcribed more robustly at 50° C. whereas SuperScript™ III best transcribes at 55° C. Amplification at 55° C. for some applications that require higher annealing temperatures for gene specific priming and/or to remove secondary structure from an RNA template may be performed with the polypeptides of the invention. This will allow the reduction of non-specific priming during reverse transcription with gene specific primers and/or the increased reverse transcription of refractory templates.

SuperScript™ III RT: Two different purification techniques. SuperScript™ III has been purified by two different methods (see above). In brief, Method A is similar to the purification technique used for SuperScript™ II, Method B differs from method A by the use of a membrane permeabilization protocol and filtration protocol to reduce cellular debris which results in a high-purity preparation. RT-PCR was performed using 200 U of SuperScript™ III purified by Method A or Method B. RT-PCR was performed using the Pol ϵ 6.8 kb primers and β-act 353 bp primers. Product yield and quality were compared for both purification methods. The methods yield similar results and either are viable methods for purification of SuperScript™ III.

Optimum SuperScript™ III RT enzyme concentration. RT reactions containing 0.1 pg to 1000 ng of total HeLa RNA and 25 to 250 units of SuperScript™ II, EFN, or LEFN RT were run at 45° C. for 50 min (hot start). 2 μl of the resulting cDNA were then added to 50 μl PCR reactions containing the β-actin 353 bp, CBP 1.6 kb, TSC 5.3 kb, Pol ϵ 6.8 kb, or APC 8.5 kb primer set. Resulting PCR products were then run on a 0.8% or 1.5% agarose gel containing 0.4 μg/ml ethidium bromide. No significant differences was obtained from 25 units to 250 units of SuperScript™ III RT. (FIG. 18). However, higher amount of SuperScript™ III RT (400 units) shows higher RT-PCR product yield at an elevated RT temperature (55 degrees, FIG. 19). In FIG. 19, RT reactions containing 10 to 1000 ng of total HeLa RNA and 200 or 400 units of SuperScript™ II or LEFN RT were run at 50° C. to 60° C. for 50 min (hot start). 2 μl of the resulting cDNA were then added to 50 μl PCR reactions containing the Pol ϵ 6.8 kb primer set. Resulting PCR products were then nm on a 0.8% agarose gel containing 0.4 μg/ml ethidium bromide. Unlike SuperScript™ II RT, increased amount of SuperScript™ III RT (up to 400 units) did not inhibit subsequent PCR amplification (FIG. 20). In FIG. 20, RT reactions containing 0.1 to 100 pg of total HeLa RNA and 50 to 800 units of LEFN RT were run at 50° C. for 50 min in hot start conditions (Oligo$(dT)_{20}$). 2 μl of the resulting cDNA were then added to 50 μl PCR reactions containing the GADPH 532 bp primer set. Resulting PCR products were then run on a 0.8% agarose gel containing 0.4 μg/ml ethidium bromide.

SuperScript™ III RT has been engineered to increase the temperature at which the enzyme can perform RT activity. The enzyme has been optimized for RT-PCR for sensitivity, yield, and target length. With this optimized system, it was demonstrated that SuperScript™ III RT was able to detect mRNA targets with as little as 1 pg of starting total HeLa RNA and to produce high yield cDNAs from targets up to 12.3 kb in size. It has the ability to function at elevated temperatures up to 55° C. and to detect a wide variety of targets. The performance of this enzyme is superior to any other RTs commercially available, and the optimized buffers and RT protocol provide a sensitive and robust RNA detection system.

Example 9: Use of Polypeptides of the Invention to Prepare Labeled Nucleic Acid Molecules Polypeptides of the invention can be used to prepare labeled nucleic acids from a variety of templates (e.g., total RNA, mRNA, etc.). For direct labeling using a polyA tailed RNA template, suitable reaction conditions may entail the use of from about 1 μg to about 1000 μg, from about 1 μg to about 500 μg, from about 1 μg to about 250 μg, from about 1 μg to about 100 μg, from about 10 μg to about 1000 μg, from about 10 μg to about 500 μg, from about 10 μg to about 250 μg, or from about 10 μg to about 100 μg of RNA.

RNA can be mixed with a suitable primer (e.g., an oligo dT primer or a gene specific primer). After mixing, the template primer mixture can be incubated at a suitable temperature (e.g., 70° C. for an oligo$(dT)_{25}$ primer) and incubated for a suitable period of time (e.g., 5 minutes). Those skilled in the art can readily determine incubation times and temperatures for any template primer pair using routine experimentation. The mixture may then be chilled on ice and the remaining reaction components added.

Suitable reaction components, which may be provided in a reaction mixture and/or solution either individually or in combination, include a buffering agent, reducing agent, one or more nucleotides, at least one of which may contain a label (e.g., a fluorescent label), one or more polypeptide of the invention, and suitable diluent (e.g., $H_2O$). A suitable reaction mixture can be prepared by combining 4 μl 5× first strand buffer, 2 μl 0.1M DTT, 1 μl 10 mM dNTP, 2 μl 1 mM Fluorescent dNTP, 2 μl SuperScript™ III (200 u/μl), an aliquot containing RNA, and $dH_2O$ to 20 μl. Additional reaction mixtures and/or solutions, as well as components thereof, which may be used with this aspect of the invention are described elsewhere herein. The mixture may be incubated at a suitable temperature, for example, from about 42° C. to about 60° C., from about 45° C. to about 60° C., from about 48° C. to about 60° C., from about 50° C. to about 60° C., from about 52° C. to about 60° C., from about 55° C. to about 60° C., from about 42° C. to about 55° C., from about 45° C. to about 55° C., from about 45° C. to about 50° C., from about 45° C. to about 48° C., from about 48° C. to about 60° C., from about 48° C. to about 55° C., from about 48° C. to about 52° C., from about 50° C. to about 60° C., from about 50° C. to about 55° C., or from about 50° C. to about 52° C. The mixture may be incubated until a sufficient incorporation of label is seen, for example, from about 5 minutes to about 24 hours, from about 10 minutes to about 24 hours, from about 30 minutes to about 24 hours, from about 1 hour to about 24 hours, from about 2 hours to about 24 hours, from about 4 hours to about 24 hours, from about 8 hours to about 24 hours, from about 30 minutes to about 16 hours, from about 30 minutes to about 8 hours, from about 30 minutes to about 4 hours, from about 30 minutes to about 2 hours, from about 30 minutes to about 1 hour, from about 1 hour to about 4 hours, or from about 1 hour to about 2 hours.

The reaction may be stopped, for example, by addition of a suitable stopping reagent (e.g., 5 μl of 0.5M EDTA in a 20 μl reaction). The resultant labeled nucleic acids may be purified using any standard technique (e.g., column purification using a SNAP column, Invitrogen Corporation, Carlsbad, Calif.).

Labeled nucleic acid produced by the methods of the invention may be used for a variety of purposes, for example, to detect a target sequence, which may be present on an array. Typically, labeled nucleic acid of the invention may be hybridized to one or more target sequences (e.g., a microarray).

In some embodiments, polypeptides of the invention may be used to prepare labeled nucleic acids by indirect labeling. For example, a modified nucleotide (e.g., an amino allyl nucleotide) may be incorporated into a nucleic acid molecule using the polypeptides of the invention. The nucleic acid molecules containing the modified nucleotide may then be reacted with a reactive molecule that comprises a detectable moiety (e.g., a fluorescent moiety, radiolabel and the like). All or a portion of the reactive molecule and the detectable moiety may then become attached to the nucleic acid molecule.

Suitable reaction conditions for indirect labeling include those listed above. For example, RNA (e.g., 5-50 μg) can be mixed with a suitable primer (e.g., an oligo$(dT)_{25}$ for polyA tailed RNA), mixed and incubated, for example, at 70° C. for 5 min, and then chilled on ice. To the primer: template mixture, addition reaction components may be added. For example, for a 30 μl reaction volume, suitable component may include: 6 μl 5× first strand buffer, 1.5 μl 0.1M DTT, 1 μl RNaseOUT (40 u/μl), 1.5 μl 10 mM dNTP mixture containing 10 mM dATP, 10 mM dCTP, 10 mM dGTP, 4 mM dTTP, and 6 mM Aminoallyl-dUTP), 2 μl SuperScript™ III (200 u/μl), X μl $dH_2O$ to a total volume of 30 μl. The mixture may be incubated at a suitable temperature for a suitable time such as those described above, for example, at 50° C. for 2 hours. The mixture may be treated to degrade the RNA template (e.g., by the addition of 150 μl 1N NaOH, and heating to 70° C. for 10 min). The pH of the solution may then be adjusted (e.g., by the addition of 15 μl 1N HCl) and the nucleic acid containing the modified nucleotide may be purified by standard techniques (e.g., using a SNAP column, Invitrogen Corporation, Carlsbad, Calif.). The purified nucleic acid may be concentrated (e.g., by ethanol precipitation).

After ethanol precipitation, the nucleic acid containing the modified nucleotide may be resuspended in a buffer suitable for coupling the reactive molecule containing the detectable moiety to the nucleic acid. For example, the nucleic acid may be resuspended in 5 μl coupling buffer (e.g., 0.1 M sodium borate, pH 8.5). The reactive molecule (e.g., a molecule comprising a dye and a reactive functionality) may be added (e.g., 5 μl monofunctional Cy3 or Cy5 dye from APB Cat#PA23001 and # PA25001). When the reactive molecule is a dye, the dye may be suspended in any suitable solvent (e.g., DMSO). In one embodiment, 1 pack of CyDye was resuspended in 45 DMSO and used as above. The reaction may be incubated for a suitable length of time and at a suitable temperature, for example, at room temperature for 1 hour. When the dye is light sensitive, the incubation is preferably performed in the dark. The coupling reaction is stopped by the addition of a reagent such as 5 μl of 4M hydroxylamine. The labeled nucleic acid is then purified (e.g., using a SNAP column, Invitrogen Corporation, Carlsbad, Calif.).

Labeled nucleic acids (whether prepared by direct or indirect labeling) may be hybridized to one or more target sequences, which may be in any suitable form, for example, in a microarray. The labeled nucleic acids are denatured (e.g., by heating at 95° C. for 2 min). The denatured, labeled nucleic acids are brought into contact with the target sequences in a suitable buffer. For example, a microarray slide can be placed in a hybridization buffer (e.g., 25% Formamide, 5×SSC, 50 mM MES pH 6.5, 0.1% SDS) that contains labeled nucleic acid (e.g., ~1 μg of Dye-label probe). The microarray can be incubated for a suitable time at a suitable temperature, for example, at 42° C. for 16 hours. The microarray may then be washed one or more times, for example, the hybridization solution may be removed and the microarray washed in Wash I (5×SSC, 0.2% SDS), followed by a wash in Wash II (1×SSC, 0.2% SDS) at 42° C. for 5 min, followed by a wash in Wash III (0.1×SSC) for 2 min. The microarray may be dried, for example, by spin drying the microarray at 600 rpm for 5 min.

The hybridized microarray may be analyzed using any techniques known in the art.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporate by reference.

What is claimed is:

1. A mutant M-MLV reverse transcriptase having at least 92% sequence identity to SEQ ID NO:2 and having one or more amino acid substitutions at a position corresponding to an amino acid of SEQ ID NO:2 selected from the group consisting of:

(a) leucine 52;
(b) tyrosine 64;
(c) lysine 152;
(d) methionine 289;
(e) threonine 306; and
(f) phenylalanine 309, wherein amino acid number 1 of said M-MLV reverse transcriptase corresponds to the threonine at position 34 of SEQ ID NO:2; and wherein said M-MLV reverse transcriptase synthesizes at least 50% as much full length cDNA at 50° C. as at it does at 40° C.

2. The M-MLV reverse transcriptase of claim 1, which synthesizes at least 70% as much full length cDNA at 50° C. as it does at 40° C.

3. The M-MLV reverse transcriptase of claim 1, which synthesizes at least 80% as much full length cDNA at 50° C. as at it does at 40° C.

4. The M-MLV reverse transcriptase of claim 1, which synthesizes at least 90% as much full length cDNA at 50° C. as at it does at 40° C.

5. A mutant M-MLV reverse transcriptase having at least 92% sequence identity to SEQ ID NO:2 and having one or more amino acid substitutions at a position corresponding to an amino acid of SEQ ID NO:2 selected from the group consisting of:

(a) leucine 52;
(b) tyrosine 64;
(c) lysine 152;
(d) methionine 289;
(e) threonine 306; and
(f) phenylalanine 309, wherein amino acid number 1 of said M-MLV reverse transcriptase corresponds to the threonine at position 34 of SEQ ID NO:2; and wherein said M-MLV reverse transcriptase synthesizes at least 20% as much full length cDNA at 52.5° C. as at it does at 40° C.

6. The M-MLV reverse transcriptase of claim 5, which synthesizes at least 40% as much full length cDNA at 52.5° C. as at it does at 40° C.

7. The M-MLV reverse transcriptase of claim 5, which synthesizes at least 50% as much full length cDNA at 52.5° C. as at it does at 40° C.

8. The M-MLV reverse transcriptase of claim 5, which synthesizes at least 60% as much full length cDNA at 52.5° C. as at it does at 40° C.

9. A mutant M-MLV reverse transcriptase having at least 92% sequence identity to SEQ ID NO:2 and having one or more amino acid substitutions at a position corresponding to an amino acid of SEQ ID NO:2 selected from the group consisting of:

(a) leucine 52;
(b) tyrosine 64;
(c) lysine 152;
(d) methionine 289;
(e) threonine 306; and
(f) phenylalanine 309, wherein amino acid number 1 of said M-MLV reverse transcriptase corresponds to the threonine at position 34 of SEQ ID NO:2; and wherein said M-MLV reverse transcriptase synthesizes at least 1% as much full length cDNA at 55° C. as at it does at 40° C.

10. The M-MLV reverse transcriptase of claim 9, which synthesizes at least 5% as much full length cDNA at 55° C. as at it does at 40° C.

11. The M-MLV reverse transcriptase of claim 9, which synthesizes at least 10% as much full length cDNA at 55° C. as at it does at 40° C.

12. The M-MLV reverse transcriptase of claim 9, which synthesizes at least 20% as much full length cDNA at 55° C. as at it does at 40° C.

* * * * *